United States Patent
Inagaki et al.

(10) Patent No.: US 8,952,010 B2
(45) Date of Patent: Feb. 10, 2015

(54) AMINO GROUP-CONTAINING PYRROLIDINONE DERIVATIVE

(75) Inventors: Hiroaki Inagaki, Tokyo (JP); Tetsunori Fujisawa, Tokyo (JP); Masao Itoh, Tokyo (JP); Aki Yokomizo, Chiba (JP); Toshifumi Tsuda, Tokyo (JP); Saito Higuchi, Tokyo (JP); Biswajit Das, Haryana (IN); Rita Katoch, New Delhi (IN); Dilip J. Upadhyay, Haryana (IN)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 13/983,540

(22) PCT Filed: Feb. 6, 2012

(86) PCT No.: PCT/JP2012/052598
§ 371 (c)(1),
(2), (4) Date: Oct. 16, 2013

(87) PCT Pub. No.: WO2012/108376
PCT Pub. Date: Aug. 16, 2012

(65) Prior Publication Data
US 2014/0187542 A1    Jul. 3, 2014

(30) Foreign Application Priority Data

Feb. 7, 2011 (JP) .................................. 2011-023772
Aug. 4, 2011 (JP) .................................. 2011-170823

(51) Int. Cl.
| | |
|---|---|
| A61K 31/538 | (2006.01) |
| A61K 31/498 | (2006.01) |
| C07D 498/12 | (2006.01) |
| C07D 265/36 | (2006.01) |
| C07D 413/04 | (2006.01) |
| C07D 413/14 | (2006.01) |
| C07D 487/04 | (2006.01) |
| C07D 241/44 | (2006.01) |
| A61K 31/5383 | (2006.01) |
| C07D 471/04 | (2006.01) |
| C07D 519/00 | (2006.01) |
| C07D 498/04 | (2006.01) |

(52) U.S. Cl.
CPC ............ *C07D 487/04* (2013.01); *C07D 265/36* (2013.01); *C07D 413/04* (2013.01); *C07D 413/14* (2013.01); *C07D 241/44* (2013.01); *A61K 31/5383* (2013.01); *C07D 471/04* (2013.01); *C07D 519/00* (2013.01); *C07D 498/04* (2013.01)
USPC ........... 514/249; 544/105; 544/336; 544/350; 514/228.8; 514/230.5; 514/247

(58) Field of Classification Search
CPC ... A61K 31/538; A61K 31/498; C07D 498/12
USPC ........ 544/105, 336, 350; 514/230.5, 247, 249
See application file for complete search history.

(56) References Cited

FOREIGN PATENT DOCUMENTS

| | | |
|---|---|---|
| WO | 02/50040 A1 | 6/2002 |
| WO | 2004/050036 A2 | 6/2004 |
| WO | 2008/009700 A1 | 1/2008 |
| WO | 2008/026172 A1 | 3/2008 |
| WO | 2008/126024 A2 | 10/2008 |
| WO | 2008/126034 A2 | 10/2008 |
| WO | 2009/077989 A1 | 6/2009 |
| WO | 2009/104147 A2 | 8/2009 |
| WO | 2009/104159 A1 | 8/2009 |
| WO | 2010/015985 A1 | 2/2010 |
| WO | 2010/041194 A1 | 4/2010 |
| WO | 2010/041218 A2 | 4/2010 |
| WO | 2010/041219 A1 | 4/2010 |

OTHER PUBLICATIONS

International Search Report mailed Feb. 28, 2012, issued in corresponding International Application No. PCT/JP2012/052598, filed Feb. 6, 2012, 8 pages.

*Primary Examiner* — Golam M M Shameem
(74) *Attorney, Agent, or Firm* — Christensen O'Connor Johnson Kindness PLLC

(57) ABSTRACT

A compound represented by the following formula (I) or a salt thereof:

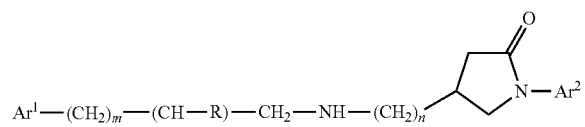

wherein R represents a hydrogen atom, a hydroxy group, or a halogen atom
$Ar^1$ represents a bicyclic heterocyclic group represented by the following formula:

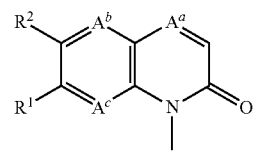

and
$Ar^2$ represents a bicyclic heterocyclic group represented by the following formulae:

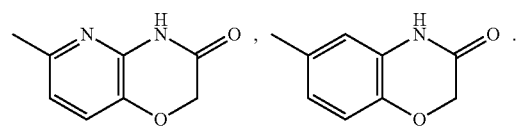

14 Claims, No Drawings

AMINO GROUP-CONTAINING PYRROLIDINONE DERIVATIVE

TECHNICAL FIELD

The present invention relates to a novel compound, a salt, or a hydrate thereof, having excellent antibacterial activity against Gram-positive bacteria and Gram-negative bacteria and also being excellent in terms of safety, and to an antibacterial agent containing the same.

BACKGROUND ART

To date, various antibiotics and synthetic antibacterial agents have been used for treatment of infectious diseases in the medical field. However, in recent years, resistant bacteria such as methicillin-resistant *Staphylococcus aureus* (MRSA), vancomycin-resistant *Enterococcus* (VRE), penicillin-resistant *Streptococcus pneumoniae* (PRSP), quinolone-resistant *Escherichia coli*, carbapenem-resistant *Klebsiella pneumoniae*, or multiple drug resistant *Pseudomonas aeruginosa* have appeared. Since these resistant bacteria are resistant to many of the existing antibiotics and antibacterial agents, the treatment of patients affected with these resistant bacteria has assumed a global importance.

Accordingly, there is a need for the development of an antibacterial agent in a different category, which has a structure different from those of the existing antibacterial agents.

As such antibacterial compounds in a different category, a group of compounds are known which have two aromatic rings that may be heterocyclic rings, and which comprise a heterocyclic ring, such as oxazolidinone, as a structural moiety for connecting these aromatic rings to each other (see Patent Literature 1 to 12, for example). However, it is considered that the compounds having such a structure must be improved in terms of safety, in order to apply them to the clinical field. With regard to the compounds of the above-described structure, a compound has not been known having a structure in which pyrrolidinone is comprised in the structure connecting the two aromatic rings.

CITATION LIST

Patent Literature

[Patent Literature 1] International Publication WO 2002/50040
[Patent Literature 2] International Publication WO 2004/50036
[Patent Literature 3] International Publication WO 2008/26172
[Patent Literature 4] International Publication WO 2008/126024
[Patent Literature 5] International Publication WO 2008/126034
[Patent Literature 6] International Publication WO 2009/77989
[Patent Literature 7] International Publication WO 2009/104147
[Patent Literature 8] International Publication WO 2009/104159
[Patent Literature 9] International Publication WO 2010/15985
[Patent Literature 10] International Publication WO 2010/41194
[Patent Literature 11] International Publication WO 2010/41218
[Patent Literature 12] International Publication WO 2010/41219

SUMMARY OF INVENTION

Problems to be Solved by the Invention

There is a need for the development of an agent which exhibits wide and strong antibacterial activity against Gram-positive bacteria, Gram-negative bacteria, and the resistant bacteria thereof, and also having excellent safety.

Means for Solving the Problems

As a result of intensive studies, the present inventors have found that a compound represented by formula (I) as described below, a salt, or a hydrate thereof, which has two heteroaryl groups, at each end of a molecule thereof, and which comprises pyrrolidinone in a structural moiety for connecting these groups to each other, exhibits wide and strong antibacterial activity against Gram-positive bacteria and Gram-negative bacteria and also has excellent safety, thereby completing the present invention.

Specifically, the invention of the present application includes the following:

[1] A compound represented by the following formula (I) or a salt thereof:

[Formula 1]

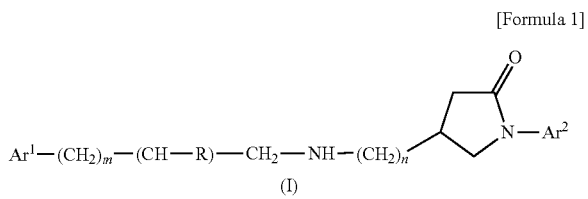

wherein R represents a hydrogen atom, a hydroxy group, or a halogen atom, m represents an integer 0, 1 or 2, n represents an integer 0 or 1

$Ar^1$ represents a bicyclic heterocyclic group represented by the following formula:

[Formula 2]

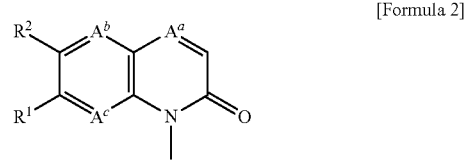

wherein $A^a$ represents a nitrogen atom or C—$R^a$, $A^b$ represents a nitrogen atom or C—$R^b$, and $A^c$ represents a nitrogen atom or C—$R^c$, $R^a$, $R^b$, and $R^c$ independently represent a hydrogen atom or an alkyl group containing 1 to 6 carbon atoms, $R^1$ and $R^2$ independently represent a hydrogen atom, an alkoxy group containing 1 to 6 carbon atoms, a halogenoalkoxy group containing 1 to 6 carbon atoms, a halogen atom, or a cyano group, and $Ar^2$ represents a bicyclic heterocyclic group represented by one of the following formulae:

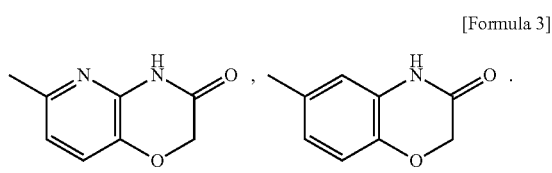

[Formula 3]

In addition, the invention of the present application includes the following [2] to [15].

[2] The compound or a salt thereof according to [1], wherein $Ar^1$ is a group selected from the bicyclic heterocyclic groups shown in the following formulae:

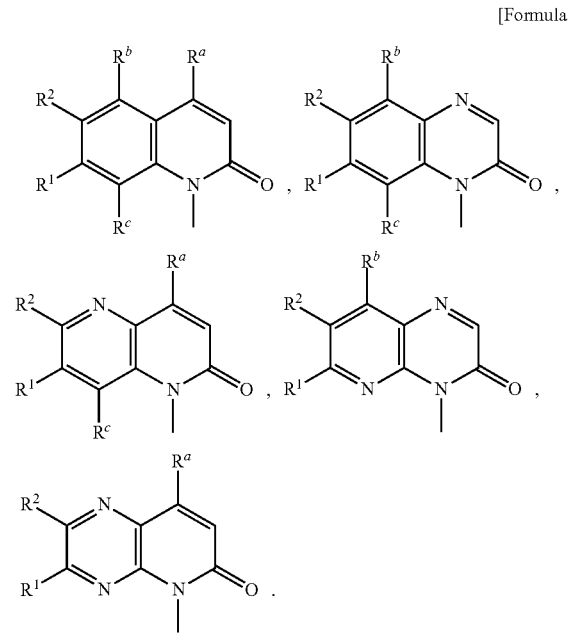

[Formula 4]

wherein, $R^1$, $R^2$, $R^a$, $R^b$ and $R^c$ are as defined above.

[3] The compound or a salt thereof according to [2], wherein $R^a$, $R^b$ and $R^c$ independently represent a hydrogen atom or a methyl group.

[4] The compound or a salt thereof according to [3], wherein $R^b$ and $R^c$ represent a hydrogen atom.

[5] The compound or a salt thereof according to [1], wherein $Ar^1$ is a group selected from the bicyclic heterocyclic groups shown in the following formulae:

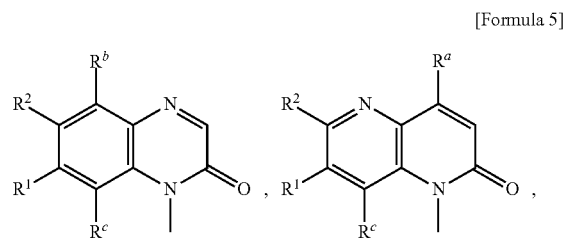

[Formula 5]

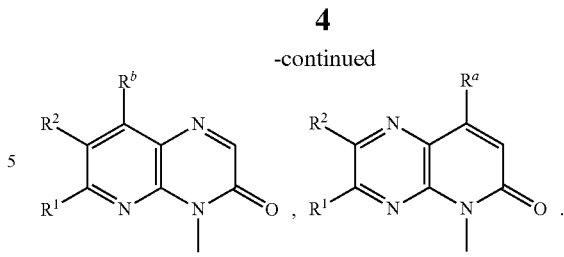

-continued

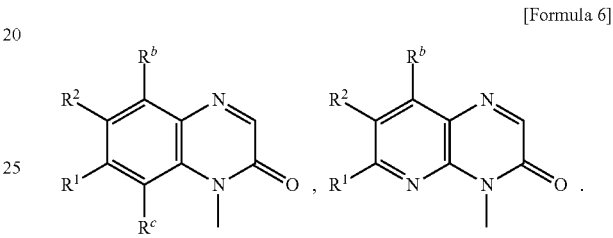

wherein, $R^1$, $R^2$, $R^a$, $R^b$, and $R^c$ are as defined above.

[6] The compound or a salt thereof according to [1], wherein $A^a$ represents a nitrogen atom.

[7] The compound or a salt thereof according to [6], wherein $Ar^1$ is a group selected from the bicyclic heterocyclic groups shown in the following formulae:

[Formula 6]

wherein, $R^1$, $R^2$, $R^b$ and $R^c$ are as defined above.

[8] The compound or a salt thereof according to [6] or [7], wherein both $R^b$ and $R^c$ are a hydrogen atom.

[9] The compound or a salt thereof according to any one of [1] to [8], wherein m is an integer 1 or 2, and the sum of m and n is 1 or 2.

[10] The compound or a salt thereof according to any one of [1] to [9], wherein $R^1$ is an alkoxy group containing 1 to 6 carbon atoms.

[11] The compound or a salt thereof according to any one of [1] to [10], wherein $R^1$ is a methoxy group.

[12] The compound or a salt thereof according to any one of [1] to [11], wherein R is a hydrogen atom or a hydroxyl group.

[13] A pharmaceutical agent comprising the compound or a salt thereof of [1] to [12] as its active ingredient.

[14] A therapeutic agent for infectious diseases, which comprises the compound or a salt thereof of [1] to [12] as its active ingredient.

[15] A method for the treatment of infectious diseases, which comprises administering the compound or a salt thereof of [1] to [12].

Advantageous Effects of the Invention

The compound, a salt, or a hydrate thereof, of the invention of the present application, namely a compound having two heteroaryl groups, at each end of a molecule thereof, and comprising pyrrolidinone in a structural moiety for connecting these groups to each other, exhibits wide and strong antibacterial activity against Gram-positive bacteria and Gram-negative bacteria, and is excellent in terms of safety. Accordingly, the compound of the present invention is anticipated to exhibit excellent efficacy for the treatment and/or prevention of infectious diseases, and is thus useful.

MODE FOR CARRYING OUT THE INVENTION

Hereafter, the present invention is explained in detail.

The compound having the structure (I) contains bicyclic aromatic heterocyclic substituents (heteroaryl group; in the present application, each may be abbreviated as $Ar^1$ or $Ar^2$) at both end of the molecule, and the two heteroaryl groups are connected by the structural unit containing the pyrrolidinone group. The two heteroaryl groups have 6-6 fused ring systems and contain 1 to 4 nitrogen atoms as constituent members of the ring.

With regard to $Ar^1$, this contains an amide group at its 1 and 2 positions forming a cyclic amide structure with a 2-oxo group. The nitrogen atom within this amide structure is the site for connection to $Ar^2$.

$Ar^2$ has a 1,4-benzoxazine structure and cyclic amide structure whose amide group is constituted at the 3 and 4 positions with a 3-oxo group. $Ar^2$ is connected directly at the 6 position to the pyrrolidinone contained in the connecting structure moiety, and moreover on the nitrogen atom of said pyrrolidinone (these position numbers are determined based on the structure wherein $A^a$ to $A^c$ in $Ar^1$ are C—H and when $Ar^2$ is a 1,4-benzoxazine).

Within the bicyclic-aromatic-heterocyclic substituent $Ar^1$, $A^a$, $A^b$, and $A^c$, represent a nitrogen atom forming part of the bicyclic aromatic ring or a carbon atom bearing $R^a$, $R^b$, or $R^c$ and forming part of the ring structure.

Here, $R^a$, $R^b$, and $R^c$ each independently represents a hydrogen atom or an alkyl group having one to six carbon atoms. Examples of such an alkyl group include, methyl, ethyl, n-propyl, isopropyl, n-butyl, isobutyl, sec-butyl, tert-butyl, n-pentyl, isopentyl, 2-ethylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, and the like. As for the alkyl group, methyl and ethyl groups are preferable, and methyl groups are more preferable. With regard to $R^a$, $R^b$, and $R^c$, independently, a hydrogen atom or a methyl group is preferable, and a hydrogen atom is more preferable.

With regard to $Ar^1$, the following are preferred examples:

[Formula 7]

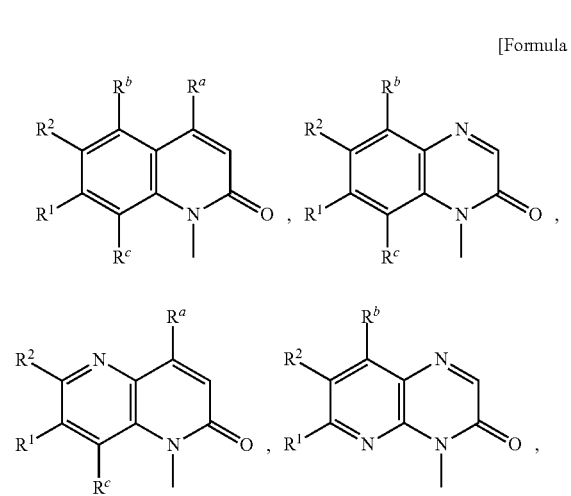

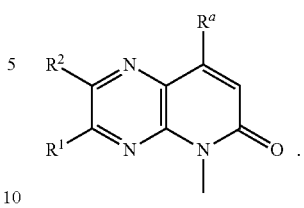

[wherein, the definition of $R^1$, $R^2$, $R^3$, $R^a$, $R^b$, or $R^c$ is the same as defined above.]

and more particularly, the following are preferable:

[Formula 8]

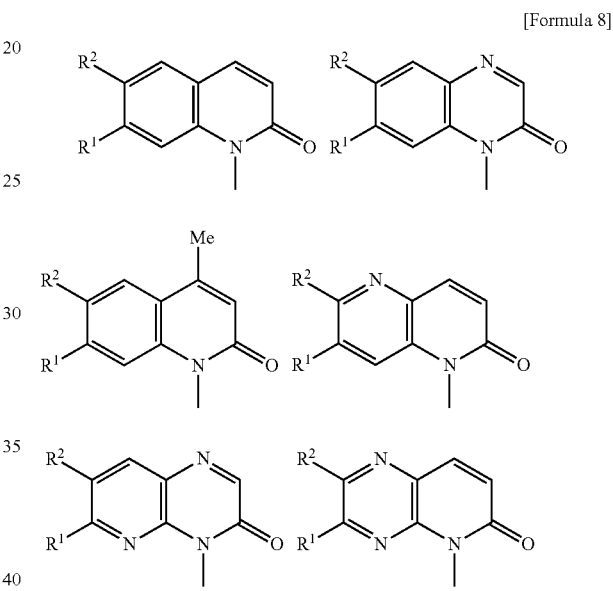

And the following are more preferable as $Ar^1$:

[Formula 9]

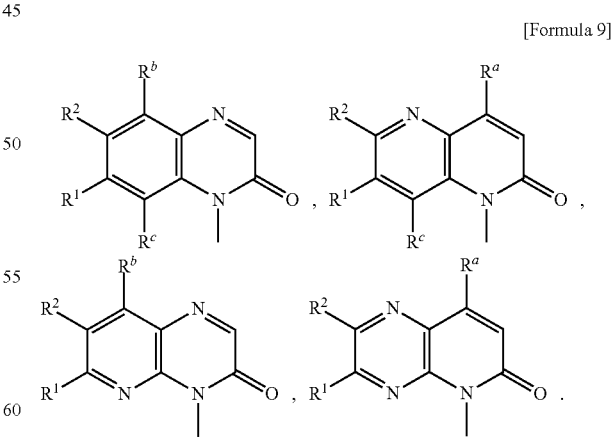

[wherein, the definition of $R^1$, $R^2$, $R^a$, $R^b$, or $R^c$ is the same as defined above.]

and more particularly, the following are the more preferred examples:

[Formula 10]

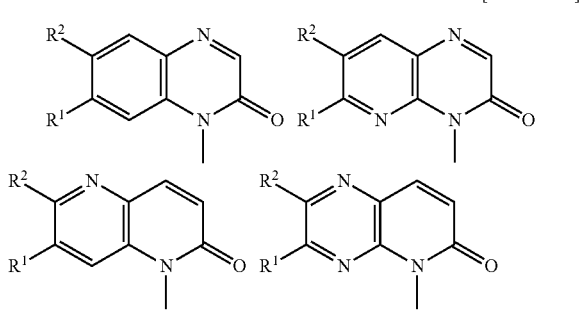

And further preferably as $Ar^1$, the following are exemplified:

[Formula 11]

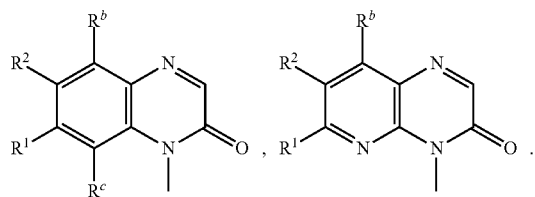

[wherein, the definition of $R^1$, $R^2$, $R^a$, $R^b$, or $R^c$ is the same as defined above.]

And more particularly, the following are further preferred examples.

[Formula 12]

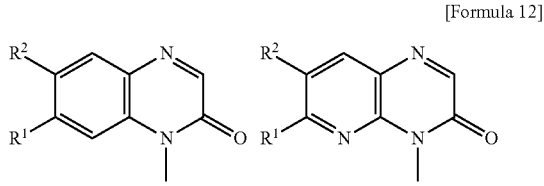

Further, $Ar^1$ has the substituents $R^1$ and $R^2$. $R^1$ or $R^2$ may be a substituent selected from the group of a hydrogen atom, an alkoxy group having 1 to 6 carbon atoms, a halogenoalkoxy group containing from 1 to 6 carbon atoms, a halogen atom, and a cyano group.

When $R^1$ or $R^2$ is an alkoxy group, the alkyl group which constitutes the alkoxy group may have 1 to 6 carbon atoms, and may be straight chain or branched chain. Examples of such an alkyl group include methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpenyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl. The alkoxy group is preferably a methoxy group, an ethoxy group or a propoxy group, and is particularly preferably a methoxy group.

When $R^1$ or $R^2$ is a halogenoalkoxy group having 1 to 6 carbon atoms, this may be the alkoxy group exemplified above substituted with halogen atoms. When $R^1$ or $R^2$ is a halogen atom, a chlorine atom or a fluorine atom is preferable, and a fluorine atom is more preferable. The number of halogen atoms substituted may be 1 or greater than 1, and in particular, when the halogen atom is a fluorine atom, perfluoro-substitution may be possible. The position of substitution is not particularly limited, and the position that is on the terminal carbon atom is more preferable. Preferred examples of a halogenoalkoxy group include a fluoromethoxy group, a difluoromethoxy group, a trifluoromethoxy group, a 2-fluoroethoxy group, and a 2,2,2-trifluoroethoxy group. Among these, a difluoromethoxy group is preferable.

When $R^1$ or $R^2$ is a halogen atom, a chlorine atom or a fluorine atom is preferable, and a fluorine atom is more preferable.

Preferred examples of $Ar^2$ include the following:

[Formula 13]

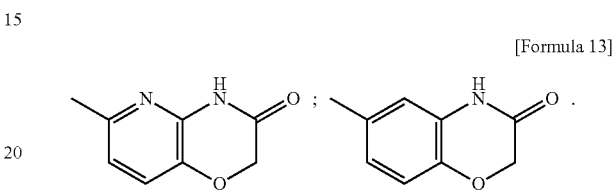

A structure for connecting the above two heteroaryl groups $Ar^1$ and $Ar^2$ to each other will be described. One characteristic of the compound of the present invention is that this structure contains pyrrolidinone. The pyrrolidinone is preferably 2-pyrrolidinone. This pyrrolidinone preferably has a structure in which the heteroaryl group $Ar^2$ is connected to the structure on a nitrogen atom thereof. Moreover, the other heteroaryl group ($Ar^1$) is also connected to the structure on a carbon atom of the pyrrolidinone ring, via another connecting moiety. The connecting position of the connecting moiety to $Ar^1$ on this 2-pyrrolidinone ring is preferably at the 4-position thereof. Further, two different isomers are formed according to the mode of connection at the 4 position of the pyrrolidinone, and all of the isomers are included in the present invention.

[Formula 14]

The connecting moiety to $Ar^1$ is characterized in that it contains an amino group. It is preferable that this amino group is directly connected to the 4-position of the 2-pyrrolidinone or is connected to it via one methylene group.

The connecting moiety from this amino group to $Ar^1$ is composed of a methylene chain containing 2 to 4 carbon atoms. Furthermore, a substituent may be present on this methylene chain. This methylene chain preferably has a structure in which a methylene chain containing 3 carbon atoms is connected to an amino group. When a substituent is present on this methylene chain, it is preferably a structure in which such a substituent is present on the second methylene from the amino group.

As a substituent on the methylene chain that is the binding structure from the amino group to $Ar^1$, a hydroxy group or a fluorine atom is preferable. A hydroxy group is more preferable. When such a substituent is present, an optical isomer is also present. This may be any type of isomer.

Thus, the following structures are constructed:

Ar$^1$—CH$_2$—CH$_2$—NH-(2-Pyrrolidinone-1-Ar$^2$-4-yl)
Ar$^1$—CH$_2$—CH$_2$—CH$_2$—NH-(2-Pyrrolidinone-1-Ar$^2$-4-yl)
Ar$^1$—CH$_2$—CH$_2$—CH$_2$—CH$_2$—NH-(2-Pyrrolidinone-1-Ar$^2$-4-yl)
Ar$^1$—CH$_2$—CHF—CH$_2$—NH-(2-Pyrrolidinone-1-Ar$^2$-4-yl)
Ar$^1$—CH$_2$—CH$_2$—CHF—CH$_2$—NH-(2-Pyrrolidinone-1-Ar$^2$-4-yl)
Ar$^1$—CH$_2$—CH(OH)—CH$_2$—NH-(2-Pyrrolidinone-1-Ar$^2$-4-yl)
Ar$^1$—CH$_2$—CH$_2$—CH(OH)—CH$_2$—NH-(2-Pyrrolidinone-1-Ar$^2$-4-yl)
Ar$^1$—CH$_2$—CH$_2$—NH—CH$_2$-(2-Pyrrolidinone-1-Ar$^2$-4-yl)
Ar$^1$—CH$_2$—CH$_2$—CH$_2$—NH—CH$_2$-(2-Pyrrolidinone-1-Ar$^2$-4-yl)
Ar$^1$—CH$_2$—CH$_2$—CH$_2$—CH$_2$—NH—CH$_2$-(2-Pyrrolidinone-1-Ar$^2$-4-yl)
Ar$^1$—CH$_2$—CHF—CH$_2$—NH—CH$_2$-(2-Pyrrolidinone-1-Ar$^2$-4-yl)
Ar$^1$—CH$_2$—CH$_2$—CHF—NH—CH$_2$-(2-Pyrrolidinone-1-Ar$^2$-4-yl)
Ar$^1$—CH$_2$—CH(OH)—CH$_2$—NH—CH$_2$-(2-Pyrrolidinone-1-Ar$^2$-4-yl)
Ar$^1$—CH$_2$—CH$_2$—CH(OH)—CH$_2$—NH—CH$_2$-(2-Pyrrolidinone-1-Ar$^2$-4-yl)

[(2-Pyrrolidinone-1-Ar$^2$-4-yl) means that the 4-position is the connecting position of the 2-pyrrolidinone to which Ar$^2$ is bonded at the 1-position.]

Among these, the following structures are more preferable:

Ar$^1$—CH$_2$—CH$_2$—CH$_2$—NH-(2-Pyrrolidinone-1-Ar$^2$-4-yl)
Ar$^1$—CH$_2$—CHF—CH$_2$—NH-(2-Pyrrolidinone-1-Ar$^2$-4-yl)
Ar$^1$—CH$_2$—CH$_2$—CH$_2$—CH$_2$—NH-(2-Pyrrolidinone-1-Ar$^2$-4-yl)
Ar$^1$—CH$_2$—CH(OH)—CH$_2$—NH-(2-Pyrrolidinone-1-Ar$^2$-4-yl)
Ar$^1$—CH$_2$—CH$_2$—CHF—CH$_2$—NH-(2-Pyrrolidinone-1-Ar$^2$-4-yl)
Ar$^1$—CH$_2$—CH$_2$—NH—CH$_2$-(2-Pyrrolidinone-1-Ar$^2$-4-yl)
Ar$^1$—CH$_2$—CH$_2$—CH$_2$—NH—CH$_2$-(2-Pyrrolidinone-1-Ar$^2$-4-yl)
Ar$^1$—CH$_2$—CH(OH)—CH$_2$—NH—CH$_2$-(2-Pyrrolidinone-1-Ar$^2$-4-yl)
Ar$^1$—CH$_2$—CHF—CH$_2$—NH—CH$_2$-(2-Pyrrolidinone-1-Ar$^2$-4-yl)

Preferred compounds of the invention of the present application include the following compounds:

6-(4-{[4-(7-methoxy-2-oxoquinoxalin-1(2H)-yl)butyl]amino}-2-oxopyrrolidin-1-yl)-2H-1,4-benzoxazin-3(4H)-one;
6-(4-{[3-(7-methoxy-2-oxoquinoxalin-1-(2H)-yl)propyl]amino}-2-oxopyrrolidin-1-yl)-2H-1,4-benzoxazin-3(4H)-one;
6-[(4R)-4-{[3-(7-methoxy-2-oxoquinoxalin-1(2H)-yl)propyl]amino}-2-oxopyrrolidin-1-yl]-2H-1,4-benzoxazin-3(4H)-one;
6-[(4S)-4-{[3-(7-methoxy-2-oxoquinoxalin-1(2H)-yl)propyl]amino}-2-oxopyrrolidin-1-yl]-2H-1,4-benzoxazin-3(4H)-one;
6-[(4R)-4-{[3-(7-methoxy-2-oxoquinoxalin-1(2H)-yl)propyl]amino}-2-oxopyrrolidin-1-yl]-2H-pyrido[3,2-b][1,4]oxazin-3(4H)-one;
6-[(4S)-4-{[3-(7-methoxy-2-oxoquinoxalin-1(2H)-yl)propyl]amino}-2-oxopyrrolidin-1-yl]-2H-pyrido[3,2-b][1,4]oxazin-3(4H)-one;
6-methoxy-4-(4-{[5-oxo-1-(3-oxo-3,4-dihydro-2H-1,4-benzoxazin-6-yl)pyrrolidin-3-yl]amino}butyl)pyrido[2,3-b]pyrazin-3(4H)-one;
6-[(4R)-4-({[2-(7-methoxy-2-oxoquinoxalin-1(2H)-yl)ethyl]amino}methyl)-2-oxopyrrolidin-1-yl]-2H-1,4-benzoxazin-3(4H)-one;
6-[(4R)-4-({[3-(7-methoxy-2-oxoquinoxalin-1(2H)-yl)propyl]amino}methyl)-2-oxopyrrolidin-1-yl]-2H-1,4-benzoxazin-3(4H)-one;
3-methoxy-5-[2-({[(3R)-5-oxo-1-(3-oxo-3,4-dihydro-2H-1,4-benzoxazin-6-yl)pyrrolidin-3-yl]methyl}amino)ethyl]pyrido[2,3-b]pyrazin-6 (5H)-one;
6-[(4R)-4-({[2-(7-methoxy-2-oxoquinoxalin-1(2H)-yl)ethyl]amino}methyl)-2-oxopyrrolidin-1-yl]-2H-pyrido[3,2-b][1,4]oxazin-3(4H)-one;
6-[(4R)-4-({[2-(7-fluoro-2-oxo-1,5-naphthyridin-1(2H)-yl)ethyl]amino}methyl)-2-oxopyrrolidin-1-yl]-2H-pyrido[3,2-b][1,4]oxazin-3(4H)-one;
6-[(4R)-4-({[2-hydroxy-3-(6-methoxy-3-oxopyrido[2,3-b]pyrazin-4(3H)-yl)propyl]amino}methyl)-2-oxopyrrolidin-1-yl]-2H-pyrido[3,2-b][1,4]oxazin-3(4H)-one;
6-[(4R)-4-({[(2S)-2-hydroxy-3-(6-methoxy-3-oxopyrido[2,3-b]pyrazin-4(3H)-yl)propyl]amino}methyl)-2-oxopyrrolidin-1-yl]-2H-pyrido[3,2-b][1,4]oxazin-3(4H)-one;
6-[(4R)-4-({[2-fluoro-3-(7-methoxy-2-oxoquinoxalin-1(2H)-yl)propyl]amino}methyl)-2-oxopyrrolidin-1-yl]-2H-1,4-benzoxazin-3(4H)-one;
6-[(4R)-4-{[(2S)-2-hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one;
6-[(4S)-4-{[(2S)-2-hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one;
6-[(4R)-4-{[(2R)-2-hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one;
6-[(4S)-4-{[(2R)-2-hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one;
6-(4-{[3-(7-methoxy-2-oxoquinoxalin-1(2H)-yl)propyl]amino}-2-oxopyrrolidin-1-yl)-2H-pyrido[3,2-b][1,4]oxazin-3(4H)-one;
3-methoxy-5-(3-{[5-oxo-1-(3-oxo-3,4-dihydro-2H-1,4-benzoxazin-6-yl)pyrrolidin-3-yl]amino}propyl)pyrido[2,3-b]pyrazin-6 (5H)-one;
6-(4-{[4-(7-methoxy-2-oxoquinoxalin-1(2H)-yl)butyl]amino}-2-oxopyrrolidin-1-yl)-2H-pyrido[3,2-b][1,4]oxazin-3(4H)-one;
6-methoxy-4-(3-{[5-oxo-1-(3-oxo-3,4-dihydro-2H-1,4-benzoxazin-6-yl)pyrrolidin-3-yl]amino}propyl)pyrido[2,3-b]pyrazin-3(4H)-one;
6-((4R)-4-({[3-(6-methoxy-3-oxopyrido[2,3-b]pyrazin-4(3H)-yl)propyl]amino}methyl)-2-oxopyrrolidin-1-yl)-2H-pyrido[3,2-b][1,4]oxazin-3(4H)-one;
6-[(4S)-4-({[3-(6-methoxy-3-oxopyrido[2,3-b]pyrazin-4(3H)-yl)propyl]amino}methyl)-2-oxopyrrolidin-1-yl]-2H-pyrido[3,2-b][1,4]oxazin-3(4H)-one;
6-[(4R)-4-({[3-(6,7-difluoro-2-oxoquinoxalin-1(2H)-yl)propyl]amino}methyl)-2-oxopyrrolidin-1-yl]-2H-pyrido[3,2-b][1,4]oxazin-3(4H)-one;
6-[(4R)-4-({[3-(6-fluoro-2-oxoquinoxalin-1(2H)-yl)propyl]amino}methyl)-2-oxopyrrolidin-1-yl]-2H-pyrido[3,2-b][1,4]oxazin-3(4H)-one;

6-[(4R)-4-{[3-(6,7-difluoro-2-oxoquinoxalin-1(2H)-yl)propyl]amino}-2-oxopyrrolidin-1-yl]-2H-pyrido[3,2-b][1,4]oxazin-3(4H)-one;

6-[(4R)-4-{[3-(7-fluoro-2-oxoquinoxalin-1(2H)-yl)propyl]amino}-2-oxopyrrolidin-1-yl]-2H-pyrido[3,2-b][1,4]oxazin-3(4H)-one;

6-[(4S)-4-{[3-(6-methoxy-3-oxopyrido[2,3-b]pyrazin-4(3H)-yl)propyl]amino}-2-oxopyrrolidin-1-yl]-2H-pyrido[3,2-b][1,4]oxazin-3(4H)-one;

6-[(4R)-4-{[3-(6-methoxy-3-oxopyrido[2,3-b]pyrazin-4(3H)-yl)propyl]amino}-2-oxopyrrolidin-1-yl]-2H-pyrido[3,2-b][1,4]oxazin-3(4H)-one;

6-[(4R)-4-({[3-(7-fluoro-2-oxoquinoxalin-1(2H)-yl)propyl]amino}methyl)-2-oxopyrrolidin-1-yl]-2H-pyrido[3,2-b][1,4]oxazin-3(4H)-one;

6-[(4R)-4-{[3-(7-methoxy-4-methyl-2-oxoquinolin-1(2H)-yl)propyl]amino}-2-oxopyrrolidin-1-yl]-2H-pyrido[3,2-b][1,4]oxazin-3(4H)-one;

6-[(4R)-4-{[3-(3-methoxy-6-oxopyrido[2,3-b]pyrazin-5(6H)-yl)propyl]amino}-2-oxopyrrolidin-1-yl]-2H-pyrido[3,2-b][1,4]oxazin-3(4H)-one;

6-[(4R)-4-({[3-(3-methoxy-6-oxopyrido[2,3-b]pyrazin-5(6H)-yl)propyl]amino}methyl)-2-oxopyrrolidin-1-yl]-2H-pyrido[3,2-b][1,4]oxazin-3(4H)-one.

Next, a method for producing the compound of the present invention will be described.

The compound represented by the formula (1) of the present invention (which may be abbreviated as compound 1; compounds of other structures with different numbers will be abbreviated in the same way) is produced by various methods. For example, it can be produced by the following method.

For example, the compound represented by the formula (1) of the present invention can be produced by performing a reductive alkylation reaction (a reductive amination reaction) between compound 2 as an aldehyde compound and compound 3 as an amine compound (Scheme 1). That is to say, an imine compound or an iminium compound which is initially generated from the reaction between the compound 2 and the compound 3 is reduced, so that it is converted to the compound 1. This reaction may be carried out either as a one-pot reaction or as a stepwise reaction.

Scheme 1

[Formula 15]

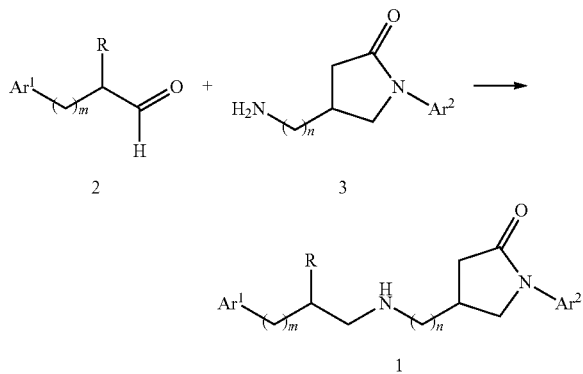

This reaction can be carried out by the method described in Advanced Organic Chemistry, 4$^{th}$ edition (written by Jerry March), pp. 898-900, 1991, John Wiley & Sons, Inc. etc., or by methods equivalent thereto. As a reducing agent used in this reaction, a hydrogenated complex compound can preferably be used. As such a hydrogenated complex compound, a boron-containing compound is preferable, and examples of such a boron-containing compound include sodium borohydride, sodium triacetoxy borohydride, and sodium cyano borohydride. In addition, catalytic reduction using a metal catalyst such as palladium carbon, Raney nickel, platinum oxide or palladium black can preferably be used. As a reduction reaction, reduction using a boron-containing hydrogenated complex compound is simple to carry out, and thus it is preferably used.

With regard to reaction temperature, both the imine/iminium ion formation reaction and the reduction reaction can be carried out within a temperature range between −100° C. and 150° C., and preferably between −20° C. and 50° C.

Various functional groups of the compounds 2 and 3 may be protected by suitable protective groups during the present reaction, as desired. After completion of the reaction, such functional groups are deprotected, so that the compounds can be converted to the compound 1.

Moreover, the compound 1 can also be produced by allowing compound 5 to react with compound 4 having a leaving group L$^1$ and performing an alkylation reaction on the amino group of a pyrrolidinone compound, as described below (Scheme 2).

Scheme 2

[Formula 16]

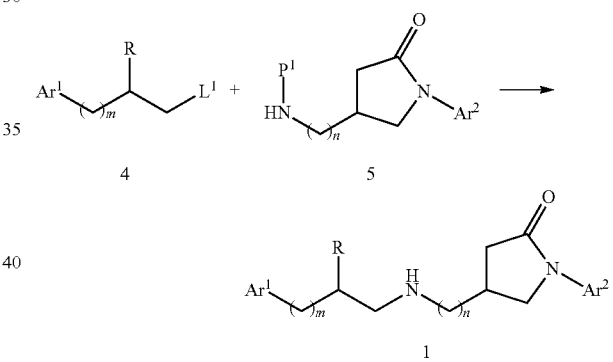

This reaction can be carried out by the method described in Advanced Organic Chemistry, 4$^{th}$ edition (written by Jerry March), pp. 411-413 and pp. 425-427, 1991, John Wiley & Sons, Inc., or by the method described in Chemical Communications, 2004, pp. 353-359, etc., or by methods equivalent thereto. This reaction is generally carried out in the presence of a base. Examples of suitable bases include: inorganic bases such as potassium carbonate or cesium carbonate; organic bases such as triethylamine or N,N-diisopropylethylamine; and sodium hydride, lithium N,N-diisopropylamide, lithium hexamethyldisilazide, sodium hexamethyldisilazide, and potassium hexamethyldisilazide.

The reaction can be carried out within a temperature range between −100° C. and 250° C., and preferably between −20° C. and 150° C.

P$^1$ may be either hydrogen or a protective group. Examples of such a protective group include: aralkyl group-type protective groups such as a benzyl group, a benzhydryl group and a trityl group; acyl group (alkylcarbonyl, aralkylcarbonyl, arylcarbonyl, etc.)-type protective groups such as a formyl group, a trifluoroacetyl group and a trichloroacetyl group; alkyl- and aralkyloxycarbonyl-type protective groups such as a benzyloxycarbonyl group and a tert-butoxycarbonyl group; and other protective groups such as a tosyl group, a nosyl group, a tert-butylsulfinyl group and a sulfo group. Such a protective group is removed under suitable conditions after completion of the present alkylation reaction, so that the compounds can be converted to the compound 1.

Examples of the leaving group $L^1$ include: leaving groups such as a mesylate group, a tosylate group, a trifluoroacetoxy group and a trifluoromethanesulfonyloxy group; as well as a halogen atom.

Various functional groups of the compounds 4 and 5 may be protected by suitable protective groups during the present reaction, as desired. In this case, such functional groups are deprotected after completion of the reaction, so that the compounds can be converted to the compound 1.

Furthermore, the compound 1 can also be produced by carrying out a cross-coupling reaction between a lactam compound 6 and a compound 7 to introduce an aromatic ring on the nitrogen atom of the lactam compound (Scheme 3).

Scheme 3

[Formula 17]

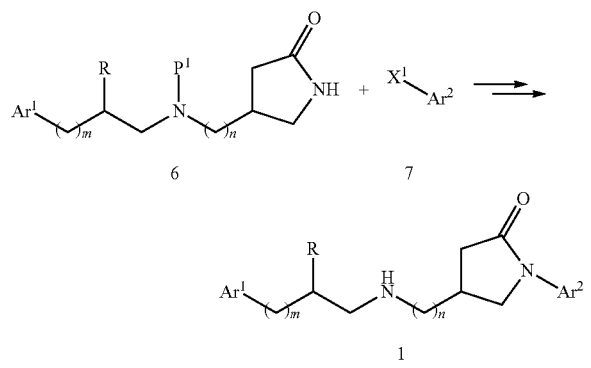

This reaction can be carried out by the method described in Strategic Applications of Name Reactions in Organic Synthesis (edited by L. Kuerti et al.), pp. 70-71, 2005, Elsevier Inc., Metal-Catalyzed Cross-Coupling Reactions, Vol. 2, $2^{nd}$ edition (edited by Armin de meijere et al.), pp. 699-760, 2004, WILEY-VCH Verlag GmbH & Co., KGaA Publishing Company, or Journal of The American Chemical Society, Vol. 124, No. 25, pp. 7421-7428, 2002, etc., or by methods equivalent thereto.

$X^1$ may be a tosyloxy group, a mesyloxy group, a trifluoromethanesulfonyloxy group, etc., as well as a halogen atom such as chlorine, bromine or iodine.

Various functional groups of the compounds 6 and 7 may be protected by suitable protective groups during the present reaction, as desired. Such protective groups are deprotected after completion of the reaction, so that the compounds can be converted to the compound 1.

This coupling reaction may be carried out in the presence of a catalyst, which is composed of a metal atom and a ligand. Examples of the catalyst metal include palladium and copper. These metals can be added to the reaction in the form of palladium(II) acetate, tris(dibenzilideneacetone)dipalladium (0), copper(I) iodide, etc. When the catalyst metal is palladium for instance, examples of the catalyst ligand include BINAP and S-Phos. When the catalyst metal is copper for instance, examples of the ligand include N,N'-dimethylethylenediamine and trans-1,2-diaminocyclohexane. A catalyst may be prepared by mixing a catalyst metal with a ligand compound before initiation of the reaction. Alternatively, the catalyst metal and the ligand compound may be added to the reaction mixture separately, so that a catalyst may be generated in the reaction mixture. This coupling reaction is preferably carried out in the presence of a base, as well as the catalyst compound. Examples of a suitable base include inorganic bases such as potassium carbonate, cesium carbonate, and potassium phosphate.

The reaction can be carried out within a temperature range between 0° C. and 250° C., and preferably between 50° C. and 150° C.

Moreover, it may also be possible that a cross-coupling reaction be carried out between the compound 6 and a compound 8 having a monocyclic structure, instead of the compound 7 having a fused ring structure, and that functional groups R11 and R12 then be converted to construct a condensed ring structure, and that the compounds then be converted to the compound 1 (Scheme 4). R11 may be a nitro group, a halogen atom, or the like, which can then be converted to an amino group. R12 may be, for example, hydrogen, a suitable protective group, an alkoxycarbonylmethyl group, or the like. For example, when R11 is a nitro group and R12 is an alkoxycarbonylmethyl group, the compounds may be converted to the compound 1 by carrying out a thermal treatment in the presence of iron/acetic acid, or a catalytic reductive reaction.

Scheme 4

[Formula 18]

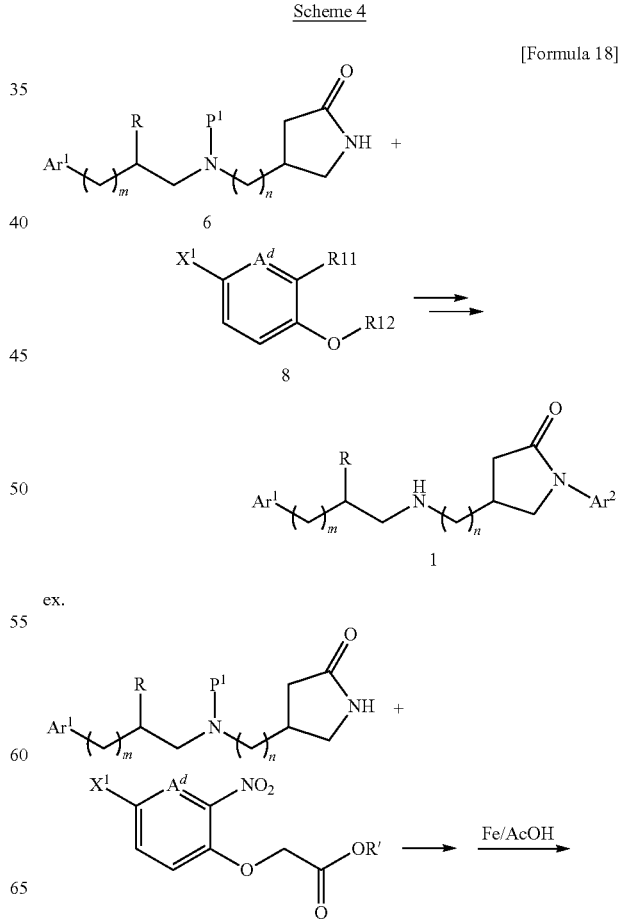

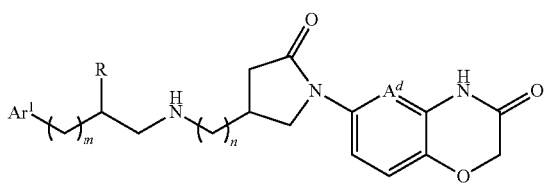

Further, the compound 1 can also be produced by allowing compound 9 to react with compound 10 to carry out an alkylation reaction on the nitrogen atom of a cyclic amide, as described below (Scheme 5).

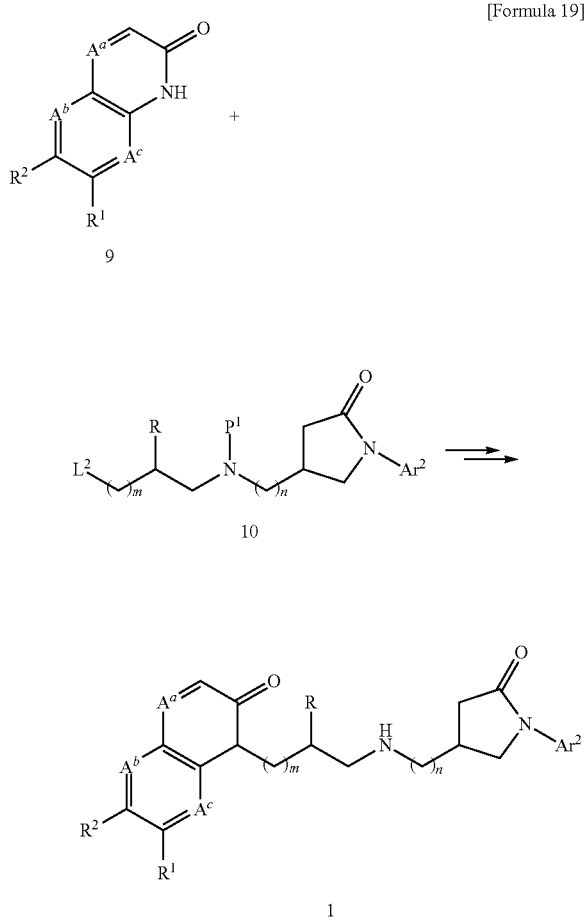

This reaction can be carried out by the method described in Advanced Organic Chemistry, 4th edition (written by Jerry March), pp. 425-427, 1991, John Wiley & Sons, Inc., etc., or by methods equivalent thereto.

This reaction may be carried out in the presence of a base. Examples of a suitable base include: inorganic bases such as potassium carbonate, cesium carbonate or potassium phosphate; organic bases such as triethylamine or N,N-diisopropylethylamine; and sodium hydride, lithium N,N-diisopropylamide, lithium hexamethyldisilazide, sodium hexamethyldisilazide, and potassium hexamethyldisilazide.

The reaction can be carried out within a temperature range between −100° C. and 200° C., and preferably between −20° C. and 150° C.

Examples of the leaving group $L^2$ include: leaving groups such as a mesylate group, a tosylate group, a trifluoroacetoxy group and a trifluoromethanesulfonyloxy group; as well as a halogen atom.

Various functional groups of the compounds 9 and 10 may be protected by suitable protective groups during the present reaction, as desired. In this case, such protective groups are deprotected after completion of the reaction, so that the compounds can be converted to the compound 1.

Moreover, when n=1, the compound 1 can be produced by carrying out a reductive alkylation reaction (a reductive amination reaction) between a compound 11 as an amine compound and a compound 12 as an aldehyde compound, as described below. Furthermore, the compound 1 can also be produced by carrying out an alkylation reaction between a compound 13 that may be protected by a protective group $P^2$ and a compound 14 having a leaving group $L^3$ (Scheme 6). The reductive alkylation reaction (reductive amination reaction) can be carried out by the same method as that applied to produce the compound 1 from the above described compound 2 and amine compound 3. Furthermore, the alkylation reaction can be carried out by the same method as that applied to produce the compound 1 from the compound 4 and the compound 5. Herein, $P^2$ may be hydrogen, and it may also be an aralkyl-type protective group such as a benzyl group, a benzhydryl group or a trityl group, an acyl-type protective group such as a formyl group, a trifluoroacetyl group or a trichloroacetyl group, an alkyl- or aralkyloxycarbonyl-type protective group such as a benzyloxycarbonyl group or a tert-butoxycarbonyl group, or another protective group such as a tosyl group, a nosyl group, a tert-butylsulfinyl group or a sulfonic acid group. Such a protective group is removed under suitable conditions after completion of the present alkylation reaction, so that the compounds can be converted to the compound 1. Examples of the leaving group $L^3$ include: leaving groups such as a mesylate group, a tosylate group, a trifluoroacetoxy group and a trifluoromethanesulfonyloxy group; as well as a halogen atom.

Various functional groups of the compounds 11, 12, 13 and 14 may be protected by suitable protective groups during the present reaction, as desired. Such protective groups are deprotected after completion of the reaction, so that the compounds can be converted to the compound 1.

Scheme 6

[Formula 20]

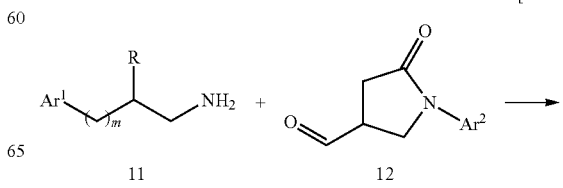

-continued

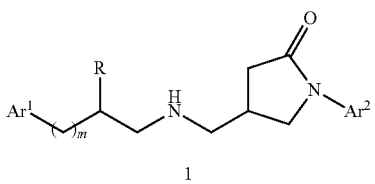

1

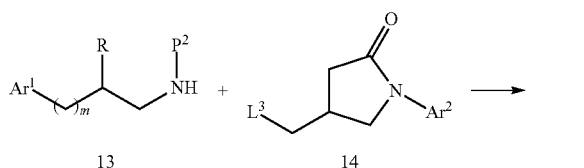

13 14

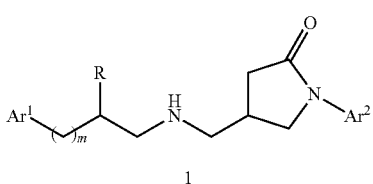

1

Still further, when R is a hydroxy group, the compound 1 can be produced by carrying out a reaction between a compound 15 as an oxirane compound and a compound 16 as an amine compound that may be protected by a protective group $P^3$, as described below (Scheme 7). This reaction can be carried out by the method described in Advanced Organic Chemistry, 4$^{th}$ edition (written by Jerry March), p. 416, 1991, John Wiley & Sons, Inc., etc., or by methods equivalent thereto.

Scheme 7

[Formula 21]

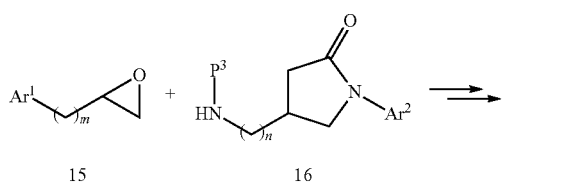

15 16

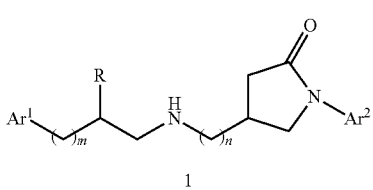

1

This reaction can be carried out in the presence or absence of a suitable solvent. In addition, a suitable reagent may be added to the reaction mixture. Examples of suitable solvents include: alcohols such as methanol, ethanol and isopropyl alcohol; ethers such as tetrahydrofuran, 1,4-dioxane and 1,2-dimethoxypropane; aromatic hydrocarbons such as toluene and benzene; esters such as ethyl acetate; water; N,N-dimethylformamide; and acetonitrile. Moreover, these solvents can also be used in the form of a mixed solvent. Examples of the reagent that can be added to the reaction mixture include: Brønsted acids such as hydrogen chloride, acetic acid, trifluoroacetic acid, and tosic acid; alkalis such as potassium carbonate, sodium carbonate, sodium hydrogen carbonate, and cesium carbonate; Lewis acids such as lithium tetrafluoroborate, lithium perchlorate, ytterbium(III) triflate, bismuth (III) chloride, and zinc(II) chloride; and strong bases such as sodium hydride, lithium diisopropylamide, lithium hexamethyldisilazide, sodium hexamethyldisilazide, potassium hexamethyldisilazide, and P4-phosphazene.

The reaction can be carried out within a temperature range between −100° C. and 200° C., and preferably between −80° C. and 150° C.

Herein, $P^3$ may be hydrogen, and it may also be an aralkyl-type protective group such as a benzyl group, a benzhydryl group or a trityl group, an acyl-type protective group such as a formyl group, a trifluoroacetyl group or a trichloroacetyl group, an alkyl- or aralkyloxycarbonyl-type protective group such as a benzyloxycarbonyl group or a tert-butoxycarbonyl group, or another protective group such as a tosyl group, a nosyl group, a tert-butylsulfinyl group or a sulfo group. Such a protective group is removed under suitable conditions after completion of the present reaction, so that the compounds can be converted to the compound 1.

Various functional groups of the compounds 15 and 16 may be protected by suitable protective groups during the present reaction, as desired. Such protective groups are deprotected after completion of the reaction, so that the compounds can be converted to the compound 1.

Next, a method for producing each synthetic intermediate compound will be described.

[Compound 2]

Compound 2 can be produced by the method described in International Publication WO2009/104159, or by methods equivalent thereto, for example (Scheme 8). That is to say, for example, a compound 17, in which a formyl group is protected by a protective group such as dimethylacetal, and a compound 9 are subjected to an alkylation reaction, and the formyl-protecting group is then removed from the obtained compound 18 to produce the compound 2. The leaving group $L^4$ may be a halogen atom, or may also be a leaving group such as a mesylate group, a tosylate group, a trifluoroacetoxy group or a trifluoromethanesulfonyloxy group.

Moreover, a compound 19, in which a hydroxy group is protected by a protective group $P^4$, and a compound 9 are subjected to an alkylation reaction. Thereafter, the protective group $P^4$ is removed from the obtained compound 20, and the hydroxy group is oxidized to a formyl group to produce the compound 2. Various functional groups of the compounds 9, 17, 18, 19 and 20 may be protected by suitable protective groups during these reactions, as desired. The protective groups can be removed at an appropriate stage.

Scheme 8

[Formula 22]

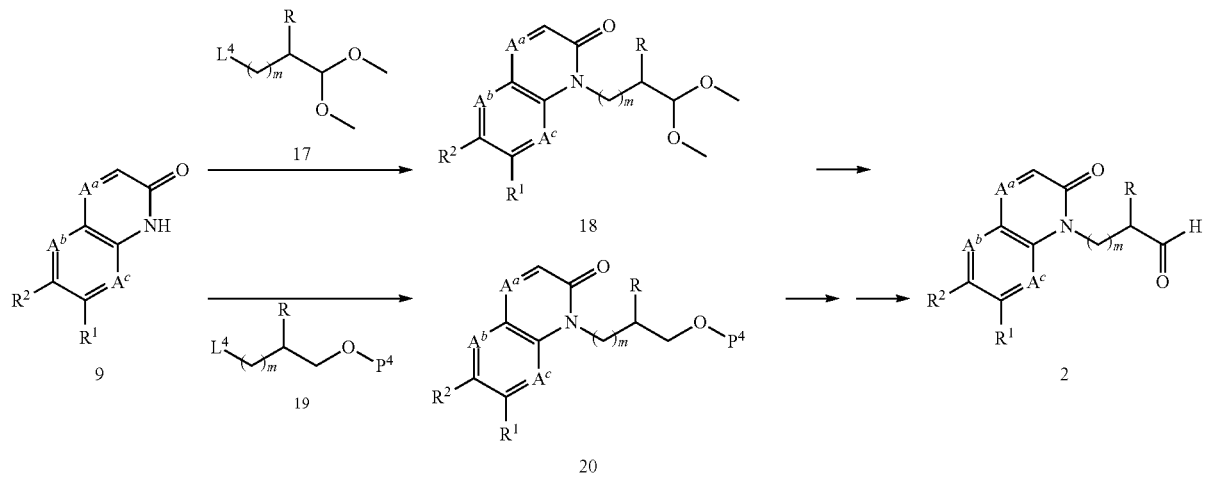

Furthermore, for example, the alkylation reaction of the compound 9 is carried out with compounds 21, 23 and the like, which are unsaturated compounds. Thereafter, hydroboration/oxidation is carried out on the unsaturated bond of the obtained compound 22, or a reaction such as conversion to diol/oxidative fission is carried out on a compound 24, so that the compound 2 can also be produced (Scheme 9). Herein, each of R13 and R14 is hydrogen, an alkyl group, etc. Various functional groups of the compounds 9, 21, 22, 23 and 24 may be protected by suitable protective groups during these reactions, as desired. The protective groups can be removed at an appropriate stage.

which are not commercially available, can be produced by generally known methods of synthetic organic chemistry.

[Compound 3]

Compound 3 can be produced by performing a cross-coupling reaction between a compound 25 and a compound 8, and then converting the functional groups R11 and R12 of the obtained compound 26. Alternatively, the compound 3 can be produced by performing a cross-coupling reaction between a compound 25 and a compound 7 (Scheme 10). Herein, each of protective groups $P^5$ and $P^6$ is hydrogen or a protective group. When they are protective groups, they can be removed at an appropriate stage. As reaction conditions for these cross- Scheme 9

[Formula 23]

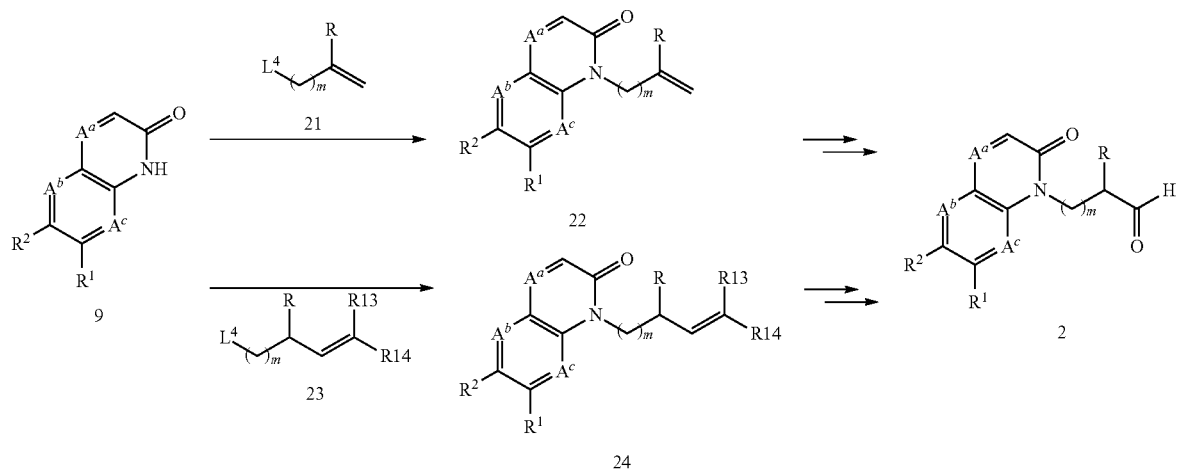

The compound 9 in Scheme 9 can be produced by the method described in International Publication WO2006/134378, International Publication WO2006/137485, International Publication WO2009/1126, etc. or by methods equivalent thereto.

Some of the compounds 17, 19, 21 and 23 are commercially available, and thus, they can be used. Also, compounds, coupling reactions, there can be applied the same reaction conditions as the reaction conditions for the production of the compound 1 from the compounds 6 and 7, or the reaction conditions for the production of the compound 1 from the compounds 6 and 8, which are described above. Various functional groups of the compounds 7, 8, 25 and 26 may be protected by suitable protective groups during these reac- Scheme 10

[Formula 24]

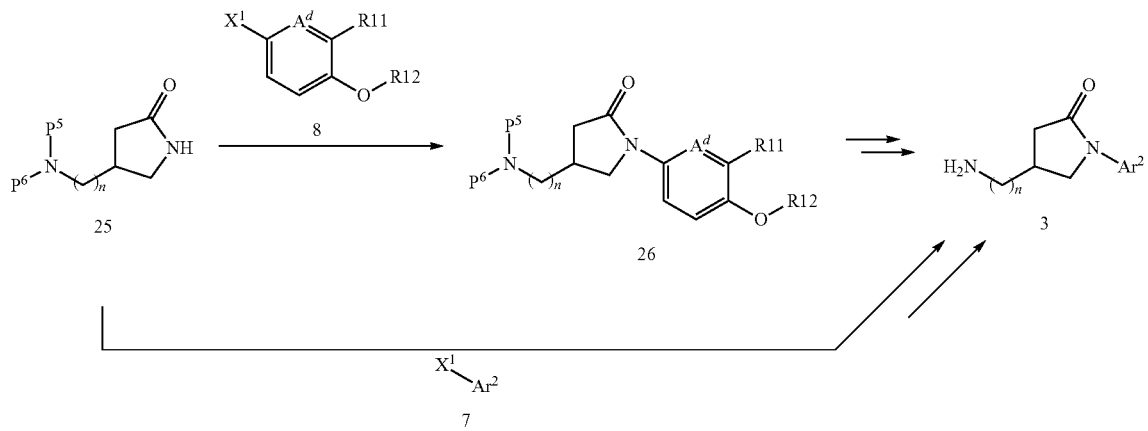

The compounds 7 and 8 can be produced by the method described in International Publication WO2010/41194, International Publication WO2007/118130, International Publication WO2007/16610, etc. or by methods equivalent thereto.

When n=0 (compound 28), the compound 25 may be commercially available. Alternatively, the compound 25 can also be produced from a commercially available 4-hydroxy-2-pyrrolidinone derivative such as a compound 27, for example (Scheme 11). Specifically, a series of reactions, such as mesylation, azidation, and reduction of an azide group, are carried out on the compound 27, so that it can be converted to a compound 28. The lactam moiety of a commercially available 4-hydroxy-2-pyrrolidinone derivative used as a raw material may be protected, as appropriate, and such a protective group may be removed at an appropriate stage. Moreover, this 4-hydroxy-2-pyrrolidinone derivative may be an optically active substance, and, using such an optically active substance, an optically active compound 1 can be produced. Furthermore, the compound 28 can be produced by synthesizing a compound 31 from a compound 29 as a primary amine and an itaconic acid 30, and then converting the carboxy group thereof to an amino group. Various functional groups of the compounds 28, 29, 30 and 31 may be protected by suitable protective groups during these reactions, as desired. The protective groups may be removed at an appropriate stage.

As such a compound 29, 4-methoxyaniline or benzylamine, in which the $P^7$ portion thereof functions as a protective group that can be removed later, or optically active 1-phenylethylamine, 1-(4-methoxyphenyl)ethylamine, and the like can preferably be used. In addition, using an optically active compound such as a compound 29, a stereoisomer can be easily separated on the basis of the steric configuration of the 4-position of pyrrolidinone at the stage of, for example, the compound 31, an ester compound thereof or the like. Even in a case in which a compound that is not optically active is used, a stereoisomer can be separated by column chromatography using a column capable of separating an optical isomer. In order to synthesize the compound 31 from the compounds 29 and 30, a mixture of the compounds 29 and 30 is heated, or such compounds are heated together with a suitable solvent such as benzene, toluene, water or alcohol. During such treatments, a suitable catalyst such as tosic acid can be used. Otherwise, using a Dean-Stark apparatus or the like, water generated as a result of the reaction may be removed. The carboxy group of the compound 31 can be converted to an amino group, for example, by performing a series of reactions such as acid azide synthesis/Curtius rearrangement/carbamate synthesis (Cbz protection using benzyl alcohol and tert-butanol, or the synthesis of a Boc-protected amino group)/deprotection. Otherwise, after the carboxy group has been converted to an amide group, it can be converted to an amino group by Hofmann rearrangement or the like. When the $P^7$ group is a 4-methoxyphenyl group, a 1-(4-methoxyphenyl)ethyl group or the like, for example, deprotection can be carried out under oxidative conditions using diammonium cerium(IV) nitrate or the like, or under acidic conditions using trifluoroacetic acid or the like, or other conditions. When it is a benzyl group, a 1-phenylethyl group or the like, deprotection can be carried out under reaction conditions for Birch reduction or the like.

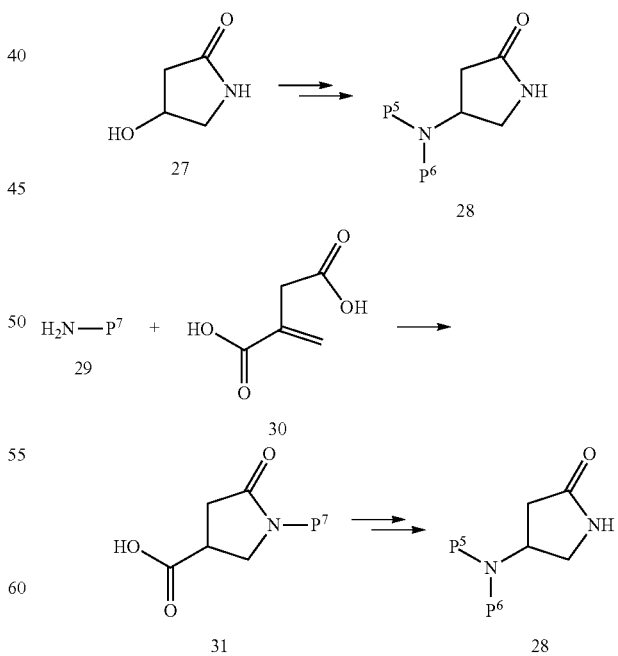

When n=1 (compound 33), the compound 25 may be commercially available. Alternatively, the compound 25 can also be produced from a commercially available 4-(hydroxymethyl)-2-pyrrolidinone derivative such as a compound 32, for example (Scheme 12). Specifically, a series of reactions, such as mesylation, azidation, and reduction of an azide group, are carried out on the compound 32, so that it can be converted to the compound 33. The lactam part of a commercially available 4-(hydroxymethyl)-2-pyrrolidinone derivative used as a raw material may be protected, as appropriate, and such a protective group may be removed at an appropriate stage. Moreover, this 4-(hydroxymethyl)-2-pyrrolidinone derivative may be an optically active substance, and using such an optically active substance, an optically active compound 1 can be produced. The compound 32 may be commercially available, and it can also be produced by synthesizing the compound 31 from the compound 29 as a primary amine and the itaconic acid 30, and then reducing the carboxy group. This reduction reaction can be carried out under ordinary reductive conditions for converting a carboxy group to a hydroxymethyl group, or the carboxy group can also be reduced mediated by a carboxylic acid ester compound.

Scheme 12

[Formula 26]

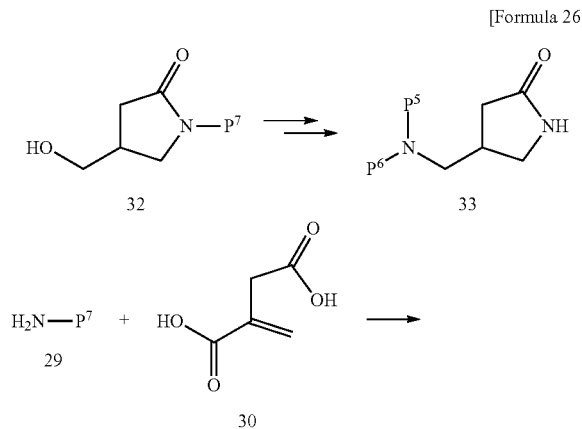

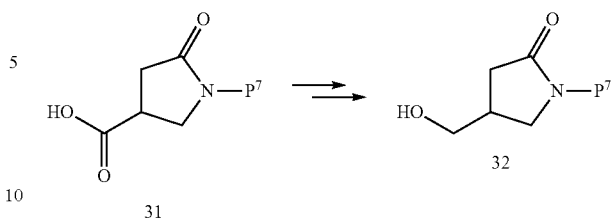

Moreover, the compound 3 can be produced by carrying out a cross-coupling reaction between a hydroxy compound 34 that may be protected and a compound 7 or a compound 8, and then converting the hydroxy group to an amino group at an appropriate stage (Scheme 13). Herein, a protective group $P^8$ is hydrogen or a protective group. When the protective group $P^8$ is a protective group, it can be removed at an appropriate stage. As reaction conditions for these cross-coupling reactions, there can be applied the same reaction conditions as the reaction conditions for the production of the compound 1 from the compounds 6 and 7, or the reaction conditions for the production of the compound 1 from the compounds 6 and 8, which are described above. Various functional groups of the compounds 7, 8, 34, 35 and 36 may be protected by suitable protective groups during these reactions, as desired. The protective groups can be removed at an appropriate stage.

Some of compounds 34 are commercially available. Also, compounds 34, which are not commercially available, can be produced by generally known methods of synthetic organic chemistry, using the compounds 31, 32 or the like, or using commercially available reagents.

Scheme 13

[Formula 27]

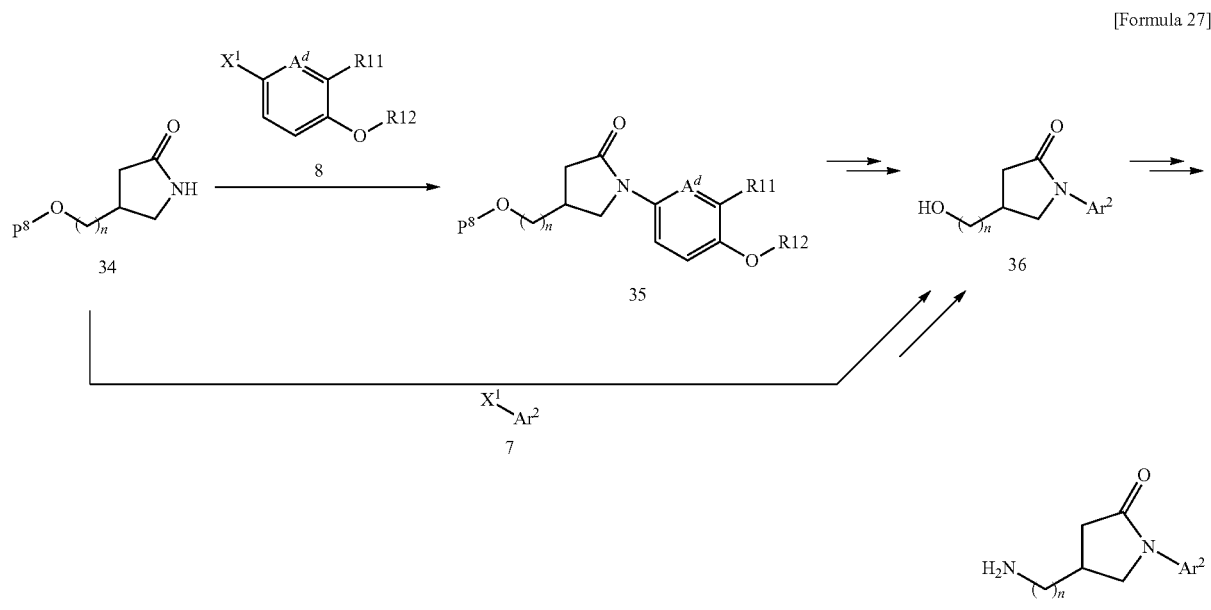

25

[Compound 4]

Compound 4 can be produced by a method similar to the method for producing the compound 2 (Scheme 14). That is to say, for example, deacetalization/reduction of an aldehyde functional group is performed on the compound 18 that is a synthetic intermediate of the compound 2 to convert the compound 18 to a compound 37 that is an alcohol compound. Thereafter, the hydroxy group of the compound 37 is converted to a leaving group to produce the compound 4. Production of this compound 37 facilitates the production of the compound 4. Alternatively, the compound 37 can also be obtained by deprotection of the hydroxy group of the compound 20 that is a synthetic intermediate of the compound 2. Moreover, the compound 37 can also be synthesized by performing hydroboronation on the compound 22 that is a synthetic intermediate of the compound 2, or by performing ozone oxidation/reduction treatment on the compound 24 that is a synthetic intermediate of the compound 2, or by conversion to diol/oxidative fission/reduction of an aldehyde group. On the other hand, the compound 4 can also be produced by carrying out a selective alkylation reaction on the compound 9, using a compound 38 having two leaving groups.

During a series of reactions, various functional groups of all of these compounds may be protected by suitable protective groups, as desired. Thereafter, the protective groups can be removed at an appropriate stage.

Some of compounds 38 in Scheme 14 are commercially available. Also, compounds 38, which are not commercially available, can be produced by generally known methods of synthetic organic chemistry, using commercially available reagents.

Scheme 14

[Formula 28]

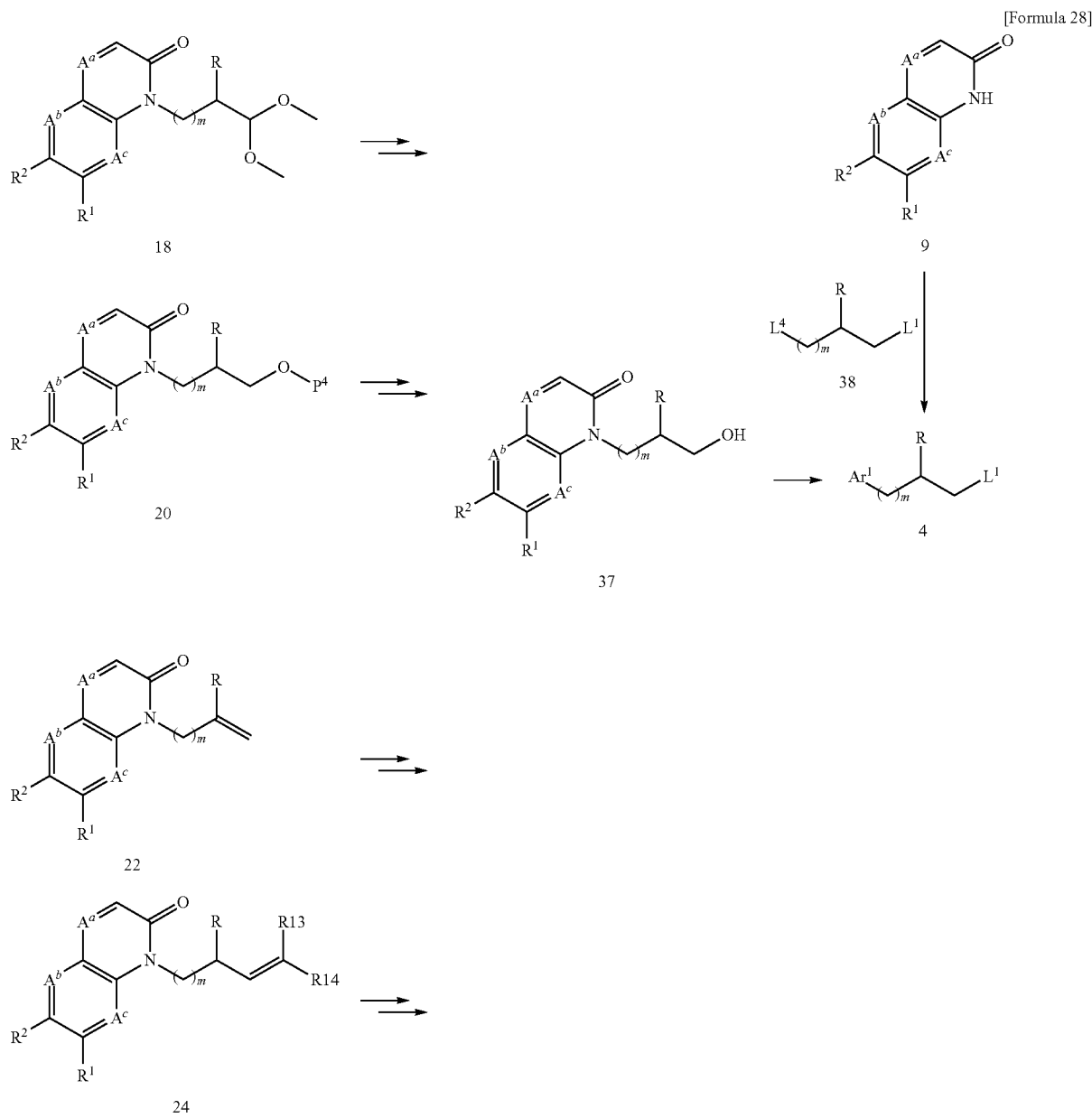

[Compound 5]

Compound 5 may be the compound 3 itself, or it may be produced by a method similar to the method for producing the compound 3 or may easily be produced from the compound 3.

[Compound 6]

Compound 6 can be produced by carrying out a reductive amination (reductive alkylation) reaction between a pyrrolidinone derivative that may be protected, such as a compound 39, and the compound 2. It can also be produced by carrying out an alkylation reaction between the compound 4 and the compound 39 or the like (Scheme 15). $P^9$ and $P^{10}$ are protective groups, and they may be hydrogen unless it affects the reaction. $P^{10}$ is preferably an acyl group, an alkoxycarbonyl group, a benzyl group, a substituted benzyl group, a 1-phenylethyl group, a 1-(substituted)phenylethyl group or the like, which can be removed later. $P^9$ is an aralkyl-type protective group such as a benzyl group. When the compound 39 is used in the alkylation reaction, $P^9$ may be various types of protective groups capable of stabilizing an anion, such as an acyl, alkoxycarbonyl, sulfonyl or sulfenyl group. During these reactions, various functional groups of all of these compounds may be protected by suitable protective groups, as desired. Thereafter, the protective groups can be removed at an appropriate stage.

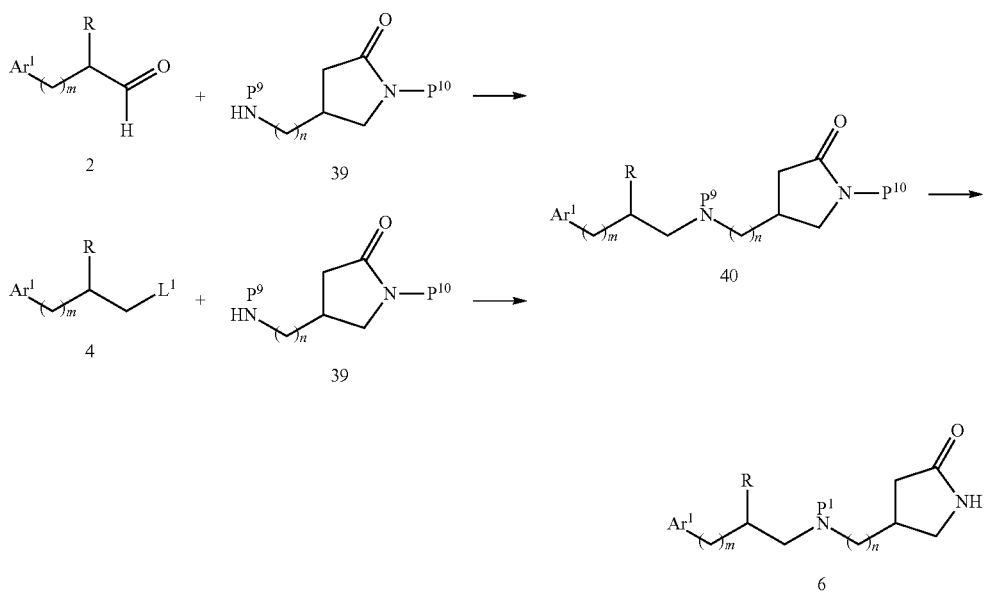

Scheme 15

[Formula 29]

Also, the compound 6 can be produced by performing a reaction, such as reductive alkylation or alkylation, between the pyrrolidinone compound 39 or the like that may be protected and a suitable compound such as a compound 38, 41, 42 or 43, then performing, as necessary, the removal of the protective group, conversion to a leaving group, etc. to convert it to a compound 44, and then carrying out the alkylation reaction of the compound 44 with a compound 9 (Scheme 16). $P^{11}$ may be an alcohol protecting group, and it may also be hydrogen unless it affects the reaction. During these reactions, various functional groups of all of these compounds may be protected by suitable protective groups, as desired. Thereafter, the protective groups can be removed at an appropriate stage.

Scheme 16

[Formula 30]

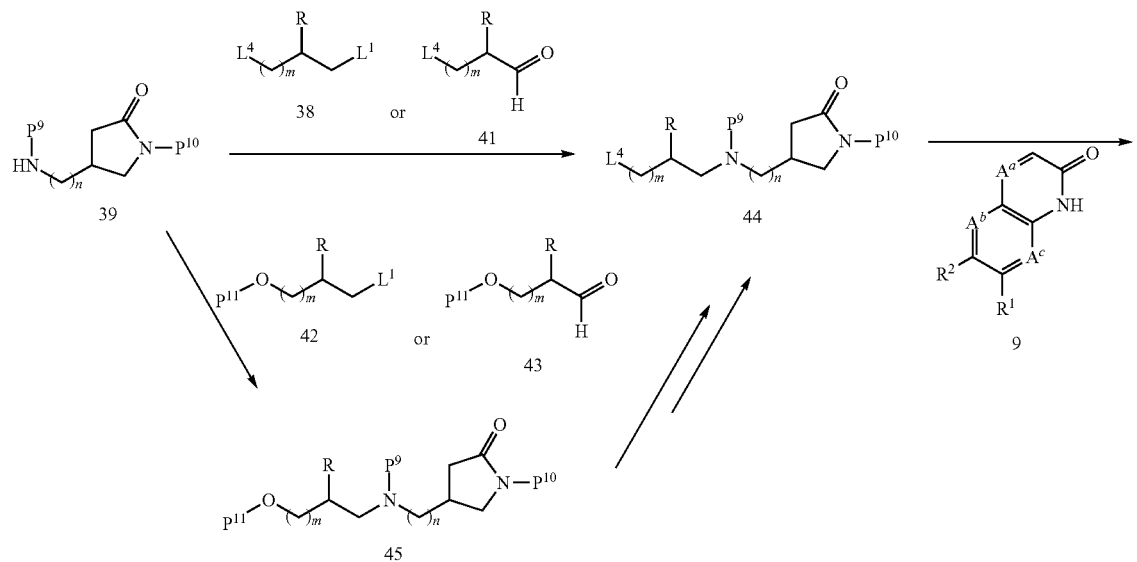

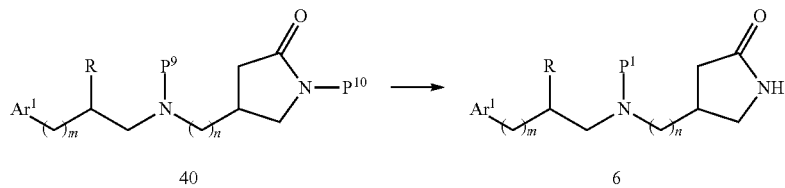

The compound 39 in Schemes 15 and 16 may be the above described compound 25 itself, or it may also be synthesized from the compound 25 or may be synthesized by a method similar to that for synthesizing the compound 25. In addition, some of the compounds 41, 42 and 43 are commercially available. Also, the compounds, which are not commercially available can be produced by generally known methods of synthetic organic chemistry, using commercially available reagents.

Moreover, when n=1, the compound 6 can be produced by carrying out a reductive alkylation (reductive amination) reaction between a compound 11 and a compound 46 or by carrying out an alkylation reaction between a compound 13 and a compound 47 (Scheme 17). Various functional groups of all of these compounds may be protected by suitable protective groups, and thereafter, the protective groups can be removed at an appropriate stage.

Scheme 17

[Formula 31]

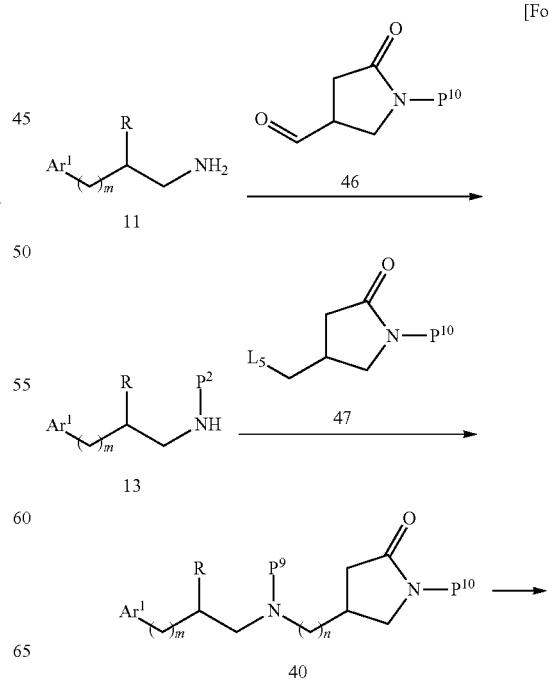

31

-continued

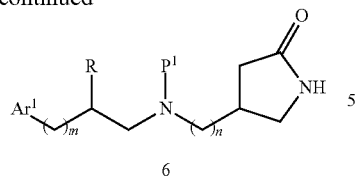

Furthermore, when n=1, the compound 6 can be produced by first carrying out a reductive alkylation (reductive amination) reaction between a compound 46 and a compound 48 or a compound 49 to yield a compound 44, and then applying a method similar to that in Scheme 16 (Scheme 18). This compound 44 can also be obtained by carrying out an alkylation reaction between the compound 47 and the compound 48 or the compound 49, and then carrying out, as necessary, the removal of the protective group, conversion of the hydroxy group to a leaving group, etc. Various functional groups of all of these compounds may be protected by suitable protective groups, and thereafter, the protective groups can be removed at an appropriate stage.

Scheme 18

[Formula 32]

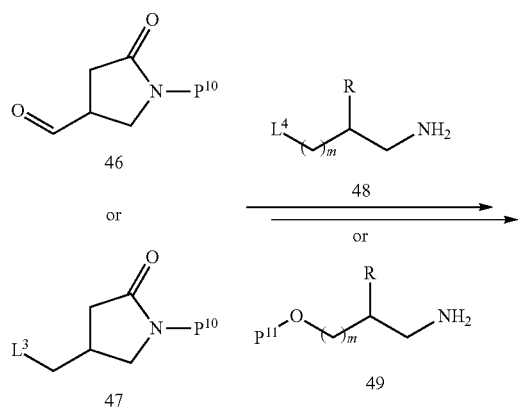

32

-continued

The compounds 46 and 47 in Schemes 17 and 18 can be produced from the above described compounds 31, 32 and 34, etc. by generally known methods of synthetic organic chemistry. Some of the compounds 48 and 49 are commercially available. The compounds which are not commercially available can be produced by generally known methods of synthetic organic chemistry, using commercially available reagents.

[Compound 10]

Compound 10 can be produced by carrying out an alkylation reaction between a compound 5 and a suitable compound such as a compound 38 or 42, and then carrying out, as necessary, the removal of the protective group, conversion to a leaving group, etc. (Scheme 19). Alternatively, the compound 10 can also be produced by carrying out a reaction, such as reductive alkylation, between the compound 5 and a suitable compound such as a compound 41 or 43, and then carrying out, as necessary, the removal of the protective group, conversion to a leaving group, etc., as described above (Scheme 19). A leaving group $L^4$ may be either identical to or different from $L^2$. When the leaving group $L^4$ is different from $L^2$, $L^4$ can be converted to $L^2$ later. Various functional groups of all of these compounds may be protected by suitable protective groups, as desired, during these reactions, and thereafter, the protective groups can be removed at an appropriate stage.

Scheme 19

[Formula 33]

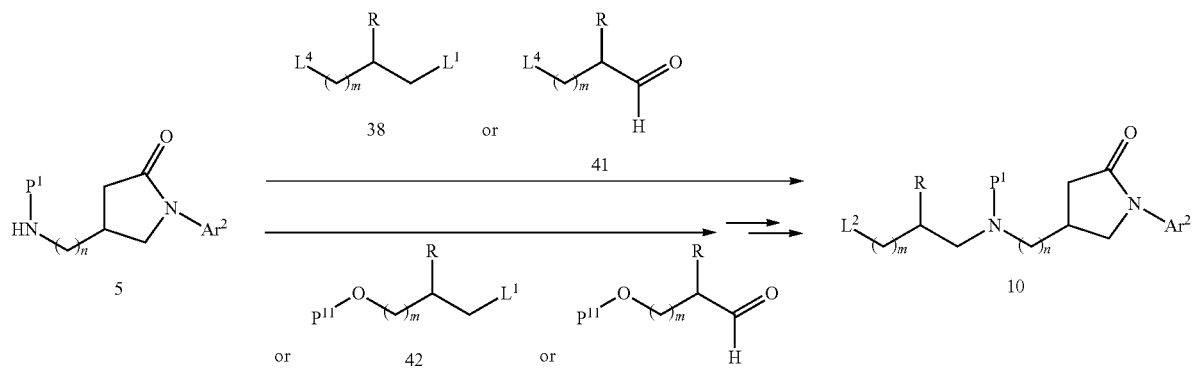

Moreover, the compound 10 can also be produced by removing a protective group P''' from a compound 44 or 45, then carrying out a cross-coupling reaction of the compound 44 or 45 with a compound 7 or a compound 8, and then converting various functional groups, as necessary (Scheme 20). Various functional groups of all of these compounds may be protected by suitable protective groups, as desired, during these reactions, and thereafter, the protective groups can be removed at an appropriate stage.

Some of the compounds 48 and 49 in Scheme 21 are commercially available. The compounds which are not commercially available can be produced by generally known methods of synthetic organic chemistry, using commercially available reagents.

[Compounds 11 and 13]

Compound 11 or 13 can be produced by carrying out reductive alkylation on a compound 2 using ammonium acetate, or by carrying out such reductive alkylation on the compound 2

Scheme 20

[Formula 34]

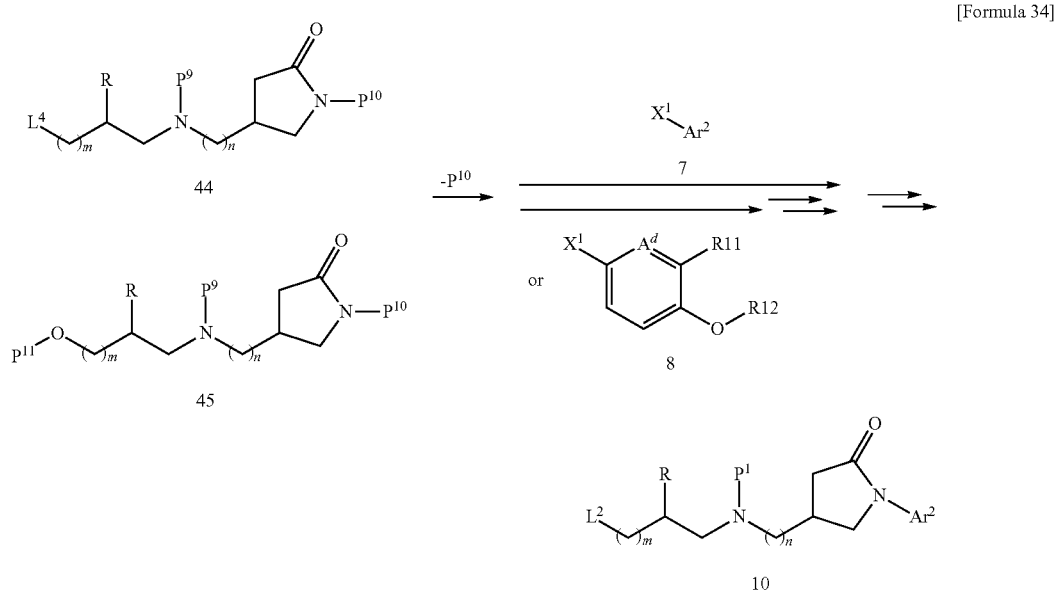

Furthermore, when n=1, the compound 10 can be produced by carrying out a reductive alkylation reaction between a compound 12 and a compound 48 or a compound 49, or carrying out an alkylation reaction between a compound 14 and the compound 48 or the compound 49, and then carrying out, as necessary, conversion of protective groups or functional groups (Scheme 21). Various functional groups of all of these compounds may be protected by suitable protective groups, as desired, during these reactions, and thereafter, the protective groups can be removed at an appropriate stage.

using benzylamine and then removing a benzyl group, etc. Moreover, the compound 11 or 13 can also be produced by carrying out an azidation/reduction reaction on a compound 4 (Scheme 22). Furthermore, the compound 11 or 13 can also be produced by carrying out an alkylation reaction between a compound 9 and a compound 50 having an amine functional group that may be protected. $P^{12}$ and $P^{13}$ are protective groups for amine. $P^{12}$ and $P^{13}$ may be hydrogen unless it affects the reaction. Various functional groups of all of these compounds may be protected by suitable protective groups, as desired, Scheme 21

[Formula 35]

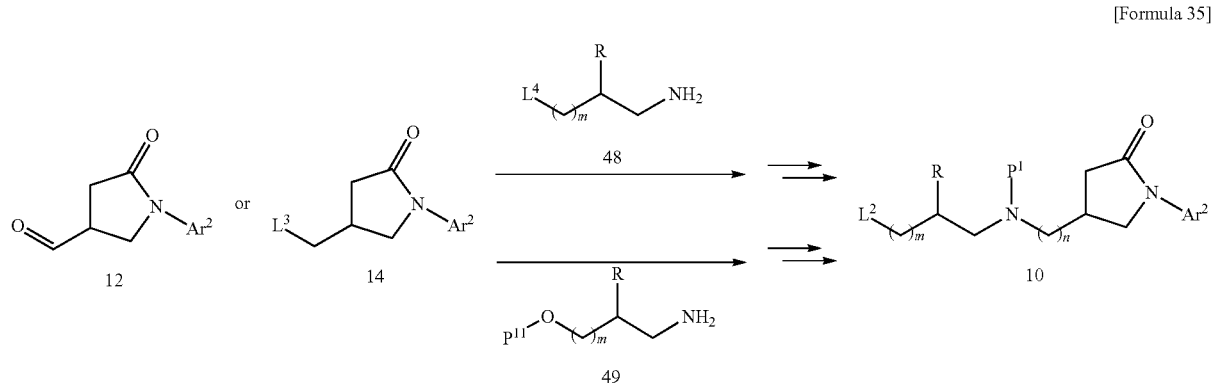

during these reactions, and thereafter, the protective groups can be removed at an appropriate stage.

Some of the compounds 50 in Scheme 22 are commercially available. The compounds which are not commercially available can be produced by generally known methods of synthetic organic chemistry, using commercially available reagents.

react on the compound (Scheme 23). Moreover, the compound 15 can also be synthesized by carrying out an alkylation reaction between a compound 9 and a compound 54 having an oxirane moiety. Furthermore, the compound 15 can also be synthesized by carrying out an alkylation reaction between the compound 9 and a compound 55 in which two hydroxy groups are appropriately protected, and then going Scheme 22

[Formula 36]

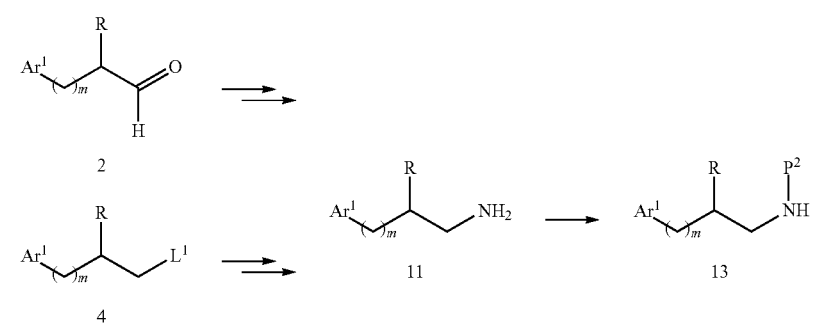

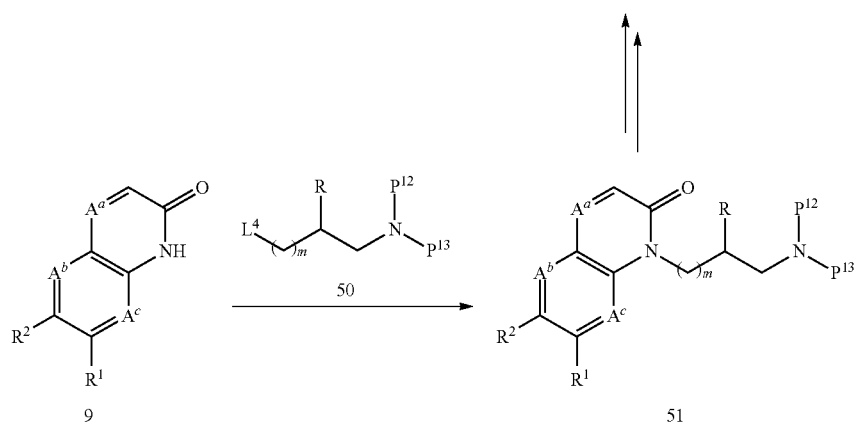

[Compounds 12 and 14]

Compounds 12 and 14 can be produced from the compounds 35, 36, etc. by generally known methods of synthetic organic chemistry.

[Compound 15]

Compound 15 can be synthesized by epoxidizing the olefin moiety of a compound 22, for example. In addition, the compound 15 can also be synthesized by converting the olefin moiety of the compound 22 to dihydroxy (compound 52), then selectively converting a primary alcohol to a leaving group $L^5$ (compound 53), and then allowing suitable alkali to through compound 56, 52 and 53. Various functional groups of all of these compounds may be protected by suitable protective groups, as desired, during these reaction, and thereafter, the protective groups can be removed at an appropriate stage.

Some of the compounds 54 or 55 in Scheme 23 are commercially available. The compounds which are not commercially available can be produced by generally known methods of synthetic organic chemistry, using commercially available reagents.

Scheme 23

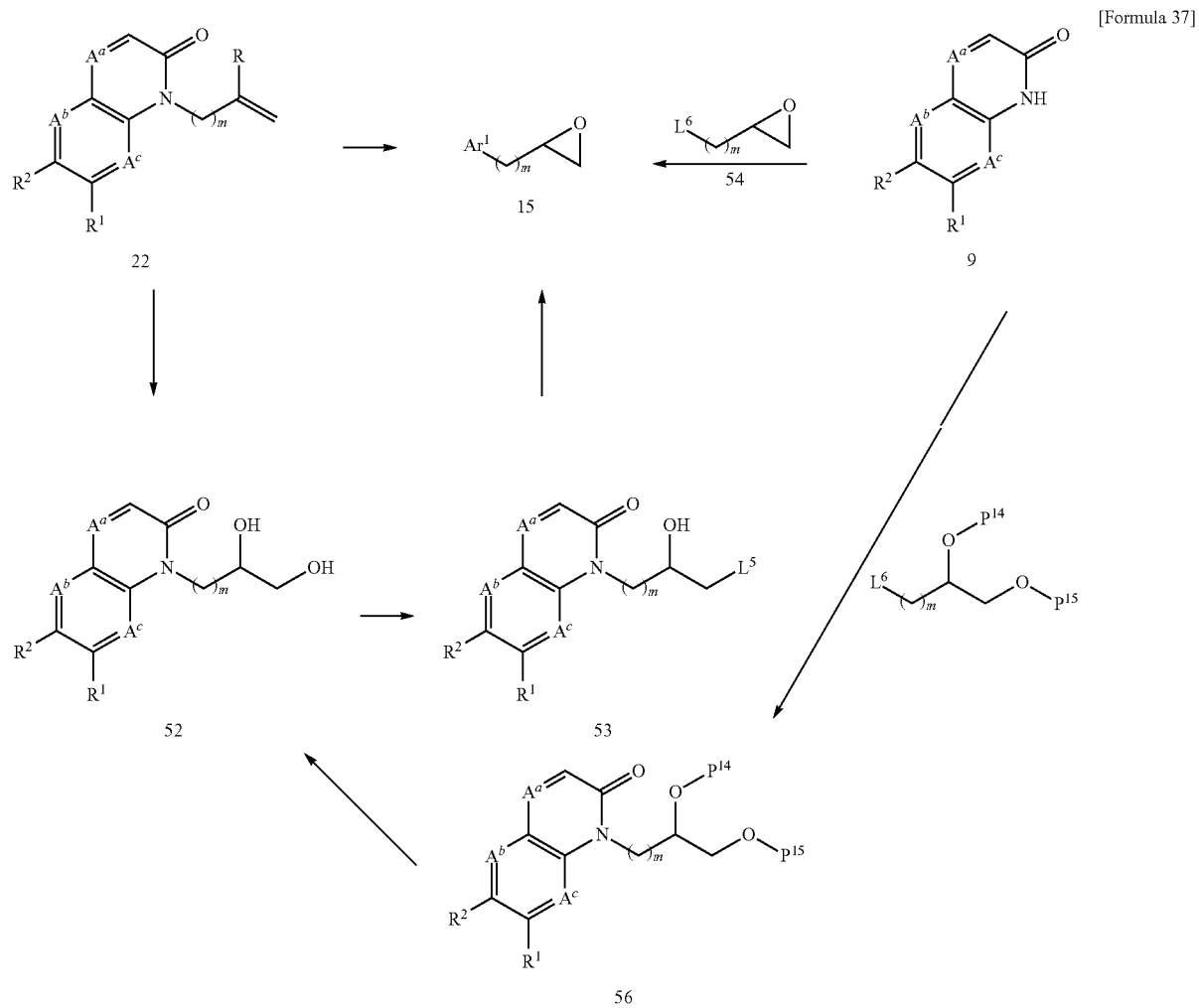

[Formula 37]

[Compound 16]

Compound 16 may be the compound 3 or 5 itself, or it can be produced from the compound 3, 5, or the like by generally known methods of synthetic organic chemistry. Alternatively, the compound 16 can be produced by a method similar to the method for producing the compounds 3, 5 and the like.

Protective groups used in the above described reactions can be selected from the following groups in accordance with common knowledge in this technical field.

Protective groups for amino groups are not particularly limited, as long as they are commonly used in this technical field. Examples of such protective groups for amino groups include: alkoxycarbonyl groups such as a tert-butoxycarbonyl group and a 2,2,2-trichloroethoxycarbonyl group; aralkyloxycarbonyl groups such as a benzyloxycarbonyl group, a paramethoxybenzyloxycarbonyl group, and a paranitrobenzyloxycarbonyl group; acyl groups such as an acetyl group, a methoxyacetyl group, a trifluoroacetyl group, a chloroacetyl group, a pivaloyl group, a formyl group, and a benzoyl group; alkyl groups or aralkyl groups such as a tert-butyl group, a benzyl group, a paranitrobenzyl group, a paramethoxybenzyl group, and a triphenylmethyl group; ethers such as a methoxymethyl group, a tert-butoxymethyl group, a tetrahydropyranyl group, and a 2,2,2-trichloroethoxymethyl group; (alkyl and/or aralkyl)-substituted silyl groups such as a trimethylsilyl group, an isopropyldimethylsilyl group, a tert-butyldimethylsilyl group, a tribenzylsilyl group, and a tert-butyldiphenylsilyl group; arylsulfonyl groups such as a p-toluenesulfonyl group, a benzenesulfonyl group, and a 2-nitrobenzenesulfonyl group (nosyl group); sulfinyl groups such as a benzenesulfinyl group, a p-toluenesulfinyl group, and a tert-butylsulfinyl group; and a sulfo group and an allyl group. The acyl group may be an alkylcarbonyl group, an arylcarbonyl group, or an aralkylcarbonyl group.

Protective groups for hydroxy groups are not particularly limited, as long as they are commonly used in this technical field. Examples of such protective groups for hydroxy groups include: alkyl groups such as a tert-butyl group and an allyl group; aralkyl groups such as a benzyl group, a paramethoxybenzyl group, a 3,4-dimethoxybenzyl group, a paranitrobenzyl group, a diphenylmethyl group, and a triphenylmethyl group; 1-(alkoxy)alkyl or 1-(aralkoxy)alkyl groups such as a methoxymethyl group, a 2-(trimethylsilyl)ethoxymethyl group, a tetrahydropyranyl group, a 1-ethoxyethyl group, a tert-butoxymethyl group, and a benzyloxymethyl group; (alkyl and/or aralkyl)-substituted silyl groups such as a trimethylsilyl group, a triethylsilyl group, a triisopropylsilyl group, a tert-butyldimethylsilyl group, and a tert-butyldiphenylsilyl group; acyl groups such as a formyl group, an acetyl group, a chloroacetyl group, a trichloroacetyl group, a trifluoroacetyl group, a pivaloyl group, a benzoyl group, and a 2,4,6-trimethylbenzoyl group; oxycarbonyl groups such as a methoxymethyloxycarbonyl group, a 9-fluorenylmethyloxycarbonyl group, a 2,2,2-trichloroethyloxycarbonyl group, a 2-(trimethylsilyl)ethyloxycarbonyl group, an isobutyloxycarbonyl group, an allyloxycarbonyl group, a paranitrophenyloxycarbonyl group, a benzyloxycarbonyl group, a paramethoxybenzyloxycarbonyl group, and a paranitrobenzyloxycarbonyl group; and sulfonyl groups such as a methanesulfonyl group and a paratoluenesulfonyl group. When two hydroxy groups are present adjacent to each other, having a 1,2- or 1,3-relation, the two hydroxy groups may be simultaneously protected. Examples of such a protective group include: cyclic acetals/ketals such as a methylidene group, a tert-butylmethylidene group, an isopropylidene group, and a benzylidene group; and orthoesters such as a methoxymethylene group.

Protective groups for carbonyl groups are not particularly limited, as long as they are commonly used in this technical field. Examples of such protective groups for carbonyl groups include: noncyclic acetals/ketals such as a dimethylacetal group; cyclic acetals/ketals such as 1,3-dioxane, 1,3-dioxolane, chiral or achiral 4,5-dimethyl-1,3-dioxolane, chiral or achiral 4,5-diphenyl-1,3-dioxolane, and trans-1,2-cyclohexanediol ketal; thioacetals/thioketals such as dimethyl dithioacetal, 1,3-dithiane, and 1,3-dithiolane; cyanohydrins such as O-trimethylsilylcyanohydrin and O-acetylcyanohydrin; hydrazones such as N,N-dimethylhydrazone and tosylhydrazone; and oximes such as O-methyloxime and O-benzyloxime.

Protective groups for carboxy groups are not particularly limited, as long as they are commonly used in this technical field. Examples of such protective groups for carboxy groups include: alkyl esters such as a methyl ester, an ethyl ester, a tert-butyl ester, a 9-fluorenylmethyl ester, a cyanomethyl ester, a cyclohexyl ester, an allyl ester, a methoxymethyl ester, a tetrahydropyranyl ester, a 2-(trimethylsilyl)ethoxymethyl ester, a benzyloxymethyl ester, a pivaloyloxymethyl ester, a phenacyl ester, a 2,2,2-trichloroethyl ester, and a 2-(trimethylsilyl)ethyl ester; aralkyl esters such as a benzyl ester, a diphenylmethyl ester, a triphenylmethyl ester, a 2,4,6-trimethylbenzyl ester, an orthonitrobenzyl ester, a paranitrobenzyl ester, and a paramethoxybenzyl ester; aryl esters such as a phenyl ester, a 2,6-dimethylphenyl ester, a 2,6-di-tert-butyl-4-methylphenyl ester, and a pentafluorophenyl ester; silyl esters such as a trimethylsilyl ester, a triethylsilyl ester, a triisopropylsilyl ester, and a tert-butyldimethylsilyl ester; and ortho esters such as a triethoxymethyl group.

Protective groups for N-mono-substituted amide groups are not particularly limited, as long as they are commonly used in this technical field. Examples of such protective groups for N-mono-substituted amide groups include: substituted alkyl groups such as an allyl group, a tert-butyl group, a methoxymethyl group, a benzyloxymethyl group, a 2,2,2-trichloroethyl group, a tert-butyldimethylsilyloxymethyl group, a pivaloyloxymethyl group, and a cyanomethyl group; aralkyl groups such as a benzyl group, a 4-methoxybenzyl group, a 2,4-dimethoxybenzyl group, an ortho-nitrobenzyl group, a triphenylmethyl group, an (R)-1-phenylethyl group, an (S)-1-phenylethyl group, an (R)-1-(4-methoxyphenyl) ethyl group, and an (S)-1-(4-methoxyphenyl)ethyl group; substituted aryl groups such as a 4-methoxyphenyl group and a 3,4-dimethoxyphenyl group; alkyl/aralkyloxy groups such as a methoxy group and a benzyloxy group; substituted silyl groups such as a triisopropylsilyl group and a tert-butyldimethylsilyl group; carbamates such as a tert-butoxycarbonyl group, a benzyloxycarbonyl group, and a methoxycarbonyl group; and sulfonyl groups such as a paratoluenesulfonyl group.

Bases used in the above described reactions can be selected from the following substances in accordance with common knowledge in this technical field. Specifically, examples of such bases include: alkali metal or alkaline-earth metal hydrides (e.g. lithium hydride, sodium hydride, potassium hydride, and calcium hydride); alkali metal or alkaline-earth metal amides (e.g. lithium amide, sodium amide, lithium diisopropylamide, lithium dicyclohexylamide, lithium hexamethyldisilazide, sodium hexamethyldisilazide, and potassium hexamethyldisilazide); alkali metal or alkaline-earth metal lower alkoxides (e.g. sodium methoxide, sodium ethoxide, and potassium t-butoxide); alkali metal or alkaline-earth metal hydroxides (e.g. sodium hydroxide, potassium hydroxide, lithium hydroxide, or barium hydroxide); alkali metal, alkaline-earth metal, or silver carbonates (e.g. sodium carbonate, potassium carbonate, cesium carbonate, and silver carbonate); alkali metal hydrogencarbonates (e.g. sodium hydrogen carbonate, and potassium hydrogen carbonate); alkyl lithium (e.g. n-butyl lithium) or alkyl Grignard (e.g. methyl magnesium bromide); inorganic bases such as silver oxide, or amines (e.g. triethylamine, diisopropylethylamine, and N-methylmorpholine); organic bases such as basic heterocyclic compounds (e.g. 4-dimethylaminopyridine, imidazole, 2,6-lutidine, collidine, 1,8-diazabicyclo[5,4,0]undec-7-ene, 1,5-diazabicyclo[4,3,0]non-5-ene, and 1,4-diazabicyclo[2,2,2]octane); and phosphazenes such as P4-phosphazene.

The solvents used in the above described reactions can be selected from the following solvents in accordance with common knowledge in this technical field. Examples of such solvents include alcohol solvents, ether solvents, halogen solvents, aromatic solvents, nitrile solvents, amide solvents, ketone solvents, sulfoxide solvents, and water. These solvents may be used as combinations of two or more types thereof.

The compound of the present invention may be either a free compound or an acid-addition salt. Examples of such an acid-addition salt include: halogen acid salts such as a hydrofluorde, a hydrochloride, a hydrobromide, and a hydriodide; inorganic acid salts such as a hydrochloride, a nitrate, a perchlorate, a sulfate, and a phosphate; lower alkanesulfonates such as a methanesulfonate, a trifluoromethanesulfonate, and an ethanesulfonate; arylsulfonates such as a benzenesulfonate and a p-toluenesulfonate; and organic acid salts such as an acetate, a malate, a lactate, a fumarate, a succinate, a citrate, an ascorbate, a tartrate, an oxalate, and a maleate.

There may be a case in which the compound of the present invention contains water molecules in the crystals thereof or it absorbs water content and has adsorption water, so that it becomes a hydrate, for example during a crystal-generating step or a purification step, or by being left in the atmosphere. Such a hydrate is also included in the salt of the present invention.

The compound of the present invention has one or more asymmetric carbon atoms in the molecule thereof, and optical isomers are present. These isomers and a mixture of these isomers are all represented by a single formula, namely, general formula (I). Accordingly, the compound of the present invention includes all of such optical isomers and mixtures containing optical isomers at any given ratio.

The present invention may also include a compound in which one or more atoms constituting the compound of the present invention are substituted with isotopes of the atoms.

There are two types of isotopes, namely, a radioisotope and a stable isotope. Examples of such isotopes include: hydrogen isotopes ($^{2}$H and $^{3}$H), carbon isotopes ($^{11}$C, $^{13}$C and $^{14}$C), nitrogen isotopes ($^{13}$N and $^{15}$N), oxygen isotopes ($^{15}$O, $^{17}$O and $^{15}$O), and a fluorine isotope ($^{18}$F). A composition comprising a compound labeled with an isotope is useful, for example, as a therapeutic agent, a preventive agent, a study reagent, an assay reagent, a diagnostic agent, an in vivo diagnostic imaging reagent, etc. A compound labeled with an isotope is also included in the compound of the present invention, and mixtures containing such isotope-labeled compounds at any given ratio are also all included in the compound of the present invention. The compound of the present invention, which is labeled with an isotope, can be produced by a method well known in the present technical field, for example, using an isotope-labeled raw material, instead of a raw material used in the production method of the present invention as described later.

Since the salt and/or crystal of the present invention has strong antibacterial action, it can be used as a pharmaceutical agent for humans, animals and fish, or as an agricultural chemical or a preservative agent for food products. When the compound of the invention of the present application is used as a pharmaceutical agent for human bodies, the dosage thereof is set from 100 mg to 10000 mg, and more preferably from 300 to 5000 mg, per adult per day. On the other hand, the dosage of the compound of the present invention for use in animals is different depending on the purpose of administration, the size of the animal to be treated, the type of pathogen infected, and the degree of symptoms. The dosage is generally set from 1 to 200 mg, and more preferably from 5 to 100 mg, per kg of body weight of the animal per day. Such a daily dosage is administered to the animal once a day, or divided over 2 to 4 administrations. It is to be noted that a daily dosage may exceed the aforementioned amounts.

The salt and/or crystal of the invention of the present application is active on a wide range of microorganisms that cause various types of infectious diseases. Thus, the salt and/or crystal of the present invention is able to treat, prevent or alleviate diseases caused by these pathogens. Examples of bacteria or bacteria-like microorganisms for which the compound of the invention of the present application is effective include *Staphylococcus, Streptococcus pyogenes, Streptococcus haemolyticus, Enterococcus, Diplococcus pneumoniae, Peptostreptococcus, Neisseria gonorrhoeae, Escherichia coli, Citrobacter, Shigella, Klebsiella pneumoniae, Enterobacter, Serratia, Proteus, Pseudomonas aeruginosa, Haemophilus influenzae, Acinetobacter, Campylobacter, Mycoplasma*, and *Chlamydia trachomatis*.

Examples of diseases caused by these pathogens include folliculitis, furuncle, carbuncle, erysipelas, cellulitis, lymphangitis (lymphadenitis), whitlow, subcutaneous abscess, hidradenitis, acne conglobata, infectious atheroma, anal abscess, mastitis, superficial secondary infection of external injury/burn injury/operative wound, pharyngolarynx, acute bronchitis, tonsillitis, chronic bronchitis, bronchiectasis, diffuse panbronchiolitis, secondary infection of chronic respiratory disease, pneumonia, pyelonephritis, cystitis, prostatitis, epididymitis, gonorrheal urethritis, nongonococcal urethritis, cholecystitis, cholangitis, bacillary dysentery, enteritis, uterine adnexitis, intrauterine infection, bartholinitis, blepharitis, hordeolum, dacryocystitis, meibomianitis, corneal ulcer, otitis media, sinusitis, periodontoclasia, pericoronitis, jaw inflammation, peritonitis, endocarditis, septicemia, meningitis, and skin infection.

Moreover, examples of acid-fast bacteria, for which the salt and/or crystal of the invention of the present application is effective, include a group of tubercle bacillus (*Mycobacterium tuberculosis, M. bovis*, and M. *africanum*) and a group of atypical mycobacteria (*M. kansasii, M. marinum, M. scrofulaceum, M. avium, M. intracellulare, M. xenopi, M. fortuitum*, and *M. chelonae*). Based on causative microorganisms, mycobacterial infections caused by these pathogens are broadly divided into three types of infections, namely, tuberculosis, atypical mycobacteriosis and leprosy. Tuberculosis is observed in the thoracic cavity, trachea/bronchus, lymph node, whole body, articulation of the bone, meninges/brain, digestive organs (bowel/liver), skin, mammary gland, eye, middle ear/pharynx, urinary tract, male genital organ, female genital organ, as well as in the lung. A main organ affected with atypical mycobacteriosis (non-tuberculous mycobacterial infection) is lung, and other organs affected with this disease include local lymph node, skin soft tissues, articulation of the bone, and whole body.

Furthermore, the salt and/or crystal of the invention of the present application is useful for various types of microorganisms causing infectious diseases of animals, such as genus *Escherichia*, genus *Salmonella*, genus *Pasteurella*, genus *Haemophilus*, genus *Bordetella*, genus *Staphylococcus*, and genus *Mycoplasma*. Examples of specific diseases that infect birds include colibacillosis, white diarrhea, avian paratyphoid, fowl cholera, infectious coryza, staphylococcosis, and mycoplasma infection. Examples of specific diseases that infect swine include colibacillosis, salmonellosis, pasteurellosis, hemophilus infection, atrophic rhinitis, exudative dermatitis, and mycoplasma infection. Examples of specific diseases that infect cattle include colibacillosis, salmonellosis, hemorrhagic septicemia, mycoplasma infection, contagious bovine pleuropneumonia, and mastitis. Examples of specific diseases that infect dogs include coliform septicemia, salmonella infection, hemorrhagic septicemia, pyometra, and cystitis. Examples of specific diseases that infect cats include exudative pleurisy, cystitis, chronic rhinitis, hemophilus infection, cat diarrhea, and mycoplasma infection.

A pharmaceutical agent comprising the salt and/or crystal of the present invention as an active ingredient is preferably provided in the form of a pharmaceutical composition comprising the salt and/or crystal of the present invention used as an active ingredient and one or two or more types of additives used for pharmaceutical agents. The pharmaceutical agent of the present invention is not particularly limited in terms of administration form, and it can be administered orally or parenterally.

An antibacterial agent comprising the salt and/or crystal of the invention of the present application can be prepared by selecting a suitable pharmaceutical agent depending on its administration method, according to a commonly used method for preparing various types of pharmaceutical agents. Examples of the dosage form of an antibacterial agent comprising the compound of the present invention as a main agent include a tablet, a powder, a granule, a capsule, a solution, a syrup, an elixir, and an oily or aqueous suspension. In the case of an injection, a stabilizer, an antiseptic, a solubilizing agent, a pH adjuster, an isotonizing agent, etc. may be added to the pharmaceutical agent. A solution that may comprise the aforementioned agents may be contained in a vessel and may then be freeze-dried to prepare a solid agent, by means of which a pharmaceutical formulation may be prepared at time of use. Otherwise, a single dosage amount of agent may be contained in a vessel, or several dosage amounts of agents may also be contained in a single vessel. Examples of an external preparation include a solution, a suspension, an emulsion, an ointment, a gel, a cream, a lotion, and a spray. In the case of a solid agent, it may comprise pharmaceutically acceptable additives as well as an active compound. Examples of such additives include fillers, binders, disintegrants, solution promoters, wetting agents, and lubricants. Examples of a liquid agent include a solution, a suspension, and an emulsion. Such a liquid agent may comprise a suspending agent, an emulsifier, and the like as additives.

Next, an example of the formulation of a pharmaceutical agent will be given. Pharmaceutical Agent Example 1. [Solution Agent]:

| | |
|---|---|
| Compound of Example 2 | 0.2 to 2 g |
| Lactic acid | 0.1 to 10 g |
| Sorbitol | 1 to 5 g |
| Purified water | 83 to 98.7 g |
| Total | 100 g |

EXAMPLES

Hereinafter, the present invention will be described in more detail in the following examples and the like. However, these examples are not intended to limit the scope of the present invention.

Reference Example 1

1-(4-{[tert-Butyl(dimethyl)silyl]oxy}butyl)-7-methoxyquinoxalin-2(1H)-one

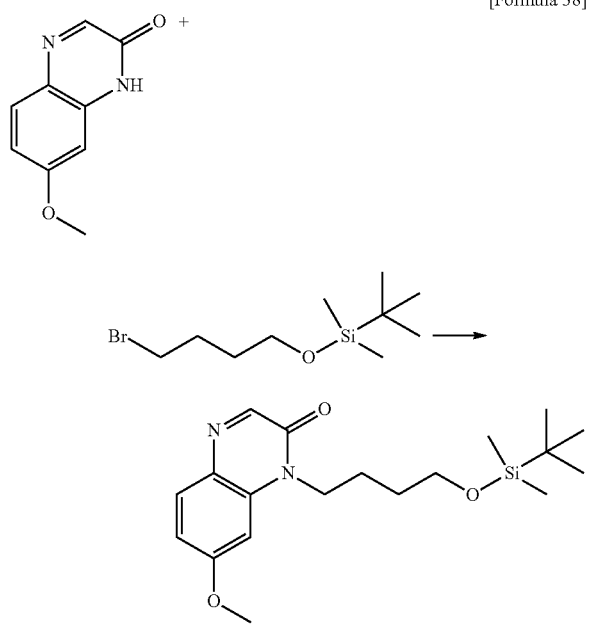

[Formula 38]

7-Methoxyquinoxalin-2(1H)-one (synthesized with reference to WO2009/1126; 400 mg, 2.27 mmol) was dissolved in N,N-dimethylformamide (8 ml). The solution was cooled in an ice bath, lithium hydride (purity 90%, 26 mg, 2.95 mmol) was then added thereto and the mixture was stirred at room temperature for 40 minutes. The reaction solution was cooled in an ice bath again, (4-bromobutoxy)(tert-butyl)dimethylsilane (synthesized with reference to Journal of Medicinal Chemistry, 2008, vol. 51, No. 18, pages 5690-5701; 580 mg, 2.17 mmol) and sodium iodide (442 mg, 2.95 mmol) were added thereto, and the mixture was stirred overnight at room temperature. The reaction mixture was diluted with ethyl acetate, washed sequentially with saturated sodium chloride solution (×2), water and saturated sodium chloride solution, dried over anhydrous magnesium sulfate and the solvent was removed under reduced pressure. The obtained residue was purified by silica gel column chromatography (n-hexane/ethyl acetate) to yield 363 mg (44%) of the title compound in the form of a light yellow syrup.

$^1$H-NMR(400 MHz,CDCl$_3$)δ:0.05(6H,s), 0.88(9H,s), 1.63-1.69(2H,m), 1.82-1.88(2H,m), 3.69(2H,t,J=6.0Hz), 3.92(3H,s), 4.25 (2H,t, J=7.7 Hz), 6.79(1H,d, J=2.3 Hz), 6.92 (1H,dd, J=8.9, 2.6 Hz), 7.79(1H,d, J=8.6 Hz), 8.13(1H,s).

MS(ESI)m/z:363(M+H)$^+$.

Reference Example 2

1-(4-Hydroxybutyl)-7-methoxyquinoxalin-2(1H)-one

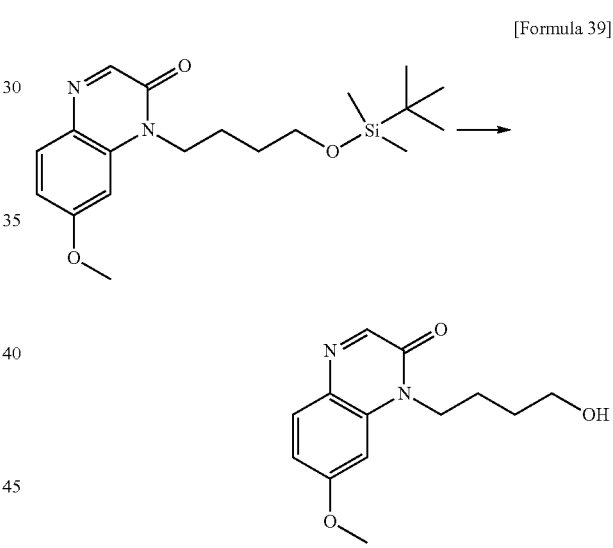

[Formula 39]

1-(4-{[Tert-butyl(dimethyl)silyl]oxy}butyl)-7-methoxyquinoxalin-2(1H)-one (363 mg, 1.0 mmol) was dissolved in tetrahydrofuran (10.9 ml). Tetrabutyl ammonium fluoride (1M tetrahydrofuran solution; 1.1 ml, 1.1 mmol) was added to this solution and the mixture was stirred at room temperature for 3 hours. The reaction mixture was diluted with ethyl acetate, washed with water and saturated sodium chloride solution, dried over magnesium sulfate and the solvent was removed under reduced pressure. The obtained residue was purified by silica gel column chromatography (chloroform/methanol) to yield 247 mg (100%) of the title compound in the form of a light yellow syrup.

$^1$H-NMR(400 MHz,CDCl$_3$)δ:1.68-1.78(3H,m),1.87-1.93 (2H,m),3.73-3.79(2H,m),3.93(3H,s),4.27(2H,t,J=7.5 Hz), 6.83(1H,d, J=2.3 Hz),6.93(1H,dd,J=9.2,2.3 Hz),7.80(1H,d, J=8.6 Hz),8.13(1H, s).

MS(FAB)m/z:249(M+H)$^+$.

Reference Example 3

4-(7-Methoxy-2-oxoquinoxalin-1(2H)-yl)butanal

[Formula 40]

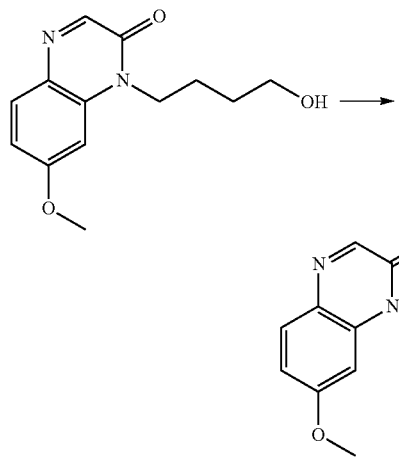

A solution of oxalyl chloride (0.171 ml, 1.99 mmol) in dichloromethane (5 ml) was cooled to −78° C., a solution of dimethyl sulfoxide (0.283 ml, 3.99 mmol) in dichloromethane (5 ml) was added dropwise under a stream of argon and the reaction mixture was stirred at the same temperature for 15 minutes. A solution of 1-(4-hydroxybutyl)-7-methoxyquinoxalin-2(1H)-one (198 mg, 0.797 mmol) in dichloromethane (5 ml) was added dropwise and the reaction mixture was further stirred at the same temperature for 1 hour. Triethylamine (0.833 ml, 5.98 mmol) was added thereto, the temperature was raised to room temperature and a saturated ammonium chloride aqueous solution and dichloromethane were added. After stirring, the organic layer was separated, washed with water and saturated sodium chloride solution, dried over magnesium sulfate and the solvent was removed under reduced pressure. The obtained residue was purified by silica gel column chromatography (n-hexane/ethyl acetate) to yield 114 mg (58%) of the title compound in the form of a yellow solid.

$^1$H-NMR(400 MHz,CDCl$_3$)δ:2.03-2.10(2H,m), 2.74(2H, t,J=6.4 Hz), 4.04(3H,s), 4.23(2H,t,J=8.0 Hz), 6.95(1H,dd, J=8.9,2.5 Hz), 7.19(1H,d,J=2.3 Hz), 7.79(1H,d, J=8.7 Hz), 8.14(1H,s), 9.89(1H,s).

MS(ESI)m/z:247(M+H)$^+$.

Reference Example 4

5-Oxo-1-(3-oxo-3,4-dihydro-2H-1,4-benzoxazin-6-yl)pyrrolidin-3-carboxylic acid

[Formula 41]

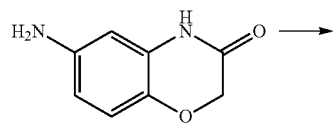

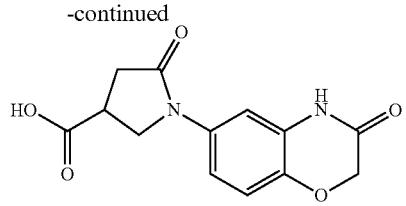

A mixture of 6-amino-2H-1,4-benzoxazin-3(4H)-one (4.93 g, 30.0 mmol), itaconic acid (4.06 g, 31.2 mmol) and water (80 ml) was heated under reflux overnight. The reaction solution was cooled, and the insoluble material was collected by filtration and washed with water and diethyl ether. The filtrate was dried at 50° C. under reduced pressure to yield 7.92 g (96%) of the title compound in the form of a brownish solid.

$^1$H-NMR(400 MHz,DMSO-d$_6$)δ:2.67(1H,dd,J=17.1,6.8 Hz),2.76(1H,dd,J=16.8,9.3 Hz), 3.30-3.37(1H, m), 3.90(1H, dd,J=9.8,5.6 Hz), 3.98(1H,t,J=9.2 Hz), 4.54(2H,s), 6.94(1H, d,J=8.8 Hz), 7.03(1H,dd,J=8.5,6.1 Hz), 7.40(1H,d,J=2.4 Hz), 10.70(1H,s), 12.76(0.7H,brs).

MS(ESI)m/z:277(M+H)$^+$.

Reference Example 5

[5-Oxo-1-(3-oxo-3,4-dihydro-2H-1,4-benzoxazin-6-yl)pyrrolidin-3-yl]carbamic acid tert-butyl ester

[Formula 42]

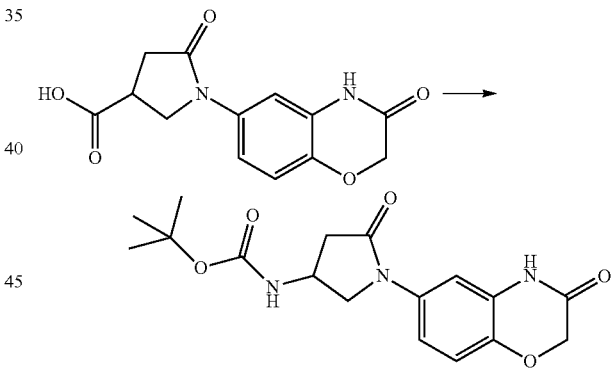

A mixture of 5-oxo-1-(3-oxo-3,4-dihydro-2H-1,4-benzoxazin-6-yl)pyrrolidin-3-carboxylic acid (300 mg, 1.09 mmol), diphenyl phosphoryl azide (351 μl, 1.63 mmol), triethylamine (380 μl, 2.73 mmol) and tert-butyl alcohol (10 ml) was heated under reflux for 24 hours. The reaction solution was cooled, the solvent was then removed under reduced pressure, and the obtained residue was suspended in ethyl acetate to collect the insoluble material by filtration. The obtained residue was purified by silica gel column chromatography (chloroform/methanol) to yield 230 mg (61%) of the title compound in the form of a colorless solid.

$^1$H-NMR(400 MHz, DMSO-d$_6$)δ:1.37(9H,s), 2.37(1H,dd, J=17.0,4.6 Hz), 2.27(1H,dd,J=17.0,8.3 Hz), 3.51(1H,dd, J=9.9,3.9 Hz),3.98(1H,dd,J=9.9,7.1 Hz), 4.14(1H,brs), 4.51 (2H,s),6.90(1H,d,J=8.7 Hz), 6.99(1H,dd, J=8.9,2.5 Hz),7.36 (1H,d,J=2.8 Hz), 7.41(1H,d,J=6.0 Hz), 10.68(1H,s).

MS(ESI)m/z:348(M+H)$^+$.

Reference Example 6

6-(4-Amino-2-oxopyrrolidin-1-yl)-2H-1,4-benzoxazin-3(4H)-one

[Formula 43]

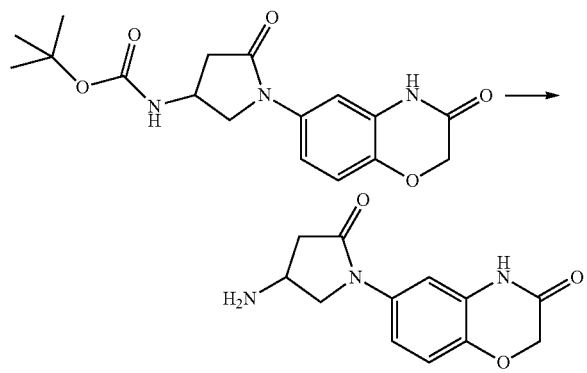

[5-Oxo-1-(3-oxo-3,4-dihydro-2H-1,4-benzoxazin-6-yl) pyrrolidin-3-yl]carbamic acid tert-butyl ester (1.02 g, 2.94 mmol) was added to a solution mixture of trifluoroacetic acid (10 ml) and dichloromethane (10 ml), and the mixture was stirred at room temperature for 3 hours. The reaction solution was concentrated under reduced pressure, the obtained residue was dissolved in water and neutralized by adding a saturated sodium hydrogen carbonate aqueous solution. The solvent of the mixture was removed under reduced pressure and the obtained residue was purified by NH-silica gel column chromatography (chloroform/methanol) to yield 642 mg (88%) of the title compound in the form of a light brown solid.

$^1$H-NMR(400 MHz,DMSO-$d_6$)δ:2.17(1H,dd,J=16.6,4.6 Hz),2.55-2.70(3H,m),3.36(1H,dd,J=9.7,4.0 Hz),3.59-3.63 (1H,m),3.87(1H,dd,J=9.7,6.3 Hz),4.51(2H,s), 6.89-6.92(1H, m),6.97-7.01(1H,m), 7.38(1H,d,J=2.9 Hz),10.69(1H,brs).
MS(ESI)m/z:248(M+H)$^+$.

Example 1

6-(4-{[4-(7-Methoxy-2-oxoquinoxalin-1(2H)-yl) butyl]amino}-2-oxopyrrolidin-1-yl)-2H-1,4-benzoxazin-3(4H)-one

[Formula 44]

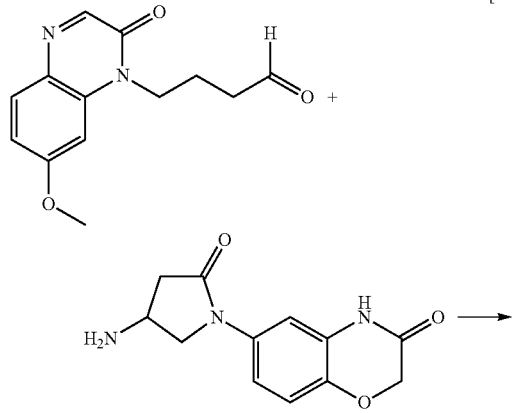

6-(4-Amino-2-oxopyrrolidin-1-yl)-2H-1,4-benzoxazin-3 (4H)-one (56.9 mg, 0.230 mmol) and 4-(7-methoxy-2-oxoquinoxalin-1(2H)-yl)butanal (Reference Example 3; 56.6 mg, 0.230 mmol) were dissolved in chloroform/methanol (10:1, v/v, 3 ml), molecular sieve 3 A (powder 700 mg) was further added, and the mixture was stirred at 60° C. for 4.5 hours. After cooling, sodium triacetoxyborohydride (154 mg, 0.69 mmol) was added to the reaction solution and the mixture was stirred at room temperature for 1.5 hours. After completion of the reaction, the molecular sieve was removed by filtration and a saturated sodium hydrogen carbonate aqueous solution was added to the filtrate and stirred. After separating the organic layer, the aqueous layer was extracted twice with chloroform/methanol (10:1, v/v) and combined with the organic layer. The organic layer was dried over anhydrous magnesium sulfate and the solvent was removed under reduced pressure. The obtained residue was purified by silica gel column chromatography (chloroform/methanol) to yield 92.6 mg (84%) of the title compound in the form of a colorless solid.

$^1$H-NMR(400 MHz,CDCl$_3$)δ:1.47(1H,brs),1.62-1.68(2H, m), 1.81-1.89(2H,m), 2.56(1H,dd,J=17.2,5.2 Hz), 2.70-2.79 (2H,m),2.94(1H,dd,J=17.2,7.5 Hz),3.56-3.64(2H,m),3.91 (3H,s),3.99(1H,dd,J=9.5,6.0 Hz), 4.17-4.28(2H,m),4.57(2H, s),6.82(2H,m),6.90-6.95(2H,m),7.75(1H,d,J=2.3 Hz),7.80 (1H,d,J=8.6 Hz), 8.13(1H,s),8.95(1H,s).
MS(ESI)m/z:478(M+H)$^+$.

Reference Example 7

1-(3,3-Dimethoxypropyl)-7-methoxyquinoxalin-2 (1H)-one

[Formula 45]

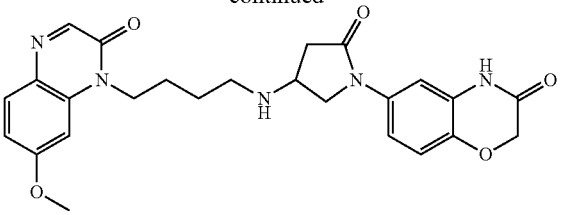

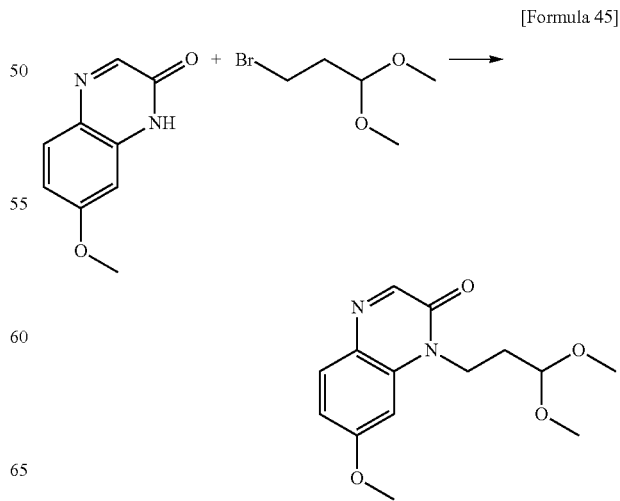

7-Methoxyquinoxalin-2(1H)-one (synthesized with reference to WO2009/1126; 4.13 g, 23.4 mmol) was dissolved in N,N-dimethylformamide (103 ml). The solution was cooled in an ice bath, lithium hydride (purity 90%, 248 mg, 28.1 mmol) was then added thereto and the mixture was stirred at room temperature for 40 minutes. The reaction solution was cooled in an ice bath again, 3-bromo-1,1-dimethoxypropane (3.78 ml, 28.1 mmol) and sodium iodide (4.21 g, 28.1 mmol) were added and then the mixture was stirred at room temperature for 2 days. The reaction solution was diluted with ethyl acetate, washed sequentially with saturated sodium chloride solution (×2), water and saturated sodium chloride solution, dried over magnesium sulfate and the solvent was removed under reduced pressure. The obtained residue was purified by silica gel column chromatography (n-hexane/ethyl acetate) to yield 4.68 g (72%) of the title compound in the form of a yellow syrup.

$^1$H-NMR(400 MHz,CDCl$_3$)δ:2.02-2.09(2H,m),3.38(6H, s),3.92(3H,s),4.27-4.30(2H,m),4.50(1H,t,J=5.2 Hz),6.90-6.93(2H,m),7.77(1H,t,8.6 Hz),8.12(1H,s).

MS(ESI)m/z:279(M+H)$^+$.

Reference Example 8

3-(7-Methoxy-2-oxoquinoxalin-1(2H)-yl)propanal

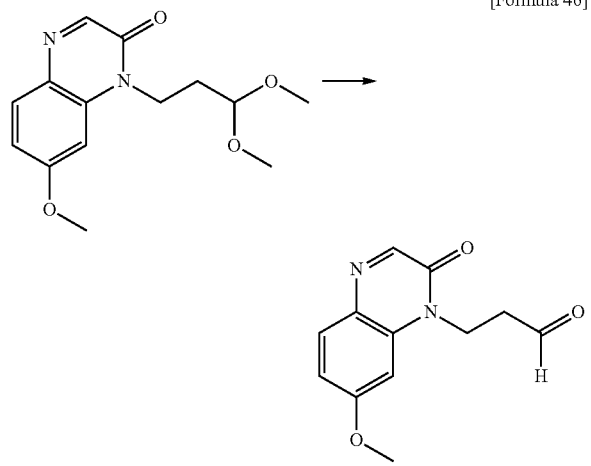

[Formula 46]

1-(3,3-Dimethoxypropyl)-7-methoxyquinoxalin-2(1H)-one (300 mg, 1.08 mmol) was dissolved in tetrahydrofuran (3 ml). 1N Hydrochloric acid (3 ml) was added to this solution and the mixture was stirred at room temperature for 3.5 hours. The reaction solution was diluted with dichloromethane and stirred, and the organic layer was then separated. The organic layer was washed with saturated sodium chloride solution, dried over magnesium sulfate and then the solvent was removed under reduced pressure to yield 236 mg (94%) of the title compound in the form of a light brown solid.

$^1$H-NMR(400 MHz,CDCl$_3$)δ:2.97(2H,dd,J=11.0,4.1 Hz), 3.93(3H, s),4.53(2H,t,J=7.1 Hz),6.81(1H,d,J=2.3 Hz),6.94 (1H,dd,J=8.7,2.8 Hz),7.80(1H,d,J=9.2 Hz),8.12(1H,s),9.89 (1H,s).

MS(FAB)m/z:233(M+H)$^+$.

Example 2

6-(4-{[3-(7-Methoxy-2-oxoquinoxalin-1(2H)-yl) propyl]amino}-2-oxopyrrolidin-1-yl)-2H-1,4-benzoxazin-3(4H)-one

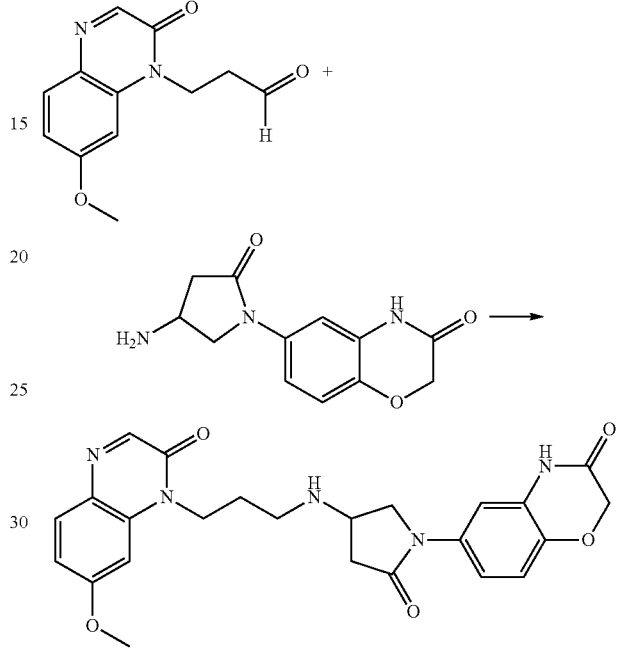

[Formula 47]

6-(4-Amino-2-oxopyrrolidin-1-yl)-2H-1,4-benzoxazin-3 (4H)-one (Reference Example 6; 106 mg, 0.431 mmol) and 3-(7-methoxy-2-oxoquinoxalin-1(2H)-yl)propanal (100 mg, 0.431 mmol) were dissolved in N,N-dimethylformamide (2 ml), and the mixture to which sodium sulfate (400 mg) was added was stirred overnight at room temperature. The reaction solution was diluted with dichloromethane (12 ml), sodium triacetoxyborohydride (110 mg, 0.517 mmol) was added thereto and the mixture was stirred at room temperature for 3 hours. After completion of the reaction, a saturated sodium hydrogen carbonate aqueous solution was added thereto, the organic layer was separated, washed sequentially with saturated sodium chloride solution, water (×3) and saturated sodium chloride solution, dried over anhydrous magnesium sulfate, and the solvent was removed under reduced pressure. The obtained residue was purified by silica gel column chromatography (chloroform/methanol) to yield 193 mg (97%) of the title compound in the form of a light brown solid.

$^1$H-NMR(400 MHz,DMSO-d$_6$)δ:1.70-1.80(2H,m),2.27 (2H,dd,J=16.7,4.4 Hz),2.55-2.63(2H,m), 2.70(1H,dd, J=17.0,7.3 Hz),3.34-3.42(1H,m),3.48(1H,dd,J=10.1,3.7 Hz),3.86-3.91(4H,m),4.23(2H,t,J=7.3 Hz),4.51(2H,s),6.90 (1H,d,J=8.7 Hz),6.96-7.00(2H,m),7.05(1H,d,J=2.8 Hz),7.42 (1H,d,J=2.3Hz),7.72(1H,d,J=8.7 Hz),8.01(1H,s), 10.69(1H, s).

MS(ESI)m/z:464(M+H)$^+$.

Reference Example 9

1-(2,3-Dihydroxypropyl)-7-methoxyquinoxalin-2(1H)-one

[Formula 48]

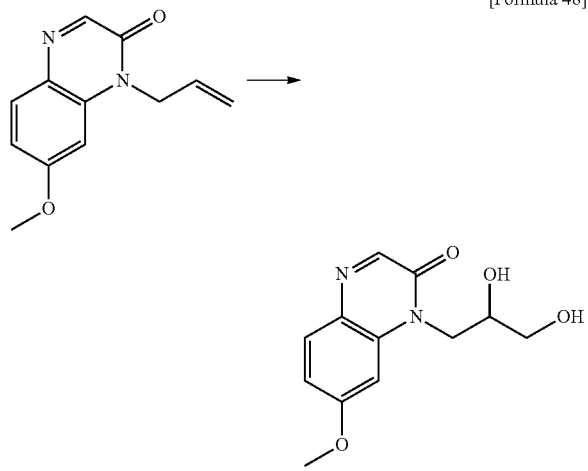

7-Methoxy-1-(2-propen-1-yl)quinoxalin-2(1H)-one (synthesized with reference to WO2008/9700; 2.77 g, 12.82 mmol) was dissolved in a mixed solvent (100 ml) of tetrahydrofuran/water/acetone (2:1:2). N-methylmorpholineoxide (3.47 g, 25.64 mmol) was added to this solution under cooling on ice and a 4% aqueous solution of osmium tetroxide (1.6 ml, 0.256 mmol) was subsequently added. The reaction solution was stirred for 2 days while the temperature was raised to room temperature. The reaction solution was diluted with ethyl acetate and washed with saturated sodium bicarbonate water and saturated sodium chloride solution. The organic layer was dried over anhydrous sodium sulfate and the solvent was removed under reduced pressure to yield 3.16 g (99%) of the title compound in the form of a brown oily product.

$^1$H-NMR(400 MHz,CDCl$_3$)δ:2.95-3.30(2H,m),3.55(1H, dd,J=12.2,3.2 Hz),3.66-3.74(1H,m),3.94(3H,s),4.06-4.14 (1H,m),4.24(1H,dd,J=14.3,5.7 Hz),4.52(1H,dd,J=14.3,7.2 Hz),6.97-7.01(2H,m),7.83(1H,d,J=8.3 Hz),8.18(1H,s).

Reference Example 10

1-(3-{[tert-Butyl(dimethyl)silyl]oxy}-2-hydroxypropyl)-7-methoxyquinoxalin-2(1H)-one

[Formula 49]

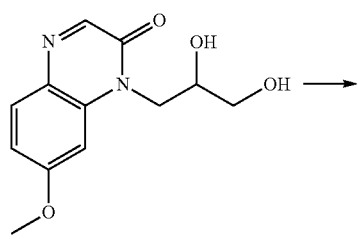

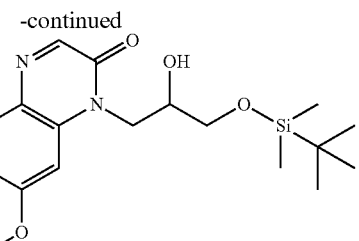

1-(2,3-Dihydroxypropyl)-7-methoxyquinoxalin-2(1H)-one (3.06 g, 12.22 mmol) was dissolved in dichloromethane (75 ml). To the solution, tert-butyldimethylsilyl chloride (2.03 g, 13.44 mmol), triethylamine (2.21 ml, 15.89 mmol) and 4-dimethylamino pyridine (299 mg, 2.44 mmol) were added under cooling on ice, and the reaction mixture was stirred for 12 hours while the temperature was rising to room temperature. The reaction solution was diluted with dichloromethane, washed with water and dried over anhydrous sodium sulfate. The solvent was removed under reduced pressure and the residue was purified by silica gel column chromatography (chloroform/methanol) to yield 5.29 g (quantitative) of the title compound in the form of a dark orange oily product.

$^1$H-NMR(400 MHz,CDCl$_3$)δ:0.12(6H,s), 0.94(9H,s),3.21 (1H,d,J=4.9 Hz),3.72-3.75(2H,m),3.91(3H,s),4.09(1H,dd, J=10.6,5.5 Hz),4.39(2H,d,J=5.6 Hz),6.95(1H,dd,J=8.9,2.6 Hz),7.02(1H,d,J=2.4 Hz),7.80(1H,d,J=9.0 Hz),8.16(1H, s).

Reference Example 11

1-[3-{[tert-Butyl(dimethyl)silyl]oxy}-2-(methoxymethoxy)propyl]-7-methoxyquinoxalin-2(1H)-one

[Formula 50]

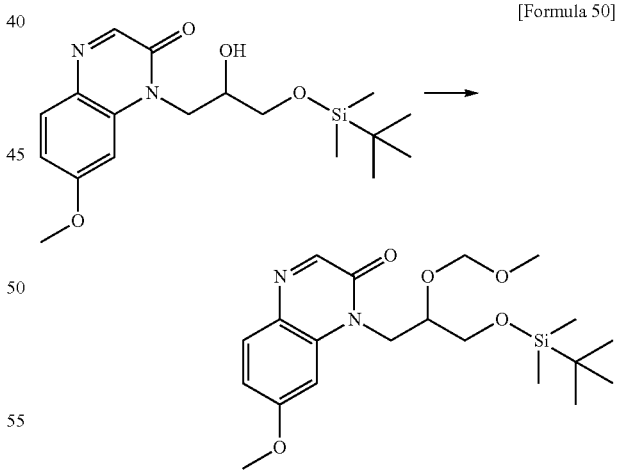

1-(3-{[Tert-butyl(dimethyl)silyl]oxy}-2-hydroxypropyl)-7-methoxyquinoxalin-2(1H)-one (2.0 g, 5.49 mmol) was dissolved in dichloromethane (30 ml). N,N-Diisopropylethylamine (3.35 ml, 19.22 mmol) and chloromethylmethyl ether (1.04 ml, 13.73 mmol) were added to this solution under cooling on ice, and the mixture was stirred for 2 hours. N,N-Diisopropylethylamine (3.35 ml, 19.22 mmol) and chloromethylmethyl ether (1.04 ml, 13.73 mmol) were further added to the reaction solution and stirred for 14 hours, and the reaction solution was diluted with dichloromethane and washed with water. The organic layer was dried over anhydrous sodium sulfate, the solvent was removed under reduced pressure, and the residue was purified by silica gel column chromatography (hexane/ethyl acetate) to yield 863 mg (39%) of the title compound in the form of a yellow oily product.

$^1$H-NMR(400 MHz,CDCl$_3$)δ:0.09(6H,s), 0.92(9H,s),3.09 (3H,s),3.73-3.84(2H,m),3.91(3H,s),4.05-4.14(1H,m),4.34-4.46(2H,m),4.48(1H,d,J=7.1 Hz), 4.63(1H,d,J=6.8 Hz),6.91 (1H,dd,J=8.8,2.4 Hz), 7.06(1H,d, J=2.7 Hz), 7.76(1H,d, J=8.8 Hz), 8.13(1H,s).

Reference Example 12

1-[3-Hydroxy-2-(methoxymethoxy)propyl]-7-methoxyquinoxalin-2(1H)-one

[Formula 51]

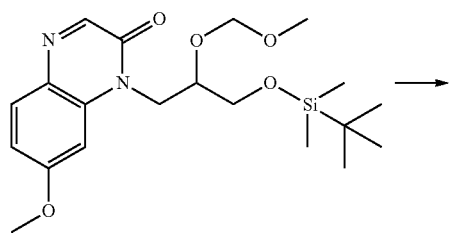

↓

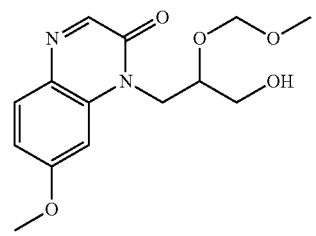

1-[3-{[Tert-butyl(dimethyl)silyl]oxy}-2-(methoxymethoxy)propyl-7-methoxyquinoxalin-2(1H)-one (863 mg, 2.11 mmol) was dissolved in tetrahydrofuran (10 ml). Tetrabutyl ammonium fluoride (1M tetrahydrofuran solution; 2.74 ml, 2.74 mmol) was added to this solution under cooling on ice, and the mixture was stirred for 3 hours. The reaction solution was diluted with dichloromethane and washed with saturated sodium bicarbonate water. After drying with anhydrous sodium sulfate, the solvent was removed under reduced pressure and the residue was purified by silica gel column chromatography (chloroform/methanol) to yield 495 mg (80%) of the title compound in the form of a yellowish solid.

$^1$H-NMR(400 MHz,CDCl$_3$)δ:3.38-3.43(4H,m),3.51-3.58 (1H,m),3.69-3.76(1H,m),3.94(3H,s),3.95-4.01(1H,m),4.25 (1H,dd,J=14.2,5.1 Hz),4.65(1H,dd,J=14.0,7.9 Hz),4.73(1H, d,J=6.8 Hz),4.79 (1H,d,J=6.8 Hz),6.96(1H,dd,J=9.0,2.4 Hz), 7.09(1H,d,J=2.4 Hz),7.80(1H,d,J=8.8 Hz),8.16(1H,s).

Reference Example 13

2-(Methoxymethoxy)-3-(7-methoxy-2-oxoquinoxalin-1(2H)-yl)propanal

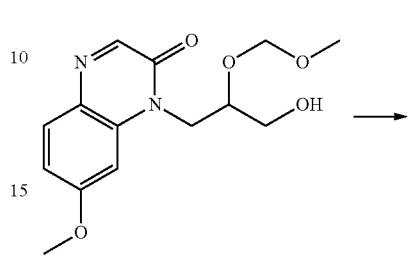

[Formula 52]

↓

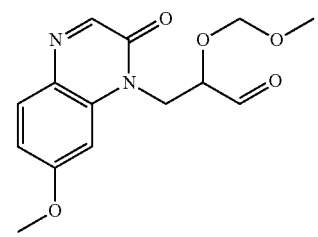

Oxalyl chloride (0.032 ml, 0.374 mmol) was dissolved in dichloromethane (2 ml). A solution of dimethyl sulfoxide (0.053 ml, 0.748 mmol) in dichloromethane (0.5 ml) was added to this solution at −78° C. and the mixture was stirred for 30 minutes. While maintaining the temperature at −78° C., a solution of 1-[3-hydroxy-2-(methoxymethoxy)propyl]-7-methoxyquinoxalin-2(1H)-one (100 mg, 0.340 mmol) in dichloromethane (3 ml) was further added and the mixture was stirred for 40 minutes. While maintaining the temperature at −78° C., triethylamine (0.261 ml, 1.870 mmol) was added and the mixture was stirred for 30 minutes. The temperature was raised to 0° C., the reaction solution was stirred for 2 hours, then diluted with dichloromethane and washed with water. After drying over anhydrous sodium sulfate, the solvent was removed under reduced pressure to yield 109 mg (quantitative) of the title compound in the form of an orange oily product. The product was used as such for the next step without purification.

Reference Example 14

6-(4-{[2-(Methoxymethoxy)-3-(7-methoxy-2-oxoquinoxalin-1(2H)-yl)propyl]amino}-2-oxopyrrolidin-1-yl)-2H-1,4-benzoxazin-3(4H)-one

[Formula 53]

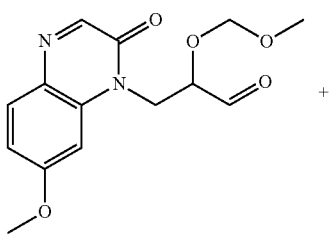 +

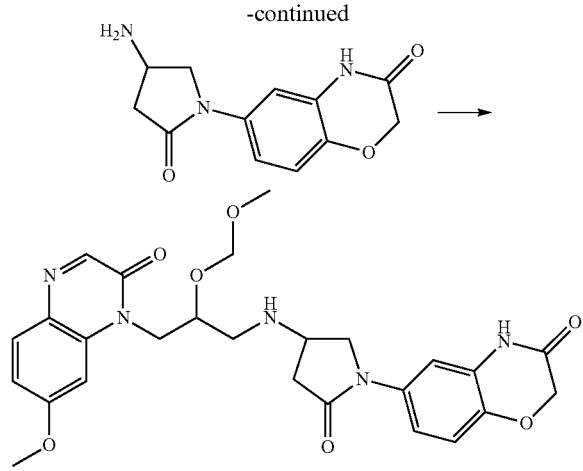

2-(Methoxymethoxy)-3-(7-methoxy-2-oxoquinoxalin-1 (2H)-yl)propanal (0.340 mmol) and 6-(4-amino-2-oxopyrrolidin-1-yl)-2H-1,4-benzoxazin-3(4H)-one (Reference Example 6; 84 mg, 0.340 mmol) were dissolved in a mixed solvent of dichloromethane/N,N-dimethylformamide (10:1, 11 ml). Acetic acid (0.039 ml, 0.680 mmol) and anhydrous sodium sulfate (200 mg) were added to this solution, and the mixture was stirred at room temperature for two and a half hours. Sodium triacetoxyborohydride (144 mg, 0.680 mmol) was added thereto, the mixture was stirred for 14 hours and then the solvent was removed under reduced pressure. Chloroform was added to the residue, the resultant was alkalized by adding saturated sodium bicarbonate water under cooling on ice and extracted with chloroform. After drying over anhydrous sodium sulfate, the solvent was removed under reduced pressure. The residue was purified by silica gel column chromatography (chloroform/methanol) to yield 115 mg (65%) of the title compound in the form of a colorless clear oily product.

$^1$H-NMR(400 MHz,CDCl$_3$)δ:2.49-2.57(1H,m),2.74-2.94 (3H,m),3.29-3.31(3H,m),3.53-3.67(2H,m),3.90-3.91(3H, m),3.94-4.02(1H,m),4.03-4.11(1H,m),4.20-4.28(1H,m), 4.58(2H,m), 4.60-4.76(3H,m), 6.78-6.84(1H,m),6.91-6.96 (2H,m), 7.09-7.13(1H,m),7.62-7.67(1H,m), 7.76-7.80(1H, m), 8.12(1H,s),8.26(1H,brs).

MS(ESI)m/z:524(M+H)$^+$.

Example 3

6-(4-{[2-Hydroxy-3-(7-methoxy-2-oxoquinoxalin-1 (2H)-yl)propyl]amino}-2-oxopyrrolidin-1-yl)-2H-1, 4-benzoxazin-3(4H)-one

[Formula 54]

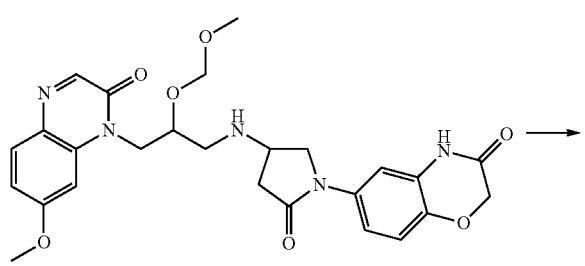

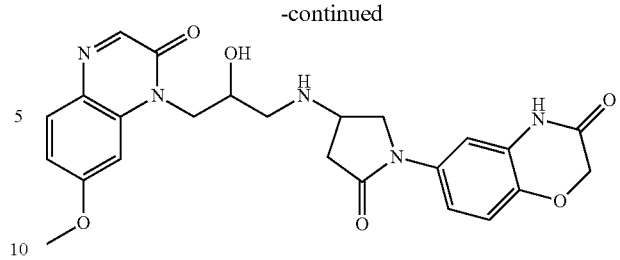

6-(4-{[2-(Methoxymethoxy)-3-(7-methoxy-2-oxoquinoxalin-1(2H)-yl)propyl]amino}-2-oxopyrrolidin-1-yl)-2H-1,4-benzoxazin-3(4H)-one (115 mg, 0.220 mmol) was dissolved in a mixed solvent of methanol/tetrahydrofuran (1:1,2 ml). To this solution was added 4N hydrochloric acid aqueous solution (1 ml) under cooling on ice and the mixture was stirred at 60° C. for 7 hours. The reaction solution was cooled in the air, and the solvent was then removed under reduced pressure. To the residue was added 1N aqueous sodium hydroxide solution under cooling on ice to neutralize the residue which was then extracted using a lower layer solvent of chloroform/methanol/water (7:3:1). The extract was dried over anhydrous sodium sulfate and the solvent was removed under reduced pressure. The residue was purified by silica gel column chromatography (chloroform/methanol) to yield 65 mg (61%) of the title compound in the form of a yellowish solid.

$^1$H-NMR(400 MHz,DMSO-d$_6$)δ:2.20-2.37(2H,m),2.61-2.78(3H,m),3.42-3.49(1H,m),3.50-3.57(1H,m),3.85-3.98 (5H,m),4.23-4.29(2H,m),4.53(2H,s),5.02-5.09(1H,m),6.91-7.04(3H,m),7.15-7.19(1H,m),7.44(1H,d,J=2.4 Hz),7.73(1H, d,J=8.8 Hz),8.04(1H,d,J=2.7 Hz),10.70(1H,s).

MS(ESI)m/z:480(M+H)$^+$.

Reference Example 15

1-[5-(2-Ethoxy-2-oxoethoxy)-6-nitropyridin-2-yl]-5-oxopyrrolidin-3-carboxylic acid methyl ester

[Formula 55]

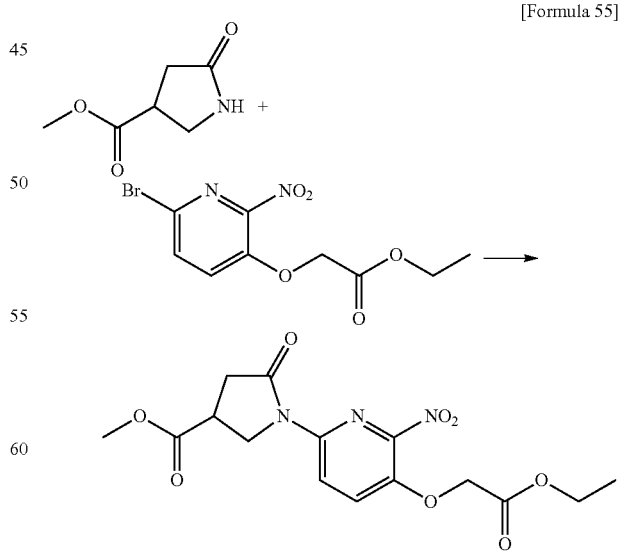

A mixture of 5-oxopyrrolidin-3-carboxylic acid methyl ester (synthesized with reference to Tetrahedron Asymmetry, 2001, vol. 12, pages 3241-3250; 1.0 g, 6.99 mmol), [(6-bromo-2-nitropyridin-3-yl)oxy]acetic acid ethyl ester (synthesized with reference to WO2004/2992; 2.13 g, 6.99 mmol), palladium acetate (157 mg, 0.699 mmol), 2,2'-bis(diphenylphosphino)-1,1'-binaphthyl (417 mg, 0.699 mmol), potassium phosphate (4.83 g, 21 mmol) and 1,4-dioxane (50 ml) was stirred under a stream of nitrogen gas at 100° C. for 5 hours. After cooling, ethyl acetate was added to the reaction solution, the insoluble material was removed by filtration, the obtained filtrate was washed with water and saturated sodium chloride solution, dried over anhydrous magnesium sulfate and the solvent was removed under reduced pressure. The obtained residue was purified by silica gel column chromatography (n-hexane/ethyl acetate) to yield 1.95 g (76%) of the title compound in the form of a light brown syrup.

$^1$H-NMR(400 MHz,CDCl$_3$)δ:1.29(3H,t,J=7.2 Hz),2.90(1H,dd,J=17.5,9.5 Hz),3.03(1H,dd,J=17.8,60.9 Hz),3.31-3.39(1H,m),3.78(3H,s),4.20-4.36(4H,m),4.76(2H,s),7.52(1H,d,J=9.2 Hz),8.63(1H,d,J=9.2 Hz).

MS(ESI)m/z:368(M+H)$^+$.

Reference Example 16

5-Oxo-1-(3-oxo-3,4-dihydro-2H-pyrido[3,2-b][1,4]oxazin-6-yl)pyrrolidin-3-carboxylic acid methyl ester

[Formula 56]

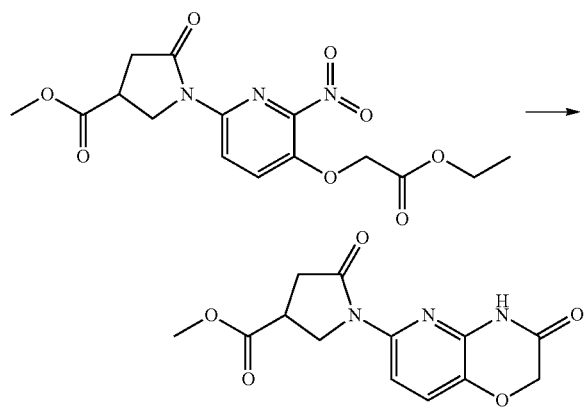

Reduced iron (55.7 mg, 0.996 mmol) was added to a solution of 1-[5-(2-ethoxy-2-oxoethoxy)-6-nitropyridin-2-yl]-5-oxopyrrolidin-3-carboxylic acid methyl ester (122 mg, 0.332 mmol) in acetic acid (1.2 ml) and the mixture was stirred at 85° C. for 2 hours. After cooling, the insoluble material was removed by filtration and the filtrate was concentrated under reduced pressure. The residue was dissolved in dichloromethane, a saturated sodium hydrogen carbonate aqueous solution was added thereto and the mixture was stirred for 10 minutes. The organic layer was separated, dried over anhydrous magnesium sulfate and then the solvent was removed under reduced pressure to yield 81 mg (84%) of the title compound in the form of a colorless solid.

$^1$H-NMR(400 MHz,CDCl$_3$)δ:2.94(2H,ddd,J=44.0,17.4,8.7 Hz),3.28-3.36(1H,m),3.78(3H,s),4.22(2H,ddd,J=31.9,11.5,7.6 Hz),4.65(2H,s),7.30(1H,d,J=8.7 Hz),7.90(1H,s),8.01(1H,d,J=8.7 Hz).

MS(ESI)m/z:292(M+H)$^+$.

Reference Example 17

5-Oxo-1-(3-oxo-3,4-dihydro-2H-pyrido[3,2-b][1,4]oxazin-6-yl)pyrrolidin-3-carboxylic acid

[Formula 57]

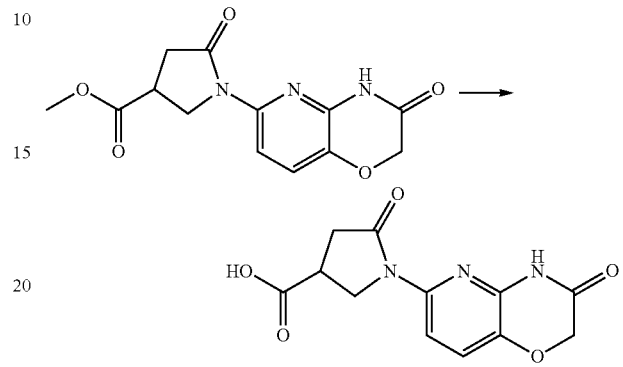

An aqueous solution (0.1 ml) of lithium hydroxide monohydrate (8.62 mg, 0.206 mmol) was added to a solution of 5-oxo-1-(3-oxo-3,4-dihydro-2H-pyrido[3,2-b][1,4]oxazin-6-yl)pyrrolidin-3-carboxylic acid methyl ester (40 mg, 0.137 mmol) in methanol (0.8 ml) and the mixture was stirred overnight at room temperature. The reaction solution was neutralized by adding 1N hydrochloric acid (0.206 ml), methanol was removed under reduced pressure, the obtained residue was triturated with water and the insoluble material was collected by filtration and dried to yield 32.9 mg (87%) of the title compound in the form of a colorless solid.

$^1$H-NMR(400 MHz,DMSO-d$_6$)δ:2.76(2H,ddd,J=39.8,17.2,8.3 Hz),3.26-3.33(2H,m),4.04-4.12(2H,m),4.59(2H,s),7.38(1H,d,J=9.2 Hz),7.79(1H,d,J=8.6 Hz),11.15(1H,s).

MS(ESI)m/z:278(M+H)$^+$.

Reference Example 18

[5-Oxo-1-(3-oxo-3,4-dihydro-2H-pyrido[3,2-b][1,4]oxazin-6-yl)pyrrolidin-3-yl]carbamic acid benzyl ester

[Formula 58]

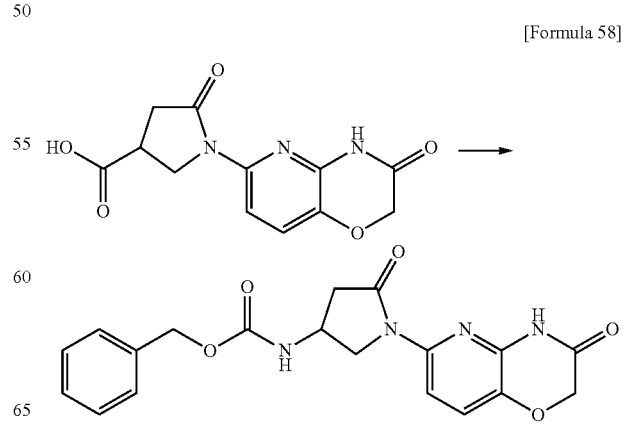

A mixture of 5-oxo-1-(3-oxo-3,4-dihydro-2H-pyrido[3,2-b][1,4]oxazin-6-yl)pyrrolidin-3-carboxylic acid (764 mg, 2.76 mmol), diphenyl phosphoryl azide (0.891 ml, 4.13 mmol), triethylamine (0.626 ml, 4.49 mmol) and benzene (35 ml) was heated under reflux for 3 hours. Benzyl alcohol (21 ml) was added to the reaction solution, which was further heated under reflux overnight. After cooling, the insoluble material was removed by filtration, the filtrate was diluted with ethyl acetate, washed with a saturated sodium hydrogen carbonate aqueous solution and saturated sodium chloride solution, dried over anhydrous magnesium sulfate and the solvent was removed under reduced pressure. The obtained residue was purified by silica gel column chromatography (n-hexane/ethyl acetate and chloroform/methanol) to yield 496 mg (47%) of the title compound in the form of a light yellow solid.

$^1$H-NMR(400 MHz,DMSO-d$_6$)δ:2.44(1H,d,J=4.0 Hz), 2.90(1H,dd,J=17.2,8.0 Hz),3.80(1H,dd,J=11.2,3.7 Hz),4.11 (1H,dd, J=11.2,6.6 Hz),4.19(1H,s),4.58(2H,s),5.01(2H,s), 7.27-7.40(6H,m), 7.78-7.85(2H,m), 11.14(1H,s).

MS(ESI)m/z: 383(M+H)$^+$.

Reference Example 19

6-(4-Amino-2-oxopyrrolidin-1-yl)-2H-pyrido[3,2-b][1,4]oxazin-3(4H)-one

[Formula 59]

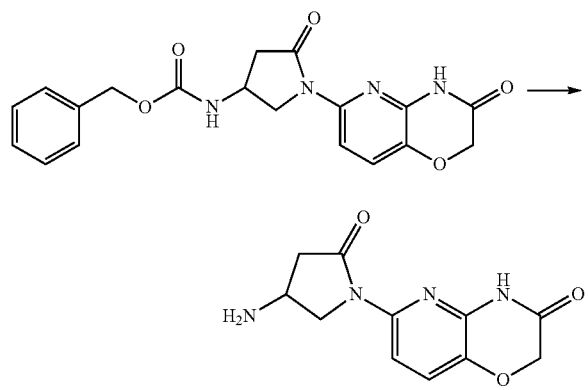

[5-oxo-1-(3-oxo-3,4-dihydro-2H-pyrido[3,2-b][1,4]oxazin-6-yl)pyrrolidin-3-yl]carbamic acid benzyl ester (66.8 mg, 0.175 mmol) was dissolved in methanol (4 ml), 10% palladium on carbon (50% wet, 50 mg) was added thereto and catalytic hydrogenation was carried out at room temperature for 1 hour and at 50° C. for 45 minutes. The catalyst was removed by filtration and washed with methanol, and the filtrate and washings were concentrated under reduced pressure to yield 40.1 mg (92%) of the title compound in the form of a colorless solid.

$^1$H-NMR(400 MHz,DMSO-d$_6$)δ:2.19(1H,dd,J=16.3,4.4 Hz),2.69-2.75(1H,m),3.53-3.61(2H,m),3.94(1H,dd,J=11.7, 6.7 Hz),4.58(2H,s),7.34-7.39(1H,m),7.81(1H,d,J=8.7 Hz).

MS(ESI)m/z:249(M+H)$^+$.6-(4-{[3-(7-Methoxy-2-oxoquinoxalin-1(2H)-yl)propyl]amino}-2-oxopyrrolidin-1-yl)-2H-pyrido[3,2-b][1,4]oxazin-3(4H)-one Example 4

[Formula 60]

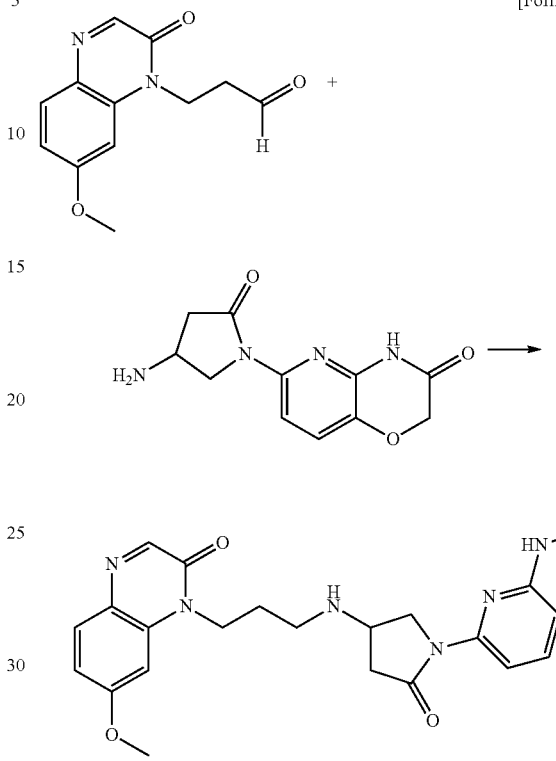

6-(4-Amino-2-oxopyrrolidin-1-yl)-2H-pyrido[3,2-b][1,4]oxazin-3(4H)-one (174 mg, 0.650 mmol) and 3-(7-methoxy-2-oxoquinoxalin-1(2H)-yl)propanal (Reference Example 8; 143 mg, 0.615 mmol) were dissolved in dichloromethane (8 ml) and N,N-dimethylformamide (2.4 ml). Sodium sulfate (3.0 g) was added to this solution and the mixture was stirred at 40° C. for 8 hours. After cooling, sodium triacetoxyborohydride (417 mg, 1.95 mmol) was added to the reaction mixture and the mixture was stirred overnight at room temperature. The insoluble material was removed by filtration, the solvent was removed under reduced pressure, dichloromethane and a saturated sodium hydrogen carbonate aqueous solution were added to the obtained residue, and the mixture was stirred for 10 minutes. The organic layer was separated, washed with water (×3) and saturated sodium chloride solution, dried over anhydrous magnesium sulfate and the solvent was removed under reduced pressure. The obtained residue was purified by silica gel column chromatography (chloroform/methanol) to yield 104 mg (34%) of the title compound in the form of a light yellow solid.

$^1$H-NMR(400 MHz,CDCl$_3$)δ:2.02-2.12(3H,m),2.59(1H, dd,J=17.2,4.0 Hz),2.73-2.89(3H,m),3.49-3.55(1H,m),3.88 (3H,s),4.02-4.08(2H,m),4.30-4.39(2H,m),4.56(2H,dd, J=33.8,15.5 Hz),6.80(1H,d,J=2.9 Hz),6.91(1H,dd,J=9.2,2.3 Hz),7.10(1H,d,J=8.6 Hz),7.78(1H,d,J=9.2 Hz),7.89(1H, J=8.6 Hz),8.12(1H,s),10.29(1H, brs).

MS(ESI)m/z:465(M+H)$^+$.

Reference Example 20

[(6-{(4S)-4-[(tert-Butoxycarbonyl)amino]-2-oxopyrrolidin-1-yl}-2-nitropyridin-3-yl)oxy]acetic acid ethyl ester

[Formula 61]

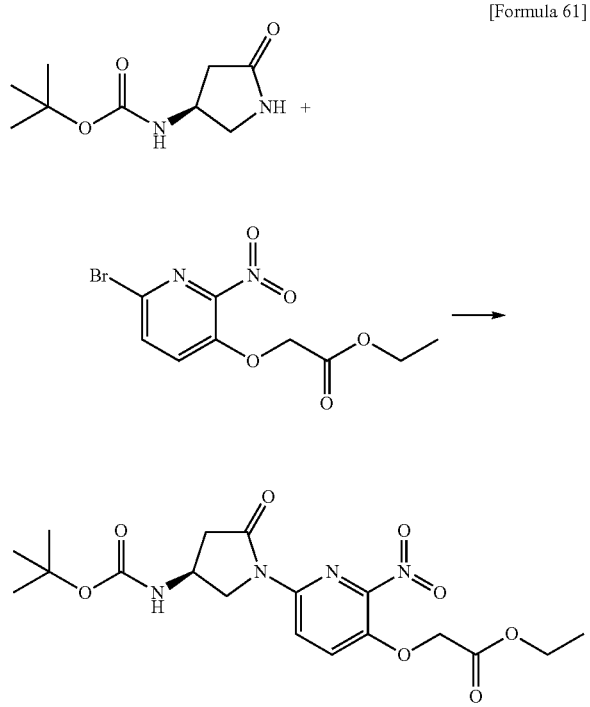

A mixture of [(3S)-5-oxopyrrolidin-3-yl]carbamic acid tert-butyl ester (synthesized with reference to WO2004/22536; 505 mg, 2.52 mmol), [(6-bromo-2-nitropyridin-3-yl)oxy]acetic acid ethyl ester (synthesized with reference to WO2004/2992; 769 mg, 2.52 mmol), palladium acetate (56.6 mg, 0.252 mmol), 2,2'-bis(diphenylphosphino)-1,1'-binaphthyl (157 mg, 0.252 mmol), potassium phosphate (1.74 g, 7.56 mmol) and 1,4-dioxane (25 ml) was stirred under a stream of nitrogen gas at 100° C. for 6 hours. After cooling, ethyl acetate was added to the reaction solution to remove the insoluble material by filtration. The obtained filtrate was washed with water and saturated sodium chloride solution, dried over anhydrous magnesium sulfate and the solvent was removed under reduced pressure. The obtained residue was purified by silica gel column chromatography (n-hexane/ethyl acetate) to yield 380 mg (36%) of the title compound in the form of a light brown syrup.

$^1$H-NMR(400 MHz,CDCl$_3$)δ:1.25-1.33(3H,m),1.45(9H,s),2.61(1H,dd,J=17.8,4.6 Hz),3.02(1H,dd,J=17.8,8.0 Hz),3.93-3.99(1H, m),4.24-4.32(3H,m),4.40(1H,s),4.76(2H,s),4.77-4.88(1H,m),7.52(1H,d,J=9.2 Hz),8.61(1H,d,J=9.2 Hz).

MS(ESI)m/z:425(M+H)$^+$.

Reference Example 21

[(3S)-5-Oxo-1-(3-oxo-3,4-dihydro-2H-pyrido[3,2-b][1,4]oxazin-6-yl)pyrrolidin-3-yl]carbamic acid tert-butyl ester

[Formula 62]

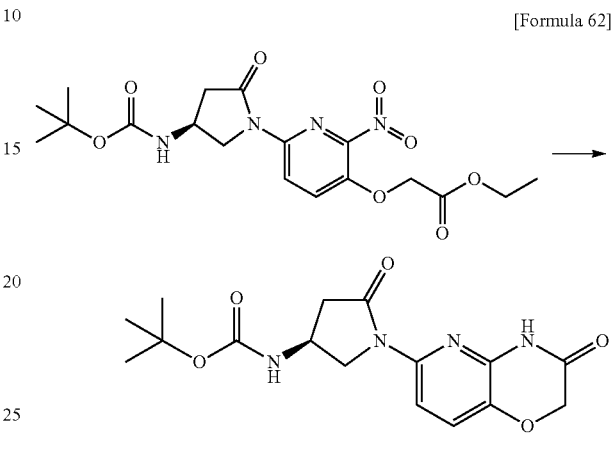

Reduced iron (150 mg, 2.69 mmol) was added to a solution of [(6-{(4S)-4-[(tert-butoxycarbonyl)amino]-2-oxopyrrolidin-1-yl}-2-nitropyridin-3-yl)oxy]acetic acid ethyl ester (380 mg, 0.895 mmol) in acetic acid (3.8 ml) and the mixture was stirred at 85° C. for 1.5 hours. After cooling, the insoluble material was removed by filtration and the filtrate was concentrated under reduced pressure. The residue was dissolved in dichloromethane, a saturated sodium hydrogen carbonate aqueous solution was added thereto and the mixture was stirred for 10 minutes. The solvent was removed under reduced pressure and the obtained residue was purified by silica gel column chromatography (chloroform/methanol) to yield 305 mg (98%) of the title compound in the form of a colorless solid.

$^1$H-NMR(400 MHz,DMSO-d$_6$)δ:1.37(9H,s),2.42-2.54 (1H,m),2.84(1H,dd,J=17.2,8.0 Hz),3.70-3.75(1H,m),4.06-4.16(2H,m),4.58(2H,s),7.36-7.42(2H,m),7.80(1H,d,J=9.2 Hz),11.14(1H, s).

MS(ESI)m/z:349(M+H)$^+$.

Reference Example 22

6-[(4S)-4-Amino-2-oxopyrrolidin-1-yl]-2H-pyrido[3,2-b][1,4]oxazin-3(4H)-one

[Formula 63]

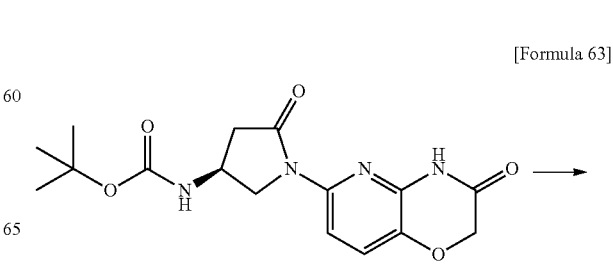

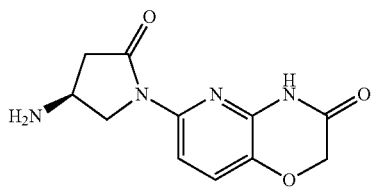

Aqueous trifluoroacetic acid (trifluoroacetic acid/water=95:5, v/v, 3.5 ml) was added to [(3S)-5-oxo-1-(3-oxo-3,4-dihydro-2H-pyrido[3,2-b][1,4]oxazin-6-yl)pyrrolidin-3-yl]carbamic acid tert-butyl ester (148 mg, 0.425 mmol) and the mixture was stirred in an ice bath for 2 hours. The reaction solution was diluted with ethyl acetate, neutralized by adding a saturated sodium hydrogen carbonate aqueous solution and the solvent was concentrated under reduced pressure. The obtained residue was purified by silica gel column chromatography (NH silica gel, chloroform/methanol) to yield 84.5 mg (80%) of the title compound in the form of a colorless solid.

MS(ESI)m/z:249(M+H)$^+$.

Example 5

6-[(4S)-4-{[3-(7-Methoxy-2-oxoquinoxalin-1(2H)-yl)propyl]amino}-2-oxopyrrolidin-1-yl]-2H-pyrido[3,2-b][1,4]oxazin-3(4H)-one

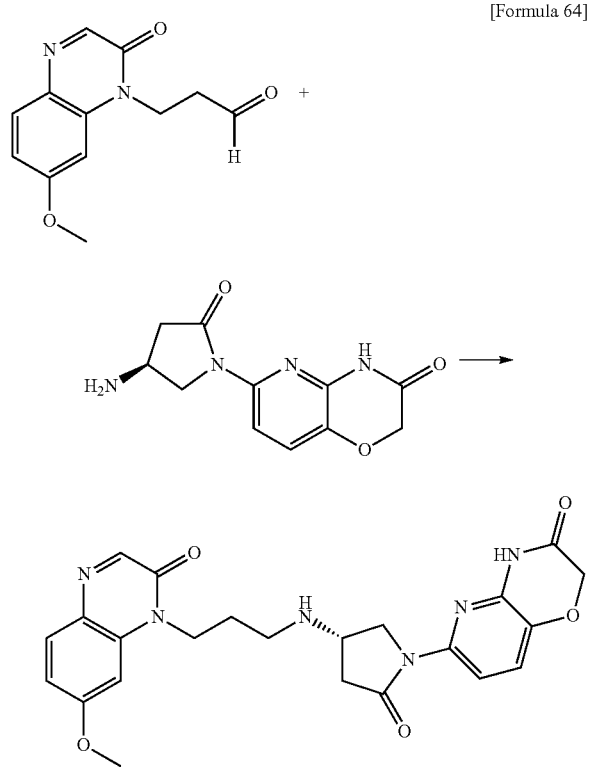

[Formula 64]

6-[(4S)-4-Amino-2-oxopyrrolidin-1-yl]-2H-pyrido[3,2-b][1,4]oxazin-3(4H)-one (94.1 mg, 0.379 mol) and 3-(7-methoxy-2-oxoquinoxalin-1(2H)-yl)propanal (Reference Example 8; 106 mg, 0.456 mmol) were dissolved in chloroform/methanol (10:1, v/v, 6 ml). Molecular sieve 3 A (powder, 1.0 g) was added to the solution and heated under reflux for 3 hours. After cooling, sodium triacetoxyborohydride (145 mg, 0.684 mmol) was added to the reaction mixture and the mixture was stirred overnight at room temperature. After completion of the reaction, the molecular sieve was removed by filtration and a saturated sodium hydrogen carbonate aqueous solution was added to the filtrate and stirred. After separating the organic layer, the aqueous layer was extracted twice with chloroform/methanol (10:1, v/v) and combined with the organic layer. The organic layer was dried over anhydrous magnesium sulfate and the solvent was removed under reduced pressure. The obtained residue was purified by thin-layer chromatography (chloroform/methanol) to yield 56 mg (32%) of the title compound in the form of a colorless solid.

$^1$H-NMR(400 MHz,CDCl$_3$)δ:2.05-2.20(3H,s),2.62(1H,dd,J=17.4,3.7 Hz),2.73-2.93(3H,m),3.48-3.60(1H,m),3.87(3H,s),4.01(1H,dd,J=11.5,6.4 Hz),4.11-4.21(1H,m),4.36(2H,s),4.54(2H,dd,J=36.7,15.6 Hz),6.78(1H,d, J=2.3 Hz),6.90(1H,dd, J=8.9, 2.5 Hz),7.04(1H,d,J=8.7 Hz),7.77(1H,d,J=9.2 Hz),7.85(1H,d,J=8.7 Hz),8.11(1H,s),11.00(1H,brs).

MS(ESI)m/z:465(M+H)$^+$.

Reference Example 23

5-[2-(1,3-Dioxolan-2-yl)ethyl]-3-methoxypyrido[2,3-b]pyrazin-6(5H)-one

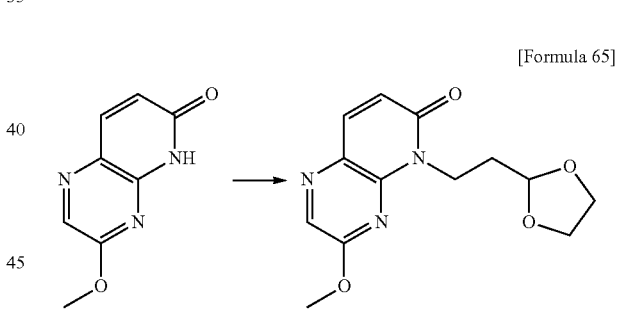

[Formula 65]

3-Methoxypyrido[2,3-b]pyrazin-6(5H)-one (400 mg, 2.26 mmol) was dissolved in N,N-dimethylformamide (12 ml). Lithium bromide (206 mg, 2.37 mmol) and sodium hydride (55%, 104 mg, 2.37 mmol) were added to the solution under cooling on ice and stirred for one and a half hours while the temperature of the reaction solution was raised to room temperature. The reaction solution was cooled on ice again, 2-(2-bromoethyl)-1,3-dioxolane (0.345 mmol, 2.94 mmol) was added thereto and the mixture was stirred at room temperature for 22 hours. Water was added to the reaction solution, which was then extracted with ethyl acetate and washed with saturated sodium chloride solution. After drying over anhydrous sodium sulfate, the solvent was removed under reduced pressure. The residue was purified by silica gel column chromatography (chloroform/methanol) to yield 731 mg (quantitative) of the title compound in the form of a yellow oily product.

¹H-NMR(400 MHz,CDCl₃)δ:2.15(2H,td,J=7.3,4.6 Hz), 3.82-3.89(2H,m),3.92-3.98(2H,m),4.09(3H,s),4.60(2H,t, J=7.3 Hz),5.03(1H,t,J=4.6 Hz),6.76(1H,d,J=9.5 Hz),7.83 (1H,d,J=9.8 Hz),8.11(1H,s).

Reference Example 24

3-(3-Methoxy-6-oxopyrido[2,3-b]pyrazin-5(6H)-yl) propanal

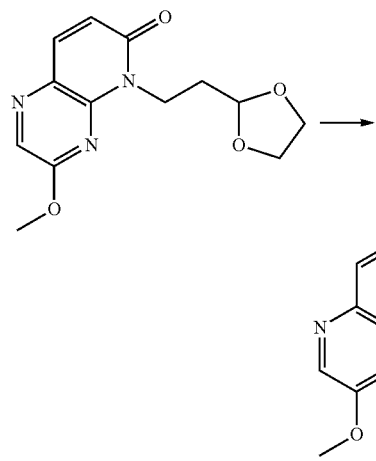

[Formula 66]

5-[2-(1,3-Dioxolan-2-yl)ethyl]-3-methoxypyrido[2,3-b] pyrazin-6(5H)-one (397 mg, 1.43 mmol) was dissolved in tetrahydrofuran (15 ml). To the solution was added a 1N hydrochloric acid aqueous solution (5 ml) under cooling on ice and the mixture was stirred at room temperature for two and a half hours and at 50° C. for 4 hours. After cooling in the air, the solvent was removed under reduced pressure and the residue was alkalized by adding saturated sodium bicarbonate water under cooling on ice. The resultant was extracted with dichloromethane, the extract was dried over anhydrous sodium sulfate and the solvent was removed under reduced pressure to yield 292 mg (87%) of the title compound in the form of a yellowish solid.

¹H-NMR(400 MHz,CDCl₃)δ:2.88-2.96(2H,m),4.05(3H, s),4.79(2H,t, J=7.1 Hz),6.77(1H,d,J=9.8 Hz),7.87(1H,d, J=9.8 Hz),8.14(1H,s),9.89(1H,s).

Example 6

3-Methoxy-5-(3-{[5-oxo-1-(3-oxo-3,4-dihydro-2H-1,4-benzoxazin-6-yl)pyrrolidin-3-yl]amino}propyl) pyrido[2,3-b]pyrazin-6(5H)-one

[Formula 67]

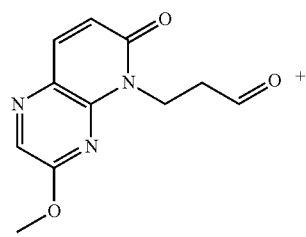

+

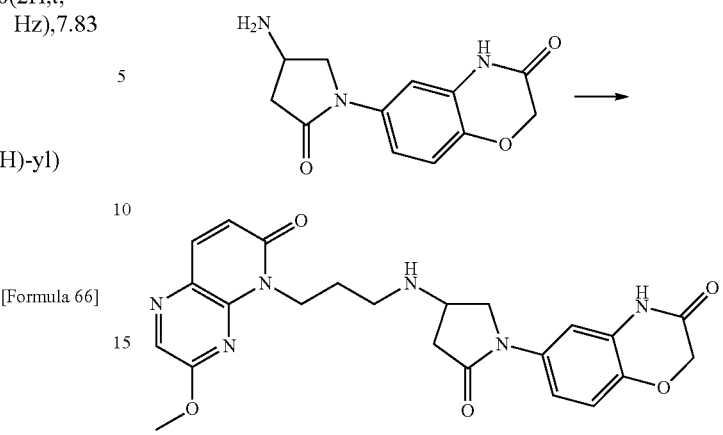

3-(3-Methoxy-6-oxopyrido[2,3-b]pyrazin-5(6H)-yl)propanal (292 mg, 1.25 mmol) and 6-(4-amino-2-oxopyrrolidin-1-yl)-2H-1,4-benzoxazin-3(4H)-one (Reference Example 6; 310 mg, 1.25 mmol) were dissolved in a mixed solvent (33 ml) of dichloromethane/N,N-dimethylformamide (10:1). Acetic acid (0.143 ml, 2.50 mmol) and anhydrous sodium sulfate (600 mg) were added to the solution and the mixture was stirred at room temperature for 13 hours. Sodium triacetoxyborohydride (531 mg, 2.50 mmol) was added to the reaction solution, the mixture was stirred for 4 hours and the solvent was removed under reduced pressure. A lower layer solvent of chloroform/methanol/water (7:3:1) was added to the residue, the resultant was alkalized by adding saturated sodium bicarbonate water under cooling on ice and extracted with a lower layer solvent of chloroform/methanol/water (7:3:1). After drying the extract with anhydrous sodium sulfate, the solvent was removed under reduced pressure and the residue was purified by silica gel column chromatography (chloroform/methanol) to yield 170 mg (29%) of the title compound in the form of a white solid.

¹H-NMR(400 MHz,DMSO-d₆)δ:1.78-1.86(2H,m),2.09-2.18(1H,m),2.22-2.29(1H,m),2.56-2.63(2H,m),2.65-2.73 (1H,m),3.36-3.49(2H,m),3.89(1H,dd,J=9.6, 6.2 Hz),4.04 (3H,s),4.38(2H,t,J=7.3 Hz),4.53(2H,s),6.71(1H,d,J=9.8 Hz)6.93(1H,d,J=8.8 Hz),7.00(1H,dd,J=8.9,2.3 Hz),7.43(1H, d,J=2.4 Hz),7.94(1H,d, J=9.5 Hz),8.22(1H,s),10.70(1H,s).

MS(ESI)m/z:465(M+H)⁺.

Reference Example 25

3-Ethoxy-2-fluoro-3-oxopropionic acid

[Formula 68]

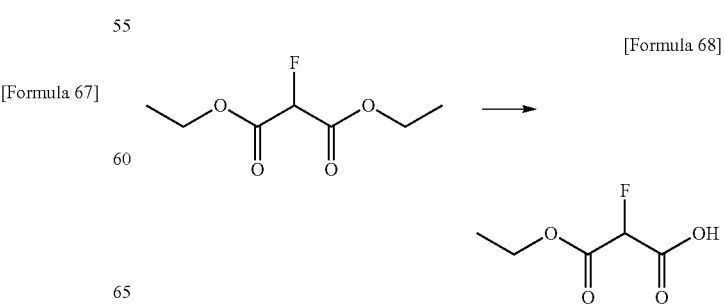

Diethyl fluoromalonate (15.0 g, 84.19 mmol) was suspended in ethanol (50 ml), a solution of potassium hydroxide (5.56 g, 84.19 mmol) in ethanol (50 ml) was added dropwise under cooling on ice and the mixture was stirred at room temperature for 14 hours. The solvent was removed under reduced pressure, the residue was dissolved in water and acidified by adding a 6N hydrochloric acid aqueous solution under cooling on ice. The mixture was extracted with diethyl ether and the extract was dried over anhydrous sodium sulfate. The solvent was removed under reduced pressure to yield 14.42 g of a crude product of the title compound in the form of a colorless clear oily product.

$^1$H-NMR(400 MHz,CDCl$_3$)δ:1.35(3H,t,J=7.2 Hz), 4.36 (2H,q,J=7.2 Hz),5.29-5.41(1H,m),5.57(1H,brs).

Reference Example 26

2-Fluoro-3-hydroxypropionic acid ethyl ester

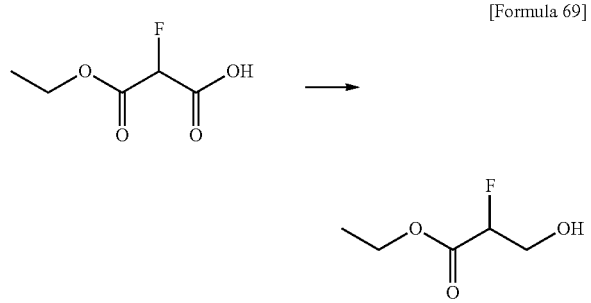

[Formula 69]

Oxalyl chloride (17.10 ml, 202.06 mmol) was added dropwise to a solution of N,N-dimethylformamide (7.17 ml, 92.61 mmol) in dichloromethane (100 ml) under cooling on ice and the mixture was stirred at the same temperature for 1 hour. The solvent was removed under reduce pressure, the residue was then suspended in acetonitrile (70 ml) and tetrahydrofuran (140 ml) and the suspension was cooled to −30° C. A solution of 3-ethoxy-2-fluoro-3-oxopropionic acid crude product (14.42 g) in tetrahydrofuran (100 ml) was added dropwise thereto, the mixture was stirred for 1 hour and then cooled to −78° C. A solution of sodium borohydride (7.33 g, 193.64 mmol) in N,N-dimethylformamide (40 ml) was added dropwise to the mixture and stirred for 19 hours while raising the temperature of the reaction solution to room temperature. The reaction was quenched by adding a 4N hydrochloric acid aqueous solution to the reaction solution under cooling on ice and the resulting solution was extracted with ethyl acetate. The extract was washed with a 1N hydrochloric acid aqueous solution, saturated sodium bicarbonate water and saturated sodium chloride solution, dried over anhydrous sodium sulfate and the solvent was removed under reduced pressure to yield 13.06 g of a crude product of the title compound in the form of a yellowish clear oily product.

$^1$H-NMR(400 MHz,CDCl$_3$)δ:1.33(3H,t,J=7.0 Hz),3.93-4.16(2H,m),4.31(2H,q, J=7.2 Hz),4.92-5.08(1H,m).

Reference Example 27

3-{[tert-Butyl(diphenyl)silyl]oxy}-2-fluoropropionic acid ethyl ester

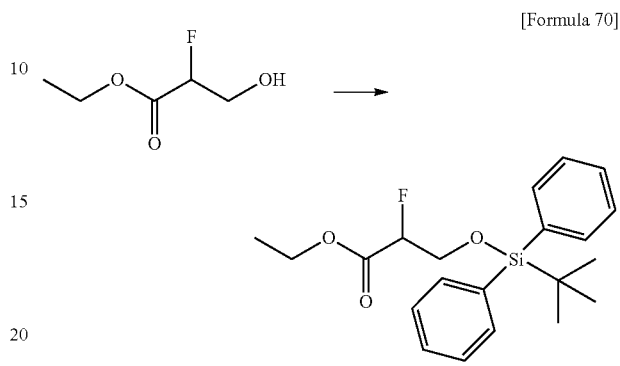

[Formula 70]

A crude product of 2-fluoro-3-hydroxypropionic acid ethyl ester (13.06 g) was dissolved in dichloromethane (300 ml). Imidazole (17.2 g, 252.57 mmol) and tert-butyldiphenylsilyl chloride (25 ml, 96.14 mmol) were added to the solution under cooling on ice, and the reaction solution was stirred for 18 hours while raising the reaction solution temperature to room temperature. Saturated sodium bicarbonate water was added to the reaction solution and the resultant was extracted with dichloromethane. The extract was dried over anhydrous sodium sulfate and the solvent was removed under reduced pressure. The residue was purified by silica gel column chromatography (hexane/ethyl acetate) to yield 17.98 g (three steps, 57%) of the title compound in the form of a colorless clear oily product.

$^1$H-NMR(400 MHz,CDCl$_3$)δ:1.04(9H,s),1.33(3H,t,J=7.1 Hz),3.98-4.15(2H,m),4.22-4.34(2H,m), 4.89-5.04(1H,m), 7.36-7.47(6H,m),7.59-7.76(4H,m).

Reference Example 28

3-{[tert-Butyl(diphenyl)silyl]oxy}-2-fluoropropan-1-ol

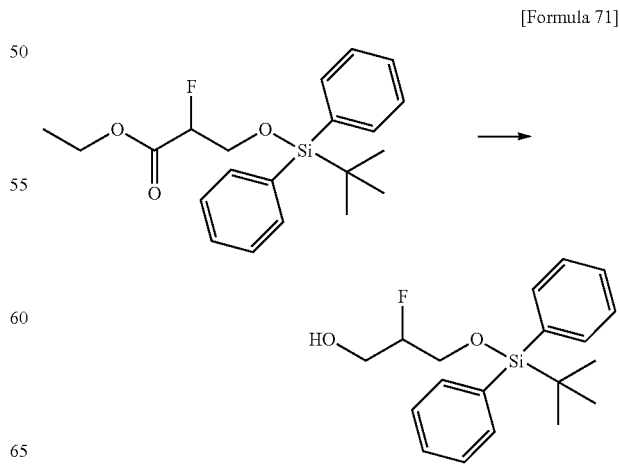

[Formula 71]

3-{[Tert-butyl(diphenyl)silyl]oxy}-2-fluoropropionic acid ethyl ester (17.98 g, 48.01 mmol) was dissolved in tetrahydrofuran (250 ml). Lithium borohydride (2.32 g, 96.02 mmol) was added to the solution under cooling on ice and the mixture was stirred for 24 hours. To the reaction solution was added 1N sodium hydroxide aqueous solution under cooling on ice to quench the reaction. The resulting solution was extracted with ethyl acetate, and the resultant was washed with saturated sodium chloride solution. The organic layer was dried over anhydrous sodium sulfate and the solvent was removed under reduced pressure. The residue was purified by silica gel column chromatography (hexane/ethyl acetate) to yield 12.10 g (76%) of the title compound in the form of a colorless clear oily product.

$^1$H-NMR(400 MHz,CDCl$_3$)δ:1.06(9H,s),3.80-3.98(4H,m),4.53-4.74(1H,m),7.37-7.50(6H,m),7.64-7.76(4H,m).

Reference Example 29 tert-Butyl (2-fluoro-3-iodopropoxy)diphenyl silane

[Formula 72]

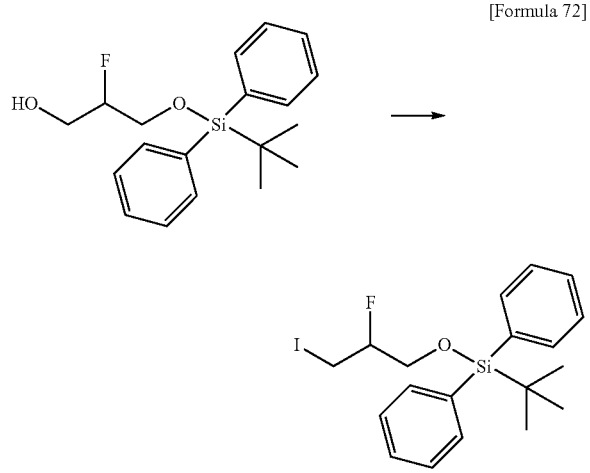

3-{[Tert-Butyl(diphenyl)silyl]oxy}-2-fluoropropan-1-ol (2.03 g, 6.12 mmol) was dissolved in dichloromethane (20 ml). Iodine (4.66 g, 18.36 mmol), triphenyl phosphine (4.82 g, 18.36 mmol) and imidazole (1.25 g, 18.36 mmol) were added to the solution under cooling on ice and the mixture was stirred at room temperature for 23 hours. A saturated sodium thiosulfate aqueous solution was added to the reaction solution under cooling on ice and stirred for a while, the solution was extracted with dichloromethane and the extract was dried over anhydrous sodium sulfate. The solvent was removed under reduced pressure, and the residue was purified by silica gel column chromatography (hexane/ethyl acetate) to yield 1.58 g (58%) of the title compound in the form of a yellowish solid.

$^1$H-NMR(400 MHz,CDCl$_3$)δ:1.06(9H,s),3.33-3.55(2H,m),3.82-3.99(2H,m),4.48-4.67(1H,m), 7.37-7.48(6H,m), 7.65-7.70(4H,m).

Reference Example 30

4-(3-{[tert-Butyl(diphenyl)silyl]oxy}-2-fluoropropyl)-6-methoxypyrido[2,3-b]pyrazin-3(4H)-one

[Formula 73]

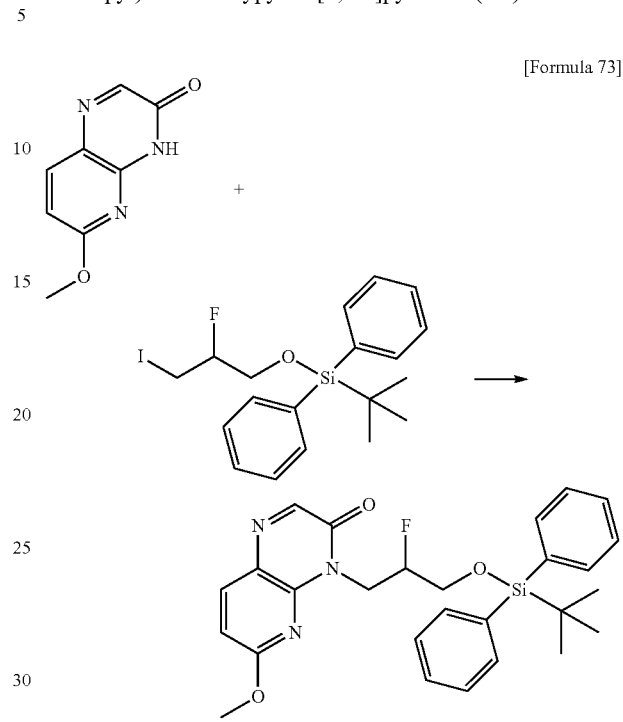

6-Methoxypyrido[2,3-b]pyrazin-3(4H)-one (215 mg, 1.213 mmol) and tert-butyl(2-fluoro-3-iodopropoxy)diphenylsilane (805 mg, 1.820 mmol) were dissolved in N,N-dimethylformamide (6 ml). Cesium carbonate (553 mg, 1.698 mmol) was added to the solution and the mixture was stirred at room temperature for 7 hours. Water was added to the reaction solution and the mixture was extracted with ethyl acetate. The extract was washed with saturated sodium chloride solution, dried over anhydrous sodium sulfate and the solvent was removed under reduced pressure. The residue was purified by silica gel column chromatography (hexane/ethyl acetate) to yield 399 mg (67%) of the title compound in the form of a light orange solid.

$^1$H-NMR(400 MHz,CDCl$_3$)δ:1.08(9H,s), 3.92-3.96(4H,m),3.99-4.02(1H,m),4.35-4.50(1H,m),4.94-5.13(1H,m), 5.16-5.27(1H,m),6.72-6.75(1H,m), 7.34-7.47(6H,m), 7.65-7.70(4H,m), 8.00-8.04(1H,m), 8.16(1H,s).

Reference Example 31

4-(2-Fluoro-3-hydroxyopropyl)-6-methoxypyrido[2,3-b]pyrazin-3(4H)-one

[Formula 74]

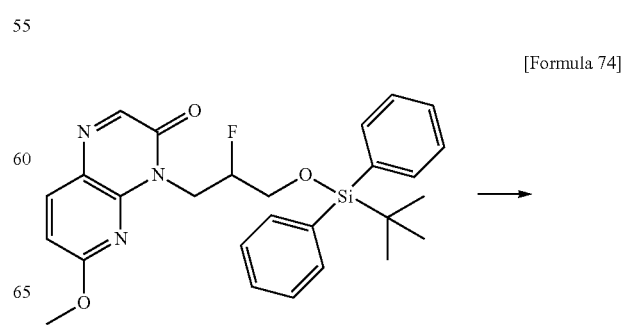

-continued

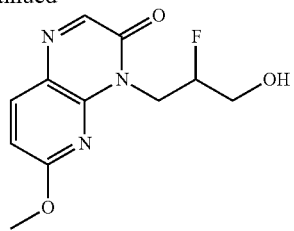

4-(3-{[Tert-butyl(diphenyl)silyl]oxy}-2-fluoropropyl)-6-methoxypyrido[2,3-b]pyrazin-3(4H)-one (564 mg, 1.15 mmol) was dissolved in tetrahydrofuran (5 ml). Tetrabutyl ammonium fluoride (1M tetrahydrofuran solution; 1.5 ml, 1.50 mmol) was added to the solution under cooling on ice and the mixture was stirred at room temperature for 24 hours. Saturated sodium bicarbonate water was added to the reaction solution and the resultant was extracted with dichloromethane. The extract was dried over anhydrous sodium sulfate and the solvent was removed under reduced pressure. The obtained residue was purified by silica gel column chromatography (hexane/ethyl acetate) to yield 232 mg (80%) of the title compound in the form of a yellow noncrystalline solid.

$^1$H-NMR(400 MHz,CDCl$_3$)δ:3.05(1H,t,J=7.1 Hz),3.63-3.93(2H,m),4.06(3H,s),4.64-5.09(3H,m),6.79(1H,d,J=8.5 Hz),8.06(1H,d,J=8.8 Hz),8.21(1H,s).

Reference Example 32

2-Fluoro-3-(6-methoxy-3-oxopyrido[2,3-b]pyrazin-4(3H)-yl)propanal

[Formula 75]

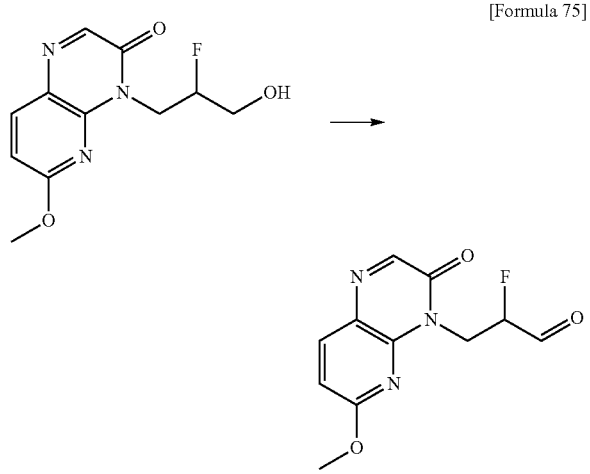

Oxalyl chloride (0.086 ml, 1.01 mmol) was dissolved in dichloromethane (4 ml). A solution of dimethyl sulfoxide (0.143 ml, 2.02 mmol) in dichloromethane (1 ml) was added dropwise while cooled to −78° C., and the mixture was stirred at the same temperature for 40 minutes. A solution of 4-(2-fluoro-3-hydroxyopropyl)-6-methoxypyrido[2,3-b]pyrazin-3(4H)-one (232 mg, 0.917 mmol) in dichloromethane (6 ml) was added dropwise to the reaction solution, the mixture was stirred at the same temperature for 1 hour after which triethylamine (0.703 ml, 5.04 mmol) was added and the mixture was stirred for 30 minutes. The temperature of the reaction solution was raised to 0° C., the reaction solution was stirred for 1 hour after which water was added and extracted with dichloromethane. The extract was dried over anhydrous sodium sulfate and the solvent was removed under reduced pressure to yield 323 mg of a crude product of the title compound in the form of a yellow oily product.

Example 7

4-(2-Fluoro-3-{[5-oxo-1-(3-oxo-3,4-dihydro-2H-1,4benzoxazin-6-yl)pyrrolidin-3-yl]amino}propyl)-6-methoxypyrido[2,3-b]pyrazin-3(4H)-one

[Formula 76]

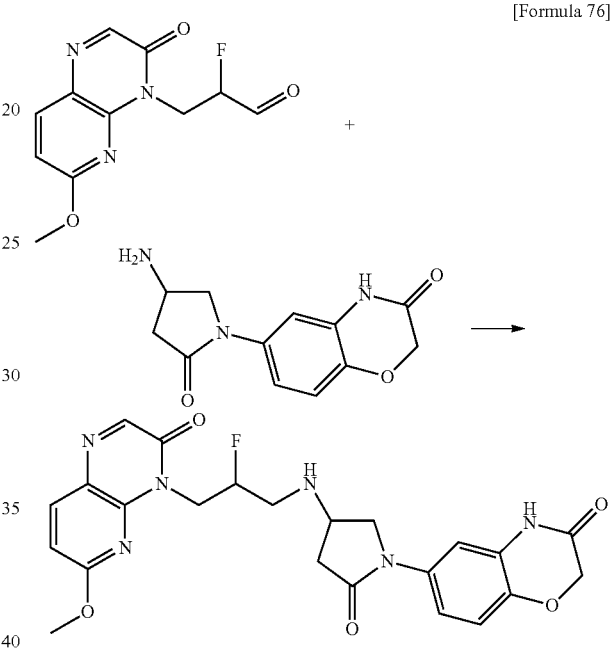

A crude product of 2-Fluoro-3-(6-methoxy-3-oxopyrido[2,3-b]pyrazin-4(3H)-yl)propanal (323 mg), 6-(4-amino-2-oxopyrrolidin-1-yl)-2H-1,4-benzoxazin-3(4H)-one (Reference Example 6; 227 mg, 0.917 mmol) were mixed in a mixed solution of dichloromethane (30 ml) and N,N-dimethylformamide (3 ml). Acetic acid (0.105 ml, 1.834 mmol) and anhydrous sodium sulfate (450 mg) were added to the solution and the mixture was stirred for 12 hours. Sodium triacetoxyborohydride (389 mg, 1.834 mmol) was added to the reaction solution, the mixture was stirred for 4 hours and then the solvent was removed under reduced pressure. A lower layer solvent of chloroform/methanol/water (7:3:1) was added to the residue and the resultant was alkalized by adding saturated sodium bicarbonate water under cooling on ice. The mixture was extracted with a lower layer solvent of chloroform/methanol/water (7:3:1), the extract was dried over anhydrous sodium sulfate and the solvent was removed under reduced pressure. The residue was purified by silica gel column chromatography (chloroform/methanol) and preparative layer chromatography (silica gel, chloroform/methanol=20:1) to yield 180 mg (41%) of the title compound in the form of a light orange solid.

$^1$H-NMR(400 MHz,DMSO-d$_6$)δ:2.28-2.36(1H,m),2.38-2.47(1H,m),2.68-2.75(1H,m),2.86-3.01(2H,m),3.43-3.56 (2H,m),3.88-3.96(1H,m),3.97(3H,d,J=6.3 Hz),4.35-4.49 (1H,m),4.53(2H,s),4.78-4.89(1H,m),4.90-5.11(1H,m),6.86

(1H,d,J=8.5 Hz),6.93(1H,d,J=8.5 Hz),7.00(1H,d,J=8.5 Hz), 7.43(1H,d,J=2.4 Hz),8.14(2H,s),10.71(1H.s).

MS(ESI)m/z:483(M+H)⁺.

Reference Example 33

1-(3-{[tert-Butyl(diphenyl)silyl]oxy}-2-fluoropropyl)-7-methoxyquinoxalin-2(1H)-one

[Formula 77]

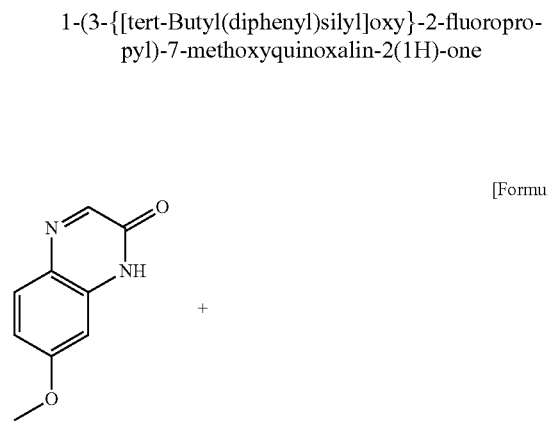

7-Methoxyquinoxalin-2(1H)-one (synthesized with Reference to WO2009/1126; 1.50 g, 8.50 mmol) and tert-butyl(2-fluoro-3-iodopropoxy)diphenylsilane (Reference Example 29; 5.64 mmol, 12.75 mmol) were dissolved in N,N-dimethylformamide (60 ml). Cesium carbonate (3.88 g, 11.90 mmol) was added to the solution, and the mixture was stirred at room temperature for 16 hours. After completion of the reaction, water was added to the reaction solution which was then extracted with ethyl acetate. The extract was washed with saturated sodium chloride solution, dried over anhydrous sodium sulfate and the solvent was removed under reduced pressure. The obtained residue was purified by silica gel column chromatography (hexane/ethyl acetate) to yield 690 mg (17%) of the title compound in the form of a light brown solid.

¹H-NMR(400 MHz,CDCl₃)δ:1.12(9H,s),3.86(3H,s),3.91-4.10(2H,m),4.57-4.69(2H,m),4.87-5.01(1H,m),6.92-6.96 (1H,m),6.98(1H,brs), 7.38-7.48(6H,m),7.67-7.73(4H,m), 7.78(1H,d, J=8.8 Hz),8.14(1H,s).

Reference Example 34

1-(2-Fluoro-3-hydroxypropyl)-7-methoxyquinoxalin-2(1H)-one

[Formula 78]

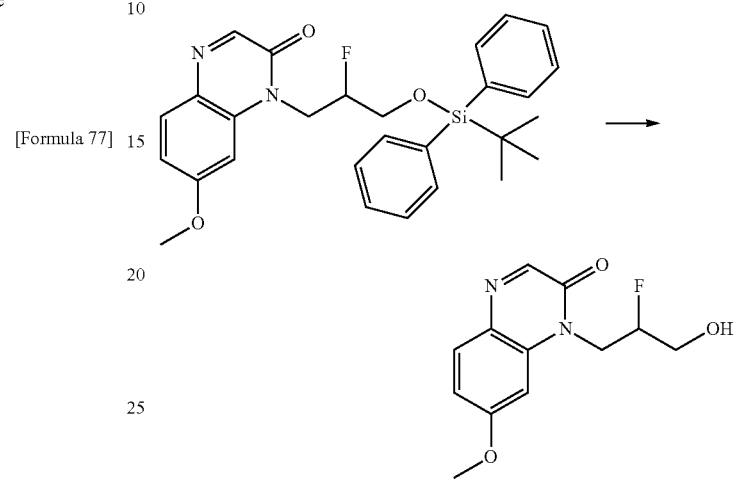

1-(3-{[tert-Butyl(diphenyl)silyl]oxy}-2-fluoropropyl)-7-methoxyquinoxalin-2(1H)-one (690 mg, 1.41 mmol) was dissolved in tetrahydrofuran (7 ml). Tetrabutyl ammonium fluoride (1M tetrahydrofuran solution; 1.83 ml, 1.83 mmol) was added to the solution under cooling on ice and the mixture was stirred at room temperature for 5 hours. Saturated sodium bicarbonate water was added to the reaction solution and the resultant was extracted with dichloromethane. The extract was dried over anhydrous sodium sulfate and the solvent was removed under reduced pressure. The residue was purified by silica gel column chromatography (chloroform/methanol) to yield 348 mg (98%) of the title compound in the form of a yellowish solid.

¹H-NMR(400 MHz,CDCl₃)δ:3.24(1H,t,J=7.1 Hz),3.67-3.84(2H,m),3.93(3H,s),4.57(1H,d,J=4.6 Hz),4.62(1H,d, J=5.0 Hz), 4.88-5.07(1H,m),6.96-7.01(2H,m),7.80-7.84(1H, m),8.18(1H,s).

Reference Example 35

2-Fluoro-3-(7-methoxy-2-oxoquinoxalin-1(2H)-yl) propanal

[Formula 79]

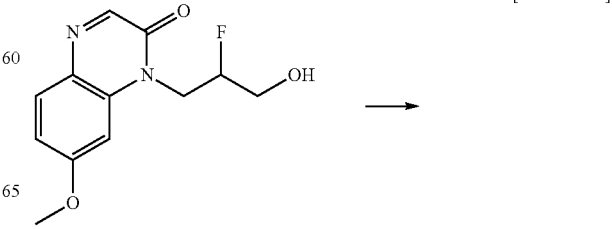

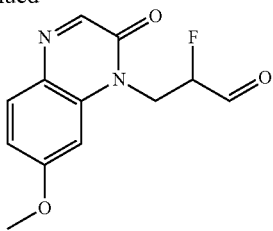

Oxalyl chloride (0.055 ml, 0.655 mmol) was dissolved in dichloromethane (3 ml). A solution of dimethyl sulfoxide (0.093 ml, 1.309 mmol) in dichloromethane (1 ml) was added dropwise to the solution at −78° C. and the mixture was stirred at the same temperature for 50 minutes. A solution of 1-(2-fluoro-3-hydroxyopropyl)-7-methoxyquinoxalin-2(1H)-one (150 mg, 0.595 mmol) in dichloromethane (5 ml) was added dropwise to the reaction solution, the mixture was stirred at the same temperature for 50 hours to which triethylamine (0.456 ml, 3.273 mmol) was then added, and the mixture was stirred for 1 hour. The temperature of the reaction solution was raised to 0° C., the reaction solution was stirred for 1 hour to which water was added and extracted with dichloromethane. The extract was dried over anhydrous sodium sulfate and the solvent was removed under reduced pressure to yield 196 mg of a crude product of the title compound in the form of a yellow oily product.

Example 8

6-(4-{[2-Fluoro-3-(7-methoxy-2-oxoquinoxalin-1(2H)-yl)propyl]amino}-2-oxopyrrolidin-1-yl)-2H-1,4-benzoxazin-3(4H)-one

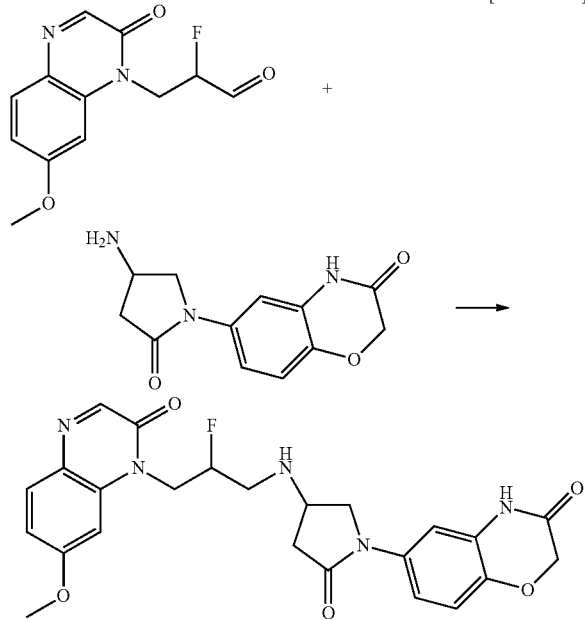

[Formula 80]

A crude product of 2-Fluoro-3-(7-methoxy-2-oxoquinoxalin-1(2H)-yl)propanal (196 mg) and 6-(4-amino-2-oxopyrrolidin-1-yl)-2H-1,4-benzoxazin-3(4H)-one (Reference Example 6; 147 mg, 0.595 mmol) were dissolved in a mixed solution of dichloromethane (20 ml) and N,N-dimethylformamide (2 ml). Acetic acid (0.068 ml, 1.190 mmol) and anhydrous sodium sulfate (300 mg) were added to the solution at room temperature and the mixture was stirred for 14 hours. Sodium triacetoxyborohydride (252 mg, 1.190 mmol) was added to the reaction solution, the mixture was stirred for 4 hours and then the solvent was removed under reduced pressure. A lower layer solvent of chloroform/methanol/water (7:3:1) was added to the residue and the resultant was alkalized by adding saturated sodium bicarbonate water under cooling on ice. The mixture was extracted with a lower layer solvent of chloroform/methanol/water (7:3:1), the extract was dried over anhydrous sodium sulfate and the solvent was removed under reduced pressure. The residue was purified by silica gel column chromatography (chloroform/methanol) and preparative thin layer chromatography (silica gel, chloroform/methanol=20:1) to yield 50 mg (18%) of the title compound in the form of a white solid.

$^1$H-NMR(400 MHz,DMSO-d$_6$)δ:2.31-2.35(1H,m),2.36-2.40(1H,m),2.70-2.79(1H,m),2.85-3.07(2H,m),3.43-3.59(2H,m), 3.87(3H,s),3.89-3.96(1H,m) 4.34-4.48(1H,m),4.54(2H,s),4.61-4.75(1H,m),4.78-4.99(1H,m),6.94(1H,d,J=8.5 Hz),6.99-7.03(2H,m),7.10(1H,s),7.43-7.46(1H,m),7.76(1H,d,J=9.0 Hz),8.07(1H,s),10.71(1H,s).

MS (ESI)m/z:482(M+H)$^+$.

Example 9

6-(4-{[2-Fluoro-3-(7-methoxy-2-oxoquinoxalin-1(2H)-yl)propyl]amino}-2-oxopyrrolidin-1(2H)-yl)-2H-pyrido[3,2-b][1,4]oxazin-3(4H)-one

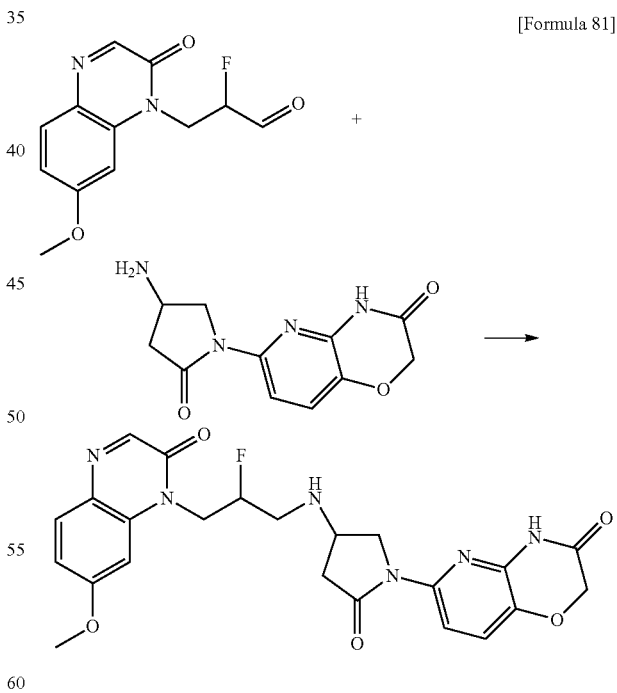

[Formula 81]

A crude product of 2-Fluoro-3-(7-methoxy-2-oxoquinoxalin-1(2H)-yl)propanol (Reference Example 35; 300 mg), and 6-(4-amino-2-oxopyrrolidin-1-yl)-2H-pyrido[3,2-b][1,4]oxazin-3(4H)-one (Reference Example 19; 97 mg, 0.391 mmol) were dissolved in a mixed solution of dichloromethane (15 ml) and N,N-dimethylformamide (2 ml). Acetic acid (0.045 ml, 0.782 mmol) and anhydrous sodium sulfate (200 mg)

were added to the solution and the mixture was stirred for 12 hours. Sodium triacetoxyborohydride (166 mg, 0.782 mmol) was added to the reaction solution, the mixture was stirred for 5 hours and then the solvent was removed under reduced pressure. A lower layer solvent of chloroform/methanol/water (7:3:1) was added to the residue and the resultant was alkalized by adding saturated sodium bicarbonate water under cooling on ice. The mixture was extracted with a lower layer solvent of chloroform/methanol/water (7:3:1), the extract was dried over anhydrous sodium sulfate and the solvent was removed under reduced pressure. The residue was purified by silica gel column chromatography (chloroform/methanol) and preparative thin film chromatography (silica gel, chloroform/methanol=20:1) to yield 63 mg (33%) of the title compound in the form of a white solid.

$^1$H-NMR(400 MHz,DMSO-$d_6$)δ:2.41(1H,t,J=3.7 Hz), 2.45(1H,t,J=3.7 Hz),2.77-2.86(1H,m),2.86-3.03(2H,m), 3.44-3.52(1H,m), 3.73-3.80(1H,m), 3.87(3H,s),4.01-4.08 (1H,m),4.34-4.50(1H,m),4.61(2H,s),4.63-4.74(1H,m),4.80-5.00(1H,m),7.01(1H,dd,J=8.7,2.3 Hz),7.10(1H,d,J=2.3 Hz), 7.40(1H,d,J=8.7 Hz),7.76(1H,d, J=8.7 Hz),7.83(1H,d,J=8.7 Hz),8.07(1H,s),11.17(1H,s).

MS(ESI)m/z:483(M+H)$^+$.

Reference Example 36

6-Bromo-4-(methoxymethyl)-2H-1,4-benzoxazin-3 (4H)-one

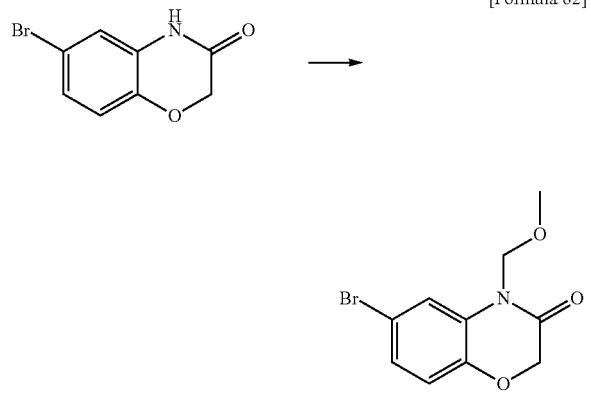

[Formula 82]

A suspension of 6-bromo-2H-1,4-benzoxazin-3(4H)-one (13 g, 57 mmol) in 1,2-dichloroethane (350 ml) was cooled in an ice bath to which N,N-diisopropylethylamine (119 ml), sodium iodide (10.25 g, 68.4 mmol) and chloromethylmethyl ether (43.3 ml, 570 mmol) were added, and the mixture was stirred at 70° C. for 3 hours. After cooling, the reaction mixture was diluted with dichloromethane, washed with cold water, dried over anhydrous magnesium sulfate, and the solvent was removed under reduced pressure. The obtained residue was purified by silica gel column chromatography (chloroform/methanol) to yield 13.6 g (88%) of the title compound in the form of a light brown solid.

$^1$H-NMR(400 MHz,CDCl$_3$)δ:3.42(3H,s),4.63(2H,s),5.29 (2H,s),6.87(1H,d, J=8.3 Hz),7.15(1H,dd,J=8.7, 2.3 Hz),7.43 (1H,d,J=2.3 Hz).

MS (ESI)m/z:273(M+H)$^+$.

Reference Example 37

{(3R)-1-[4-(Methoxymethyl)-3-oxo-3,4-dihydro-2H-1,4-benzoxazin-6-yl]-5-oxopyrrolidin-3-yl}carbamic acid tert-butyl ester

[Formula 83]

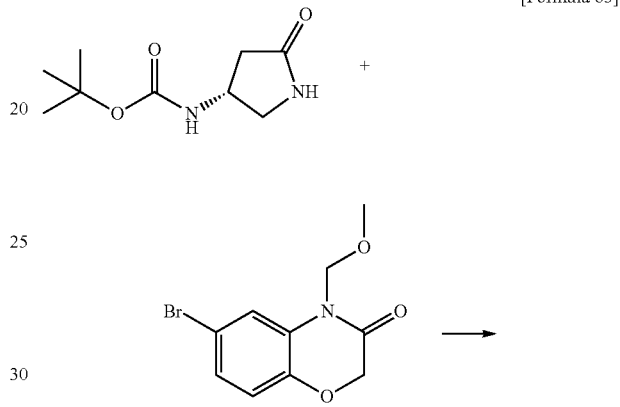

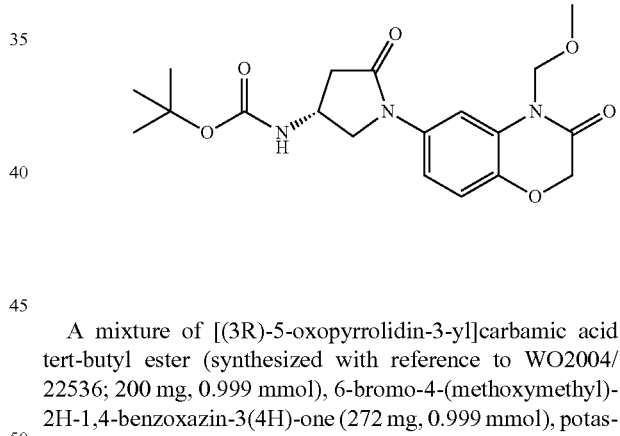

A mixture of [(3R)-5-oxopyrrolidin-3-yl]carbamic acid tert-butyl ester (synthesized with reference to WO2004/22536; 200 mg, 0.999 mmol), 6-bromo-4-(methoxymethyl)-2H-1,4-benzoxazin-3(4H)-one (272 mg, 0.999 mmol), potassium carbonate (415 mg, 3.0 mmol), copper (I) iodide (190 mg, 0.999 mmol), N,N'-dimethylethylenediamine (0.107 ml, 0.999 mmol) and toluene (4 ml) was stirred overnight at 100° C. under a stream of nitrogen gas. After cooling, dichloromethane was added to the reaction solution and insoluble material was removed by filtration. The solvent of the filtrate was removed under reduced pressure. The obtained residue was purified by silica gel column chromatography (n-hexane/ethyl acetate) to yield 375 mg (96%) of the title compound in the form of a colorless foamy solid.

$^1$H-NMR(400 MHz,CDCl$_3$)δ:1.46(9H,s),2.48(1H,dd, J=17.4,4.6 Hz),2.97(1H,dd,J=17.4, 8.3 Hz),3.42 (3H,s),3.69 (1H,dd,J=10.3, 3.9 Hz),4.10-4.17(1H,m),4.43(1H,brs),4.64 (2H,s),4.85(1H,brs), 5.32(2H,dd, J=12.8,10.6 Hz),6.99(1H,d J=9.2 Hz),7.12(1H,dd,J=8.7, 2.8),7.64(1H,d,J=2.3 Hz).

MS(ESI)m/z:392(M+H)$^+$.

Reference Example 38

6-[(4R)-4-Amino-2-oxopyrrolidin-1-yl]-2H-1,4-benzoxazin-3(4H)-one

[Formula 84]

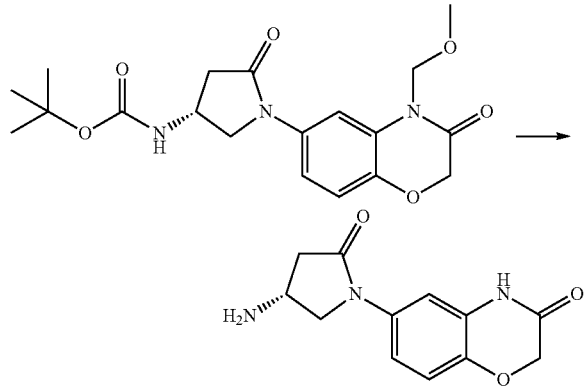

A solution of {(3R)-1-[4-(methoxymethyl)-3-oxo-3,4-dihydro-2H-1,4-benzoxazin-6-yl]-5-oxopyrrolidin-3-yl}carbamic acid tert-butyl ester (120 mg, 0.31 mmol) in methanol (2 ml) was cooled in an ice bath. Lithium chloride (80 mg, 0.92 mmol) and concentrated sulfuric acid (0.5 ml) were added thereto, and the mixture was then stirred at 80° C. for 2 hours. After cooling, the reaction solution was neutralized with a saturated sodium hydrogen carbonate aqueous solution and the solvent was concentrated under reduced pressure. The obtained residue was purified by silica gel column chromatography (NH silica gel, chloroform/methanol) to yield 58 mg (75%) of the title compound in the form of a colorless solid.

$^1$H-NMR(400 MHz,CDCl$_3$)δ:1.81(2H,brs),2.14(1H,dd, J=16.5,4.1 Hz),2.66(1H,dd,J=16.5,7.3 Hz),3.33(1H,dd, J=9.6,3.7 Hz),3.55-3.62(1H,m),3.86(1H,dd, J=9.6,6.0 Hz), 4.51(2H,s),6.90(1H,dd,J=8.7 Hz),6.97-7.00(1H,m),7.39(1H, d, J=2.3 Hz),10.69(1H,brs).

MS(ESI)m/z:248(M+H)$^+$.

Example 10

6-[(4R)-4-{[3-(7-Methoxy-2-oxoquinoxalin-1(2H)-yl)propyl]amino}-2-oxopyrrolidin-1-yl]-2H-1,4-benzoxazin-3(4H)-one

[Formula 85]

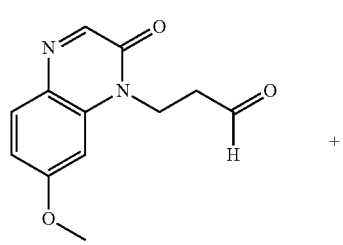

+

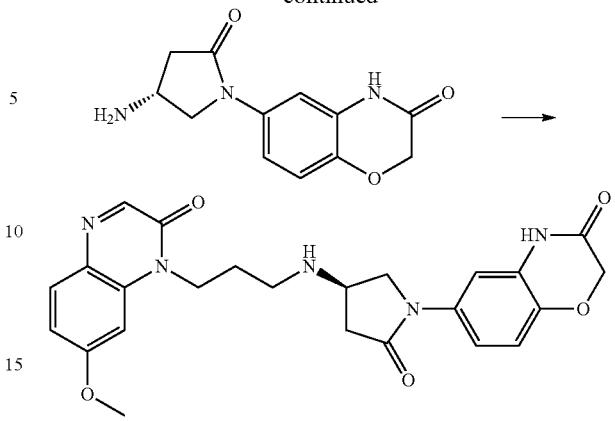

6-[(4R)-4-Amino-2-oxopyrrolidin-1-yl]-2H-1,4-benzoxazin-3(4H)-one (23.9 mg, 0.0967 mmol) and 3-(7-methoxy-2-oxoquinoxalin-1(2H)-yl)propanal (Reference Example 8; 22.4 mg, 0.0967 mmol) were dissolved in N,N-dimethylformamide (0.5 ml). Sodium sulfate (100 mg) was added to the obtained solution, and the mixture was then stirred at room temperature overnight. Thereafter, sodium triacetoxy borohydride (30.7 mg, 0.145 mmol) was added to the reaction solution, and the obtained mixture was then stirred at room temperature for 2 days. After completion of the reaction, dichloromethane and a saturated sodium hydrogen carbonate aqueous solution were added to the reaction solution, and the organic layer was separated. The organic layer was washed with water (4×) and saturated sodium chloride solution, and was then dried over anhydrous magnesium sulfate. Thereafter, the solvent was removed under reduced pressure. The obtained residue was purified by preparative thin layer chromatography (chloroform/methanol) to yield 18.4 mg (41%) of the above captioned compound in the form of a light brown solid.

$^1$H-NMR(400 MHz,CDCl$_3$) δ: 1.81(1H, brs), 1.95-2.0 (2H, m), 2.61 (1H, dd, J=17.5, 4.9 Hz), 2.65-2.76 (2H, m), 2.95 (1H, dd, J=17.5, 7.7), 3.54-3.60 (1H, m), 3.64 (1H, dd, J=9.7, 4.0 Hz), 3.98 (3H, s), 3.99 (1H, dd, J=9.7, 6.9 Hz), 4.32 (2H, td, J=13.9, 7.1), 4.55 (2H, s), 6.73 (1H, dd, J=8.9, 2.6 Hz), 6.84 (1H, d, J=2.3), 6.90-6.93 (2H,m), 7.79 (1H, d, J=9.2 Hz), 7.86 (1H, d, J=2.3 Hz), 8.12 (1H, s), 9.50 (1H, s).

MS (ESI)m/z: 464 (M+H)$^+$.

Example 11

6-[(4R)-4-{[3-(7-Methoxy-2-oxoquinoxalin-1(2H)-yl)propyl]amino}-2-oxopyrrolidin-1-yl]-2H-1,4-benzoxazin-3(4H)-one hydrochloride monohydrate

[Formula 86]

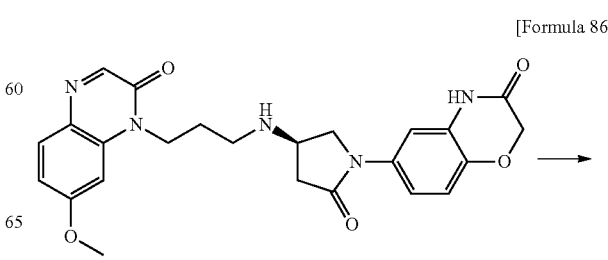

81

-continued

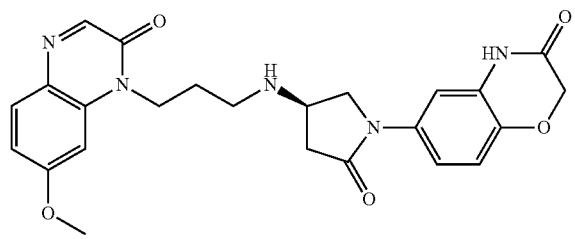

HCl/H2O

6-[(4R)-4-{[3-(7-Methoxy-2-oxoquinoxalin-1(2H)-yl) propyl]amino}-2-oxopyrrolidin-1-yl]-2H-1,4-benzoxazin-3 (4H)-one (2.86 g, 6.17 mmol) was dissolved in dichloromethane (50 ml) and ethanol (2 ml). To this solution was added 4 N hydrogen chloride/dioxane solution (1.59 ml, 6.37 mmol) under cooling in an ice bath. The precipitated insoluble material was collected by filtration and was then dried. The obtained residue was suspended in ethanol (20 ml), and the suspension was then stirred at 50° C. for 20 minutes. The suspension was cooled in an ice bath, and the insoluble material was collected by filtration. The filtrate was dried at 70° C. overnight under reduced pressure to yield 2.36 g (74%) of the above-captioned compound in the form of a colorless solid.

$^1$H-NMR (400 MHz, DMSO-$d_6$) δ: 1.98-2.09 (2H, m), 2.78 (1H, dd, J=17.7, 3.4 Hz), 2.95 (1H, dd, J=17.9, 8.3 Hz), 3.11 (2H, brs), 3.91-4.04 (5H, m), 4.13 (1H, dd, J=10.8, 7.1 Hz), 4.31 (2H, t, J=7.1 Hz), 4.53 (2H, s), 6.94-7.09 (4H, m), 7.39 (1H, d, J=2.8 Hz), 7.76 (1H, d, J=8.7 Hz), 8.05 (1H, s), 9.38 (2H, d, J=41.7 Hz), 10.78 (1H, s).

MS (ESI) m/z: 464 (M+H)$^+$.

Example 12

6-(4-{[4-(7-Methoxy-2-oxoquinoxalin-1(2H)-yl) butyl]amino}-2-oxopyrrolidin-1-yl)-2H-pyrido[3,2-b][1,4]oxazin-3(4H)-one

82

-continued

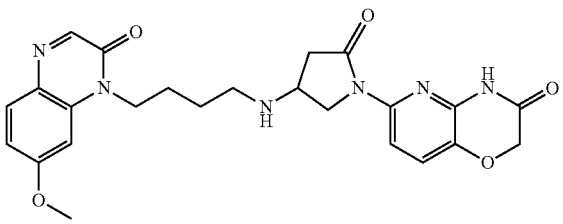

6-(4-Amino-2-oxopyrrolidin-1-yl)-2H-pyrido[3,2-b][1,4] oxazin-3(4H)-one (Reference Examples 19; 67 mg, 0.250 mmol) and 4-(7-methoxy-2-oxoquinoxalin-1(2H)-yl)butanal (Reference Examples 3; 58 mg, 0.250 mmol) were dissolved in N,N-dimethylformamide (4 ml). Sodium sulfate (800 mg) was added to this solution and the mixture was stirred at room temperature for 8 hours. Sodium triacetoxyborohydride (80 mg, 0.375 mmol) was added to the reaction solution and the mixture was stirred overnight at room temperature. After completion of the reaction, the reaction solution was diluted with dichloromethane, a saturated sodium hydrogen carbonate aqueous solution was added thereto and the mixture was stirred for 10 minutes. The organic layer was separated, washed sequentially with water (3×) and saturated sodium chloride solution, dried over anhydrous magnesium sulfate and the solvent was removed under reduced pressure. The obtained residue was purified by silica gel column chromatography (chloroform/methanol) to yield 93 mg (76%) of the title compound in the form of a yellow solid.

$^1$H-NMR(400 MHz,CDCl$_3$)δ:1.66-1.75(2H,m), 1.80-1.91 (2H,m),2.55(1H,dd,J=17.5,3.7 Hz),2.74-2.88(4H,m),2.94 (1H,s),3.49-3.51(1H,m),3.86(3H,s),3.90-3.95(1H,m),4.00 (1H,dd,J=11.5,3.4 Hz), 4.18-4.24(2H,m),4.52(2H,dd, J=35.5,15.5 Hz),6.72(1H,d, J=2.3 Hz),6.86(1H,dd,J=8.9,2.6 Hz),7.04 (1H,d,J=8.6 Hz),7.74(1H,d,J=9.2 Hz),7.80-7.84 (1H,m),8.05(1H,s).

MS(ESI)m/z:479(M+H)$^+$.

Reference Example 39

{(3S)-1-[4-(Methoxymethyl)-3-oxo-3,4-dihydro-2H-1,4-benzoxazin-6-yl]-5-oxopyrrolidin-3-yl}carbamic acid tert-butyl ester

[Formula 87]

[Formula 88]

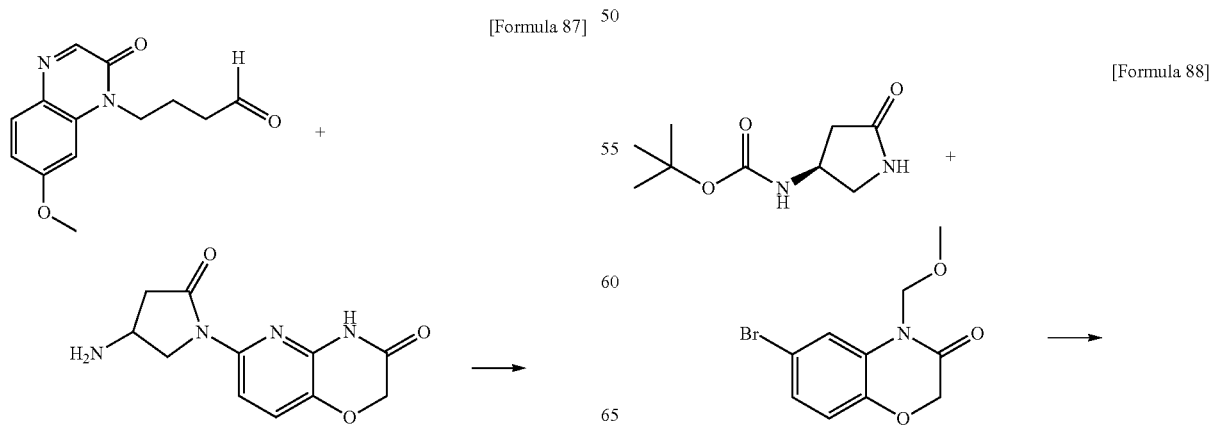

-continued

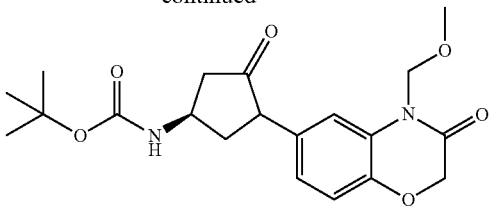

A mixture of [(3R)-5-oxopyrrolidin-3-yl]carbamic acid tert-butyl ester (synthesized with reference to WO2004/22536; 1.5 g, 7.49 mmol), 6-bromo-4-(methoxymethyl)-2H-1,4-benzoxazin-3(4H)-one (Reference Examples 36; 2.04 g 7.49 mmol), potassium carbonate (3.11 g, 22.5 mmol), copper (I) iodide (1.43 g, 7.49 mmol), N,N'-dimethylethylenediamine (0.80 ml, 7.49 mmol) and toluene (95 ml) was stirred overnight at 100° C. under a stream of nitrogen gas. After cooling, dichloromethane was added to the reaction solution to remove insoluble material by filtration and the solvent was removed under reduced pressure. The obtained residue was purified by silica gel column chromatography (n-hexane/ethyl acetate) to yield 1.79 g (61%) of the title compound in the form of a colorless foamy solid.

$^1$H-NMR(400 MHz,CDCl$_3$)δ:1.46(9H,s),2.48(1H,dd, J=17.4,4.6 Hz),2.96(1H,dd,J=17.4,7.8 Hz),3.42(3H,s),3.69 (1H,dd,J=10.1,3.7 Hz),4.09-4.18(1H,m),4.43(1H,brs),4.62 (2H,s),4.88(1H,brs),5.32(2H,dd,J=12.8,10.6 Hz),6.98(1H,d, J=8.7 Hz),7.12(1H,dd,J=8.7,2.8 Hz),7.64(1H,d,J=2.8 Hz).

MS(ESI)m/z:392(M+H)$^+$.

Reference Example 40

6-[(4S)-4-Amino-2-oxopyrrolidin-1-yl]-2H-1,4-benzoxazin-3(4H)-one

[Formula 89]

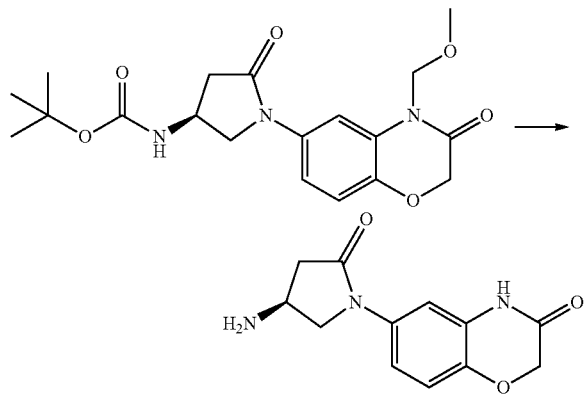

To a solution of {(3S)-1-[4-(methoxymethyl)-3-oxo-3,4-dihydro-2H-1,4-benzoxazin-6-yl]-5-oxopyrrolidin-3-yl}carbamic acid tert-butyl ester (1.79 g, 4.57 mmol) in tetrahydrofuran (24 ml) was added 6N Hydrochloric acid (11.9 ml) and the mixture was stirred at 80° C. for 1.5 hours. After cooling, the reaction solution was basified by adding a saturated sodium hydrogen carbonate aqueous solution and the solvent was removed under reduced pressure. The obtained residue was purified by silica gel column chromatography (NH silica gel, chloroform/methanol) to yield 337 mg (30%) of the title compound in the form of a light yellow solid.

$^1$H-NMR(400 MHz,DMSO-d$_6$)δ:1.82(2H,brs),2.14(1H, dd,J=16.7,4.4 Hz),2.66(1H,dd,J=16.5,7.4 Hz),3.33-3.38(1H, m),3.55-3.61(1H,m),3.86(1H,dd,J=9.6,6.0 Hz),4.51(2H,s), 6.88-6.93(1H,m),6.98(1H,dd,J=8.9,2.5 Hz),7.39(1H,d,J=2.3 Hz),10.66(1H,brs).

MS(ESI)m/z:248(M+H)$^+$.

Example 13

6-[(4S)-4-{[3-(7-methoxy-2-oxoquinoxalin-1(2H)-yl)propyl]amino}-2-oxopyrrolidin-1-yl]-2H-1,4-benzoxazin-3(4H)-one

[Formula 90]

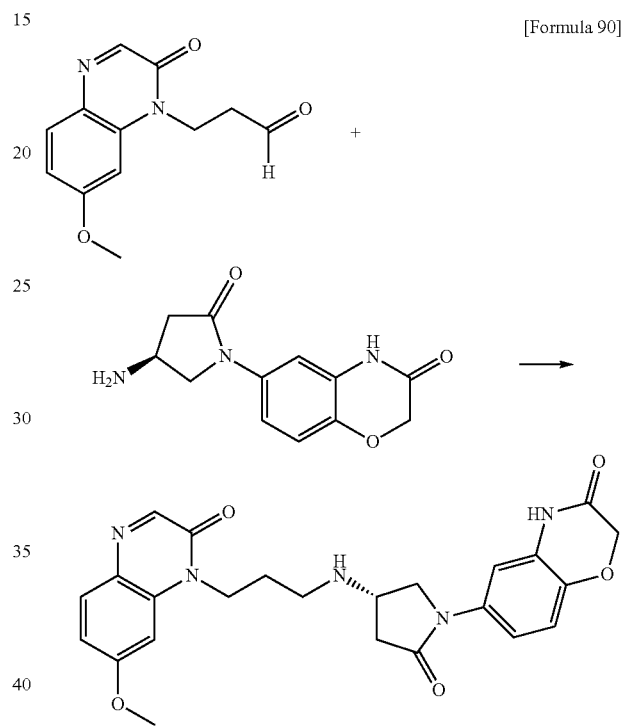

6-[(4S)-4-Amino-2-oxopyrrolidin-1-yl]-2H-1,4-benzoxazin-3(4H)-one (330 mg, 1.21 mmol) and 3-(7-methoxy-2-oxoquinoxalin-1(2H)-yl)propanal (Reference Example 8; 281 mg, 1.21 mmol) were dissolved in N,N-dimethylformamide (8.8 ml). Sodium sulfate (1.4 g) was added to this solution and the mixture was stirred at room temperature for 5.5 hours. Sodium triacetoxyborohydride (386 mg, 1.82 mmol) was added to the reaction solution and the mixture was stirred at room temperature for 2 days. After completion of the reaction, dichloromethane and a saturated sodium hydrogen carbonate aqueous solution were added to the reaction solution and the organic layer was separated. The organic layer was washed with water (3x) and saturated sodium chloride solution, dried over anhydrous magnesium sulfate and the solvent was removed under reduced pressure. The obtained residue was purified by flash column chromatography (chloroform/methanol) to yield 324 mg (58%) of the title compound in the form of light brown foamy crystals.

$^1$H-NMR(400 MHz,CDCl$_3$)δ:1.96-2.01(2H,m),2.58(1H, dd,J=17.2,5.2 Hz),2.64-2.76(2H,m),2.94(1H,dd,J=17.2,7.5 Hz),3.55-3.60(1H,m),3.63(1H,dd,J=9.7,4.6 Hz),3.91(3H,s), 4.00(1H,dd,J=9.7,6.9 Hz),4.32(2H,td,J=14.2,7.3 Hz),4.57 (2H,s),6.77(1H,dd,J=8.9,2.6 Hz),6.85(1H,d,J=2.9 Hz),6.92-6.94(2H,m),7.78-7.83(2H,m),8.12(1H,s),8.90(1H,s).

MS(ESI)m/z:464(M+H)$^+$.

Example 14

6-Methoxy-4-(3-{[5-oxo-1-(3-oxo-3,4-dihydro-2H-1,4-benzoxazin-6-yl)pyrrolidin-3-yl]amino}propyl)pyrido[2,3-b]pyrazin-3(4H)-one

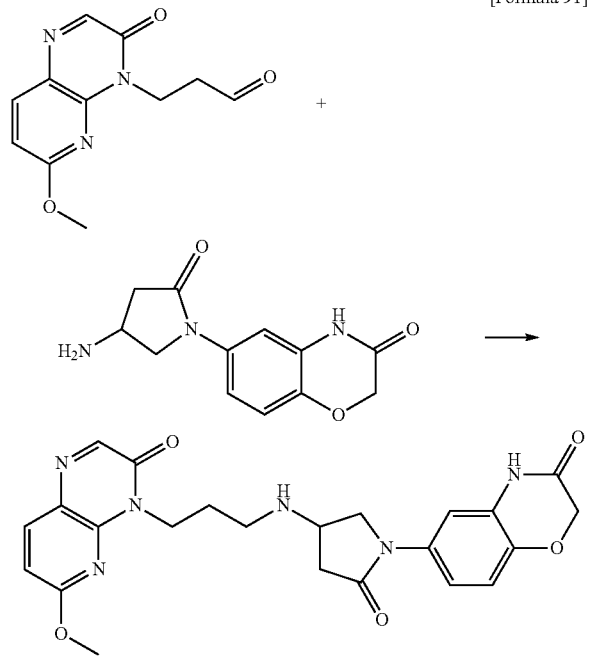

[Formula 91]

In N,N-dimethylformamide (3 ml) were dissolved 6-(4-Amino-2-oxopyrrolidin-1-yl)-2H-1,4-benzoxazin-3(4H)-one (Reference Example 6; 159 mg, 0.643 mmol) and 3-(6-methoxy-3-oxopyrido[2,3-b]pyrazin-4(3H)-yl)propanal (synthesized with reference to WO2008/9700; 150 mg, 0.643 mmol). Sodium sulfate (1.0 g) was added to the solution and the mixture was stirred overnight at room temperature. Sodium triacetoxyborohydride (164 mg, 0.772 mmol) was added to the reaction solution and the mixture was stirred at room temperature for 2 hours. After completion of the reaction, the reaction solution was diluted with dichloromethane, basified by adding a saturated sodium hydrogen carbonate aqueous solution and the organic layer was then separated. The organic layer was washed sequentially with saturated sodium chloride solution, water (3×) and saturated sodium chloride solution, dried over anhydrous magnesium sulfate and the solvent was removed under reduced pressure. The obtained residue was purified by silica gel column chromatography (chloroform/methanol) to yield 219 mg (73%) of the title compound in the form of a colorless foamy solid.

$^1$H-NMR(400 MHz,CDCl$_3$)δ:1.66(1H,brs),2.02-2.09(2H,m),2.57(1H,dd,J=17.0,5.0 Hz),2.63-2.76(2H,m),2.93(1H,dd,J=17.4,7.3 Hz),3.53-3.64(2H,m),3.96-4.03(4H,m),4.53(2H,t,J=6.7 Hz),4.57(2H,s),6.73-6.77(2H,m),6.93(1H,d,J=8.7 Hz),7.82(1H,d,J=2.3 Hz),8.03(1H,d,J=8.7 Hz),8.16(1H,s),9.07(1H,s).

MS(ESI)m/z:465(M+H)$^+$.

Reference Example 41

4-[4-(Benzyloxy)butyl]-6-methoxypyrido[2,3-b]pyrazin-3(4H)-one

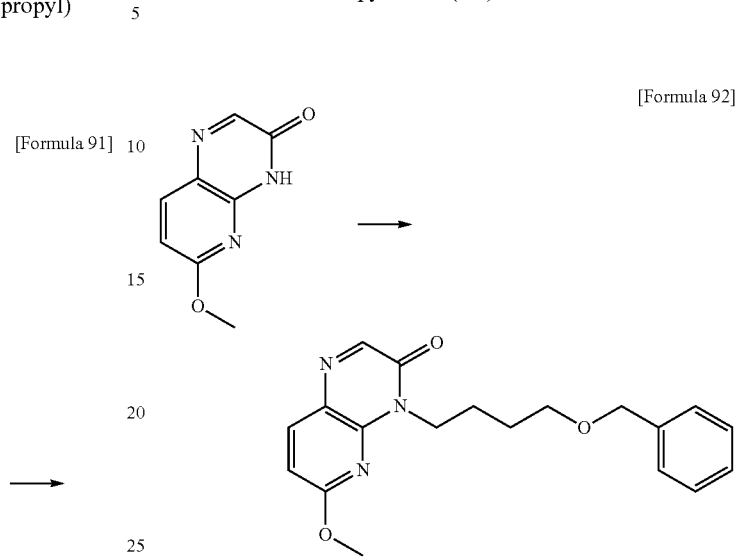

[Formula 92]

In N,N-dimethylformamide (15 ml) was dissolved 6-Methoxypyrido[2,3-b]pyrazin-3(4H)-one (600 mg, 3.39 mmol). The solution was cooled in an ice bath, lithium hydride (purity 90%, 35.9 mg, 4.06 mmol) was then added thereto and the mixture was stirred at room temperature for 40 minutes. The reaction solution was cooled again in an ice bath, benzyl 4-bromobutyl ether (0.774 ml, 4.06 mmol) and sodium iodide (609 g, 4.06 mmol) were added and then the mixture was stirred overnight at room temperature. The reaction solution was diluted with ethyl acetate, washed sequentially with saturated sodium chloride solution (2×), water and saturated sodium chloride solution, dried over anhydrous magnesium sulfate and the solvent was removed under reduced pressure. The obtained residue was purified by silica gel column chromatography (n-hexane/ethyl acetate) to yield 847 mg (74%) of the title compound in the form of a light yellow syrup.

$^1$H-NMR(400 MHz,CDCl$_3$)δ:1.71-1.78(2H,m),1.88-1.95(2H,m),3.53(2H,t,J=6.4 Hz),3.99(3H,s),4.44-4.51(4H,m),6.72(1H,d,J=8.7 Hz),7.27-7.35(5H,m),8.01(1H,d,J=8.7 Hz),8.16(1H,s).

MS(ESI)m/z:340(M+H)$^+$.

Reference Example 42

4-(4-Hydroxybutyl)-6-methoxypyrido[2,3-b]pyrazin-3(4H)-one

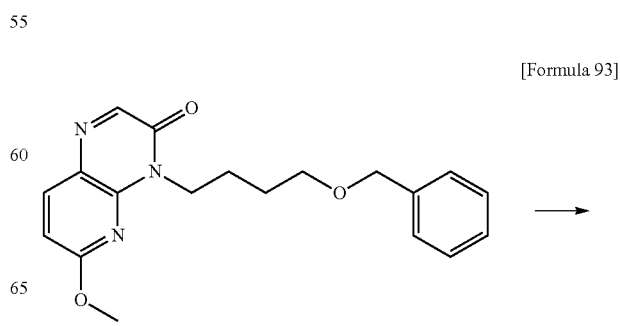

[Formula 93]

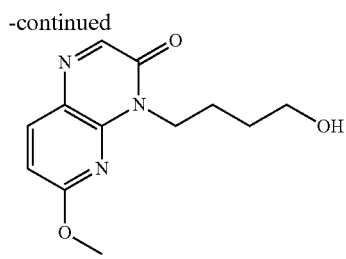

To a solution of 4-[4-(benzyloxy)butyl]-6-methoxypyrido[2,3-b]pyrazin-3(4H)-one (847 mg, 2.5 mmol) in ethyl acetate (20 ml) 20% palladium hydroxide (400 mg) was added and the catalytic hydrogenation was carried out at room temperature for 90 minutes. After removing the catalyst by filtration, the solvent was removed under reduced pressure, the obtained residue was dissolved in dichloromethane (20 ml) to which manganese dioxide (1.09 g, 12.5 mmol) was then added, and the mixture was stirred overnight at room temperature. After removing manganese dioxide by filtration, the solvent of the filtrate was removed under reduced pressure and the obtained residue was purified by silica gel column chromatography (n-hexane/ethyl acetate) to yield 548 mg (88%) of the title compound in the form of a light brown solid.

$^1$H-NMR(400 MHz,CDCl$_3$)δ:1.64-1.73(2H,m),1.77-1.82(1H,m),1.87-1.94(2H,m),3.69-3.76(2H,m),4.04(3H,s),4.48(2H,t,J=7.3 Hz),6.73(1H,d,J=8.7 Hz),8.02(1H,d,J=8.7 Hz),8.16(1H,s).

MS(FAB)m/z:250(M+H)$^+$.

Reference Example 43

4-(6-Methoxy-3-oxopyrido[2,3-b]pyrazin-4(3H)-yl)butanal

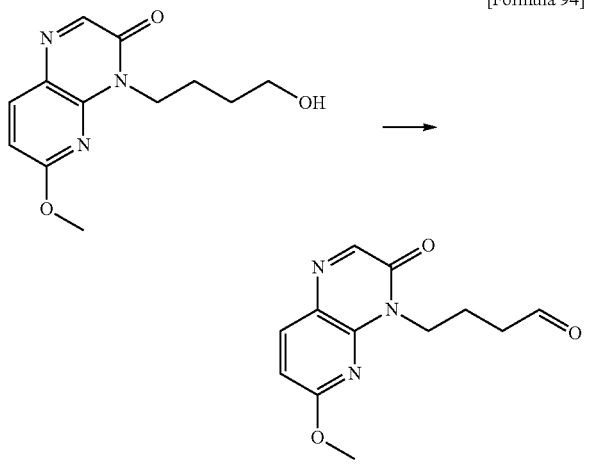

[Formula 94]

A solution of oxalyl chloride (0.155 ml, 1.81 mmol) in dichloromethane (1.5 ml) was cooled to −78° C., a solution of dimethyl sulfoxide (0.128 ml, 1.81 mmol) in dichloromethane (1.5 ml) was added dropwise under a stream of argon and the solution was stirred at the same temperature for 15 minutes. A solution of 4-(4-hydroxybutyl)-6-methoxypyrido[2,3-b]pyrazin-3(4H)-one (150 mg, 0.60 mmol) in dichloromethane (1.5 ml) was added dropwise to the reaction solution and the mixture was further stirred at the same temperature for 1.5 hours. Triethylamine (0.503 ml, 3.61 mmol) was added to the reaction solution, the temperature was raised to room temperature and a saturated ammonium chloride solution and dichloromethane were added. The organic layer was separated, washed with water and saturated sodium chloride solution, dried over anhydrous magnesium sulfate and then the solvent was removed under reduced pressure to yield 148 mg (100%) of the title compound in the form of a yellow solid. The product was used as such for the next step without purification.

$^1$H-NMR(400 MHz,CDCl$_3$)δ:2.56-2.61(2H,m),3.06-3.13(2H,m),4.04(3H,s),4.47(2H,t,J=7.1 Hz),6.73(1H,d,J=8.7 Hz),8.01(1H,d,J=8.7 Hz),8.14(1H,s),9.79(1H,s).

MS(ESI)m/z:248(M+H)$^+$.

Example 15

6-Methoxy-4-(4-{[5-oxo-1-(3-oxo-3,4-dihydro-2H-1,4-benzoxazin-6-yl)pyrrolidin-3-yl]amino}butyl)pyrido[2,3-b]pyrazin-3(4H)-one

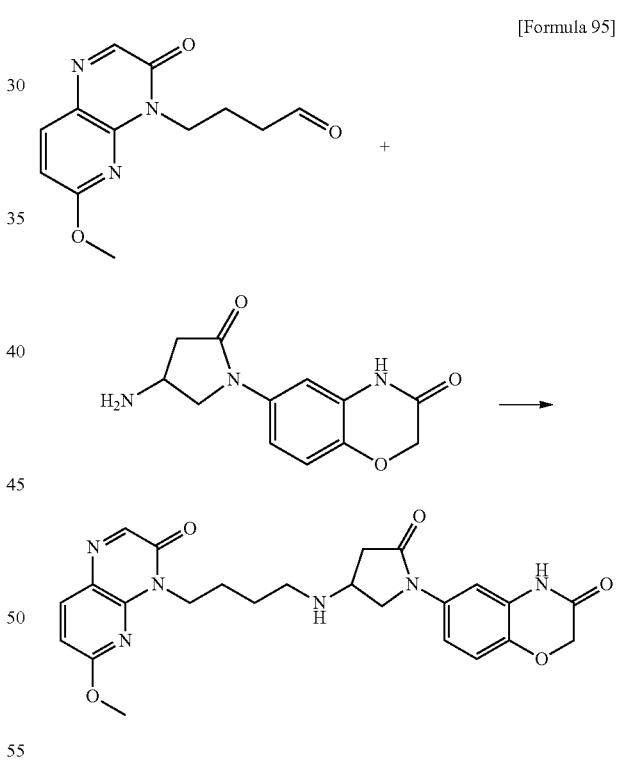

[Formula 95]

In N,N-dimethylformamide (5 ml) were dissolved 6-(4-Amino-2-oxopyrrolidin-1-yl)-2H-1,4-benzoxazin-3(4H)-one (Reference Example 6; 148 mg, 0.60 mmol) and 4-(6-methoxy-3-oxopyrido[2,3-b]pyrazin-4(3H)-yl)butanal (148 mg, 0.60 mmol). Sodium sulfate (1.0 g) was added to this solution and the mixture was stirred overnight at room temperature. Sodium triacetoxyborohydride (508 mg, 2.40 mmol) was added to the reaction solution and the mixture was stirred at room temperature for 6 hours. After completion of the reaction, the reaction solution was diluted with dichloromethane, basified by adding a saturated sodium hydrogen carbonate aqueous solution, and the organic layer was then separated and washed in the order of saturated sodium chloride solution, water (3×) and saturated sodium chloride solution. The organic layer was dried over anhydrous magnesium sulfate and the solvent was removed under reduced pressure. The obtained residue was purified by silica gel column chromatography (chloroform/methanol) to yield 53 mg (18%) of the title compound in the form of a light yellow foamy solid.

$^1$H-NMR(400 MHz,CDCl$_3$)δ:1.58-1.65(3H,m),1.83-1.90 (2H,m),2.59(1H,dd,J=17.4,4.6 Hz),2.66-2.78(2H,m),2.96 (1H,dd,J=17.4,7.3 Hz),3.53-3.63(2H,m),3.96-4.05(4H,m), 4.44(2H,t,J=7.3 Hz),4.54(2H,s),6.67-6.75(2H,m),6.89(1H, dd,J=8.7,1.9 Hz),7.86(1H,s),8.01(1H,d,J=8.7 Hz),8.15(1H, s),9.60-9.79(1H,m).

MS(ESI)m/z:479(M+H)$^+$.

Reference Example 44

(4S)-4-[(Methoxymethoxy)methyl]-1-[(1R)-phenylethyl]pyrrolidin-2-one

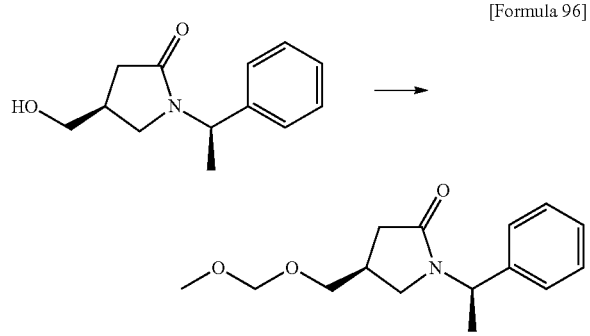

[Formula 96]

Under a nitrogen gas atmosphere, chloromethylmethyl ether (6.23 ml, 82.1 mmol) was added at 0° C. to a solution of (4S)-4-(hydroxymethyl)-1-[(1R)-phenylethyl]pyrrolidin-2-one (12.0 g, 54.7 mmol) and N,N-diisopropylethylamine (28.6 ml, 164 mmol) in dichloromethane (120 ml). While raising the temperature to room temperature, the mixture was stirred for 14 hours, followed by adding pieces of ice to the reaction solution, which was then stirred. The reaction solution was poured into a mixture of dichloromethane and a saturated ammonium chloride aqueous solution and the resultant was extracted with dichloromethane. The organic layer was dried over anhydrous sodium sulfate, the drying agent was removed by filtration and the filtrate was concentrated under reduced pressure. The residue was purified by silica gel column chromatography (n-hexane/ethyl acetate) to yield 12.5 g (three steps, 87%) of the title compound in the form of a colorless oily product.

$^1$H-NMR(400 MHz,CDCl$_3$)δ:1.52(3H,d,J=7.1 Hz),2.20 (1H,m),2.52-2.63(2H,m)2.79(1H,dd,J=4.4,9.8 Hz),3.20(3H, s),3.27(1H,dd,J=7.3,9.5 Hz),3.37(1H,dd, J=5.4,9.5 Hz),3.43 (1H,m),4.45(1H,d,J=6.6 Hz),4.49(1H,d,J=6.6 Hz),5.50(1H, q,J=7.1 Hz),7.23-7.34(5H,m).

MS(ESI)m/z:264(M+H)$^+$.

Reference Example 45

(4S)-4-[(Methoxymethoxy)methyl]pyrrolidin-2-one

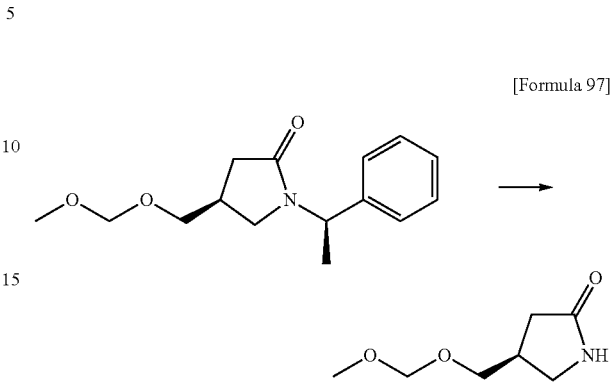

[Formula 97]

Under a nitrogen gas atmosphere, metallic sodium (3.93 g, 171 mmol) was added to liquid ammonia (about 90 ml) at −78° C. over the period of 15 minutes, and the mixture was further stirred at the same temperature for 15 minutes. A solution of (4S)-4-[(methoxymethoxy)methyl]-1-[(1R)-phenylethyl]pyrrolidin-2-one (9.00 g, 34.2 mmol) in tetrahydrofuran (20 ml)/tert-butyl alcohol (5 ml) was added to the reaction solution over a period of 10 minutes at the same temperature and the mixture was stirred for 15 minutes. Ammonium chloride (18.0 g) was added to the reaction solution, and ammonia was evaporated by gradually raising the temperature to room temperature when the color of the reaction solution changed from dark blue to colorless. Water was added to the residue to dissolve the insoluble material and the resultant was extracted with dichloromethane. The organic layer was dried over anhydrous sodium sulfate, the drying agent was removed by filtration and the filtrate was concentrated under reduced pressure. The obtained residue was purified by silica gel column chromatography (dichloromethane/methanol) to yield 5.44 g (100%) of the title compound in the form of a light yellow oily product.

$^1$H-NMR(400 MHz,CDCl$_3$)δ:2.15(1H,dd,J=6.9,16.9 Hz), 2.46(1H,dd,J=9.2,16.9 Hz),2.78(1H,m),3.23(1H,dd,J=5.5, 9.6 Hz),3.36(3H,s),3.50-3.58(3H,m),4.63(2H,s),6.09(1H, br).

MS(ESI)m/z:160(M+H)$^+$.

Reference Example 46

6-{(4S)-4-[(Methoxymethoxy)methyl]-2-oxopyrrolidin-1-yl}-2H-1,4-benzoxazin-3(4H)-one

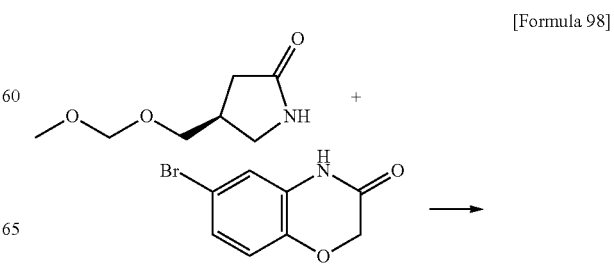

[Formula 98]

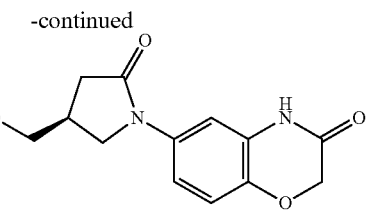

Copper iodide (1.50 g, 7.85 mmol) was added at room temperature to a suspension of (4S)-4-[(methoxymethoxy)methyl]pyrrolidin-2-one (3.00 g, 18.8 mmol), 6-bromo-2H-1,4-benzoxazin-3(4H)-one (3.58 g, 15.7 mmol) and N,N'-dimethylethylenediamine (0.84 ml, 7.85 mmol) and potassium carbonate (6.51 g, 47.1 mmol) in toluene (60 ml) and the mixture was heated to 100° C. The mixture was stirred at the same temperature for 42 hours and dichloromethane (100 ml) and methanol (10 ml) were then added thereto to dilute the reaction solution, and the insoluble material was removed by filtration. The filtrate was concentrated and the obtained residue was purified by silica gel column chromatography (hexane/ethyl acetate) to yield 1.92 g (40%) of the title compound in the form of a light yellow solid.

$^1$H-NMR(400 MHz,DMSO-$d_6$)δ:2.29(1H,dd,J=6.0,16.0 Hz),2.59-2.75(2H,m),3.26(3H,s),3.48-3.57(3H,m),3.87(1H, dd,J=7.8,9.6 Hz),4.53(2H,s), 4.59(2H,s),6.92(1H,d,J=8.7 Hz),7.03(1H,dd,J=2.8,8.7 Hz),7.41(1H,d,J=2.8 Hz),10.7 (1H,brs).

MS(ESI)m/z:307(M+H)$^+$.

Reference Example 47

6-[(4S)-4-(Hydroxymethyl)-2-oxopyrrolidin-1-yl]-2H-1,4-benzoxazin-3(4H)-one

[Formula 99]

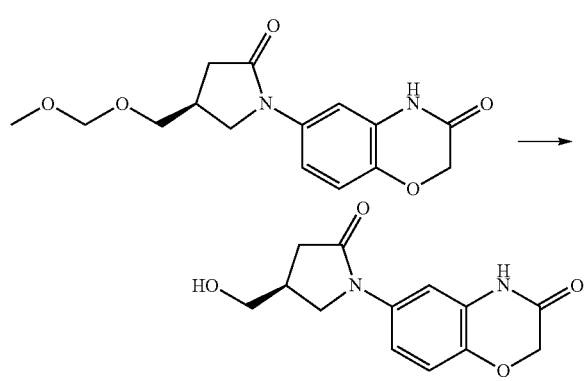

To a solution of 6-{(4S)-4-[(methoxymethoxy)methyl]-2-oxopyrrolidin-1-yl}-2H-1,4-benzoxazin-3(4H)-one (1.49 g, 4.86 mmol) in methanol (10 ml)/tetrahydrofuran (10 ml) was added 4N Hydrochloric acid (2 ml) at room temperature and the mixture was heated to 60° C. and stirred for 18 hours. The reaction solution was poured into a mixture of dichloromethane and a saturated sodium hydrogen carbonate aqueous solution and the resultant was extracted with dichloromethane. The organic layer was dried over anhydrous sodium sulfate, the drying agent was removed by filtration and the filtrate was concentrated under reduced pressure. A mixed solvent of dichloromethane/methanol (10:1) was added to the obtained solid to prepare a slurry and the solid was collected by filtration to yield 1.14 g (90%) of the title compound in the form of a light yellow solid.

$^1$H-NMR(400 MHz,DMSO-$d_6$)δ:2.27(1H,dd,J=6.1,15.9 Hz),2.51(1H,m),2.57(1H,dd,J=9.0,15.9 Hz),3.38-3.47(2H, m),3.54(1H,dd,J=5.1,9.8 Hz),3.82(1H,dd,J=7.8,9.8 Hz),4.53 (2H,s),4.85(1H,br),6.91(1H,d,J=8.8 Hz),7.02(1H,dd,J=2.5, 8.8 Hz),7.40(1H,d,J=2.5 Hz),10.7(1H,br).

MS(ESI)m/z:263(M+H)$^+$.

Reference Example 48

6-[(4S)-4-(Azidomethyl)-2-oxopyrrolidin-1-yl]-2H-1,4-benzoxazin-3(4H)-one

[Formula 100]

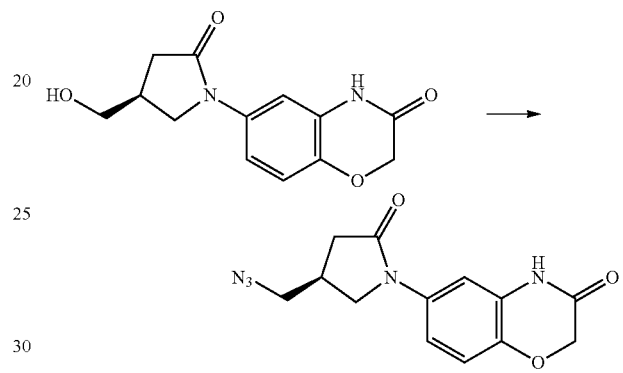

p-Toluenesulfonyl chloride (611 mg, 3.20 mmol) was added at room temperature to a solution of 6-[(4S)-4-(hydroxymethyl)-2-oxopyrrolidin-1-yl]-2H-1,4-benzoxazin-3 (4H)-one (420 mg, 1.60 mmol) in pyridine (5 ml) and the mixture was stirred for 24 hours. The reaction solution was concentrated under reduced pressure and the obtained resultant was dissolved in dichloromethane and washed with 1N hydrochloric acid. The aqueous layer was extracted with dichloromethane and the organic layer was washed sequentially with water and a saturated sodium hydrogen carbonate aqueous solution. The organic layer was dried over anhydrous sodium sulfate, the drying agent was removed by filtration and the filtrate was concentrated under reduced pressure. The obtained brown solid was dissolved in N,N-dimethylformamide (5 mL), sodium azide (208 mg, 3.20 mmol) was added thereto and the mixture was stirred at 80° C. for 2 hours. After adding water, the reaction solution was poured into a mixture of dichloromethane and a saturated sodium hydrogen carbonate aqueous solution and extracted with dichloromethane. The organic layer was dried over anhydrous sodium sulfate, the drying agent was removed by filtration and the filtrate was concentrated under reduced pressure. Dichloromethane was added to the obtained residue to prepare a slurry and the solid was collected by filtration to yield 300 mg of the title compound in the form of a light yellow solid. The residue obtained by concentrating the filtrate was purified by silica gel column chromatography (dichloromethane/methanol) to yield 132 mg of the title compound in the form of a light yellow solid. Total yield 432 mg (94%).

$^1$H-NMR(400 MHz,CD$_3$OD)δ:2.41(1H,q,J=10.5 Hz), 2.71-2.78(2H,m),3.50(1H,dd,J=6.4,12.4 Hz),3.56(1H,dd, J=5.5,12.4 Hz),3.64(1H,dd,J=5.5,10.1 Hz),3.98(1H,dd, J=7.8,10.1 Hz),4.84(2H,s), 6.94(1H,d,J=8.7 Hz),7.05(1H,dd, J=2.3,8.7 Hz),7.31(1H,d,J=2.3 Hz).

MS(ESI)m/z:288(M+H)$^+$.

Reference Example 49

6-[(4R)-4-(Aminomethyl)-2-oxopyrrolidin-1-yl]-2H-1,4-benzoxazin-3(4H)-one

[Formula 101]

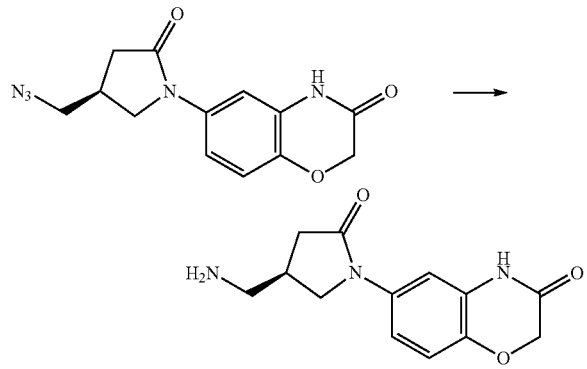

To a solution of 6-[(4S)-4-(azidomethyl)-2-oxopyrrolidin-1-yl]-2H-1,4-benzoxazin-3(4H)-one (430 mg, 1.50 mmol) in methanol (40 ml)/tetrahydrofuran (40 ml) was added 10% palladium on carbon catalyst (53% aqueous, 100 mg) at room temperature and the mixture was stirred at the same temperature for 2 hours under a hydrogen atmosphere. The catalyst was removed by filtration and the residue obtained by concentrating the filtrate was purified by silica gel column chromatography (NH silica gel, dichloromethane/methanol) to yield 336 mg (86%) of the title compound in the form of a light yellow amorphous solid.

$^1$H-NMR(400 MHz,DMSO-d$_6$)δ:2.29(1H,dd,J=6.4,16.0 Hz),2.37(1H,m),2.52-2.65(3H,m),3.55(1H,dd,J=5.5,9.6 Hz),3.81(1H,dd,J=7.8,9.6 Hz),4.52(2H,s),6.92(1H,d,J=8.7 Hz),7.02(1H,dd,2.7,8.7 Hz),7.43(1H,d,J=2.7 Hz).
MS(ESI)m/z:262(M+H)$^+$.

Example 16

6-[(4R)-4-({[2-(7-Methoxy-2-oxoquinoxalin-1(2H)-yl)ethyl]amino}methyl)-2-oxopyrrolidin-1-yl]-2H-1,4-benzoxazin-3(4H)-one

[Formula 102]

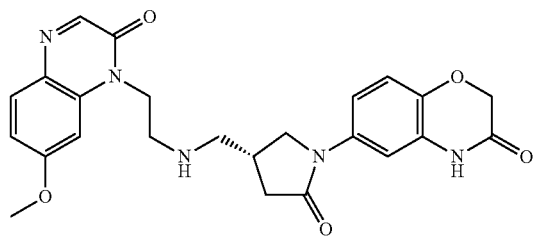

+

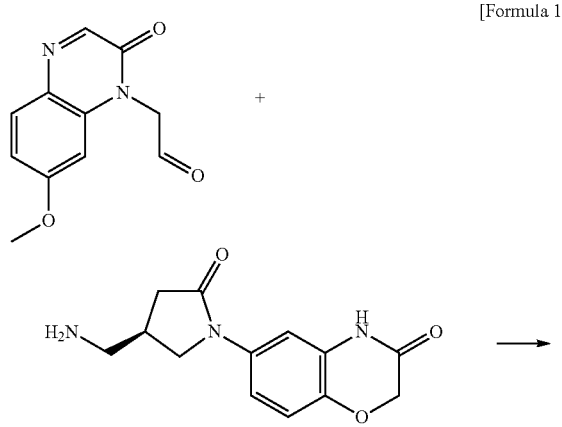

→

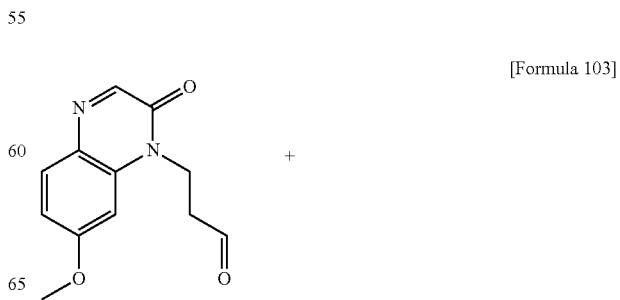

Under a nitrogen gas atmosphere, anhydrous sodium sulfate (1.4 g) was added at room temperature to a solution of (7-methoxy-2-oxoquinoxalin-1(2H)-yl)acetaldehyde (synthesized with reference to WO2009/1126; 167 mg, 0.765 mmol) and 6-[(4R)-4-(aminomethyl)-2-oxopyrrolidin-1-yl]-2H-1,4-benzoxazin-3(4H)-one (200 mg, 0.765 mmol) in dichloromethane (3 ml)/N,N-dimethylformamide (1 ml) and the mixture was stirred at the same temperature for 2 hours. Dichloromethane (3 ml) was added to the reaction solution, sodium triacetoxyborohydride (243 mg, 1.15 mmol) was subsequently added thereto and the mixture was stirred at the same temperature for 15 hours. Water (10 ml) was added to the reaction solution to dissolve the insoluble material and then a mixture of dichloromethane and a saturated sodium hydrogen carbonate aqueous solution was poured thereinto and the resultant was extracted with dichloromethane. The organic layer was dried over anhydrous sodium sulfate, the drying agent was removed by filtration and the filtrate was concentrated under reduced pressure. The obtained residue was purified by silica gel column chromatography (dichloromethane/methanol) to yield 321 mg (90%) of the title compound in the form of a light yellow amorphous solid.

$^1$H-NMR(400 MHz,CDCl$_3$)δ:2.47(1H,dd,J=6.6,16.6 Hz), 2.54(1H,m),2.73(1H,dd,J=7.6,11.8 Hz),2.79-2.85(2H,m), 2.96-3.08(2H,m),3.55(1H,dd,J=5.7,9.8 Hz),3.82(1H,m), 3.89(3H,s),4.32(2H,t,J=6.6 Hz),4.51(2H,s), 6.67(1H,dd, J=2.5,8.8 Hz),6.82(1H,d,J=2.5 Hz),6.84(1H,d,J=8.8 Hz), 6.89(1H,dd,J=2.5,8.8 Hz), 7.74(1H,d,J=8.8 Hz),7.88(1H,d, J=2.5 Hz),8.08(1H,s),10.2(1H,br).
MS(ESI)m/z:464(M+H)$^+$.

Example 17

6-[(4R)-4-({[3-(7-Methoxy-2-oxoquinoxalin-1(2H)-yl)propyl]amino}methyl)-2-oxopyrrolidin-1-yl]-2H-1,4-benzoxazin-3(4H)-one

[Formula 103]

+

-continued

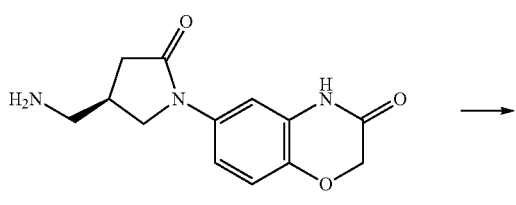

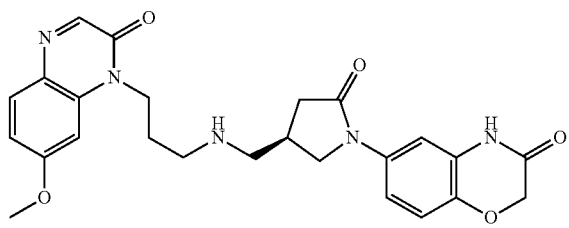

In the same manner as in Example 16, 33.0 mg (35%) of the title compound was obtained from 3-(7-methoxy-2-oxoquinoxalin-1(2H)-yl)propanal (Reference Example 8; 51.0 mg, 0.219 mmol) and 6-[(4R)-4-(aminomethyl)-2-oxopyrrolidin-1-yl]-2H-1,4-benzoxazin-3(4H)-one (Reference Example 49; 52.0 mg, 0.199 mmol) in the form of a milky white solid.

$^1$H-NMR(400 MHz,CDCl$_3$)δ:1.93-2.00(2H,m),2.52(1H,dd,J=6.4,17.1 Hz),2.60-2.75(4H,m),2.80(1H,dd,J=6.1,11.5 Hz),2.88(1H,dd,J=8.3,17.1 Hz),3.68(1H,dd,J=5.4,9.8 Hz),3.90(3H,s),3.95(1H,dd,J=7.8,9.8 Hz),4.30(2H,t,J=7.1 Hz),4.54(2H,s),6.78(1H,dd,J=2.4,8.8 Hz),6.84(1H,d,J=2.5 Hz),6.88(1H,d,J=8.8 Hz),6.91(1H,dd,J=2.5,8.8 Hz), 7.78(1H,d,J=8.8 Hz), 7.88(1H,d,J=2.4 Hz),8.11(1H,s).

MS(ESI)m/z:478(M+H)$^+$.

Example 18

3-Methoxy-5-[2-({[(3R)-5-oxo-1-(3-oxo-3,4-dihydro-2H-1,4-benzoxazin-6-yl)pyrrolidin-3-yl]methyl}amino)ethyl]pyrido[2,3-b]pyrazin-6(5H)-one

[Formula 104]

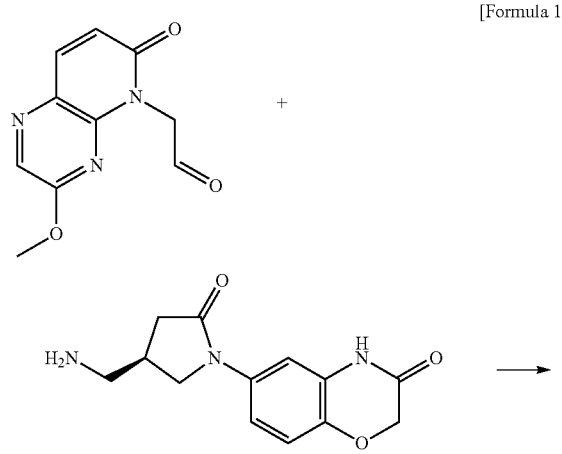

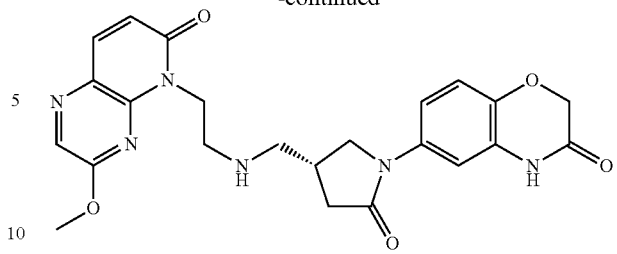

In the same manner as in Example 16, 91 mg (79%) of the title compound was obtained from (3-methoxy-6-oxopyrido[2,3-b]pyrazin-5(6H)-yl)acetaldehyde (synthesized with reference to WO2008/9700; 55 mg, 0.249 mmol) and 6-[(4R)-4-(aminomethyl)-2-oxopyrrolidin-1-yl]-2H-1,4-benzoxazin-3(4H)-one (Reference Example 49; 65 mg, 0.249 mmol) in the form of a milky white solid.

$^1$H-NMR(400 MHz,CDCl$_3$)δ:2.23(1H,dd,J=5.5,16.0 Hz), 2.46-2.57(2H,m),2.67(2H,brm),2.86(2H,brm),3.48(1H,dd, J=5.1,9.6 Hz),3.76(1H,dd,J=9.2,9.6 Hz), 4.03(3H,s),4.41 (2H,t,J=6.9 Hz),4.54(2H,s),6.71(1H,d,J=9.6 Hz),6.92(1H,d, J=8.7 Hz),6.97(1H,dd,J=1.9,8.7 Hz),7.40(1H,d,J=1.9 Hz), 7.93(1H,d,J=9.6 Hz),8.20(1H,s),10.7(1H,brs).

MS(ESI)m/z:465(M+H)$^+$.

Reference Example 50

[6-{(4S)-4-(Methoxymethyl)methyl}-2-oxopyrrolidin-1-yl]-2-nitropyridin-3-yl)oxy]acetic acid ethyl ester

[Formula 105]

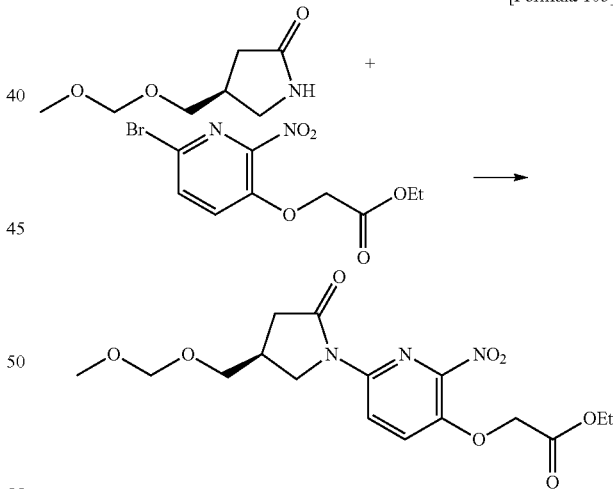

A mixture of (4S)-4-[(methoxymethoxy)methyl]pyrrolidin-2-one (Reference Example 45; 2.209 g, 13.87 mmol), [(6-bromo-2-nitropyridin-3-yl)oxy]acetic acid ethyl ester (synthesized with reference to WO2004/2992; 4.653 g, 15.25 mmol), palladium acetate (623 mg, 2.77 mmol), 2,2'-bis(diphenylphosphino)-1,1'-binaphthyl (1.727 g, 2.77 mmol), potassium phosphate (5.89 g, 27.7 mmol) and 1,4-dioxane (28 ml) was stirred at 80° C. with heating for 8 hours under a stream of nitrogen gas. After cooling, the insoluble material was removed by filtration and the filtrate was concentrated under reduced pressure. Ethyl acetate was added to the residue, which was washed with water (3×) and saturated sodium chloride solution, dried over anhydrous magnesium sulfate and the solvent was removed under reduced pressure. The obtained residue was purified by silica gel column chromatography (chloroform/ethyl acetate) to yield 3.84 mg (72%) of the title compound in the form of a reddish-brown gummy solid.

$^1$H-NMR(400 MHz,CDCl$_3$)δ:1.29(3H,t,J=7.1 Hz),2.56 (1H,dd,J=16.3,5.7 Hz),2.73-2.84(2H,m),3.37(3H,s),3.59-3.61(2H,m),3.89(1H,dd,J=11.7,6.0 Hz),4.19(1H,dd,J=11.5, 8.3 Hz),4.26(2H,q,J=7.2 Hz),4.64(2H,s),4.75(2H,s),7.51 (1H,d,J=8.7 Hz),8.68(1H,d,J=9.2 Hz).

MS(ESI)m/z:384(M+H)$^+$.

Reference Example 51

6-{(4S)-4-[(Methoxymethyl)methyl]-2-oxopyrrolidin-1-yl}-2H-pyrido[3,2-b][1,4]oxazin-3(4H)-one

[Formula 106]

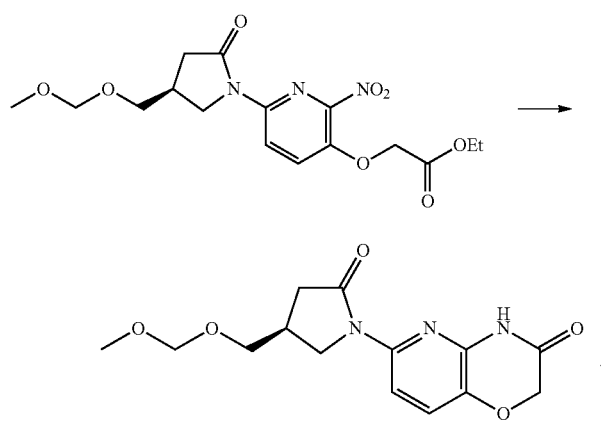

A mixture of [6-{(4S)-4-[(methoxymethyl)methyl]-2-oxopyrrolidin-1-yl}-2-nitropyridin-3-yl)oxy]acetic acid ethyl ester (3.84 g, 10.0 mmol), iron powder (5.90 g, 100 mmol) and acetic acid (100 ml) was stirred at 60° C. with heating for 8 hours. After cooling, the insoluble material was removed by filtration and the filtrate was concentrated under reduced pressure. Ethyl acetate and water were added to the residue which was then removed again by filtration. The organic layer was separated from the filtrate and washed with water and saturated sodium chloride solution. The layer was then dried over anhydrous magnesium sulfate, the solvent was removed under reduced pressure and the obtained residue was purified by silica gel column chromatography (chloroform/ethyl acetate) to yield 2.21 g (72%) of the title compound in the form of a yellow gummy solid.

$^1$H-NMR(400 MHz,CDCl$_3$)δ:2.51(1H,dd,J=16.3,5.7 Hz), 2.70-2.82(2H,m),3.38(3H,s),3.55-3.63(2H,m),3.82(1H,dd, J=11.5,5.5 Hz),4.11-4.14(1H,m),4.26(2H,q,J=7.2 Hz),4.64 (2H,s),4.65(2H,s),7.29(1H,d,J=9.2 Hz),7.87(1H,brs),8.04 (1H,d,J=8.7 Hz).

Reference Example 52

6-[(4S)-4-(Hydroxymethyl)-2-oxopyrrolidin-1-yl]-2H-pyrido[3,2-b][1,4]oxazin-3(4H)-one

[Formula 107]

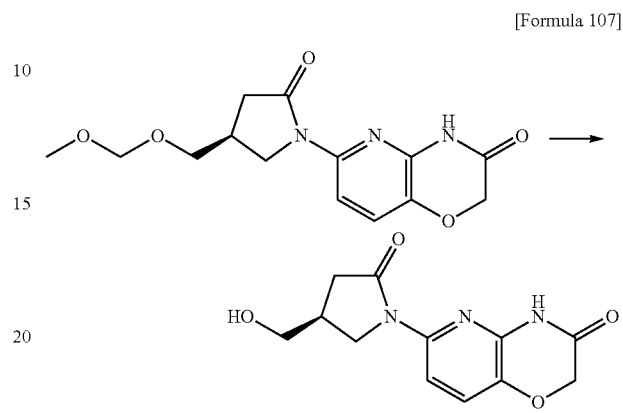

To a solution of 6-{(4S)-4-[(methoxymethyl)methyl]-2-oxopyrrolidin-1-yl}-2H-pyrido[3,2-b][1,4]oxazin-3(4H)-one (2.21 g, 7.20 mmol) in methanol (25 ml)/tetrahydrofuran (25 ml) was added 4N Hydrochloric acid (2.5 ml) at room temperature and the mixture was heated to 60° C. and stirred with heating for 16 hours. The reaction solution was poured into a saturated sodium hydrogen carbonate aqueous solution and extracted with a mixed solvent of chloroform/methanol (9:1) (3×). The organic layer was dried over anhydrous sodium sulfate, the drying agent was removed by filtration and the filtrate was concentrated under reduced pressure. 1.76 g (93%) of a crude product of the title compound was obtained in the form of a light yellow solid.

$^1$H-NMR(400 MHz,CDCl$_3$/CD$_3$OD=9/1)δ:2.47(1H,dd, J=6.4,17.0 Hz),2.62(1H,m),2.75(1H,dd,J=80.9,17.2 Hz), 3.57-3.68(2H,m),3.88(1H,dd,J=5.5,11.5 Hz),4.10(1H,dd, J=8.0,11.2 Hz),4.62(2H,s),7.28(1H,d,J=8.7 Hz),7.92(1H,d, J=8.7 Hz).

Reference Example 53

6-[(4S)-4-(Azidomethyl)-2-oxopyrrolidin-1-yl]-2H-pyrido[3,2-b][1,4]oxazin-3(4H)-one

[Formula 108]

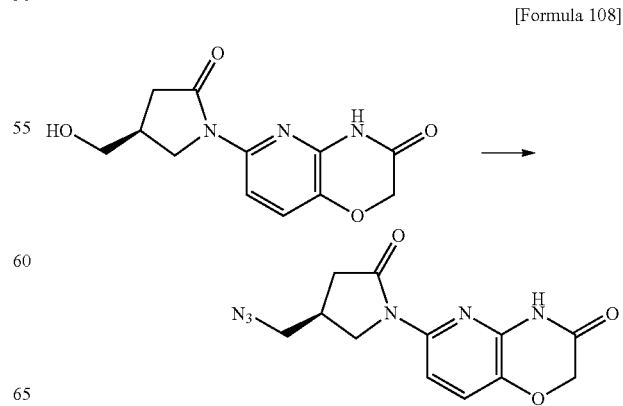

Methanesulfonyl chloride (0.229 ml, 2.96 mmol) was added under cooling on ice to a solution of 6-[(4S)-4-(hydroxymethyl)-2-oxopyrrolidin-1-yl]-2H-pyrido[3,2-b][1,4]oxazin-3(4H)-one (518 mg, 1.97 mmol) and triethylamine (0.649 ml, 3.94 mmol) in dichloromethane (10 ml) and the mixture was stirred for 6.5 hours while gradually raising the temperature to room temperature. Triethylamine (0.275 ml, 1.97 mmol) and methanesulfonyl chloride (0.229 ml, 2.96 mmol) were added to the reaction solution, which was further stirred for 1 hour, diluted with dichloromethane and washed with water. The organic layer was dried over anhydrous sodium sulfate, the drying agent was removed by filtration and the filtrate was concentrated under reduced pressure.

The obtained orangish solid was dissolved in N,N-dimethylformamide (10 mL), sodium azide (261 mg, 3.94 mmol) was added thereto and the mixture was stirred at 65° C. for 11 hours. The reaction solution was diluted with ethyl acetate and washed with water and saturated sodium chloride solution. The organic layer was dried over anhydrous sodium sulfate, the drying agent was removed by filtration and the filtrate was concentrated under reduced pressure. The obtained residue was purified by silica gel column chromatography (chloroform/ethyl acetate) to yield 441 mg (78%) of the title compound in the form of a white solid.

$^1$H-NMR(400 MHz,CDCl$_3$)δ:2.47(1H,dd,J=6.4,17.0 Hz), 2.67(1H,m),2.81(1H,dd,J=8.9,17.2 Hz),3.43-3.53(2H,m), 3.79(1H,dd,J=5.7,11.7 Hz),4.13(1H,dd,J=7.8,11.5 Hz),4.64 (2H,s),7.29(1H,d,J=8.7 Hz),7.97(1H,brs),8.01(1H,d,J=8.7 Hz).

MS(ESI)m/z:289(M+H)$^+$.

Reference Example 54

6-[(4R)-4-(Aminomethyl)-2-oxopyrrolidin-1-yl]-2H-pyrido[3,2-b][1,4]oxazin-3(4H)-one

[Formula 109]

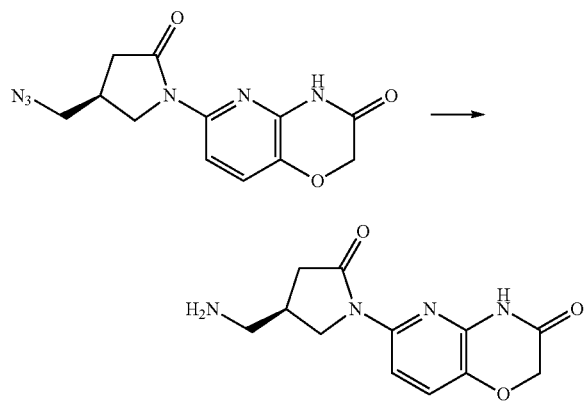

To a solution of 6-[(4S)-4-(azidomethyl)-2-oxopyrrolidin-1-yl]-2H-pyrido[3,2-b][1,4]oxazin-3(4H)-on (688 mg, 2.39 mmol) in methanol (20 ml) was added 10% palladium on carbon catalyst (about 50% aqueous, 360 mg) at room temperature and the mixture was stirred at room temperature for 1 hour under a hydrogen atmosphere. The catalyst was removed by filtration and washed with methanol, the filtrate and washings were concentrated under reduced pressure, and the obtained residue was purified by silica gel column chromatography (chloroform/methanol/triethylamine) to yield 328 mg (54%) of the title compound in the form of a colorless solid.

$^1$H-NMR(400 MHz,DMSO-d$_6$)δ:2.31-2.41(2H,m),2.56-2.66(3H,m).3.29(1H,brs), 3.66(1H,dd,J=11.2,5.4),3.97(1H,dd,J=10.9,7.4 Hz),4.58(2H,s),7.36(1H,d,J=8.59 Hz),7.80 (1H,d,J=8.6 Hz).

MS(ESI)m/z:263(M+H)$^+$.

Example 19

6-[(4R)-4-({[2-(7-Methoxy-2-oxoquinoxalin-1(2H)-yl)ethyl]amino}methyl)-2-oxopyrrolidin-1-yl]-2H-pyrido[3,2-b][1,4]oxazin-3(4H)-one

[Formula 110]

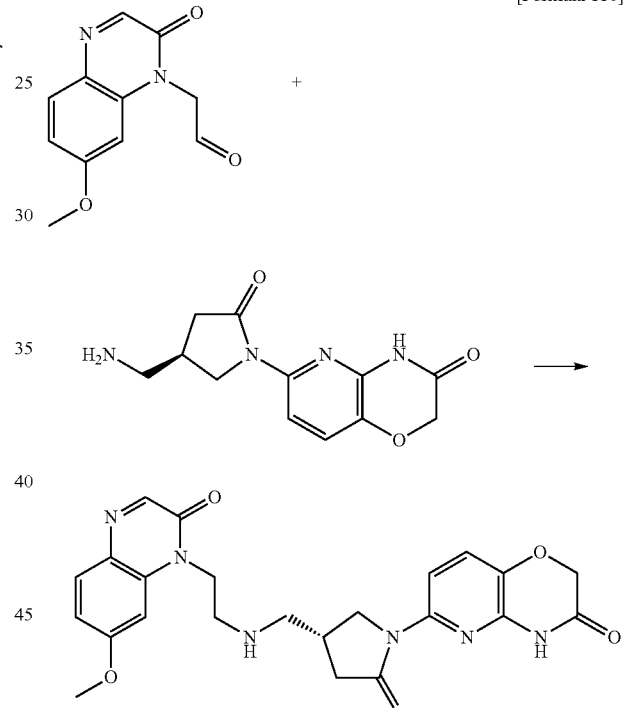

In the same manner as in Example 16, 69 mg (49%) of the title compound was obtained from (7-methoxy-2-oxoquinoxalin-1(2H)-yl)acetaldehyde (synthesized with reference to WO2009/1126; 67 mg, 0.305 mmol) and 6-[(4R)-4-(aminomethyl)-2-oxopyrrolidin-1-yl]-2H-pyrido[3,2-b][1,4]oxazin-3(4H)-one (80 mg, 0.305 mmol) in the form of a milky white solid.

$^1$H-NMR(400 MHz,DMSO-d$_6$)δ:2.34(1H,dd,J=6.4,16.5 Hz),2.45(1H,m),2.58-2.66(3H,m),2.82(2H,t,J=7.3 Hz),3.65 (1H,dd,J=5.5,11.0 Hz),3.90(3H,s),3.99(1H,dd,J=7.8,11.0 Hz),4.28(2H,t,J=6.9 Hz),4.60(2H,s),6.90(1H,dd,J=2.3,8.7 Hz),7.08(1H,d,J=2.3 Hz),7.38(1H,d,J=8.7 Hz),7.74(1H,d, J=8.7 Hz),7.81(1H,d,J=8.7 Hz),8.03(1H,s),11.1(1H,brs).

MS(ESI)m/z:465(M+H)$^+$.

Example 20

6-[(4R)-4-({[2-(7-Fluoro-2-oxo-1,5-naphthylidin-1 (2H)-yl)ethyl]amino}methyl)-2-oxopyrrolidin-1-yl]-2H-pyrido[3,2-b][1,4]oxazin-3(4H)-one

[Formula 111]

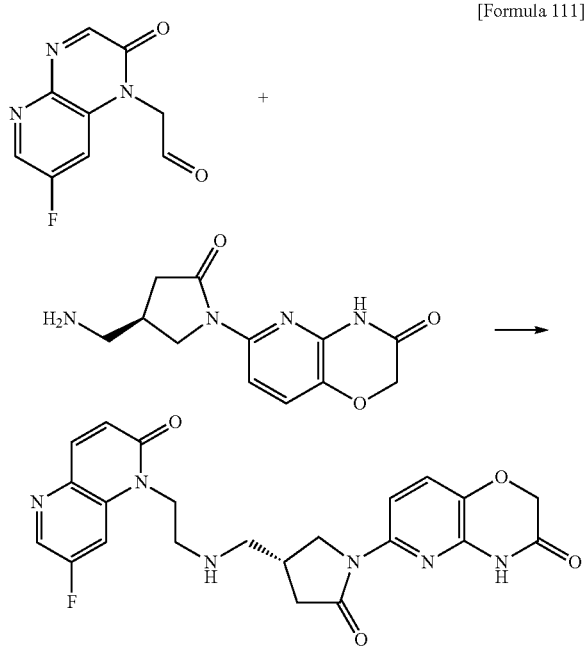

In the same manner as in Example 16, 74 mg (65%) of the title compound was obtained from (7-fluoro-2-oxo-1,5-naphthylidin-1(2H)-yl)acetaldehyde crude product (synthesized with reference to WO2007/138974; 75 mg, about 0.253 mmol) and 6-[(4R)-4-(aminomethyl)-2-oxopyrrolidin-1-yl]-2H-pyrido[3,2-b][1,4]oxazin-3(4H)-one (Reference Example 54; 66 mg, 0.253 mmol) in the form of a white solid.

$^1$H-NMR(400 MHz,DMSO-$d_6$)δ:2.32(1H,dd,J=6.6,16.7 Hz),2.45(1H,m),2.57-2.64(3H,m),2.77(2H,t,J=7.1 Hz),3.62 (1H,dd,J=6.0,11.0 Hz),3.97(1H,dd,J=7.8,11.0 Hz),4.25(2H, t,J=6.9 Hz),4.61(2H,s),6.82(1H,d,J=9.6 Hz),7.39(1H,d, J=8.7 Hz),7.81(1H,d,J=8.7 Hz),7.94(1H,d,J=9.6 Hz),8.12 (1H,dd,J=2.1,11.4 Hz),8.54(1H,d,J=2.3 Hz),11.1(1H,brs).

MS(ESI)m/z:453(M+H)$^+$.

Example 21

6-((4R)-4-({[3-(6-Methoxy-3-oxopyrido[2,3-b]pyrazin-4(3H)-yl)propyl]amino}methyl)-2-oxopyrrolidin-1-yl)-2H-pyrido[3,2-b][1,4]oxazin-3(4H)-one

[Formula 112]

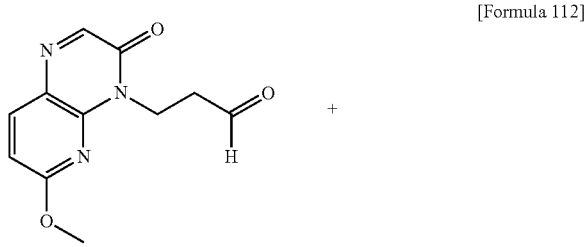

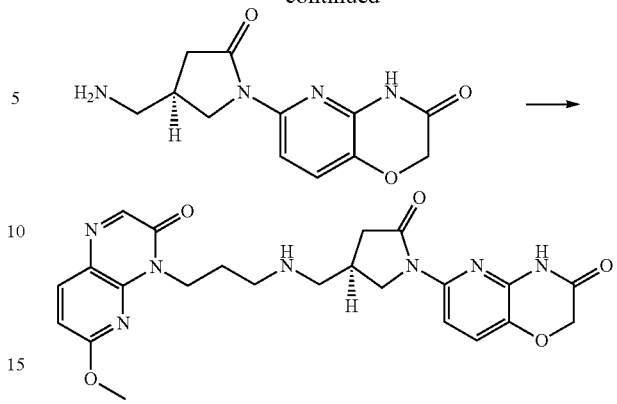

In the same manner as in Example 16, 45 mg (33%) of the title compound was obtained from 3-(6-methoxy-3-oxopyrido[2,3-b]pyrazin-4(3H)-yl)propanal (synthesized with reference to WO2008/9700; 67 mg, 0.286 mmol) and 6-[(4R)-4-(aminomethyl)-2-oxopyrrolidin-1-yl]-2H-pyrido[3,2-b][1,4]oxazin-3(4H)-one (Reference Example 54; 75 mg, 0.286 mmol) in the form of a white solid.

$^1$H-NMR(400 MHz,CDCl$_3$)δ:1.63(2H,brs),2.02-2.10(2H, m),2.37(1H,dd,J=16.9,7.2 Hz),2.44-2.55(1H,m),2.61(1H,t, J=10.0 Hz),2.68-2.81(2H,m),3.65(1H,dd,J=10.9,6.3 Hz), 3.99-4.05(4H,m),4.55(2H,t,J=6.9 Hz),4.63(2H,s),6.74(1H, d,J=8.6 Hz),7.25-7.28(1H,m),7.99(1H,d,J=8.6 Hz),8.04(1H, d,J=8.6 Hz),8.19(1H,s).

MS(ESI)m/z:480(M+H)$^+$.

Reference Example 55

6-Methoxy-4-(2-propen-1-yl)pyrido[2,3-b]pyrazin-3(4H)-one

[Formula 113]

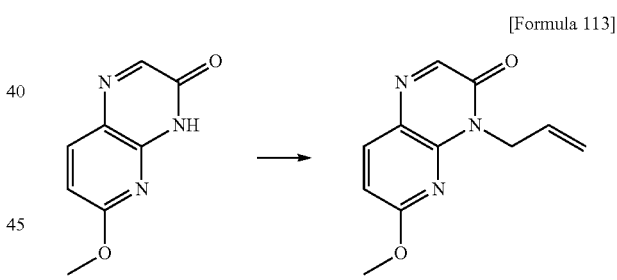

Lithium bromide (514 mg, 5.92 mmol) and subsequently sodium hydride (55%, oily, 258 mg, 5.92 mmol) were added under cooling on ice to a solution of 6-methoxypyrido[2,3-b]pyrazin-3(4H)-one (1.00 g, 5.64 mmol) in N,N-dimethylformamide (30 ml) and the mixture was stirred at room temperature for 1 hour. The reaction solution was cooled on ice again, allyl bromide (0.537 ml, 6.20 mmol) was added thereto and the mixture was stirred for 3 hours while gradually raising the temperature to room temperature. Water was added to the reaction solution, which was extracted with ethyl acetate. The extract was washed with saturated sodium chloride solution, dried over anhydrous sodium sulfate and the solvent was removed under reduced pressure. The residue was purified by silica gel column chromatography (n-hexane/ethyl acetate) to yield 1.20 g (98%) of the title compound in the form of a yellowish solid.

$^1$H-NMR(400 MHz,CDCl$_3$)δ:4.03(3H,s),5.05(2H,dt, J=5.9,1.3 Hz),5.23(1H,dd,J=10.0,1.2 Hz),5.30(1H,dd, J=17.1,1.5 Hz),6.00(1H,m),6.73(1H,d,J=8.5 Hz),8.02(1H,d, J=8.5 Hz),8.23(1H,s).

MS(ESI)m/z:218(M+H)$^+$.

Reference Example 56

4-(2,3-Dihydroxypropyl)-6-methoxypyrido[2,3-b]pyrazin-3(4H)-one

[Formula 114]

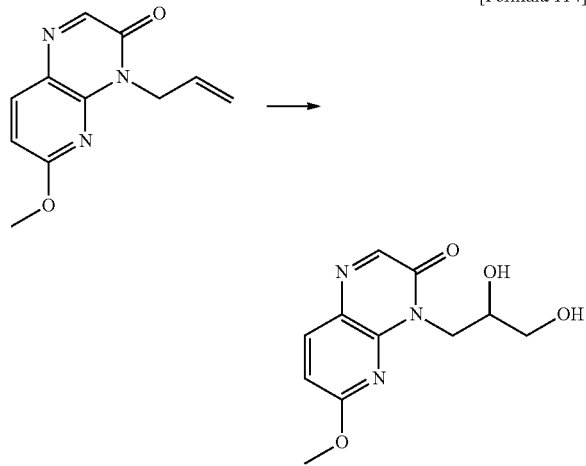

In a mixed solvent (25 ml) of tetrahydrofuran/water/acetone (2:1:2) was dissolved 6-methoxy-4-(2-propen-1-yl)pyrido[2,3-b]pyrazin-3(4H)-one (1.20 g, 5.54 mmol), to the solution N-methylmorpholineoxide (1.50 g, 11.08 mmol) was added under cooling on ice and subsequently a 4% aqueous solution of osmium tetroxide (0.70 ml, 0.11 mmol) was added thereto. The reaction solution was stirred for 24 hours while the temperature was raised to room temperature. The reaction solution was diluted with chloroform and washed with saturated sodium bicarbonate water and saturated sodium chloride solution. The organic layer was dried over anhydrous sodium sulfate and the solvent was removed under reduced pressure to yield 1.34 g (96%) of the title compound in the form of a grayish brown solid.

$^1$H-NMR(400 MHz,CDCl$_3$)δ:3.00-3.08(1H,m),3.40(1H,d,J=6.6 Hz),3.53-3.69(2H,m),4.05(3H,s),4.13-4.21(1H,m),4.59-4.74(2H,m),6.81(1H,d,J=8.8 Hz),8.08(1H,d,J=8.8 Hz),8.23(1H,s).

Reference Example 57

4-(3-{[tert-Butyl(dimethyl)silyl]oxy}-2-hydroxypropyl)-6-methoxypyrido[2,3-b]pyrazin-3(4H)-one

[Formula 115]

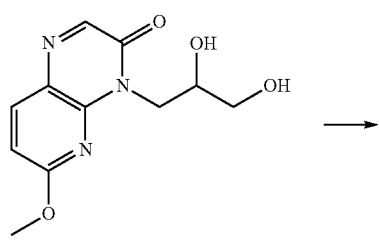

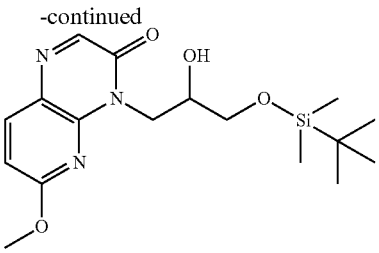

In dichloromethane (30 ml) was dissolved 4-(2,3-dihydroxypropyl)-6-methoxypyrido[2,3-b]pyrazin-3(4H)-one (1.34 g, 5.32 mmol). To the solution were added tert-butyldimethylsilyl chloride (882 mg, 5.85 mmol), triethylamine (0.96 ml, 6.92 mmol) and 4-dimethylamino pyridine (130 mg, 1.06 mmol) under cooling on ice and the reaction mixture was stirred for 15 hours while the temperature was raised to room temperature. Saturated sodium bicarbonate water was added to the reaction solution, which was extracted with dichloromethane and the extract was dried over anhydrous sodium sulfate. The solvent was removed under reduced pressure and the residue was purified by silica gel column chromatography (chloroform/methanol) to yield 1.35 g (70%) of the title compound in the form of a white solid.

$^1$H-NMR(400 MHz,CDCl$_3$)δ:0.09-0.11(6H,m),0.92(9H,s),2.98(1H,d,J=7.6 Hz),3.78(2H,d,J=4.4 Hz),4.02(3H,s),4.11-4.21(1H,m),4.52-4.57(1H,m),4.74-4.82(1H,m),6.75(1H,d,J=8.5 Hz),8.04(1H,d,J=8.5 Hz),8.19(1H,s).

Reference Example 58

4-[3-{[tert-Butyl(dimethyl)silyl]oxy}-2-(methoxymethoxy)propyl]-6-methoxypyrido[2,3-b]pyrazin-3(4H)-one

[Formula 116]

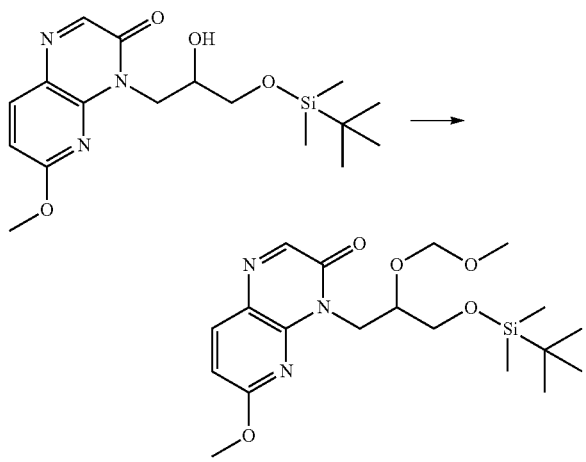

N,N-Diisopropylethylamine (1.93 ml, 11.10 mmol) and chloromethylmethyl ether (0.56 ml, 7.40 mmol) were added under cooling on ice to a solution of 4-(3-{[tert-butyl(dimethyl)silyl]oxy}-2-hydroxypropyl)-6-methoxypyrido[2,3-b]pyrazin-3(4H)-one (1.35 g, 3.70 mmol) in dichloromethane (20 ml) and the mixture was stirred for 24 hours. The reaction solution was diluted with dichloromethane and washed with water. The organic layer was dried over anhydrous sodium sulfate, the solvent was removed under reduced pressure and the residue was purified by silica gel column chromatography (hexane/ethyl acetate) to yield 1.02 g (67%) of the title compound in the form of a yellow oily product.

$^1$H-NMR(400 MHz,CDCl$_3$)δ:0.04(6H,s),0.86(9H,s),3.07 (3H,s),3.70-3.85(2H,m),4.04(3H,s),4.25-4.32(1H,m),4.45 (1H,dd,J=12.9,5.4 Hz),4.51(1H,d,J=6.8 Hz),4.63(1H,d, J=6.8 Hz),4.77(1H,dd,J=12.9,8.1 Hz),6.71-6.75(1H,m),8.01 (1H,d,J=8.8 Hz),8.16(1H,s).

Reference Example 59

4-[3-Hydroxy-2-(methoxymethoxy)propyl]-6-methoxypyrido[2,3-b]pyrazin-3(4H)-one

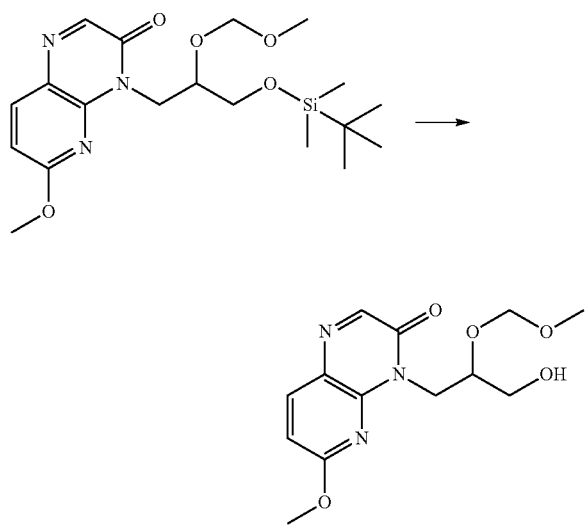

[Formula 117]

A solution of tetrabutyl ammonium fluoride in 1M tetrahydrofuran (3.22 ml, 3.22 mmol) was added to a solution of 4-[3-{[tert-Butyl(dimethyl)silyl]oxy}-2-(methoxymethoxy) propyl]-6-methoxypyrido[2,3-b]pyrazin-3(4H)-one (1.02 g, 2.48 mmol) in tetrahydrofuran (15 ml) under cooling on ice and the mixture was stirred for 15 hours. The reaction solution was diluted with dichloromethane and washed with saturated sodium bicarbonate water. The organic layer was dried over anhydrous sodium sulfate and the solvent was removed under reduced pressure. The residue was purified by silica gel column chromatography (chloroform/methanol) to yield 637 mg (87%) of the title compound in the form of an orange oily product.

$^1$H-NMR(400 MHz,CDCl$_3$)δ:3.37(3H,s),3.40-3.44(1H, m),3.49-3.56(1H,m),3.66-3.74(1H,m),4.06(3H,s),4.11-4.18 (1H,m),4.55-4.73(2H,m),4.73-4.81(2H,m),6.78(1H,d,J=8.5 Hz),8.05(1H,d,J=8.5 Hz),8.20(1H,s).

Reference Example 60

2-(Methoxymethoxy)-3-(6-methoxy-3-oxopyrido[2, 3-b]pyrazin-4 (3H)-yl)propanal

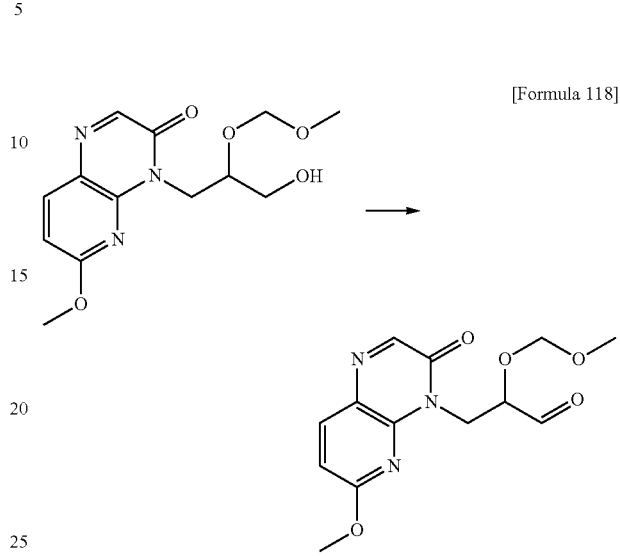

[Formula 118]

Oxalyl chloride (0.022 ml, 0.260 mmol) was dissolved in dichloromethane (1 ml), a solution of dimethyl sulfoxide (0.037 ml, 0.521 mmol) in dichloromethane (0.5 ml) was added to the solution at −78° C. and mixed for 30 minutes. While maintaining at −78° C., a solution of 4-[3-hydroxy-2-(methoxymethoxy)propyl]-6-methoxypyrido[2,3-b]pyrazin-3(4H)-one (64 mg, 0.217 mmol) in dichloromethane (3 ml) was added to the reaction solution and the mixture was stirred for 1 hour. While maintaining the temperature at −78° C., triethylamine (0.181 ml, 1.302 mmol) was added to the reaction solution and the mixture was stirred for 30 minutes. The temperature was raised to 0° C., the reaction solution was stirred for 1 hour, then diluted with dichloromethane and washed with water. The organic layer was dried over anhydrous sodium sulfate and the solvent was removed under reduced pressure to yield 67 mg (quantitative) of the title compound in the form of a yellow-orange oily product. The product was used as such for next reaction without purification.

Reference Example 61

6-[(4R)-4-({[2-(Methoxymethoxy)-3-(6-methoxy-3-oxopyrido[2,3-b]pyrazin-4(3H)-yl)propyl] amino}methyl)-2-oxopyrrolidin-1-yl)-2H-pyrido[3, 2-b][1,4]oxazin-3(4H)-one

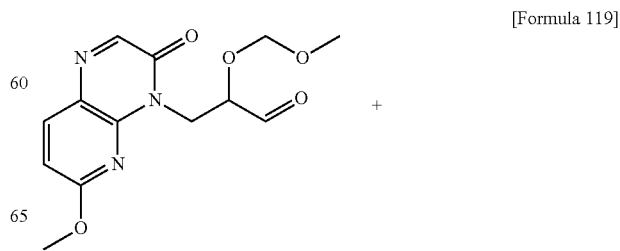

[Formula 119]

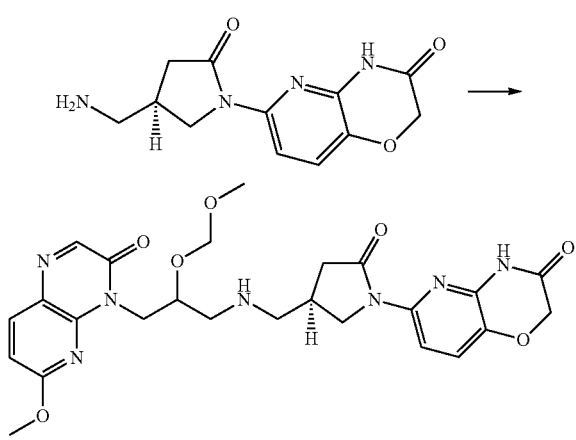

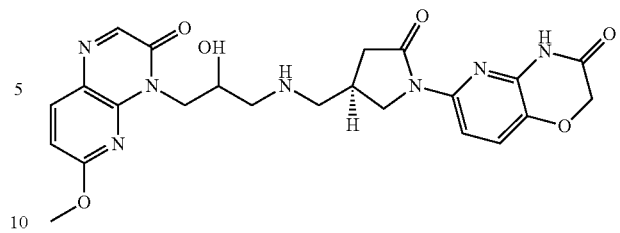

In a mixed solvent (6 ml) of dichloromethane/N,N dimethylformamide (5:1) were dissolved 2-(methoxymethoxy)-3-(6-methoxy-3-oxopyrido[2,3-b]pyrazin-4(3H)-yl)propanal (as 0.217 mmol) and 6-[(4R)-4-(aminomethyl)-2-oxopyrrolidin-1-yl]-2H-pyrido[3,2-b][1,4]oxazin-3(4H)-one (Reference Example 54; 57 mg, 0.217 mmol). Acetic acid (0.025 ml, 0.434 mmol) and anhydrous sodium sulfate (100 mg) were added to the solution and the mixture was stirred at room temperature for 14 hours. Sodium triacetoxyborohydride (92 mg, 0.434 mmol) was added to the reaction solution, the mixture was stirred for 8 hours and then the solvent was removed under reduced pressure. A lower layer solvent of chloroform/methanol/water (7:3:1) was added to the residue, the resultant was alkalized by adding saturated sodium bicarbonate water under cooling on ice and extracted with a lower layer solvent of chloroform/methanol/water (7:3:1). After drying the extract with anhydrous sodium sulfate, the solvent was removed under reduced pressure and the residue was purified by silica gel column chromatography (chloroform/methanol) to yield 41 mg (35%) of the title compound in the form of an orange oily product.

MS(EI)m/z:540(M+H)$^+$.

Example 22

6-[(4R)-4-({[2-Hydroxy-3-(6-methoxy-3-oxopyrido[2,3-b]pyrazin-4(3H)-yl)propyl]amino}methyl)-2-oxopyrrolidin-1-yl)-2H-pyrido[3,2-b][1,4]oxazin-3(4H)-one

[Formula 120]

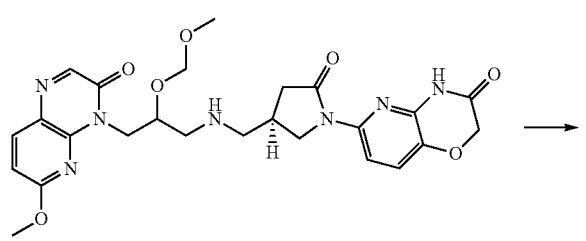

In a mixed solution (2 ml) of methanol/tetrahydrofuran (1:1) was dissolved 6-[(4R)-4-({[2-(Methoxymethoxy)-3-(6-methoxy-3-oxopyrido[2,3-b]pyrazin-4(3H)-yl)propyl]amino}methyl)-2-oxopyrrolidin-1-yl)-2H-pyrido[3,2-b][1,4]oxazin-3(4H)-one (41.3 mg, 0.077 mmol). To this solution was added a 4N hydrochloric acid aqueous solution (1 ml) under cooling on ice and the mixture was stirred at 60° C. for 4 hours. The reaction solution was cooled in the air, and the solvent was then removed under reduced pressure. The residue was dissolved in a lower layer solvent of the chloroform/methanol/water (7:3:1) and alkalized by adding saturated sodium bicarbonate water under cooling on ice. The mixture was extracted with a lower layer solvent of chloroform/methanol/water (7:3:1), the extract was dried over anhydrous sodium sulfate and the solvent was removed under reduced pressure. The residue was purified by preparative layer chromatography (chloroform/methanol) to yield 7 mg (18%) of the title compound in the form of an orangish solid.

$^1$H-NMR(400 MHz,DMSO-d$_6$)δ:2.29-2.38(2H,m),2.51-2.55(2H,m),2.55-2.68(4H,m),3.63-3.70(1H,m),3.96-4.03(4H,m),4.08-4.18(1H,m),4.21-4.30(1H,m),4.46-4.54(1H,m),4.57-4.63(2H,m),4.84-4.92(1H,m),6.83(1H,d,J=8.5 Hz),7.38(1H,d,J=7.6 Hz),7.82(1H,d,J=8.8 Hz),8.10-8.15(2H,m),11.11-11.19(1H,m).

MS(EI)m/z:496(M+H)$^+$.

Example 23

6-[(4R)-4-({[2-Fluoro-3-(7-methoxy-2-oxoquinoxalin-1(2H)-yl)propyl]amino}methyl)-2-oxopyrrolidin-1-yl)-2H-1,4-benzoxazin-3(4H)-one

[Formula 121]

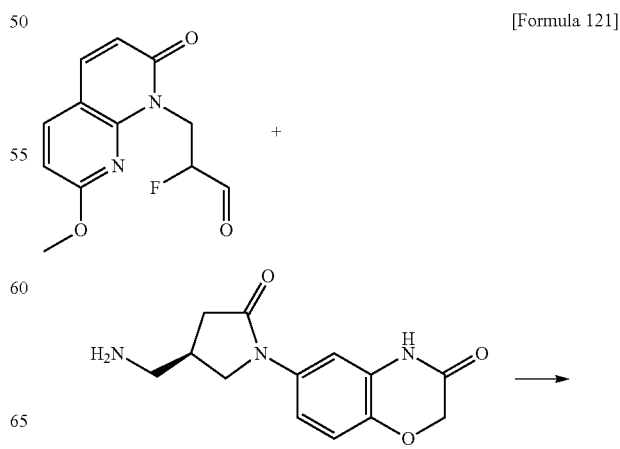

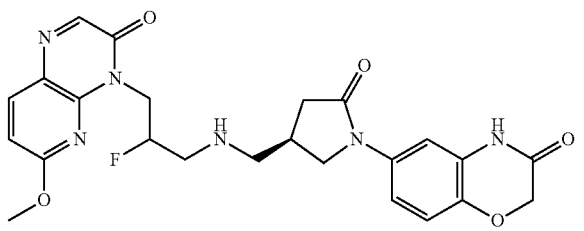

In the same manner as in Example 16, 222 mg (50%) of the title compound was obtained from 2-fluoro-3-(6-methoxy-3-oxopyrido[2,3-b]pyrazin-4(3H)-yl)propanal crude product (Reference Example 32; 293 mg, about 0.900 mmol) and 6-[(4R)-4-(aminomethyl)-2-oxopyrrolidin-1-yl]-2H-1,4-benzoxazin-3(4H)-one (Reference Example 49; 259 mg, 0.990 mmol) in the form of a light red solid.

$^1$H-NMR(400 MHz,DMSO-$d_6$)δ:2.21(1H,br),2.29(1H,dd,J=5.5,16.0 Hz),2.51-2.65(4H,m),2.89(1H,br),2.94(1H,br),3.54(1H,dd,J=5.0,9.6 Hz),3.83(1H,dd,J=7.8,9.6 Hz),3.98(3H,s),4.36-4.48(1H,m),4.53(2H,s),4.78-4.87(1H,m),4.93-5.08(1H,m),6.85(1H,d,J=8.7 Hz),6.92(1H,d,J=8.7 Hz),7.01(1H,m),7.40(1H,d,J=2.3 Hz),8.14(1H,s),8.15(1H,d,J=8.7 Hz),10.7(1H,s).

MS(ESI)m/z:497(M+H)$^+$.

Reference Example 62

(4R)-4-({[tert-Butyl(dimethyl)silyl]oxy}methyl)pyrrolidin-2-one

[Formula 122]

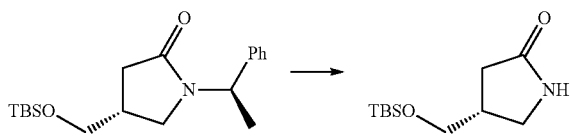

Under a nitrogen gas atmosphere, metallic sodium (920 mg, 40.0 mmol) was added to liquid ammonia (about 30 ml) at −78° C. over a period of 5 minutes, and the mixture was further stirred at the same temperature for 15 minutes. To the reaction solution, a solution of (4R)-4-({[tert-butyl(dimethyl)silyl]oxy}methyl)-1-[(1R)-1-phenylethyl]pyrrolidin-2-one (Heterocycles, 2003, vol. 60, No. 11, pages 2485-2498, or synthesized with reference to JP09136886; 3.34 g, 10.0 mmol) in tetrahydrofuran (10 ml)/tert-butyl alcohol (1 ml) was added over a period of 5 minutes and the mixture was stirred for about 1 hour. Ammonium chloride (3.21 g) was added thereto, and ammonia was evaporated by gradually raising the temperature to room temperature when the color of the reaction solution changed from dark blue to colorless. Water was added to dissolve the insoluble material and the resultant was extracted with a mixed solution of chloroform-methanol (9:1). The organic layer was dried over anhydrous sodium sulfate, the drying agent was removed by filtration and the filtrate was concentrated under reduced pressure. The obtained residue was purified by silica gel column chromatography to yield 2.29 g (100%) of the title compound in the form of a colorless oily product.

$^1$H-NMR(400 MHz,CDCl$_3$)δ:0.06(6H,s),0.89(9H,s),2.14(1H,dd,J=16.7,6.4 Hz),2.38(1H,dd,J=16.7,8.7 Hz),2.61-2.71(1H,m),3.23(1H,dd,J=9.6,5.0 Hz),3.45(1H,t,J=8.9 Hz),3.55-3.64(2H,m),5.85(1H,s).

Reference Example 63

6-[(4R)-4-({[tert-Butyl(dimethyl)silyl]oxy}methyl)-2-oxopyrrolidin-1-yl]-2H-pyrido[3,2-b][1,4]oxazin-3(4H)-one

[Formula 123]

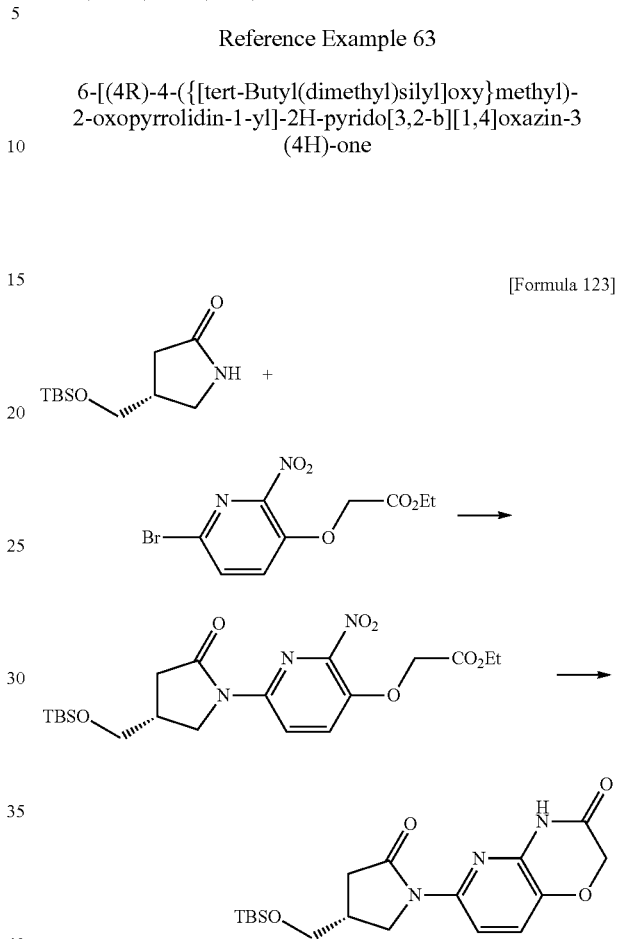

A mixture of (4R)-4-({[tert-butyl(dimethyl)silyl]oxy}methyl)pyrrolidin-2-one (1.93 g, 8.43 mmol), [(6-bromo-2-nitropyridin-3-yl)oxy]acetic acid ethyl ester (synthesized with reference to WO2004/2992, 2.57 g, 8.43 mmol), potassium carbonate (2.33 g, 16.9 mmol), copper (I) iodide (803 mg, 4.21 mmol), N,N'-dimethylethylenediamine (0.449 ml, 4.21 mmol) and toluene (40 ml) was stirred at 100° C. for 8 hours under a stream of nitrogen gas. [(6-Bromo-2-nitropyridin-3-yl)oxy]acetic acid ethyl ester (1.29 g, 4.21 mmol) was added thereto and stirred overnight at 100° C. [(6-Bromo-2-nitropyridin-3-yl)oxy]acetic acid ethyl ester (1.29 g, 4.21 mmol), copper (I) iodide (803 mg, 4.21 mmol) and N,N'-dimethylethylenediamine (0.449 ml, 4.21 mmol) were further added thereto which was stirred at 100° C. for 24 hours. After cooling, ethyl acetate was added to the reaction solution to remove the insoluble material by filtration and the filtrate was concentrated under reduced pressure. The obtained residue was purified by silica gel column chromatography (n-hexane/ethyl acetate), thereby obtaining 2.70 g (71%) of ({6-[(4R)-4-({[tert-butyl(dimethyl)silyl]oxy}methyl)-2-oxopyrrolidin-1-yl]-2-nitropyridin-3-yl}oxy)acetic acid ethyl ester in the form of a reddish brown gummy solid. The whole amount was dissolved in acetic acid (18 ml) to which reduced iron (999 mg, 17.9 mmol) was added and the mixture was stirred at 60° C. for 3 hours. After cooling, a mixed solution of chloroform-methanol (9:1) was added to remove the insoluble material by filtration and the filtrate was concentrated under reduced pressure. The residue was purified by silica gel column chromatography (chloroform/methanol) to yield 1.93 g (86%) of the title compound in the form of a yellow solid.

$^1$H-NMR(400 MHz,CDCl$_3$)δ:0.05(3H,s),0.06(3H,s),0.88 (9H,s),2.50(1H,dd,J=16.5,6.0 Hz),2.55-2.62(1H,m),2.71 (1H,dd,J=16.5,8.3 Hz),3.65(2H,t,J=5.5 Hz),3.81(1H,dd, J=11.2,5.0 Hz),4.05(1H,dd,J=11.2,8.0 Hz),4.64(2H,s),7.28 (1H,d,J=8.7 Hz),7.96(1H,s),8.03(1H,d,J=8.7 Hz).

Reference Example 64

6-[(4R)-4-(Hydroxymethyl)-2-oxopyrrolidin-1-yl]-2H-pyrido[3,2-b][1,4]oxazin-3(4H)-one

[Formula 124]

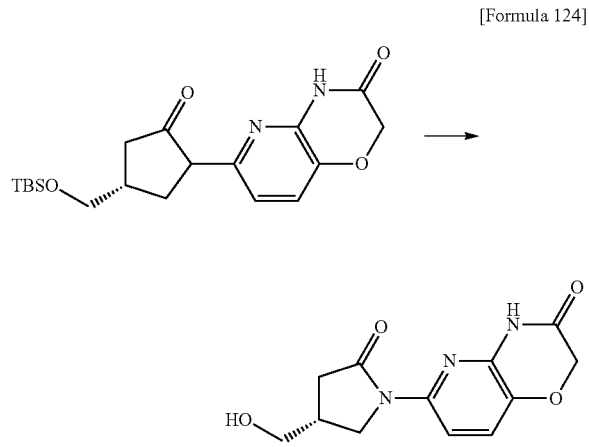

In tetrahydrofuran (20 ml) was dissolved 6-[(4R)-4-({[tert-butyl(dimethyl)silyl]oxy}methyl)-2-oxopyrrolidin-1-yl]-2H-pyrido[3,2-b][1,4]oxazin-3(4H)-one (1.93 g, 5.12 mmol). Tetrabutyl ammonium fluoride (1M tetrahydrofuran solution; 6.14 ml, 6.14 mmol) was added to this solution and the mixture was stirred at room temperature for 7 hours. The reaction solution was concentrated under reduced pressure and ethyl acetate and water were added to the obtained residue. The aqueous layer was extracted with ethyl acetate and washed with saturated sodium chloride solution. The solution was dried over anhydrous sodium sulfate, the drying agent was removed by filtration and the filtrate was concentrated under reduced pressure. The obtained residue was purified by silica gel column chromatography (hexane/ethyl acetate) to yield 667 mg (49%) of the title compound in the form of a light yellow solid.

$^1$H-NMR(400 MHz,CDCl$_3$)δ:2.50(1H,dd,J=16.9,6.1 Hz), 2.61-2.69(1H,m),2.78(1H,dd,J=16.9,8.8 Hz),3.70-3.77(2H, m),3.86(1H,dd,J=11.5,5.4 Hz),4.10(1H,dd,J=11.5,7.9 Hz), 4.64(2H,s),7.29(1H,d,J=8.5 Hz),7.75(1H,s),8.03(1H,d,J=8.5 Hz).

MS(FAB)m/z:264(M+H)$^+$.

Reference Example 65

6-[(4R)-4-(Azidomethyl)-2-oxopyrrolidin-1-yl]-2H-pyrido[3,2-b][1,4]oxazin-3(4H)-one

[Formula 125]

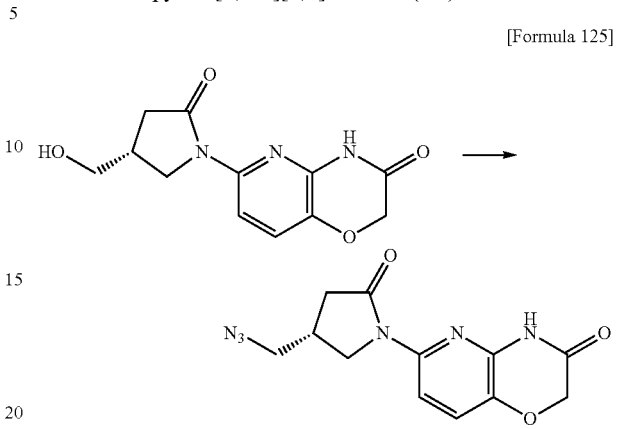

Methanesulfonyl chloride (0.198 ml, 2.56 mmol) was added to a solution of 6-[(4R)-4-(hydroxymethyl)-2-oxopyrrolidin-1-yl]-2H-pyrido[3,2-b][1,4]oxazin-3(4H)-one (450 mg, 1.71 mmol) and triethylamine (0.477 ml, 3.42 mmol) in dichloromethane (5 ml) under cooling on ice and the mixture was stirred for 0.5 hours while gradually raising the temperature to room temperature. Triethylamine (0.240 ml, 1.72 mmol) and methanesulfonyl chloride (0.100 ml, 1.29 mmol) were added thereto and the mixture was further stirred for 1 hour. The reaction solution was diluted with dichloromethane and washed with water. The obtained organic layer was dried over anhydrous sodium sulfate, the drying agent was removed by filtration and the filtrate was concentrated under reduced pressure.

The obtained orange-ish solid was dissolved in N,N-dimethylformamide (5 mL), sodium azide (217 mg, 3.34 mmol) was added thereto and the mixture was stirred at 65° C. for 18 hours. The reaction solution was diluted with ethyl acetate and washed with water and saturated sodium chloride solution. The reaction solution was dried over anhydrous sodium sulfate, the drying agent was removed by filtration and the filtrate was concentrated under reduced pressure. The obtained residue was purified by silica gel column chromatography (hexane/ethyl acetate) to yield 230 mg (48%) of the title compound in the form of a white solid.

$^1$H-NMR(400 MHz,CDCl$_3$)δ:2.47(1H,dd,J=16.9,6.4 Hz), 2.64-2.72(1H,m),2.81(1H,dd,J=16.9,8.7 Hz),3.43-3.54(2H, m),3.79(1H,dd,J=11.4,6.0 Hz),4.13(1H,dd,J=11.4,7.8 Hz), 4.64(2H,s),7.30(1H,d,J=8.7 Hz),7.80(1H,s),8.01(1H,d,J=8.7 Hz).

MS(ESI)m/z:289(M+H)$^+$.

Reference Example 66

6-[(4S)-4-(Aminomethyl)-2-oxopyrrolidin-1-yl]-2H-pyrido[3,2-b][1,4]oxazin-3(4H)-one

[Formula 126]

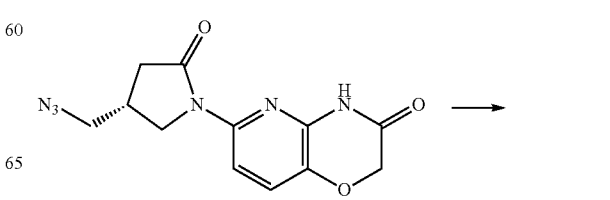

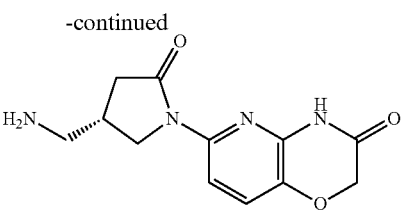

To a solution of 6-[(4R)-4-(azidomethyl)-2-oxopyrrolidin-1-yl]-2H-pyrido[3,2-b][1,4]oxazin-3(4H)-one (230 mg, 0.877 mmol) in methanol-tetrahydrofuran (5 ml-2.5 ml) was added 10% palladium on carbon catalyst (about 50% aqueous, 130 mg) at room temperature and the mixture was stirred at the same temperature for 2 hours under a hydrogen atmosphere. The catalyst was removed by filtration and washed with methanol, and the filtrate was concentrated under reduced pressure. The obtained residue was dissolved in dichloromethane and dried over anhydrous sodium sulfate. After removing the drying agent by filtration, the filtrate was concentrated under reduced pressure so as to yield 188 mg (90%) of the title compound in the form of a colorless solid.

$^1$H-NMR(400 MHz,CDCl$_3$)δ:2.39-2.52(2H,m),2.74-2.90 (3H,m).3.76(1H,dd,J=11.4,6.0 Hz),4.12(1H,dd,J=11.4,7.8 Hz),4.63(2H,s),7.28(1H,d,J=8.7 Hz),8.03(1H,d,J=8.7 Hz).
MS(ESI)m/z:263(M+H)$^+$.

Example 24

6-[(4S)-4-({[3-(6-Methoxy-3-oxopyrido[2,3-b]pyrazin-4(3H)-yl)propyl]amino}methyl)-2-oxopyrrolidin-1-yl]-2H-pyrido[3,2-b][1,4]oxazin-3(4H)-one

[Formula 127]

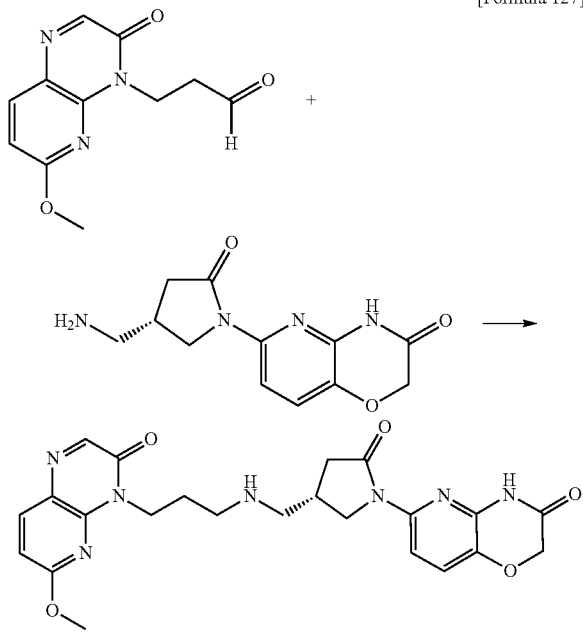

In the same manner as in Example 16, 29 mg (16%) of the title compound was obtained from 3-(6-methoxy-3-oxopyrido[2,3-b]pyrazin-4(3H)-yl)propanal (synthesized with reference to WO2008/9700; 90 mg, 0.386 mmol) and 6-[(4S)-4-(aminomethyl)-2-oxopyrrolidin-1-yl]-2H-pyrido[3,2-b][1,4]oxazin-3(4H)-one (101 mg, 0.386 mmol) in the form of a light yellow solid.

$^1$H-NMR(400 MHz,CDCl$_3$)δ:2.02-2.08(2H,m),2.34-2.41(1H,m),2.43-2.52(1H,m),2.58-2.63(1H,m),2.68-2.80(4H,m),3.64(1H,dd,J=11.2,6.2 Hz),3.97-4.02(1H,m),4.04(3H,s),4.55(2H,t,J=6.9 Hz),4.64(2H,s),6.74(1H,d,J=8.7 Hz),7.27-7.30(1H,m),7.99(1H,d,J=8.7 Hz),8.04(1H,d,J=8.7 Hz),8.19(1H,s).
MS(ESI)m/z:480(M+H)$^+$.

Reference Example 67

6-Methoxy-4-[(2R)-oxiran-2-ylmethyl]pyrido[2,3-b]pyrazin-3(4H)-one

[Formula 128]

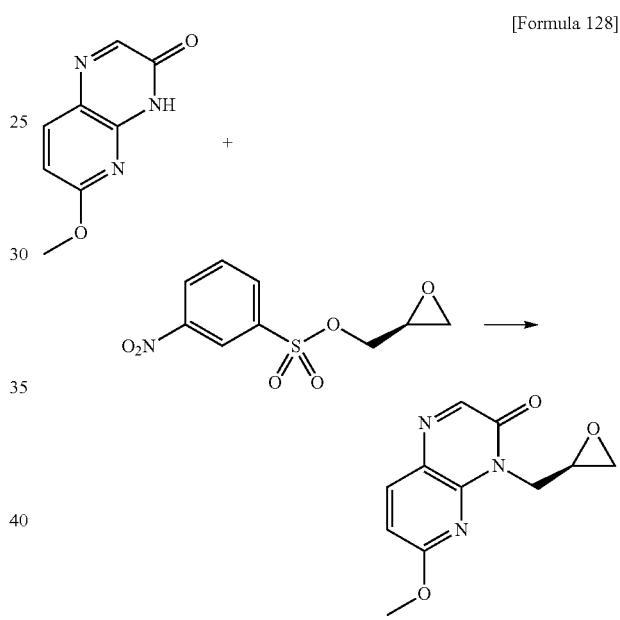

In dimethylformamide (140 ml) was dissolved 6-methoxypyrido[2,3-b]pyrazin-3(4H)-one (5.0 g, 28.22 mmol), and sodium hydride (1.35 g, 31.04 mmol) was then added to the solution under cooling on ice. The obtained mixture was stirred at room temperature for 1.5 hours. The reaction solution was cooled on ice again, and (S)-glycidyl 3-nitrobenzenesulfonate (8.78 g, 33.86 mmol) was then added thereto. While slowly raising the temperature to room temperature, the mixture was stirred for 15 hours. Thereafter, water was added to the reaction solution, and it was then extracted with ethyl acetate. The resultant was washed with saturated sodium chloride solution, and it was then dried over anhydrous sodium sulfate. The solvent was removed under reduced pressure, and the obtained residue was then purified by silica gel column chromatography (hexane/ethyl acetate) to yield 4.98 g (76%) of the above-captioned compound in the form of a white solid.

$^1$H-NMR (400 MHz, CDCl$_3$) δ: 2.79-2.83 (2H, m), 3.40-3.44 (1H, m), 4.05 (3H, s), 4.51 (1H, dd, J=13.2, 5.6 Hz), 4.76 (1H, dd, J=13.2, 4.9 Hz), 6.76 (1H, d, J=8.3 Hz), 8.04 (1H. d, J=8.8 Hz), 8.19 (1H, s).

Example 25

6-[(4R)-4-({[(2S)-2-Hydroxy-3-(6-methoxy-3-oxopyrido[2,3-b]pyrazin-4(3H)-yl)propyl]amino}methyl)-2-oxopyrrolidin-1-yl]-2H-pyrido[3,2-b][1,4]oxazin-3(4H)-one

[Formula 129]

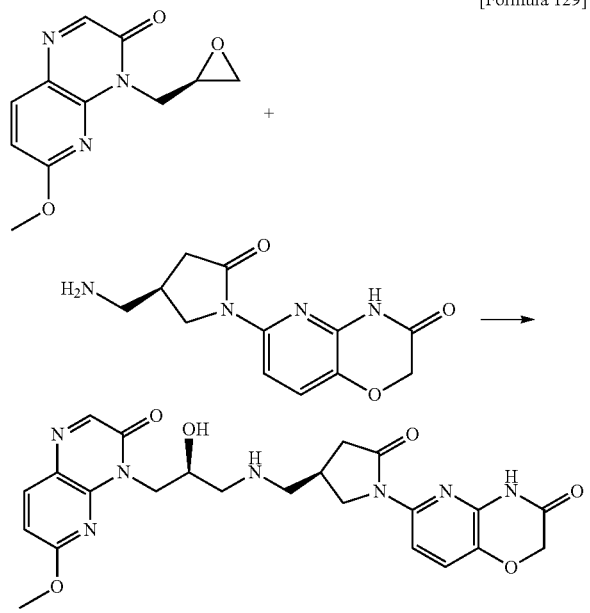

In a mixed solvent (60 ml) of ethanol and water (9:1) were dissolved 6-methoxy-4-[(2R)-oxiran-2-ylmethyl]pyrido[2,3-b]pyrazin-3(4H)-one (2.94 g, 12.60 mmol) and 6-[(4R)-4-(aminomethyl)-2-oxopyrrolidin-1-yl]-2H-pyrido[3,2-b][1,4]oxazin-3(4H)-one (Reference Example 54; 3.30 g, 12.60 mmol), and the obtained mixture was then stirred in a sealed tube at 60° C. for 15 hours. Thereafter, the reaction solution was cooled in the air, and the solvent was then removed under reduced pressure. The residue was purified by silica gel column chromatography (chloroform/methanol) to yield 1.73 g (28%) of the above-captioned compound in the form of a light yellow solid.

$^1$H-NMR (400 MHz, DMSO-d$_6$) δ: 2.30-2.36 (1H, m), 2.46-2.67 (7H, m), 3.65 (1H, dd, J=10.7, 5.9 Hz), 3.97-4.02 (4H, m), 4.09-4.15 (1H, m), 4.25 (1H, dd, J=12.8, 5.2 Hz), 4.49 (1H, dd, J=12.6, 7.7 Hz), 4.59 (2H, s), 4.89 (1H, d, J=5.9 Hz), 6.83 (1H, d, J=8.8 Hz), 7.38 (1H, d, J=8.8 Hz), 7.82 (1H, d, J=8.8 Hz), 8.12-8.14 (2H, m), 11.15 (1H, brs).

MS (ESI) m/z: 496 (M+H)$^+$.

Reference Example 68

(4S)-4-(2-Iodoethyl)-2,2-dimethyl-1,3-dioxolane

[Formula 130]

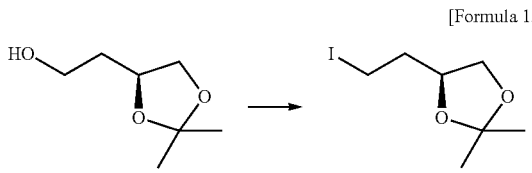

Triphenyl phosphine (31.0 g, 118.21 mmol) and imidazole (8.05 g, 118.21 mmol) were dissolved in a mixed solution (400 ml) of diethyl ether-acetonitrile (3:1), iodine (30.0 g, 118.21 mmol) was added thereto under cooling on ice and the mixture was stirred at room temperature for 3 hours. The solution was cooled on ice again, a mixed solution (100 ml) of (4S)-(+)-4-(2-hydroxyethyl)-2,2-dimethyl-1,3-dioxolane (15 g, 98.51 mmol) in diethyl ether-acetonitrile (3:1) was added thereto and stirred at room temperature for 18 hours. A saturated sodium thiosulfate aqueous solution was added to the reaction solution under cooling on ice and stirred for a while. The solution was extracted with diethyl ether and the extract was washed with saturated sodium chloride solution. The solvent was removed under reduced pressure and the obtained residue was triturated by adding a mixed solvent of ether/hexane to remove the insoluble material by filtration. The filtrate was concentrated under reduce pressure, and the obtained residue was purified by silica gel column chromatography (hexane/ethyl acetate) to yield 23.1 g (92%) of the title compound in the form of a colorless clear oily product.

$^1$H-NMR(400 MHz,CDCl$_3$)δ:1.36(3H,s),1.41(3H,s),2.00-2.15(2H,m),3.19-3.31(2H,m),3.58(1H,dd,J=7.8,6.4 Hz),4.09(1H,dd,J=8.0,6.2 Hz),4.15-4.21(1H,m).

Reference Example 69

4-{2-[(4S)-2,2-Dimethyl-1,3-dioxolan-4yl]ethyl}-6-methoxypyrido[2,3-b]pyrazin-3(4H)-one

[Formula 131]

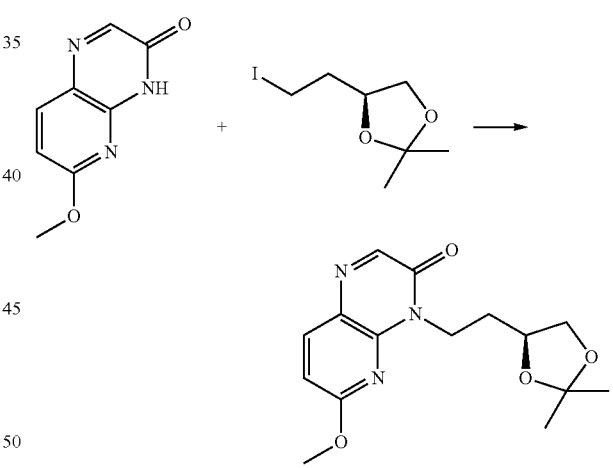

In N,N-dimethylformamide (400 ml) were dissolved 6-methoxypyrido[2,3-b]pyrazin-3(4H)-one (14.53 g, 82.00 mmol) and (4S)-4-(2-iodoethyl)-2,2-dimethyl-1,3-dioxolane (23.10 g, 90.20 mmol). Cesium carbonate (34.7 g, 1.06.6 mmol) was added to the solution and the mixture was stirred at 50° C. for 11 hours. After cooling in the air, water was added to the reaction solution and the mixture was extracted with ethyl acetate. The extract was washed with saturated sodium chloride solution, dried over anhydrous sodium sulfate and the solvent was removed under reduced pressure. The residue was purified by silica gel column chromatography (hexane/ethyl acetate) to yield 22.58 g (90%) of the title compound in the form of a yellow orange oily product.

$^1$H-NMR(400 MHz,CDCl$_3$)δ:1.32(3H,s),1.39(3H,s),1.97-2.15(2H,m),3.62(1H,t,J=7.4 Hz),4.06(3H,s),4.10(1H,dd,

J=8.1,6.1 Hz),4.19-4.26(1H,m),4.47-4.53(1H,m),4.59-4.66 (1H,m),6.74(1H,d,J=8.5 Hz),8.02(1H,d,J=8.5 Hz),8.15(1H, s).

Reference Example 70

4-[(3S)-3,4-Dihydroxybutyl]-6-methoxypyrido[2,3-b]pyrazin-3(4H)-one

[Formula 132]

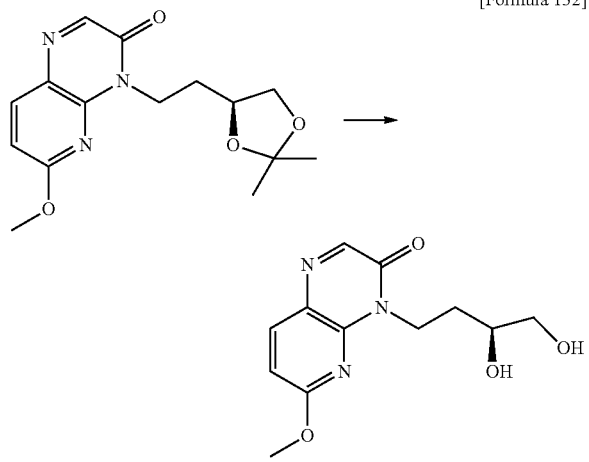

In tetrahydrofuran (1000 ml) was dissolved 4-{2-[(4S)-2, 2-dimethyl-1,3-dioxolan-4yl]ethyl}-6-methoxypyrido[2,3-b]pyrazin-3(4H)-one, 1N hydrochloric acid aqueous solution (250 ml) was added thereto under cooling on ice and the mixture was stirred at 60° C. for 14 hours. After cooling in the air, the reaction solution was concentrated under reduced pressure and alkalized by adding 1N sodium hydroxide aqueous solution (300 ml) under cooling on ice. The solution was extracted with a lower layer solvent of chloroform/methanol/water (7:3:1) and the extract was dried over anhydrous sodium sulfate. The solvent was removed under reduced pressure so as to yield 30.6 g (84%) of the title compound in the form of an orange solid.

$^{1}$H-NMR(400 MHz,CDCl$_{3}$)δ:1.83-1.92(1H,m),1.95-2.08 (1H,m),2.08-2.15(1H,m),3.47-3.62(3H,m),4.05(3H,s),4.12-4.16(1H,m),4.63(2H,dd,J=8.2,4.0 Hz),6.79(1H,d,J=8.5 Hz), 8.07(1H,d,J=8.8 Hz),8.21(1H,s).

Reference Example 71

(2S)-2-Hydroxy-4-(6-methoxy-3-oxopyrido[2,3-b]pyrazin-4(3H)-yl)butyl 4-methylbenzensulfonate

[Formula 133]

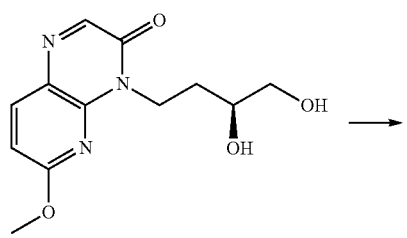

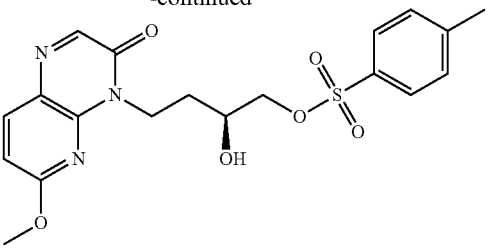

In dichloromethane (4 ml) was dissolved 4-[(3S)-3,4-dihydroxybutyl]-6-methoxypyrido[2,3-b]pyrazin-3(4H)-one (200 mg, 0.754 mmol), and triethylamine (0.126 ml, 0.905 mmol), dimethylamino pyridine (18.4 mg, 0.151 mmol) and p-toluene sulfonyl chloride (158 mg, 0.829 mmol) were added thereto under cooling on ice and the mixture was stirred at room temperature for 24 hours. After completion of the reaction, water was added to the reaction solution which was extracted with dichloromethane. After drying the extract with anhydrous sodium sulfate, the solvent was removed under reduced pressure and the obtained residue was purified by silica gel column chromatography (chloroform/methanol) to yield 227 mg (72%) of the title compound in the form of a yellow oily product.

$^{1}$H-NMR(400 MHz,CDCl$_{3}$)δ:1.83-1.90(1H,m),2.03-2.11 (1H,m),2.44(3H,s),3.66-3.74(1H,m),3.87(1H,d,J=4.1 Hz), 3.99(2H,d,J=5.0 Hz),4.04(3H,s),4.52-4.66(2H,m),6.79(1H, d,J=8.7 Hz),7.32(2H,d,J=7.8 Hz),7.76(2H,d,J=8.2 Hz),8.06 (1H,d,J=8.7 Hz),8.17(1H,s).

Reference Example 72

6-Methoxy-4-{2-[(2S)-oxiran-2-yl]ethyl}pyrido[2,3-b]pyrazin-3(4H)-one

[Formula 134]

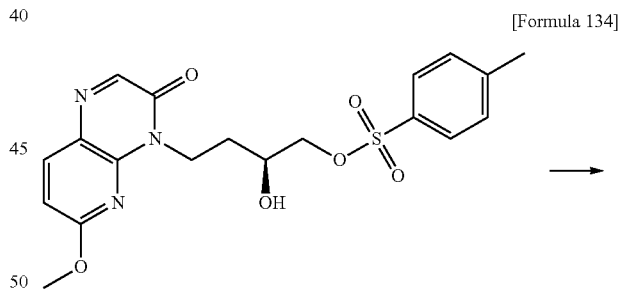

In methanol (15 ml) was dissolved (2S)-2-hydroxy-4-(6-methoxy-3-oxopyrido[2,3-b]pyrazin-4(3H)-yl)butyl 4-methylbenzenesulfonate (227 mg, 0.540 mmol), and potassium carbonate (90 mg, 0.648 mmol) was then added to the solution at room temperature. The obtained mixture was stirred for 17 hours. Thereafter, the solvent was removed from the reaction solution under reduced pressure. The obtained residue was purified by silica gel column chromatography (chloroform/methanol) to yield 83 mg (62%) of the above-captioned compound in the form of a yellow solid.

$^1$H-NMR (400 MHz, CDCl$_3$) δ: 1.91-1.99 (1H, m), 2.11-2.19 (1H, m), 2.44 (1H, dd, J=5.0, 2.6 Hz), 2.73 (1H, dd, J=4.9, 3.9 Hz), 3.02-3.07 (1H, m), 4.05 (3H, s), 4.64 (2H, t, J=7.2 Hz), 6.74 (1H, d, J=8.5 Hz), 8.03 (1H, d, J=8.8 Hz), 8.17 (1H, s).

Example 26

6-[(4R)-4-{[(2S)-2-Hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one

[Formula 135]

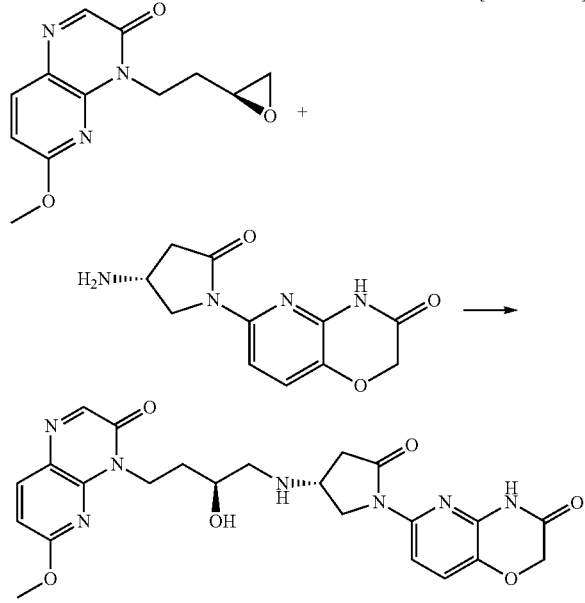

In a mixed solvent (12 ml) of ethanol and water (9:1) were suspended 6-methoxy-4-{2-[(2S)-oxiran-2-yl]ethyl}pyrido[2,3-b]pyrazin-3(4H)-one (290 mg, 1.17 mmol) and 6-[(4R)-4-amino-2-oxopyrrolidin-1-yl]-2H-pyrido[3,2-b][1,4]oxazin-3(4H)-one (which was synthesized in the same manner as those of Reference Examples 20, 21 and 22, using the [(3R)-5-oxopyrrolidin-3-yl]carbamic acid tert-butyl ester synthesized with reference to WO2004/22536; 291 mg, 1.17 mmol). The obtained mixture was stirred in a sealed tube at 80° C. for 16 hours.

Thereafter, the solvent was removed from the reaction solution under reduced pressure. The obtained residue was purified by silica gel column chromatography (chloroform/methanol) to yield 233 mg (40%) of the above-captioned compound in the form of a light yellow solid.

$^1$H-NMR (400 MHz, DMSO-d$_6$) δ: 1.68-1.77 (1H, m), 1.82-1.90 (1H, m), 1.99-2.11 (1H, m), 2.32-2.37 (1H, m), 2.51-2.62 (2H, m), 2.73-2.79 (1H, m), 3.36-3.43 (1H, m), 3.59-3.67 (1H, m), 3.71 (1H, dd, J=11.0, 3.7 Hz), 3.98-4.02 (4H, m), 4.29-4.36 (1H, m), 4.45-4.52 (1H, m), 4.60 (2H, s), 4.70 (1H, d, J=4.6 Hz), 6.84 (1H, d, J=8.7 Hz), 7.38 (1H, d, J=8.7 Hz), 7.82 (1H, d, J=8.7 Hz), 8.11 (1H, s), 8.13 (1H, d, J=8.3 Hz), 11.15 (1H, brs).

MS (ESI) m/z: 496 (M+H)$^+$.

Example 27

6-[(4S)-4-{[(2S)-2-Hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one

[Formula 136]

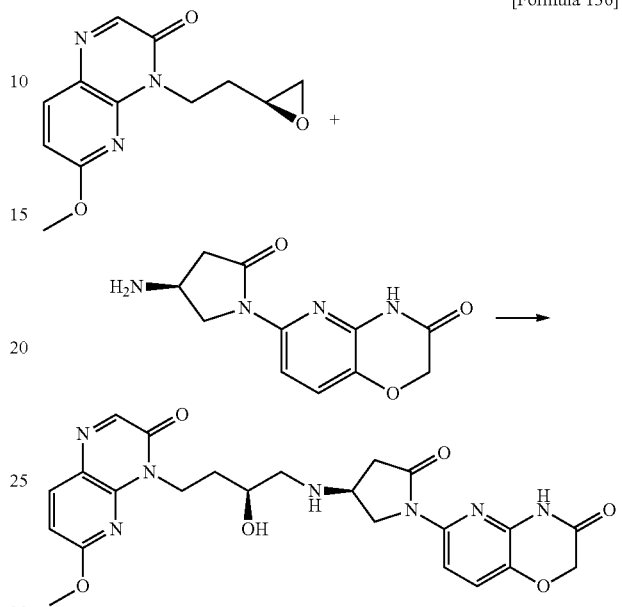

In a mixed solvent (12 ml) of ethanol-water (9:1) were suspended 6-methoxy-4-{2-[(2S)-oxiran-2-yl]ethyl}pyrido[2,3-b]pyrazin-3(4H)-one (Reference Example 72; 290 mg, 1.17 mmol) and 6-[(4S)-4-amino-2-oxopyrrolidin-1-yl]-2H-pyrido[3,2-b][1,4]oxazin-3(4H)-one (Reference Example 22; 291 mg, 1.17 mmol), and the suspension was stirred in a sealed tube at 80° C. for 16 hours. The solvent was removed from the reaction solution under reduced pressure and the obtained residue was purified by silica gel column chromatography (chloroform/methanol) to yield 182 mg (31%) of the title compound in the form of a yellowish solid.

$^1$H-NMR(400 MHz,DMSO-d$_6$)δ:1.66-1.75(1H,m),1.83-1.91(1H,m),2.01-2.10(1H,m),2.30-2.35(1H,m),2.51-2.57 (2H,m),2.75-2.81(1H,m),3.36-3.43(1H,m),3.59-3.66(1H,m),3.71(1H,dd,J=11.2,3.4 Hz),3.94-4.00(4H,m),4.28-4.35 (1H,m),4.45-4.52(1H,m),4.59(2H,s),4.70(1H,d,J=5.0 Hz), 6.83(1H,d,J=8.7 Hz),7.37(1H,d,J=8.7 Hz),7.80(1H,d,J=8.7 Hz),8.10(1H,s),8.12(1H,d,J=8.7 Hz),11.13(1H,s).

MS(ESI)m/z:496(M+H)$^+$.

Reference Example 73

(4R)-4-(2-Iodoethyl)-2,2-dimethyl-1,3-dioxolane

[Formula 137]

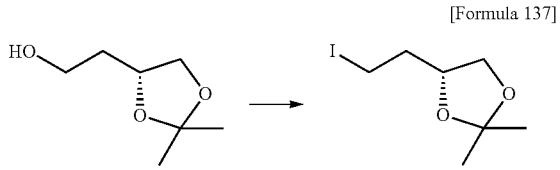

Triphenyl phosphine (5.94 g, 22.65 mmol) and imidazole (22.65 mmol) were dissolved in a mixed solution (120 ml) of diethyl ether-acetonitrile (3:1). Iodine (5.75 g, 22.65 mmol) was added thereto under cooling on ice and the mixture was stirred at room temperature for 30 minutes. The solution was cooled on ice again, (4R)-4-(2-hydroxyethyl)-2,2-dimethyl-1,3-dioxolane (3.0 mmol, 20.59 mmol) was added thereto and the mixture was stirred at room temperature for 24 hours. A saturated sodium thiosulfate aqueous solution was added to the reaction solution under cooling on ice and stirred for a while, the solution was extracted with diethyl ether and the extract was washed with saturated sodium chloride solution. The solvent was removed under reduced pressure and the residue was purified by silica gel column chromatography (hexane/ethyl acetate) to yield 3.20 g (61%) of the title compound in the form of a yellowish oily product.

$^1$H-NMR(400 MHz,CDCl$_3$)δ:1.36(3H,s),1.41(3H,s),1.99-2.15(2H,m),3.19-3.30(2H,m),3.58(1H,dd,J=7.8,6.6 Hz), 4.09(1H,dd,J=7.8,6.1 Hz),4.14-4.22(1H,m).

Reference Example 74

4-{2-[(4R)-2,2-Dimethyl-1,3-dioxolan-4-yl]ethyl}-6-methoxypyrido[2,3-b]pyrazin-3(4H)-one

[Formula 138]

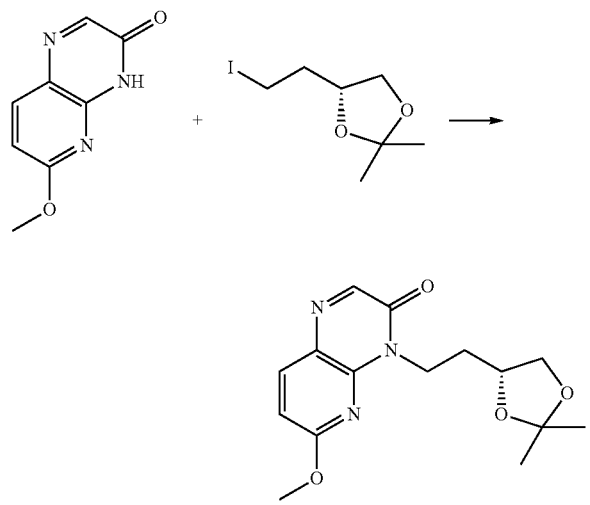

In N,N-dimethylformamide (40 ml) were dissolved 6-methoxypyrido[2,3-b]pyrazin-3(4H)-one (1.48 g, 8.34 mmol) and (4R)-4-(2-iodoethyl)-2,2-dimethyl-1,3-dioxolane (3.20 g, 12.51 mmol). Cesium carbonate (3.81 g, 11.68 mmol) was added to the solution and the mixture was stirred at 50° C. for 13 hours. After cooling in the air, water was added to the reaction solution and the mixture was extracted with ethyl acetate. The extract was washed with saturated sodium chloride solution, dried over anhydrous sodium sulfate and the solvent was removed under reduced pressure. The residue was purified by silica gel column chromatography (hexane/ethyl acetate) to yield 2.55 g (100%) of the title compound in the form of a light yellow oily product.

$^1$H-NMR(400 MHz,CDCl$_3$)δ:1.32(3H,s),1.39(3H,s),1.95-2.16(2H,m),3.62(1H,t,J=7.4 Hz),4.06(3H,s),4.07-4.12(1H,m),4.18-4.26(1H,m),4.46-4.55(1H,m),4.58-4.67(1H,m), 6.74(1H,d,J=8.5 Hz),8.02(1H,d,J=8.8 Hz),8.15(1H,s).

Reference Example 75

4-[(3R)-3,4-Dihydroxybutyl]-6-methoxypyrido[2,3-b]pyrazin-3(4H)-one

[Formula 139]

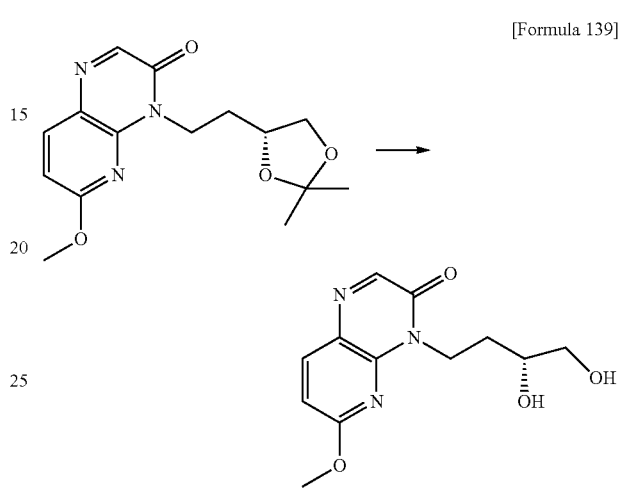

In tetrahydrofuran (100 ml) was dissolved 4-{2-[(4R)-2,2-dimethyl-1,3-dioxolan-4yl]ethyl}-6-methoxypyrido[2,3-b] pyrazin-3(4H)-one (2.55 g, 8.34 mmol), and 1N Hydrochloric acid aqueous solution (25 ml) was added thereto at room temperature and the mixture was stirred at 60° C. for 16 hours. After cooling in the air, the reaction solution was concentrated under reduced pressure and alkalized by adding 1N sodium hydroxide aqueous solution (30 ml) under cooling on ice. The solution was extracted with a lower layer solvent of chloroform/methanol/water (7:3:1) and the extract was dried over anhydrous sodium sulfate. The solvent was removed under reduced pressure so as to yield 1.95 g (88%) of the title compound in the form of an orange solid.

$^1$H-NMR(400 MHz,CDCl$_3$)δ:1.83-1.93(1H,m),1.97-2.07 (1H,m),2.13-2.25(1H,m),3.47-3.62(3H,m),4.05(3H,s),4.11-4.13(1H,m),4.63(2H,dd,J=8.0,4.4 Hz),6.79(1H,d,J=8.7 Hz), 8.07(1H,d,J=8.7 Hz),8.20(1H,s).

Reference Example 76

(2R)-2-Hydroxy-4-(6-methoxy-3-oxopyrido[2,3-b] pyrazin-4(3H)-yl)butyl 4-methylbenzensulfonate

[Formula 140]

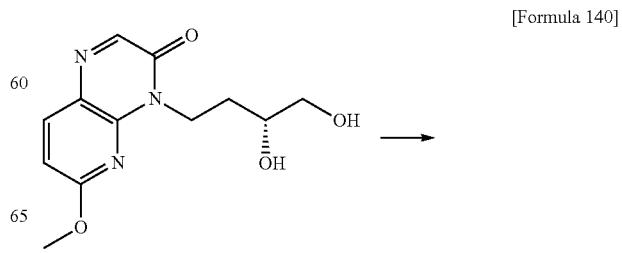

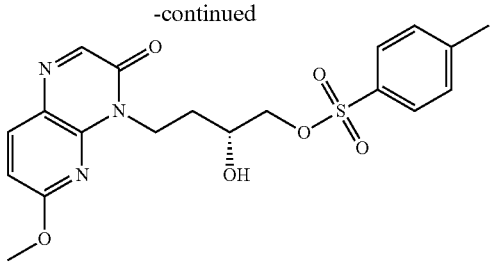

In dichloromethane (80 ml) was dissolved 4-[(3R)-3,4-dihydroxybutyl]-6-methoxypyrido[2,3-b]pyrazin-3(4H)-one (4.38 g, 16.51 mmol) and triethylamine (2.76 ml, 19.81 mmol), dimethylamino pyridine (403 mg, 3.30 mmol) and p-toluene sulfonyl chloride (3.46 g, 18.16 mmol) were added thereto under cooling on ice and the mixture was stirred at room temperature for 24 hours. After completion of the reaction, water was added to the reaction solution, which was extracted with dichloromethane. After drying the extract over anhydrous sodium sulfate, the solvent was removed under reduced pressure and the obtained residue was purified by silica gel column chromatography (chloroform/methanol) to yield 4.30 g (62%) of the title compound in the form of an orange oily product.

$^1$H-NMR(400 MHz,CDCl$_3$)δ:1.81-1.90(1H,m),2.03-2.11(1H,m),2.44(3H,s),3.66-3.73(1H,m),3.87(1H,d,J=4.4 Hz),3.99(2H,d,J=5.4 Hz),4.04(3H,s),4.53-4.65(2H,m),6.79(1H,d,J=8.5 Hz),7.32(2H,d,J=7.8 Hz),7.76(2H,d,J=8.5 Hz),8.06(1H,d,J=8.5 Hz),8.17(1H,s).

Reference Example 77

6-Methoxy-4-{2-[(2R)-oxiran-2-yl]ethyl}pyrido[2,3-b]pyrazin-3(4H)-one

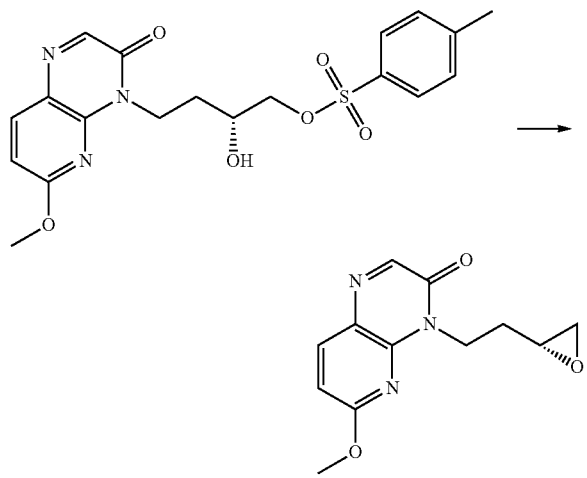

[Formula 141]

In methanol (250 ml) was dissolved (2R)-2-hydroxy-4-(6-methoxy-3-oxopyrido[2,3-b]pyrazin-4(3H)-yl)butyl 4-methylbenzensulfonate (4.30 g, 10.25 mmol), potassium carbonate (1.70 g, 12.30 mmol) was added thereto at room temperature and the mixture was stirred for 4 hours. The reaction solution was concentrated under reduced pressure and the residue was diluted with chloroform and washed with water. After drying the resultant over anhydrous sodium sulfate, the solvent was removed under reduced pressure and the obtained residue was purified by silica gel column chromatography (chloroform/methanol) to yield 2.62 g (quantitative) of the title compound in the form of a yellowish solid.

$^1$H-NMR(400 MHz,CDCl$_3$)δ:1.91-2.00(1H,m),2.11-2.19(1H,m),2.43-2.45(1H,m),2.73(1H,t,J=4.4 Hz),3.02-3.07(1H,m),4.05(3H,s),4.64(2H,t,J=7.1 Hz),6.74(1H,d,J=8.5 Hz),8.03(1H,d,J=8.8 Hz),8.17(1H,s).

Example 28

6-[(4R)-4-{[(2R)-2-Hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one

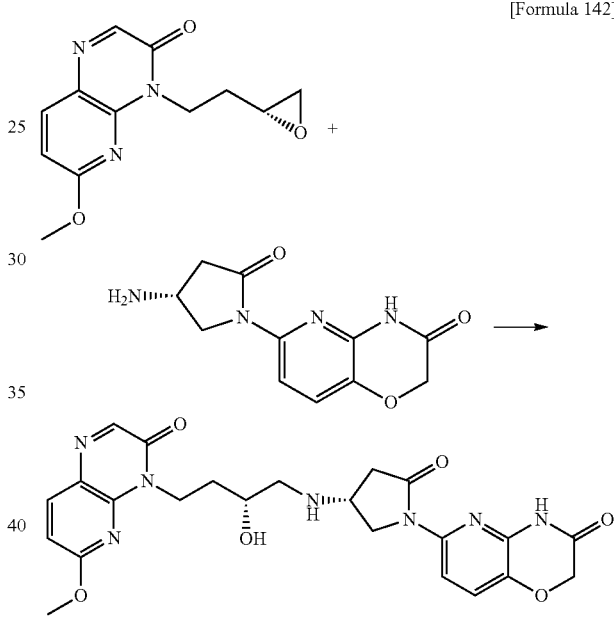

[Formula 142]

In a mixed solvent (16 ml) of ethanol-water (9:1) were suspended 6-methoxy-4-{2-[(2R)-oxiran-2-yl]ethyl}pyrido[2,3-b]pyrazin-3(4H)-one (400 mg, 1.62 mmol) and 6-[(4R)-4-amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21 and 22; 402 mg, 1.62 mmol) and stirred in a sealed tube at 80° C. for 16 hours. The solvent was removed from the reaction solution under reduced pressure and the obtained residue was purified by silica gel column chromatography (chloroform/methanol) to yield 323 mg (40%) of the title compound in the form of a yellowish solid.

$^1$H-NMR(400 MHz,DMSO-d$_6$)δ:1.66-1.76(1H,m),1.83-1.91(1H,m),2.01-2.11(1H,m),2.30-2.36(1H,m),2.49-2.56(2H,m),2.75-2.81(1H,m),3.37-3.43(1H,m),3.58-3.66(1H,m),3.71(1H,dd,J=11.0,3.7 Hz),3.95-3.97(1H,m),3.99(3H,s),4.28-4.36(1H,m),4.45-4.52(1H,m),4.60(2H,s),4.70(1H,d,J=5.0 Hz),6.83(1H,d,J=8.7 Hz),7.37(1H,d,J=8.7 Hz),7.81(1H,d,J=8.7 Hz),8.10(1H,s),8.13(1H,d,J=8.7 Hz),11.13(1H,s).

MS(ESI)m/z:496(M+H)$^+$.

Example 29

6-[(4S)-4-{[(2R)-2-Hydroxy-4-(6-methoxy-3-oxopyrido[2,3-b]pyrazin-4(3H)-yl)butyl]amino}-2-oxopyrrolidin-1-yl]-2H-pyrido[3,2-b][1,4]oxazin-3(4H)-one

[Formula 143]

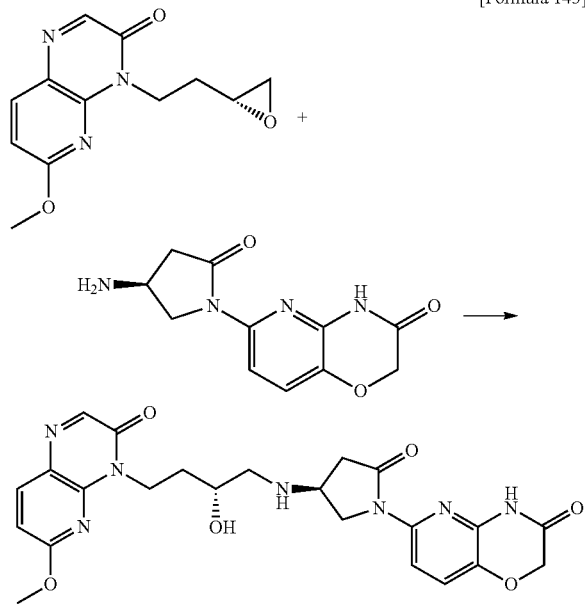

In a mixed solvent (16 ml) of ethanol-water (9:1) were suspended 6-methoxy-4-{2-[(2R)-oxiran-2-yl]ethyl}pyrido[2,3-b]pyrazin-3(4H)-one (Reference Example 77; 400 mg, 1.62 mmol) and 6-[(4S)-4-amino-2-oxopyrrolidin-1-yl]-2H-pyrido[3,2-b][1,4]oxazin-3(4H)-one (Reference Example 22; 402 mg, 1.62 mmol), and the suspension was stirred in a sealed tube at 80° C. for 16 hours. The solvent was removed from the reaction solution under reduced pressure and the obtained residue was purified by silica gel column chromatography (chloroform/methanol) to yield 288 mg (36%) of the title compound in the form of a yellowish solid.

$^1$H-NMR(400 MHz,DMSO-d$_6$)δ:1.68-1.77(1H,m),1.82-1.90(1H,m),2.00-2.11(1H,m),2.32-2.37(1H,m),2.48-2.62(2H,m),2.73-2.79(1H,m),3.36-3.43(1H,m),3.59-3.68(1H,m),3.71(1H,dd,J=11.0,3.7 Hz),3.97-4.03(4H,m),4.29-4.36(1H,m),4.45-4.52(1H,m),4.60(2H,s),4.70(1H,d,J=5.0 Hz),6.84(1H,d,J=8.3 Hz),7.38(1H,d,J=8.7 Hz),7.82(1H,d,J=8.3 Hz),8.11(1H,s),8.13(1H,d,J=8.7 Hz),11.15(1H,s).

MS(ESI)m/z:496(M+H)$^+$.

Reference Example 78

4-[(Benzyloxy)methyl]-6-bromo-2H-1,4-benzoxazin-3(4H)-one

[Formula 144]

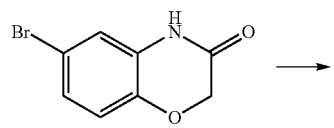

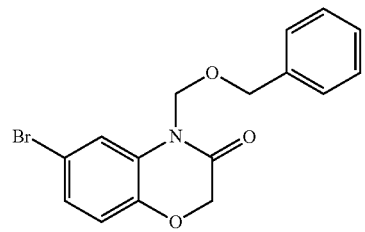

In N,N-dimethylformamide (4 ml) was dissolved 6-bromo-2H-1,4-benzoxazin-3(4H)-one (200 mg, 0.88 mmol). The solution was cooled in an ice bath, the reaction vessel was charged with nitrogen gas, lithium hydride (purity 90%, 11.7 mg, 1.32 mmol) was then added thereto and the mixture was stirred at room temperature for 10 minutes. Thereafter, benzyl chloromethyl ether (0.20 ml, 1.44 mmol) was added dropwise to the reaction solution at the same temperature and the mixture was stirred at the same temperature for 1.5 hours. Thereafter, lithium hydride (purity 90%, 2.3 mg, 0.26 mmol) and benzyl chloromethyl ether (0.04 ml, 0.29 mmol) were added while continuing stirring, whereby the reaction was quenched. The reaction solution was diluted with dichloromethane, washed with water (×4), dried over anhydrous magnesium sulfate and filtered, and the solvent was removed under reduced pressure. The obtained residue was purified by silica gel column chromatography (n-hexane/ethyl acetate) to yield 278 mg (91%) of the title compound in the form of a white solid.

$^1$H-NMR(500 MHz,CDCl$_3$)δ:4.52(2H,s),4.65(2H,s),5.40(2H,s),6.85(1H,d,J=8.6 Hz),7.14(1H,dd,J=8.6,2.3 Hz),7.28-7.36(5H,m),7.48(1H,d,J=2.3 Hz).

MS(ESI)m/z:348,350(M+H)$^+$.

Reference Example 79 tert-Butyl [(3R)-1-{4-[(Benzyloxy)methyl]-3-oxo-3,4-dihydro-2H-1,4-benzoxazin-6-yl}-5-oxopyrrolidin-3-yl]carbamate

[Formula 145]

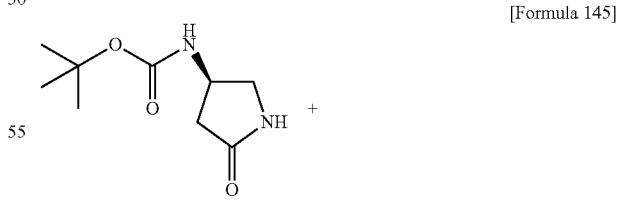

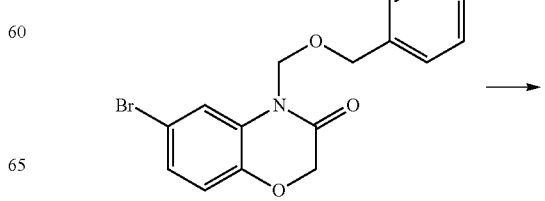

-continued

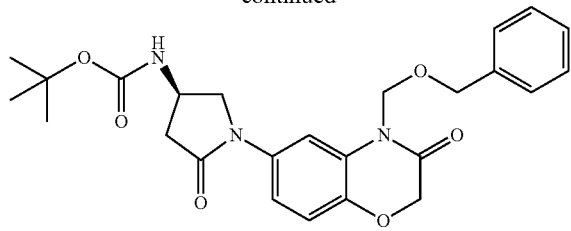

In a reaction vessel were weighed and charged 4-[(Benzyloxy)methyl]-6-bromo-2H-1,4-benzoxazin-3(4H)-one (366 mg, 1.05 mmol), tert-butyl [(3R)-5-oxopyrrolidin-3-yl]carbamate (200 mg, 1.00 mmol), cesium carbonate (652 mg, 2.00 mmol) and 1,4-dioxane (5 ml), which was purged with nitrogen gas, subsequently copper (I) iodide (190 mg, 1.00 mmol) and N,N'-dimethylethylenediamine (0.107 ml, 1.00 mmol) were added thereto, and the mixture was stirred with heating for 9 hours on an oil bath at 100° C. After lowering the temperature to room temperature, the reaction solution was diluted with a mixed solvent of chloroform-methanol (9:1) to remove insoluble material by filtration using celite. The filtrate was concentrated under reduced pressure. The residue was roughly purified by silica gel column chromatography (chloroform/methanol), subsequently crystallized in a mixed solvent of n-hexane-ethyl acetate (1:1) and collected by filtration to yield 373 mg (80%) of the title compound in the form of a white solid.

$^1$H-NMR(400 MHz,CDCl$_3$)δ:1.46(9H,s),2.48(1H,dd, J=17.2,4.8 Hz),2.97(1H,dd,J=17.4,8.3 Hz),3.66(1H,dd, J=10.5,3.7 Hz),4.12(1H,m),4.43(1H,brs),4.53(2H,s),4.66 (2H,s),4.87(1H,brs),5.43(2H,s),6.97(1H,d,J=8.7 Hz),7.15 (1H,dd,J=8.7,2.8 Hz),7.27-7.37(5H,m),7.65(1H,d,J=2.8 Hz).

MS(ESI)m/z:468(M+H)$^+$.

Reference Example 80 tert-Butyl [(3R)-5-oxo-1-(3-oxo-3,4-dihydro-2H-1,4-benzoxazin-6-yl}pyrrolidin-3-yl]carbamate

[Formula 146]

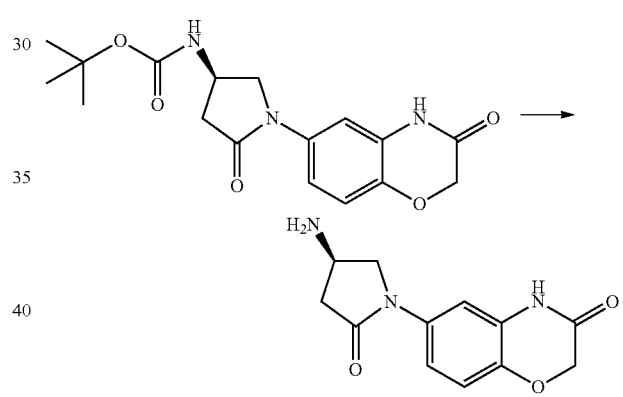

To a mixture of tert-butyl [(3R)-1-{4-[(benzyloxy)methyl]-3-oxo-3,4-dihydro-2H-1,4-benzoxazin-6-yl}-5-oxopyrrolidin-3-yl]carbamate (15.0 g, 32.1 mmol), ammonium formate (6.93 g, 110 mmol), methanol (250 ml) and tetrahydrofuran (93 ml) was added 10% Palladium on carbon (50% wet, 15.0 g) and the mixture was heated under reflux for 1 hour on an oil bath at 100° C. Ammonium formate (7.00 g, 111 mmol) was added and the mixture was further heated under reflux for 1 hour. Subsequently the catalyst was removed by filtration and the residue was washed thoroughly with a mixed solvent of chloroform-methanol (1:1). The filtrate and washings were combined to remove the solvent under reduced pressure and the residue was suspended in water from which the insoluble material was removed by filtration. The residue was washed with water and dried with heating under reduced pressure. 10.33 g (93%) of the title compound was obtained in the form of a white solid.

$^1$H-NMR(400 MHz,DMSO-d$_6$)δ:1.39(9H,s),2.40(1H,dd, J=17.0,5.0 Hz),2.79(1H,dd,J=17.0,8.3 Hz),3.53(1H,dd, J=9.9,3.9 Hz),4.40(1H,dd,J=10.1,6.9 Hz),4.17(1H,brs),4.54 (2H,s),6.93(1H,d,J=9.2 Hz),7.02(1H,dd,J=8.7,2.3 Hz),7.39 (1H,d,J=2.3 Hz),7.44(1H,m),10.72(1H,s).

MS(ESI)m/z:348(M+H)$^+$.

Reference Example 81

6-[(4R)-4-Amino-2-oxopyrrolidin-1-yl]-2H-1,4-benzoxazin-3(4H)-one

[Formula 147]

Trifluoroacetic acid (100 ml) was added to a suspension of tert-butyl [(3R)-5-oxo-1-(3-oxo-3,4-dihydro-2H-1,4-benzoxazin-6-yl)pyrrolidin-3-yl]carbamate (31.2 g, 89.8 mmol) in dichloromethane (150 ml) and the suspension was stirred at room temperature for 2 hours. The solvent was removed under reduced pressure and azeotroped with toluene (×2). The residual solid was suspended in diethyl ether and the insoluble material was collected by filtration. The residue was washed with diethyl ether (×2) and dried to yield the intended trifluoroacetate salt.

Dichloromethane (200 ml) and methanol (100 ml) were added to the obtained trifluoroacetate salt, and triethylamine (30 ml) was added thereto under cooling on ice. After heating the reaction mixture to 50° C. to dissolve the insoluble material, silica gel (NH type, 150 ml) was added thereto, and the solvent was evaporated. The residue was purified by silica gel column chromatography (NH type, chloroform/methanol) to yield 21.7 g (98%) of the title compound in the form of a white solid.

Isopropyl alcohol (60 ml) and water (60 ml) were added to the obtained solid, which was dissolved by heating to 80° C. and the mixture was cooled in the air. The solid formed was collected by filtration and the optical purity was increased. 18.51 g (83%,>99% ee/analyzed on CHIRALCEL, OD-H column).

$^1$H-NMR(500 MHz,CD$_3$OD)δ:2.35(1H,dd,J=17.2,4.6 Hz),2.86(1H,dd,J=17.2,7.4 Hz),3.53(1H,J=10.0,3.7 Hz), 3.72-3.76(1H,m),4.06(1H,dd,J=10.0,6.6 Hz),4.54(2H,s), 6.94(1H,d,J=8.6 Hz),7.05(1H,dd,J=8.9,2.6 Hz),7.33(1H,d, J=2.3 Hz).

MS(ESI)m/z:248(M+H)$^+$.

Reference Example 82

Benzyl 6-methoxy-3-oxo-3,4-dihydroquinoxalin-1 (2H)-carboxylate

[Formula 148]

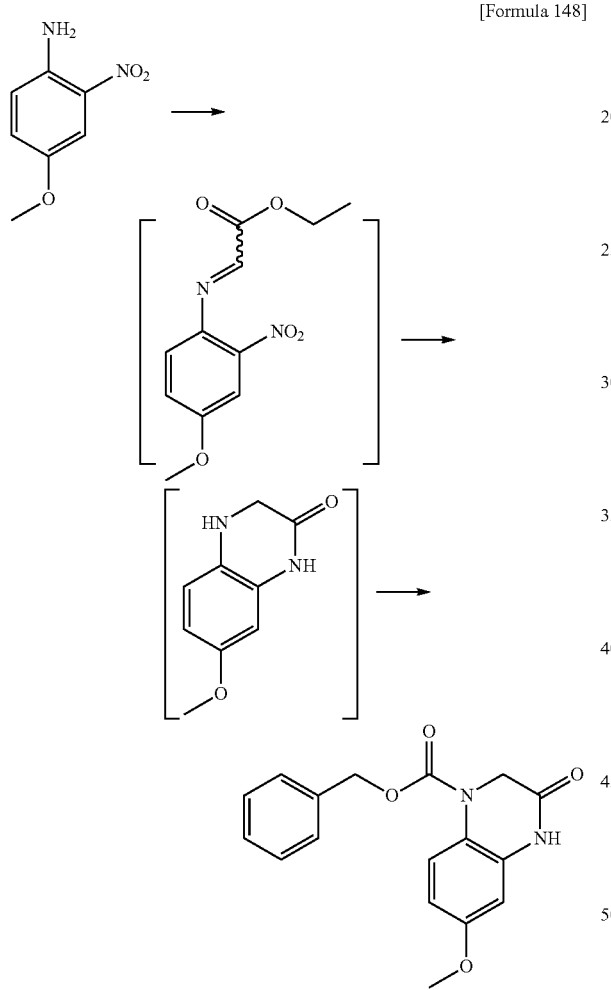

A mixture of 4-methoxy-2-nitroaniline (1.68 g, 10.0 mmol), ethyl glyoxylate/toluene solution (50 wt %, 1.98 ml, 10.0 mmol) and toluene (20 ml) was heated under reflux under a nitrogen gas atmosphere for 17 hours while removing water using a Dean-Stark apparatus. The solvent was removed under reduced pressure to yield [(4-methoxy-2-nitrophenyl)imino]ethyl acetate crude product.

The obtained [(4-methoxy-2-nitrophenyl)imino]ethyl-acetate crude product was dissolved in methanol (30 ml) and 10% palladium on carbon (50% wet, 1.20 g) was added thereto and the mixture was stirred at room temperature for 3 hours under a hydrogen gas atmosphere. The catalyst was removed by filtration using celite and the filtrate was concentrated under reduced pressure to yield 1.733 g of a crude product of 7-methoxy-3,4-dihydroquinoxalin-2(1H)-one. In dichloromethane (12 ml) was dissolved 518 mg of the obtained crude product of 7-methoxy-3,4-dihydroquinoxalin-2(1H)-one, and under a nitrogen gas atmosphere in an ice bath, N,N-diisopropylethylamine (0.604 ml, 3.47 mmol) and subsequently benzyl chloroformate (0.408 ml, 2.77 mmol) were added thereto. Then, the mixture was stirred at room temperature for 17 hours, a saturated sodium hydrogen carbonate aqueous solution was added thereto and the resultant was extracted with dichloromethane. The extract was combined, dried over anhydrous sodium sulfate and the solvent was removed under reduced pressure. The obtained residue was purified by silica gel column chromatography (n-hexane/ethyl acetate) to yield 291 mg (40%) of the title compound in the form of a light red solid.

$^1$H-NMR(400 MHz,CDCl$_3$)δ:3.79(3H,s),4.43(2H,s),5.24 (2H,s),6.35(1H,d,J=2.9 Hz),6.61(1H,brd,J=6.3 Hz),7.34-7.38(6H,m),7.64(0.8H,brs).

Reference Example 83

Benzyl 4-(3,3-dimethoxypropyl)-6-methoxy-3-oxo-3,4-dihydroquinoxalin-1(2H)-carboxylate

[Formula 149]

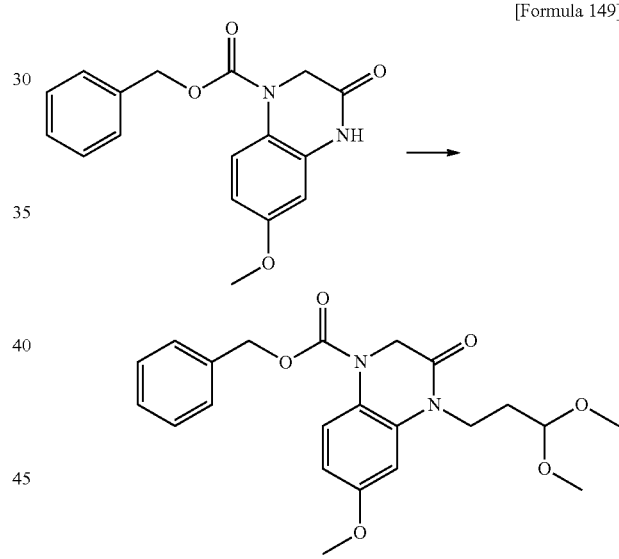

To a solution of benzyl 6-methoxy-3-oxo-3,4-dihydroquinoxalin-1(2H)-carboxylate (291 mg, 0.932 mmol) in N,N-dimethylformamide (5 ml), lithium bromide (89 mg, 1.025 mmol) and subsequently sodium hydride (55%, 45 mg, 1.025 mmol) were added under a nitrogen gas atmosphere in an ice bath. The solution was stirred at room temperature for 1 hour. The reaction solution was cooled on ice again and 3-bromopropionaldehyde dimethyl acetal (0.184 ml, 1.212 mmol) was added thereto. After stirring overnight at room temperature, the reaction solution was diluted with ethyl acetate and washed sequentially with a saturated sodium hydrogen carbonate aqueous solution and saturated sodium chloride solution. After drying the resultant over anhydrous sodium sulfate, the solvent was removed under reduced pressure and the obtained residue was purified by silica gel column chromatography (n-hexane/ethyl acetate) to yield 386 mg (quantitative) of the title compound in the form of a yellowish brown oil.

¹H-NMR(400 MHz,CDCl₃)δ:1.99(2H,m),3.33(6H,s), 3.82(3H,s),3.97(2H,t,J=7.6 Hz),4.40(2H,s),4.44(1H,t,J=5.4 Hz),5.23(2H,s),6.63(1H,brd,J=8.8 Hz),6.71(1H,d,J=2.7 Hz), 7.33-7.55(6H,m).

Reference Example 84

1-(3,3-Dimethoxypropyl)-7-methoxy-3,4-dihydro-quinoxalin-2(1H)one

[Formula 150]

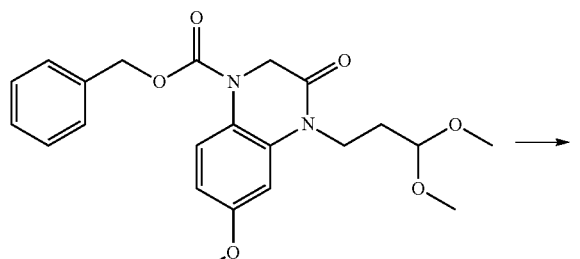

Benzyl 4-(3,3-dimethoxypropyl)-6-methoxy-3-oxo-3,4-dihydroquinoxalin-1(2H)-carboxylate (386 mg, 0.931 mmol) was dissolved in methanol (5 ml), 10% palladium on carbon (50% wet, 200 mg) was added thereto and the mixture was stirred at room temperature for 4 hours under a hydrogen gas atmosphere. After removing the catalyst by filtration using celite, the filtrate was concentrated under reduced pressure to yield 201 mg (77%) of a crude product of the title compound in the form of a yellow oil.

¹H-NMR(400 MHz,CDCl₃)δ:1.99(2H,m),3.36(6H,s), 3.63(0.8H,brs),3.78(3H,s),3.87(2H,s),3.98(2H,t,J=7.6 Hz), 4.47(1H,t,J=5.7 Hz),6.48(1H,dd,J=8.5,2.5 Hz),6.65(1H,d, J=8.3 Hz),6.66(1H,d,J=2.8 Hz).

Reference Example 85

1-(3,3-Dimethoxypropyl)-7-methoxyquinoxalin-2 (1H)one

[Formula 151]

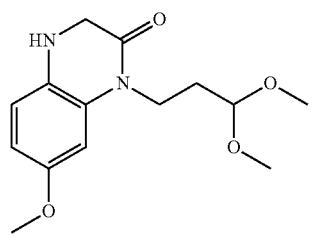

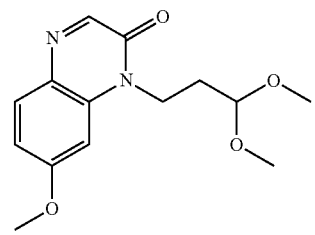

In dichloromethane (10 ml) was dissolved 1-(3,3-dimethoxypropyl)-7-methoxy-3,4-dihydroquinoxalin-2(1H) one (201 mg, 0.717 mmol) under a nitrogen gas atmosphere, manganese dioxide (733 mg, 7.17 mmol) was added thereto at room temperature and the mixture was stirred at the same temperature for 17 hours. The insoluble material was removed by filtration using celite, the filtrate was concentrated under reduced pressure, and the residue was purified by silica gel column chromatography (n-hexane/ethyl acetate) to yield 143 mg (72%) of the title compound in the form of a yellowish solid.

Reference Example 86

1-[2-(1,3-Dioxolan-2-yl)ethyl]-6,7-difluoroquinoxa-lin-2(1H)one

[Formula 152]

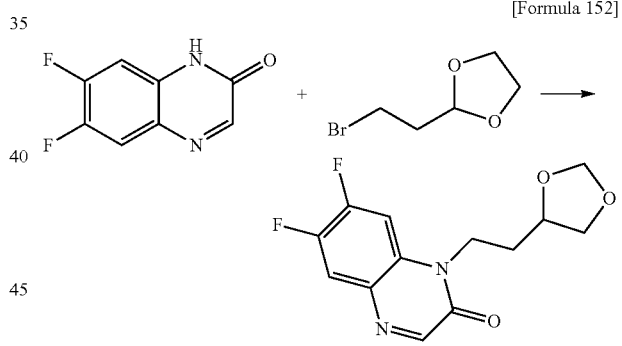

Lithium hydride (52 mg, 6.5 mmol) was added to a solution of 6,7-difluoroquinoxalin-2(1H)one (1 g, 5.4 mmol) in N,N-dimethylformamide (10 ml) under cooling on ice and the reaction mixture was stirred at room temperature for 30 minutes. The mixture was cooled on ice again, a solution of 2-(2-bromoethyl)-1,3-dioxolane (0.8 ml, 6.5 mmol) in N,N-dimethylformamide (2 ml) was gradually added thereto and the obtained mixture was stirred for 4 hours. Water was gradually added to the reaction solution and the mixture was extracted with ethyl acetate. The organic layer was dried over anhydrous sodium sulfate and the solvent was removed under reduced pressure. The residue was purified by silica gel column chromatography (hexane/ethyl acetate) to yield 0.6 g (39%) of the title compound.

¹H-NMR(400 MHz,CDCl₃)δ:2.08-2.15(2H,m),3.87-4.07 (4H,m),4.30-4.33(2H,m),5.00-5.02(1H,m),7.31-7.35(1H, m),7.67-7.71(1H,m),8.22-8.25(1H,s).

MS(ESI)m/z:283(M+H)⁺.

Reference Example 87

3-(6,7-Difluoro-2-oxoquinoxalin-1(2H)-yl)propanal

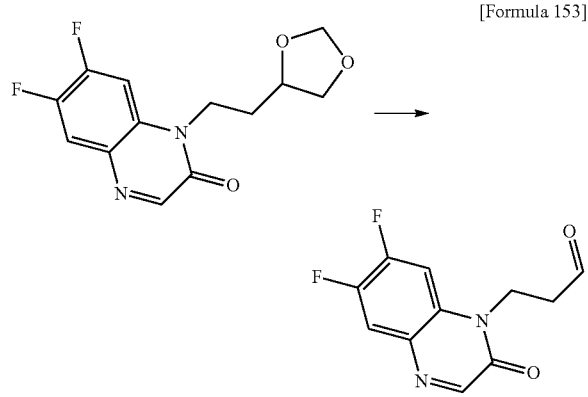

[Formula 153]

To a solution of 1-[2-(1,3-dioxolan-2-yl)ethyl]-6,7-difluoroquinoxalin-2(1H)one (0.6 g, 2.1 mmol) in dioxane (10 ml) was added 4N hydrochloric acid (10 ml) and the mixture was stirred at room temperature for 4 hours. An aqueous solution of sodium hydrogen carbonate was added thereto, the mixture was extracted with ethyl acetate, and the obtained organic layer was dried over anhydrous sodium sulfate and concentrated under reduced pressure. The obtained crude product was dried in vacuum and used as such for the next step. 0.3 g (59%).

Example 30

6-[(4R)-4-({[3-(6,7-Difluoro-2-oxoquinoxalin-1(2H)-yl)propyl]amino}methyl)-2-oxopyrrolidin-1-yl]-2H-pyrido[3,2-b][1,4]oxazin-3(4H)-one

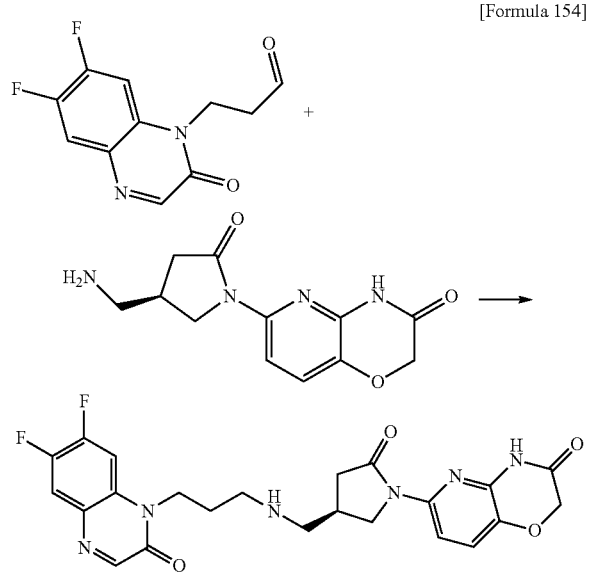

[Formula 154]

Acetic acid (32 mg, 0.58 mmol) was added to a mixture of 3-(6,7-difluoro-2-oxoquinoxalin-1(2H)-yl)propanal (0.1 g, 0.45 mmol), 6-[(4R)-4-(aminomethyl)-2-oxopyrrolidin-1-yl]-2H-pyrido[3,2-b][1,4]oxazin-3(4H)-one (Reference Examples 54, 0.11 g, 0.45 mmol), molecular sieve (4A, 0.1 g) and methanol (4 ml). The obtained mixture was stirred for 20 minutes, cooled on ice and sodium triacetoxyborohydride (0.11 g, 0.58 mmol) was gradually added thereto. Then, the mixture was stirred at room temperature for 4 hours, an aqueous solution of sodium hydrogen carbonate was added thereto and the mixture was extracted with ethyl acetate. The obtained crude product was purified by silica gel column chromatography (dichloromethane/methanol) to yield 15 mg (7%) of the title compound.

$^1$H-NMR(400 MHz,CDCl$_3$)δ:1.99(2H,m),2.40-2.46(1H,m),2.59(1H,m),2.69-2.82(4H,m),3.73-3.77(1H,m),4.08-4.13(1H,m),4.30-4.34(2H,m),4.60-4.64(3H,m),7.26-7.36(2H,m),7.70-7.75(1H,m),7.97-8.00(1H,m),8.15(1H,s).

MS(ESI)m/z:486(M+H)$^+$.

Reference Example 88

1-[2-(1,3-Dioxolan-2-yl)ethyl]-6-fluoroquinoxalin-2(1H)one

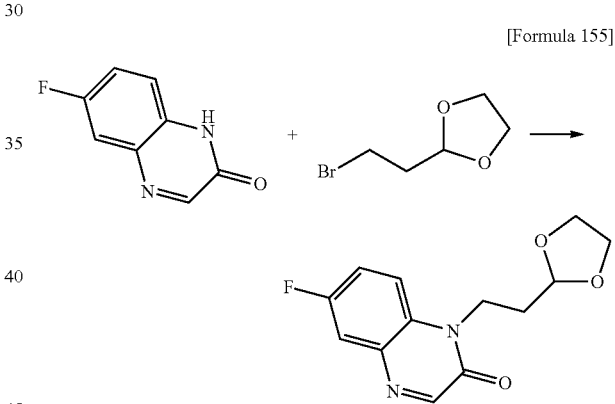

[Formula 155]

Lithium hydride (57 mg, 7.3 mmol) was added to a solution of 6-fluoroquinoxalin-2(1H)one (1 g, 6.0 mmol) in N,N-dimethylformamide (6 ml) under cooling on ice and the mixture was stirred at room temperature for 30 minutes. The mixture was cooled on ice again and a solution of 2-(2-bromoethyl)-1,3-dioxolane (0.88 ml, 7.3 mmol) in N,N-dimethylformamide (2 ml) was gradually added thereto and the mixture was stirred for 4 hours. Water was added thereto, the mixture was then extracted with ethyl acetate, and the extract was dried over anhydrous sodium sulfate and concentrated under reduced pressure. The residue was purified by silica gel column chromatography (hexane/ethyl acetate) to yield 0.5 g (32%) of the title compound.

$^1$H-NMR(400 MHz,DMSO-d$_6$)δ:1.93-1.99(2H,m),3.76-3.80(2H,m),3.89-3.92(2H,m),4.23-4.27(2H,m),4.96-4.99(1H,m),7.17-7.28(1H,m),7.45-7.48(1H,m),7.88-7.90(1H,m),8.18(1H,s).

MS(ESI)m/z:265(M+H)$^+$.

Reference Example 89

3-(6-Fluoro-2-oxoquinoxalin-1(2H)-yl)propanal

[Formula 156]

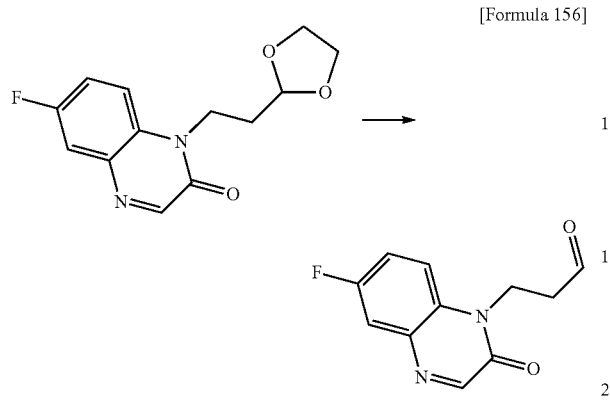

To a solution of 1-[2-(1,3-dioxolan-2-yl)ethyl]-6-difluoro-quinoxalin-2(1H)one (0.5 g, 1.9 mmol) in 1,4-dioxane (5 ml) was added 4N hydrochloric acid (10 ml) and the mixture was stirred at room temperature for 3 hours. A sodium hydrogen carbonate aqueous solution was added thereto, the mixture was extracted with ethyl acetate, and the obtained organic layer was dried over anhydrous sodium sulfate and concentrated under reduce pressure. The obtained crude product was dried under vacuum and used as such for next step. 0.2 g (48%).

MS(ESI)m/z:221(M+H)$^+$.

Example 31

6-[(4R)-4-({[3-(6-Fluoro-2-oxoquinoxalin-1(2H)-yl)propyl]amino}methyl)-2-oxopyrrolidin-1-yl]-2H-pyrido[3,2-b][1,4]oxazin-3(4H)-one

[Formula 157]

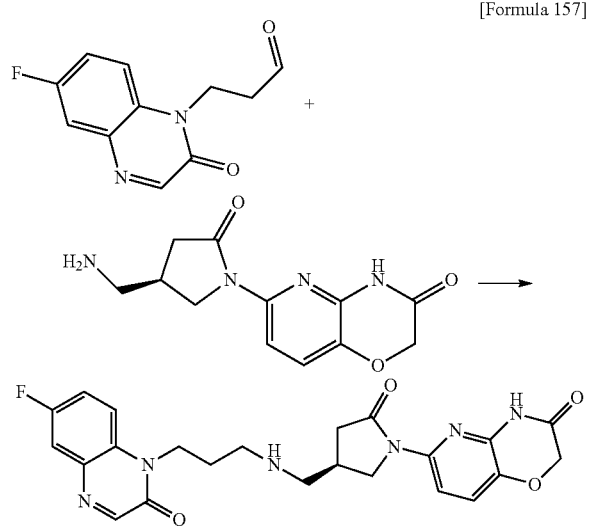

A mixture of 3-(6-fluoro-2-oxoquinoxalin-1(2H)-yl)propanal (0.1 g, 0.45 mmol), 6-[(4R)-4-(aminomethyl)-2-oxopyrrolidin-1-yl]-2H-pyrido[3,2-b][1,4]oxazin-3(4H)-one (Reference Examples 54, 0.11 g, 0.45 mmol) DMF (3 ml) and molecular sieve (4 A, 0.1 g) was stirred at room temperature for 20 minutes. The reaction mixture was cooled on ice and sodium triacetoxyborohydride (0.12 g, 0.54 mmol) was gradually added thereto. Then, the mixture was stirred at room temperature for 4 hours, a sodium hydrogen carbonate aqueous solution was added thereto and the mixture was extracted with ethyl acetate. The obtained crude product was purified by thin layer chromatography (dichloromethane/methanol) to yield the title compound. 8 mg (2%).

$^1$H-NMR(400 MHz,CDCl$_3$)δ:1.96-2.00(2H,m),2.39-2.45 (2H,m),2.55(1H,m),2.65-2.81(4H,m),3.71-3.76(1H,m), 4.06-4.11(1H,m),4.31-4.35(2H,m),4.63(2H,s),7.06-7.11 (1H,m),7.16-7.21(1H,m),7.28-7.31(1H,m), 7.88-7.92(1H,m),7.99(1H,d,J=8 Hz),8.01(1H,s).

MS(ESI)m/z:467(M+H)$^+$.

Example 32

6-[(4R)-4-{[3-(6,7-Difluoro-2-oxoquinoxalin-1(2H)-yl)propyl]amino}-2-oxopyrrolidin-1-yl]-2H-pyrido[3,2-b][1,4]-benzoxazin-3(4H)-one

[Formula 158]

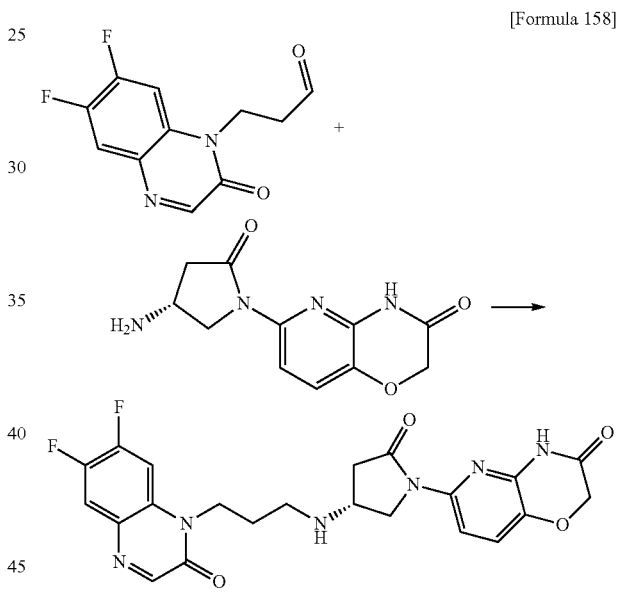

Acetic acid (32 mg, 0.54 mmol) was added to a mixture of 3-(6,7-difluoro-2-oxoquinoxalin-1(2H)-yl)propanal (0.1 g, 0.42 mmol), 6-[(4R)-4-amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21 and 22; 0.1 g, 0.42 mmol), methanol (4 ml) and molecular sieve (4 A, 0.1 g), and the mixture was stirred at room temperature for 20 minutes. After cooling on ice, sodium triacetoxyborohydride (0.11 g, 0.54 mmol) was gradually added thereto. Then, the mixture was stirred at room temperature for 4 hours, a sodium hydrogen carbonate aqueous solution was added thereto and the mixture was extracted with ethyl acetate. The obtained crude product was purified by silica gel column chromatography (dichloromethane/methanol) to yield 20 mg (10%) of the title compound.

$^1$H-NMR(400 MHz,CDCl$_3$)δ:2.00-2.03(2H,m),2.53-2.59 (1H,m),2.76-2.77(2H,m),2.86-2.92(1H,m),3.53(1H,m), 3.93-3.95(1H,m),4.09-4.14(1H,m),4.29-4.33(2H,m),4.57-

4.62(2H,m),7.20-7.26(1H,m),7.29-7.32(1H,m),7.68-7.73(1H,m),7.95-7.98(1H,d,J=12 Hz),8.26(1H,s).

MS(ESI)m/z:471(M+H)⁺.

Reference Example 90

1-[2-(1,3-Dioxolan-2-yl)ethyl]-7-fluoroquinoxalin-2(1H)one

[Formula 159]

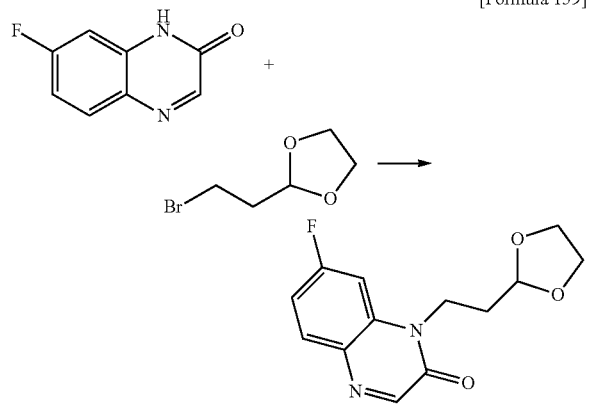

Lithium hydride (88 mg, 011 mmol) was added to a solution of 7-fluoroquinoxalin-2(1H)one (1.3 g, 7.8 mmol) in N,N-dimethylformamide (40 ml) under cooling on ice and the mixture was stirred at room temperature for 30 minutes. The mixture was cooled on ice and 2-(2-bromoethyl)-1,3-dioxolane (1.33 ml, 11 mmol) was added thereto. The obtained mixture was stirred at room temperature for 24 hours, water was then gradually added thereto and the mixture was extracted with ethyl acetate. The organic layer was dried over anhydrous sodium sulfate and concentrated under reduced pressure. The obtained crude product was purified by silica gel column chromatography (dichloromethane/methanol) to yield 0.6 g (29%) of the title compound.

¹H-NMR(400 MHz,DMSO-d₆)δ:1.91-1.99(2H,m),3.76-3.80(2H,m),3.88-3.93(2H,m),4.23-4.27(2H,m),4.96-4.98(1H,m),7.23-7.28(1H,m),7.45-7.49(1H,m),7.87-7.91(1H,m),8.18(1H,s).

MS(ESI)m/z:265(M+H)⁺.

Reference Example 91

3-(7-Fluoro-2-oxoquinoxalin-1(2H)-yl)propanal

[Formula 160]

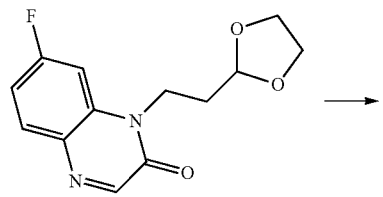

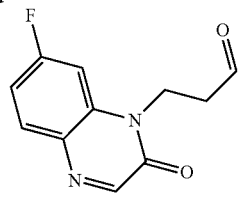

To a solution of 1-[2-(1,3-dioxolan-2-yl)ethyl]-7-fluoroquinoxalin-2(1H)-one (0.6 g, 2.3 mmol) in 1,4-dioxane (6.8 ml) was added 4N hydrochloric acid (24 ml) and the mixture was stirred at room temperature for 5 hours. An aqueous solution of sodium hydrogen carbonate was added thereto and then the mixture was extracted with ethyl acetate. The organic layer was dried over anhydrous sodium sulfate, concentrated under reduced pressure and dried under vacuum. 0.6 g (quantitative).

MS(ESI)m/z:221(M+H)⁺.

Example 33

6-[(4R)-4-{[3-(7-Fluoro-2-oxoquinoxalin-1(2H)-yl)propyl]amino}-2-oxopyrrolidin-1-yl]-2H-pyrido[3,2-b][1,4]oxazin-3(4H)-one

[Formula 161]

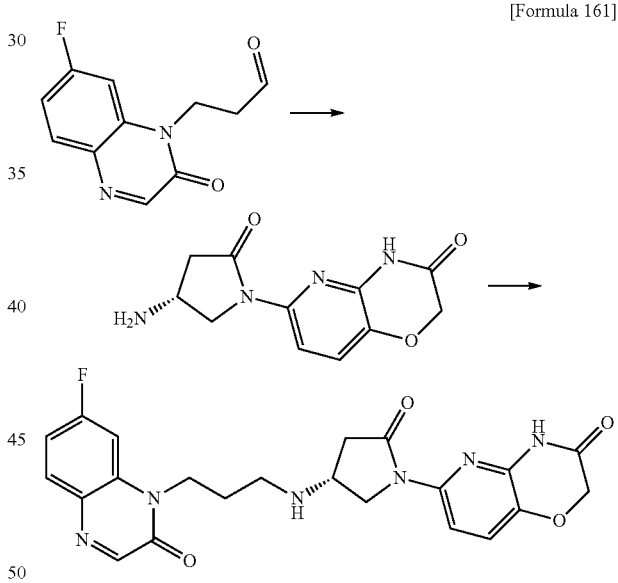

Acetic acid (0.042 ml, 0.70 mmol) was added to a mixture of 3-(7-fluoro-2-oxoquinoxalin-1(2H)-yl)propanal (0.120 g, 0.54 mmol), 6-[(4R)-4-amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21 and 22; 0.185 g, 0.70 mmol) and N,N-dimethylformamide (1.6 ml). The mixture was stirred for 0.5 hours, to which sodium triacetoxyborohydride (0.15 g, 0.70 mmol) was gradually added and stirred for 12 hours. An aqueous solution of sodium hydrogen carbonate was added to the reaction mixture under cooling on ice and the mixture was extracted with ethyl acetate. The obtained crude product was purified by thin layer chromatography (dichloromethane/methanol) to yield 70 mg (29%) of the title compound.

¹H-NMR(400 MHz,DMSO-d₆)δ:1.81(2H,m),2.36-2.42(1H,m),2.53-2.54(2H,m),2.78-2.85(1H,m),3.42(1H,m),3.76-3.82(1H,m),4.02-4.04(1H,m),4.22(2H,m),4.61(2H,s),7.26(1H,m),7.39-7.42(1H,d,J=12 Hz),7.57-7.59(1H,d,J=8 Hz),7.80-7.82(1H,d,J=8 Hz),7.89-7.92(1H,m),8.18(1H,s).

MS(ESI)m/z:453(M+H)⁺.

Example 34

6-[(4S)-4-{[3-(6-Methoxy-3-oxopyrido[2,3-b]pyrazin-4(3H)-yl)propyl]amino}-2-oxopyrrolidin-1-yl]-2H-pyrido[3,2-b][1,4]oxazin-3(4H)-one

[Formula 162]

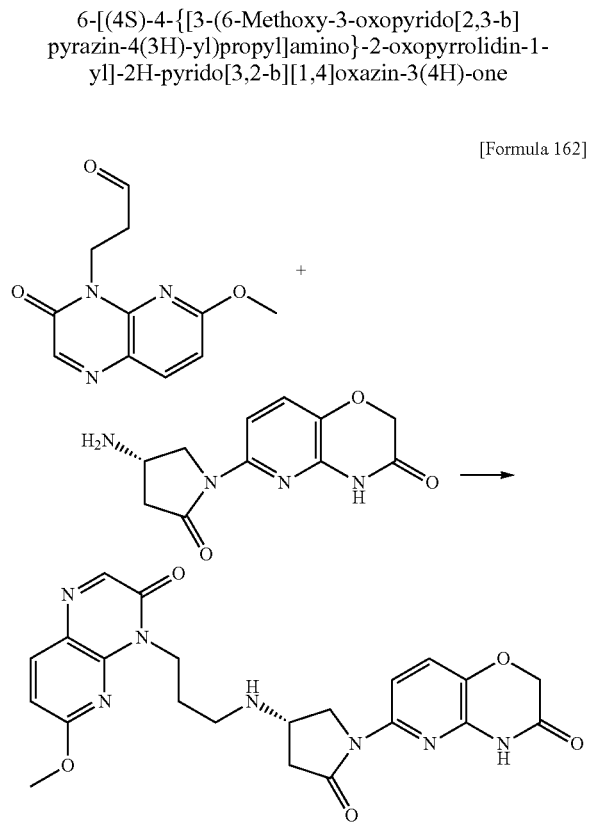

Acetic acid (0.06 g, 1 mmol) was added dropwise to a mixture of 3-(6-methoxy-3-oxopyrido[2,3-b]pyrazin-4(3H)-yl)propanal (synthesized with reference to WO2008/9700; 0.2 g, 0.85 mmol), 6-[(4S)-4-amino-2-oxopyrrolidin-1-yl]-2H-pyrido[3,2-b][1,4]oxazin-3(4H)-one (Reference Example 22; 0.25 g, 1.0 mmol) and N,N-dimethylformamide (4 ml). Sodium triacetoxyborohydride (0.23 g, 1.1 mmol) was gradually added under cooling on ice to the obtained mixture, which was then stirred for 10 minutes. The mixture was further stirred at room temperature for 2 hours, cooled on ice, a saturated sodium hydrogen carbonate aqueous solution was added thereto, and the resultant was extracted with dichloromethane. The organic layer was dried over anhydrous sodium sulfate and concentrated under reduced pressure. The obtained crude product was purified by silica gel column chromatography (dichloromethane/methanol) to yield 45 mg (11%) of the title compound.

¹H-NMR(400 MHz,DMSO-d₆)δ:1.85(2H,m),2.32(1H,m),2.59(2H,m),2.74(1H,m),3.32(1H,m),3.70(1H,m),3.98(4H,m),4.37(2H,m),4.60(2H,s),6.82-6.84(1H,d,J=8 Hz),7.37-7.40(1H,d,J=12 Hz),7.81-7.83(1H,d,J=8 Hz),8.11-8.14(2H,m).

MS(ESI)m/z:466(M+H)⁺.

Example 35

6-[(4R)-4-{[3-(6-Methoxy-3-oxopyrido[2,3-b]pyrazin-4(3H)-yl)propyl]amino}-2-oxopyrrolidin-1-yl]-2H-pyrido[3,2-b][1,4]oxazin-3(4H)-one

[Formula 163]

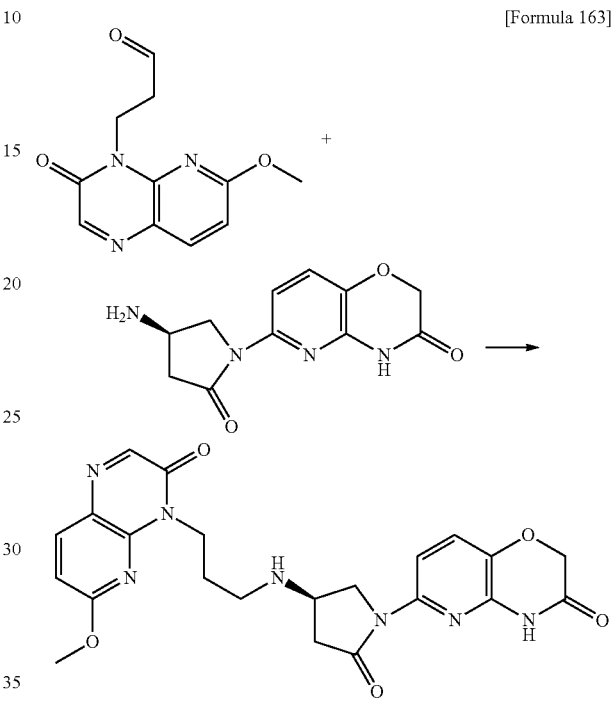

Acetic acid (0.06 g, 1 mmol) was added dropwise to a mixture of 3-(6-methoxy-3-oxopyrido[2,3-b]pyrazin-4(3H)-yl)propanal (synthesized with reference to WO2008/9700; 0.2 g, 0.85 mmol), 6-[(4R)-4-amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21 and 22; 0.25 g, 1.0 mmol) and N,N-dimethylformamide (4 ml). The mixture was cooled on ice and sodium triacetoxyborohydride (0.23 g, 1.1 mmol) was gradually added thereto. The mixture was stirred for 10 minutes under cooling on ice and subsequently stirred at room temperature for 2 hours. The reaction solution was cooled on ice again and a sodium hydrogen carbonate aqueous solution was added thereto. The obtained mixture was extracted with dichloromethane and the extract was dried over anhydrous sodium sulfate and concentrated under reduced pressure. The obtained crude product was purified by silica gel column chromatography (dichloromethane/methanol) to yield 90 mg (23%) of the title compound.

¹H-NMR(400 MHz,DMSO-d₆)δ:1.84-1.87(2H,m),2.28-2.34(1H,m),2.59(2H,m),2.73-2.79(1H,m),3.33-3.37(1H,m),3.67-3.71(1H,m),3.95-3.98(4H,m),4.35-4.38(2H,t),4.60(2H,s),6.82-6.84(1H,d,J=8 Hz),7.37-7.39(1H,d,J=8 Hz),7.81-7.85(1H,m),8.11-8.14(2H,m).

MS(ESI)m/z:466(M+H)⁺.

Example 36

6-[(4R)-4-{[3-(7-Methoxy-2-oxoquinoxalin-1(2H)-yl)propyl]amino}-2-oxopyrrolidin-1-yl]-2H-pyrido[3,2-b][1,4]oxazin-3(4H)-one

[Formula 164]

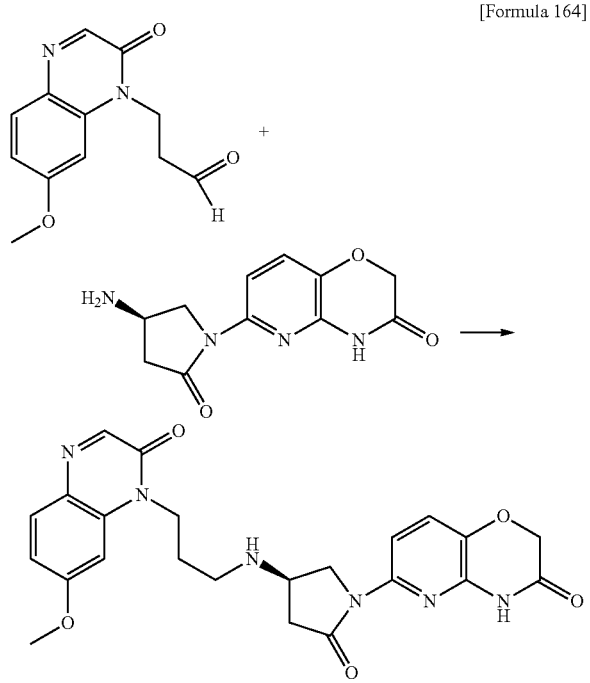

In N,N-dimethylformamide (5 ml) was dissolved 3-(7-methoxy-2-oxoquinoxalin-1(2H)-yl)propanal (Reference Example 8,200 mg, 0.86 mmol). 6-[(4R)-4-Amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21 and 22; 262 mg, 1.03 mmol) was added thereto and subsequently acetic acid (65 mg, 1.12 mmol) was added. The obtained mixture was stirred at room temperature for 1 hour, cooled on ice and sodium triacetoxyborohydride (237 mg, 1.12 mmol) was added thereto. After stirring at room temperature for 2 hours, sodium hydrogen carbonate aqueous solution was added thereto and the mixture was extracted with ethyl acetate. The obtained organic layer was washed with water and a saturated sodium chloride solution, dried over anhydrous sodium sulfate and the solvent was removed under reduced pressure. The obtained crude product was purified by thin layer chromatography (dichloromethane/methanol) to yield 80 mg (20%) of the title compound.

$^1$H-NMR(400 MHz,DMSO-$d_6$)δ:1.79-1.81(2H,m),2.36-2.39(1H,m),2.62(2H,m),2.77-2.83(1H,m),3.41(1H,brs),3.73-3.76(1H,m),3.88(3H,s),3.99-4.03(1H,m),4.24-4.27(2H,m),4.60(2H,s),6.98-7.00(1H,m),7.07(1H,s),7.38-7.40(1H,m),7.74-7.76(1H,m),7.82-7.84(1H,d,J=8 Hz),8.03(1H,s).

MS(ESI)m/z:465(M+H)$^+$.

Example 37

6-[(4R)-4-({[3-(7-Fluoro-2-oxoquinoxalin-1(2H)-yl)propyl]amino}methyl)-2-oxopyrrolidin-1-yl]-2H-pyrido[3,2-b][1,4]oxazin-3(4H)-one

[Formula 165]

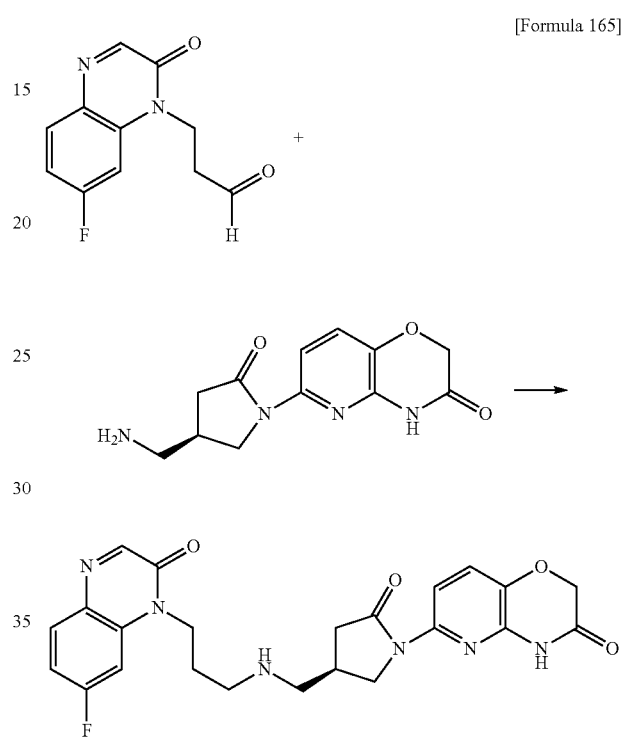

In N,N-dimethylformamide (5 ml) was dissolved 3-(7-fuoro-2-oxoquinoxalin-1(2H)-yl)propanal] (Reference Example 91, 250 mg, 1.13 mmol). 6-[(4R)-4-(Aminomethyl)-2-oxopyrrolidin-1-yl]-2H-pyrido[3,2-b][1,4]oxazin-3(4H)-one (Reference Example 54, 595 mg, 2.27 mmol) was added thereto and the mixture was stirred at room temperature for 1 hour. Then, under ice cooling, sodium triacetoxyborohydride (718 mg, 3.39 mmol) was added thereto and the reaction solution was stirred at room temperature for 2 hours. An aqueous solution of sodium hydrogen carbonate was added to the reaction solution, which was extracted with ethyl acetate and the extract was washed with water and saturated sodium chloride solution. The obtained organic layer was dried over anhydrous sodium sulfate and the solvent was removed under reduced pressure. The obtained crude product was purified by thin layer chromatography (dichloromethane/methanol) to yield 20 mg (4%) of the title compound.

$^1$H-NMR(400 MHz,DMSO-$d_6$)δ:1.78(2H,m),2.37-2.60(7H,m),3.66-3.70(1H,m),4.01-4.24(3H,m),4.59(2H,s),7.23-7.25(1H,m),7.37-7.39(1H,d,J=8 Hz),7.60-7.63(1H,d,J=12 Hz),7.81-7.84(1H,d,J=12 Hz),7.87-7.91(1H,m),8.19(1H,s).

MS(ESI)m/z:467(M+H)$^+$.

Reference Example 92

1-[2-(1,3-Dioxolan-2-yl)ethyl]-7-methoxy-4-methylquinolin-2(1H)one

[Formula 166]

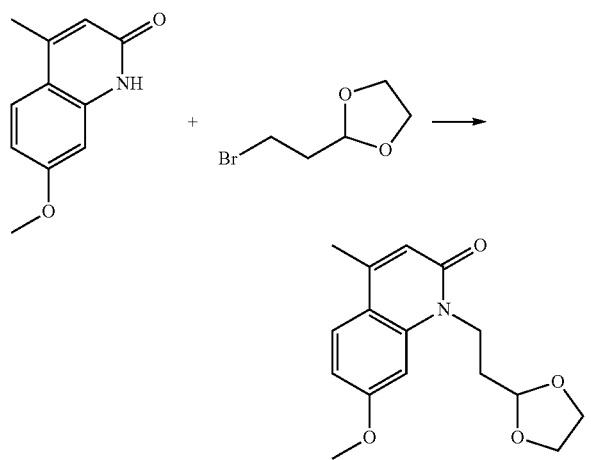

In N,N-dimethylformamide (15 ml) was dissolved 7-methoxy-4-methylquinolin-2(1H)one (1.5 g, 6.06 mmol), sodium iodide (2.3 g, 15.9 mmol) was added thereto under cooling on ice and lithium hydride (188 mg, 15.9 mmol) was gradually added thereto. After stirring for 1 hour under cooling on ice, 2-(2-bromoethyl)-1,3-dioxolane (1.6 ml, 15.9 mmol) was gradually added thereto. The reaction solution was stirred overnight at room temperature and then the extract was partitioned into ethyl acetate-water, whereby the organic layer was separated. The obtained organic layer was washed with water and saturated sodium chloride solution and dried over anhydrous sodium sulfate. The solvent was removed under reduced pressure and the obtained residue was purified by silica gel column chromatography (hexane/ethyl acetate) to yield 1 g (57%) of the title compound.

$^1$H-NMR(400 MHz,DMSO-d$_6$)δ:1.89-1.94(2H,m),2.83 (3H,s),3.81-3.83(2H,m),3.86(3H,s),3.86-3.97(2H,m),4.25-4.29(2H,m),4.96-4.98(1H,m),6.33(1H,brs),6.89-6.92(1H, m),6.97-6.98(1H,brs),7.69-7.71(1H,d,J=8 Hz).

MS(ESI)m/z:290(M+H)$^+$.

Reference Example 93

3-(7-Methoxy-4-methyl-2-oxoquinolin-1(2H)-yl)propanal

[Formula 167]

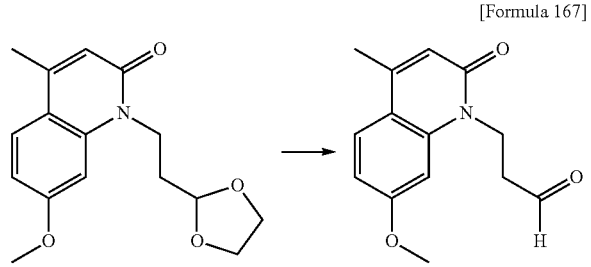 [SMILES: COc1ccc2c(C)cc(=O)n(CCC3OCCO3)c2c1 ; COc1ccc2c(C)cc(=O)n(CCC=O)c2c1]

To a solution of 1-[2-(1,3-dioxolan-2-yl)ethyl]-7-methoxy-4-methylquinolin-2(1H)one (30 ml) was added 4N hydrochloric acid (30 ml) and the mixture was stirred at room temperature for 2 hours. An aqueous solution of sodium carbonate/hydrogen carbonate was added to the reaction solution and the mixture was extracted with ethyl acetate. The obtained organic layer was washed with water and saturated sodium chloride solution and dried over anhydrous sodium sulfate. The solvent was removed under reduced pressure and the obtained crude product was purified by thin layer chromatography (hexane/ethyl acetate) to yield 630 mg (74%) of the title compound.

Example 38

6-[(4R)-4-{[3-(7-Methoxy-4-methyl-2-oxoquinolin-1(2H)-yl)propyl]amino}-2-oxopyrrolidin-1-yl]-2H-pyrido[3,2-b][1,4]oxazin-3(4H)-one

[Formula 168]

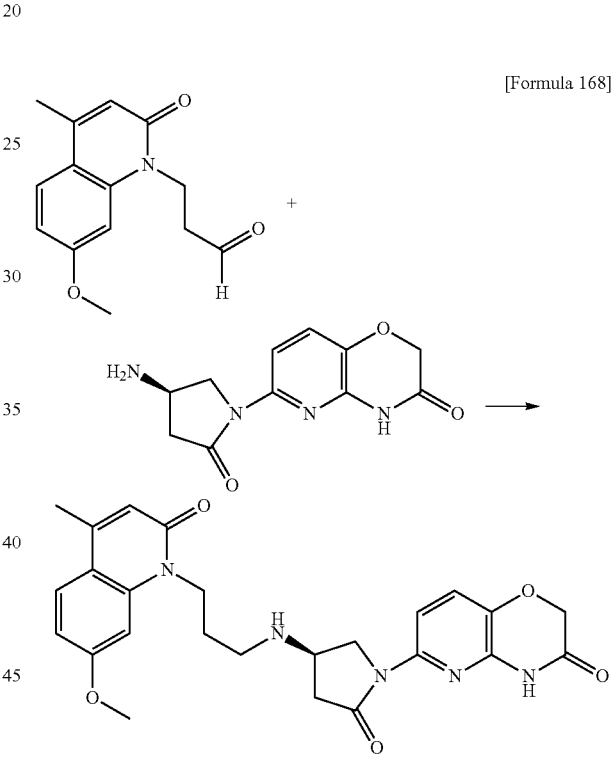

To a solution of 3-(7-methoxy-4-methyl-2-oxoquinolin-1 (2H)-yl)propanal (150 mg, 1.13 mmol) in N,N-dimethylformamide (5 ml) was added 6-[(4R)-4-amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21 and 22; 303 mg, 1.22 mmol) and the mixture was stirred at room temperature for 1 hour. After cooling the reaction solution on ice, sodium triacetoxyborohydride (388 mg, 1.83 mmol) was added thereto and the mixture was stirred at room temperature for 2 hours. A sodium hydrogen carbonate aqueous solution was added, the reaction solution was extracted with ethyl acetate and the extract was washed with water and saturated sodium chloride solution. The obtained organic layer was dried over anhydrous sodium sulfate and the solvent was removed under reduced pressure. The obtained crude product was purified by thin layer chromatography (dichloromethane/methanol) so as to yield 15 mg (3%) of the title compound.

$^1$H-NMR(400 MHz,DMSO-d$_6$)δ:1.76(2H,m),2.38-2.79 (7H,m),3.40(1H,brs),3.77(1H,m),3.85(3H,s),4.01(1H,m), 4.26(2H,m),4.60(2H,s),6.33(1H,s),6.90(1H,m),7.40(1H,m), 7.70(1H,m),7.71(1H,m),7.83(1H,m).

MS(ESI)m/z:478(M+H)$^+$.

Example 39

6-[(4R)-4-{[3-(3-Methoxy-6-oxopyrido[2,3-b]pyrazin-5 (6H)-yl)propyl]amino}-2-oxopyrrolidin-1-yl]-2H-pyrido[3,2-b][1,4]oxazin-3(4H)-one

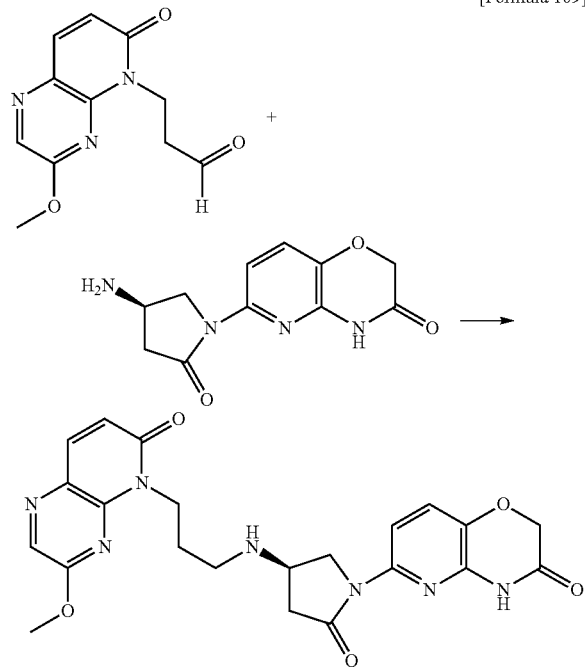

[Formula 169]

To a solution of 3-(3-methoxy-6-oxopyrido[2,3-b]pyrazin-5 (6H)-yl)propanal (Reference Example 24, 120 mg, 0.515 mmol) in N,N-dimethylformamide (1.6 ml) were added 6-[(4R)-4-amino-2-oxopyrrolidin-1-yl]-2H-pyrido[3,2-b][1,4]oxazin-3(4H)-one (synthesized using [(3R)-5-oxopyrrolidin-3-yl]carbamic acid tert-butyl ester synthesized with reference to WO2004/22536 in the same manner as in Reference Examples 20, 21, 22; 166 mg, 0.66 mmol) and acetic acid (0.04 ml, 0.66 mmol) and the mixture was stirred at room temperature for 30 minutes. The reaction solution was then cooled on ice and sodium triacetoxyborohydride (141 mg, 0.66 mmol) was added thereto. After stirring overnight, sodium triacetoxyborohydride (282 mg, 1.32 mmol) was added to the reaction solution, which was further stirred at room temperature for 2 days. A sodium hydrogen carbonate aqueous solution was added to the reaction solution, which was then extracted with ethyl acetate and the obtained organic layer was washed with water and saturated sodium chloride solution. The layer was dried over anhydrous sodium sulfate and the solvent was removed under reduced pressure. The obtained crude product was purified by thin layer chromatography (dichloromethane/methanol) to yield 21 mg (9%) of the title compound.

$^1$H-NMR(400 MHz,DMSO-d$_6$+D$_2$O)δ:1.87-1.89(2H,m), 2.33-2.37(1H,m),2.59(2H,m),2.77-2.83(1H,dd,J=7 Hz,17 Hz),3.41(1H,m),3.72-3.74(1H,m),3.96-3.98(1H,m),4.02 (3H,s),4.37-4.44(2H,m),4.60(2H,s),6.72-6.74(1H,d,J=8 Hz),7.37-7.39(1H,d,J=8 Hz),7.77-7.79(1H,d,J=8 Hz),7.94-7.96(1H,d,J=8 Hz),8.19(1H,s).

MS(ESI)m/z:466(M+H)$^+$.

Example 40

6-[(4R)-4-({[3-(3-Methoxy-6-oxopyrido[2,3-b]pyrazin-5 (6H)-yl)propyl]amino}methyl)-2-oxopyrrolidin-1-yl]-2H-pyrido[3,2-b][1,4]oxazin-3(4H)-one

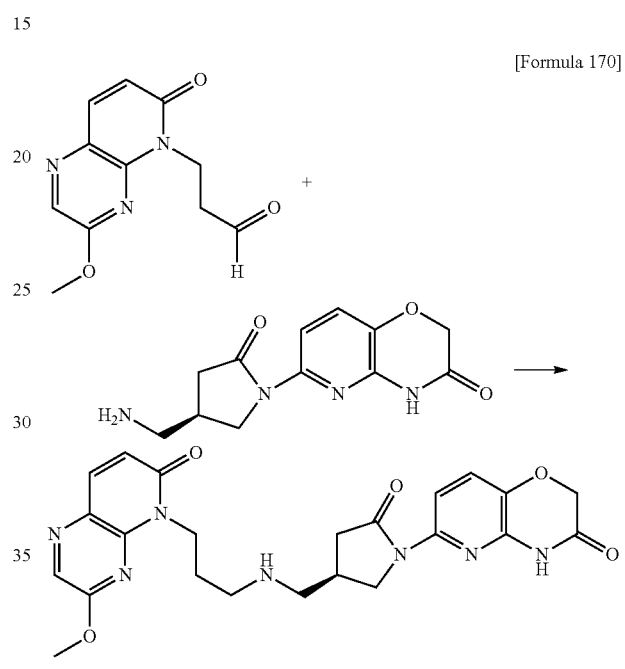

[Formula 170]

To a solution of 3-(3-methoxy-6-oxopyrido[2,3-b]pyrazin-5 (6H)-yl)propanal (Reference Example 24, 120 mg, 0.515 mmol) in N,N-dimethylformamide (1.6 ml) were added 6-[(4R)-4-(aminomethyl)-2-oxopyrrolidin-1-yl]-2H-pyrido[3,2-b][1,4]oxazin-3(4H)-one (Reference Example 54, 175 mg, 0.66 mmol) and acetic acid (0.04 ml, 0.66 mmol), and the mixture was stirred at room temperature for 30 minutes. The reaction solution was cooled on ice, sodium triacetoxyborohydride (141 mg, 0.66 mmol) was added thereto and stirred overnight at room temperature. Two equivalents of sodium triacetoxyborohydride (282 mg, 1.32 mmol) were further added thereto and the reaction solution was stirred for 2 days. A sodium hydrogen carbonate aqueous solution was added to the reaction solution, which was then extracted with ethyl acetate and the obtained organic layer was washed with water and saturated sodium chloride solution. Subsequently, the organic layer was dried over anhydrous sodium sulfate and the solvent was removed under reduced pressure. The obtained crude product was purified by thin layer chromatography (dichloromethane/methanol) to yield 27 mg (11%) of the title compound.

$^1$H-NMR(400 MHz,DMSO-d$_6$+D$_2$O)δ:2.02(2H,m),2.44-2.87(7H,m),3.65(1H,m),4.07(3H,s),4.11(1H,m),4.42(2H, m),4.62(2H,s),6.77-6.80(1H,d,J=12 Hz),7.40-7.42(1H,d,J=8 Hz),7.74-7.76(1H,d,J=8 Hz),8.00-8.02(1H,d,J=8 Hz),8.25 (1H,s).

MS(ESI)m/z:480(M+H)$^+$.

The measurement method of antibacterial activity of the compound of the present invention was carried out in accordance with the standard methods specified by the Japanese Society of Chemotherapy, and the results are shown in MIC (μg/mL) (Table 1).

TABLE 1

| Compound | bacteria MRSA DB00026 |
| --- | --- |
| Example 1 | 0.12 |
| Example 2 | ≤0.06 |
| Example 15 | ≤0.06 |
| Example 16 | ≤0.06 |
| Example 19 | ≤0.06 |
| Example 22 | 0.25 |
| Example 23 | ≤0.06 |

[Industrial Applicability]

The compound of the invention of the present application, a salt, or a hydrate thereof exhibits wide and strong antibacterial activity against Gram-positive bacteria and Gram-negative bacteria, and it also has excellent safety. Thus, the compound of the present invention, a salt, or a hydrate thereof is anticipated to exhibit excellent effects for the treatment and/or prevention of infectious diseases.

The invention claimed is:

1. A compound represented by the following formula (I) or a salt thereof:

(I)

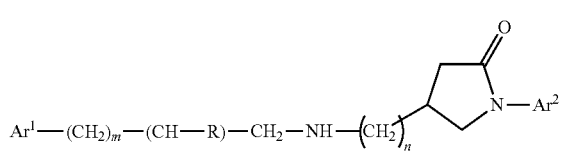

wherein R represents a hydrogen atom, a hydroxy group, or a halogen atom,
m represents an integer 0, 1, or 2,
n represents an integer 0 or 1
$Ar^1$ represents a bicyclic heterocyclic group represented by the following formula:

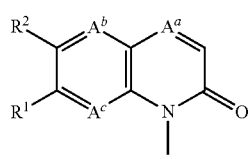

wherein $A^a$ represents a nitrogen atom or $C-R^a$, $A^b$ represents a nitrogen atom or $C-R^b$, and $A^c$ represents a nitrogen atom or $C-R^c$,
$R^a$, $R^b$, and $R^c$ independently represent a hydrogen atom or an alkyl group containing 1 to 6 carbon atoms,
$R^1$ and $R^2$ independently represent a hydrogen atom, an alkoxy group containing 1 to 6 carbon atoms, a halogenoalkoxy group containing 1 to 6 carbon atoms, a halogen atom, or a cyano group,
$Ar^2$ represents a bicyclic heterocyclic group represented by one of the following formulae:

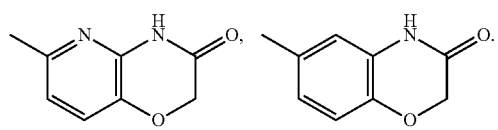

2. The compound or a salt thereof according to claim 1, wherein $Ar^1$ is a group selected from the bicyclic heterocyclic groups shown in the following formulae:

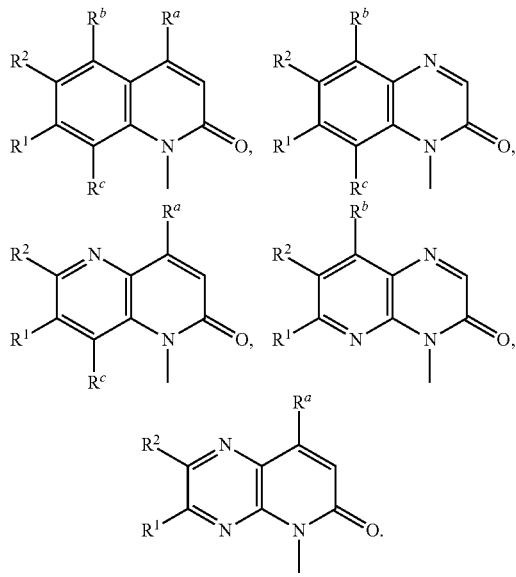

3. The compound or a salt thereof according to claim 1, wherein $R^a$, $R^b$ and $R^c$ independently represent a hydrogen atom or a methyl group.

4. The compound or a salt thereof according to claim 3, wherein $R^b$ and $R^c$ represent a hydrogen atom.

5. The compound or a salt thereof according to claim 1, wherein $Ar^1$ is a group selected from the bicyclic heterocyclic groups shown in the following formulae:

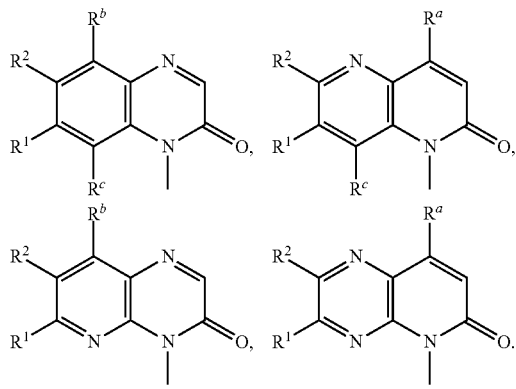

6. The compound or a salt thereof according to claim 1, wherein $A^a$ represents a nitrogen atom.

7. The compound or a salt thereof according to claim 6, wherein $Ar^1$ is a group selected from the bicyclic heterocyclic groups shown in the following formulae:

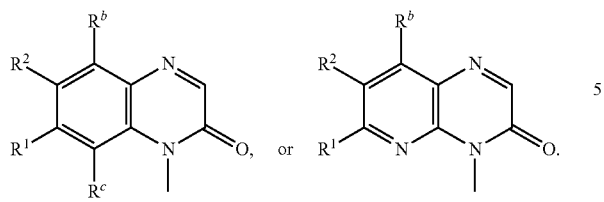

8. The compound or a salt thereof according to claim 6, wherein both $R^b$ and $R^c$ are a hydrogen atom.

9. The compound or a salt thereof according to claim 1, wherein m is an integer 1 or 2, and the sum of m and n is 1 or 2.

10. The compound or a salt thereof according to claim 1, wherein $R^1$ is an alkoxy group containing 1 to 6 carbon atoms.

11. The compound or a salt thereof according to claim 1, wherein $R^1$ is a methoxy group.

12. The compound or a salt thereof according to claim 1, wherein R is a hydrogen atom or a hydroxyl group.

13. A pharmaceutical agent comprising the compound or a salt thereof of claim 1 as its active ingredient.

14. A method for the treatment of infectious diseases, which comprises administering an effective amount of the compound or a salt thereof of claim 1 to a subject in need thereof.

* * * * *